US012060360B2

(12) United States Patent
Marais et al.

(10) Patent No.: US 12,060,360 B2
(45) Date of Patent: *Aug. 13, 2024

(54) LYSYL OXIDASE INHIBITORS

(71) Applicant: The Institute of Cancer Research: Royal Cancer Hospital, London (GB)

(72) Inventors: Richard Marais, Manchester (GB); Caroline Springer, Manchester (GB); Dan Niculescu-Duvaz, Manchester (GB); Natalie Miller, Manchester (GB); Mohammed Aljarah, Manchester (GB); Alfonso Zambon, Reggio Emilia (IT); Leo Leung, Manchester (GB); Deborah Smithen, Manchester (GB); Michael Brown, Manchester (GB); Haoran Tang, Manchester (GB)

(73) Assignee: The Institute of Cancer Research: Royal Cancer Hospital, London (GB)

( * ) Notice: Subject to any disclaimer, the term of this patent is extended or adjusted under 35 U.S.C. 154(b) by 23 days.

This patent is subject to a terminal disclaimer.

(21) Appl. No.: 17/712,541

(22) Filed: Apr. 4, 2022

(65) Prior Publication Data

US 2022/0289757 A1  Sep. 15, 2022

Related U.S. Application Data

(63) Continuation of application No. 16/755,739, filed as application No. PCT/GB2018/052934 on Oct. 12, 2018, now Pat. No. 11,325,915.

(30) Foreign Application Priority Data

Oct. 13, 2017 (GB) .................................. 1716871

(51) Int. Cl.
*C07D 471/08* (2006.01)
*A61K 31/439* (2006.01)
*A61P 35/00* (2006.01)
*C07D 487/08* (2006.01)

(52) U.S. Cl.
CPC ............ *C07D 487/08* (2013.01); *A61P 35/00* (2018.01)

(58) Field of Classification Search
CPC ...... C07D 471/08; A61K 31/439; A61P 35/00
See application file for complete search history.

(56) References Cited

U.S. PATENT DOCUMENTS

| 4,992,546 A | 2/1991 | Hutt, Jr. et al. |
| 5,532,251 A | 7/1996 | Schoen et al. |
| 11,325,915 B2 | 5/2022 | Marais et al. |
| 2015/0132258 A1 | 5/2015 | Hartman |
| 2020/0331922 A1 | 10/2020 | Marais et al. |

FOREIGN PATENT DOCUMENTS

| WO | WO-2008/008517 A2 | 1/2008 |
| WO | WO-2009/081197 A1 | 7/2009 |
| WO | WO-2010/028011 A1 | 3/2010 |
| WO | WO-2011/119345 A2 | 9/2011 |
| WO | WO-2015/073774 A1 | 5/2015 |
| WO | WO-2016/085783 A1 | 6/2016 |
| WO | WO-2016/144846 A1 | 9/2016 |
| WO | WO-2017/003862 A1 | 1/2017 |
| WO | WO-2017/136870 A1 | 8/2017 |
| WO | WO-2017/136871 A1 | 8/2017 |
| WO | WO-2017/139274 A1 | 8/2017 |
| WO | WO-2017/141049 A1 | 8/2017 |
| WO | WO-2017/210559 A1 | 12/2017 |
| WO | WO-2018/048928 A1 | 3/2018 |
| WO | WO-2018/048930 A1 | 3/2018 |
| WO | WO-2018/048943 A1 | 3/2018 |
| WO | WO-2018/157190 A1 | 9/2018 |

OTHER PUBLICATIONS

European Examination Report for EP Application No. 18792450.1 dated Nov. 25, 2021.
International Search Report and Written Opinion for International Application No. PCT/GB2018/052934 dated Apr. 18, 2019.
Peprah et al., "Structure-activity relationship studies of SYA 013, a homopiperazine analog of haloperidol," Bioorganic & Medicinal Chemistry, 20(5):1671-1678 (2012).
Singh et al., "A general and efficient synthesis of 3,6-diazabicyclo[3.2.1]octanes," Tetrahedron, 62: 4011-4017 (2006).
Tang et al., "Lysyl oxidase drives tumour progression by trapping EGF receptors at the cell surface," Nature Communications, 8:14909 (2017).
United Kingdom Search Report for Application No. GB1716871.7 dated Jun. 18, 2018.

*Primary Examiner* — Bruck Kifle
(74) *Attorney, Agent, or Firm* — Foley Hoag LLP; David P. J. Halstead D.; Benjamin A. Vaughan

(57) ABSTRACT

This invention relates to compounds useful as lysyl oxidase (LOX) and lysyl oxidase-like (LOXL) family member (LOXL1, LOXL2, LOXL3, LOXL4) inhibitors. In addition there are contemplated pharmaceutical compositions comprising the compounds and the use of the compounds in the treatment of conditions mediated by LOX and LOXL, for example cancer. In particular a LOX inhibitor such as the present compounds may be for use in the treatment of a cancer associated with EGFR. The present invention also contemplates the identification of biomarkers that predict responsiveness to a LOX inhibitor.

16 Claims, No Drawings
Specification includes a Sequence Listing.

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Forward primer used for cloning of LOX cDNA
      into pEGFP-N1/proGFP2-N1

<400> SEQUENCE: 1
gagagagcta gcatgcgttt cgcctggg                                        28

<210> SEQ ID NO 2
<211> LENGTH: 33
<212> TYPE: DNA
<213> ORGANISM: Artificial Sequence
<220> FEATURE:
<223> OTHER INFORMATION: Reverse primer used for cloning of LOX cDNA
      into pEGFP-N1/proGFP2-N1

<400> SEQUENCE: 2
tctctcctcg agatacggtg aaattgtgca gcc                                  33
```

LYSYL OXIDASE INHIBITORS

RELATED APPLICATIONS

This application is a continuation of U.S. application Ser. No. 16/755,739, filed Apr. 13, 2020; which is a § 371 national-stage application based on International Application No. PCT/GB18/52934, filed on Oct. 12, 2018; which claims the benefit of priority to GB Patent Application No. 1716871.7, filed on Oct. 13, 2017. The entire contents of U.S. application Ser. No. 16/755,739 are incorporated herein by reference.

SEQUENCE LISTING

The instant application contains a Sequence Listing which has been submitted electronically in ASCII format and is hereby incorporated by reference in its entirety. Said ASCII copy, created on Apr. 4, 2022, is named HGX-10302_ST25.txt and is 860 bytes in size.

This invention relates to compounds. More specifically, the invention relates to compounds useful as lysyl oxidase (LOX) and lysyl oxidase-like (LOXL) family members (LOXL1, LOXL2, LOXL3, LOXL4) inhibitors, to pharmaceutical compositions comprising the compounds, to the compounds for use in the treatment of conditions mediated by LOX and LOXL, for example cancer; to a LOX inhibitor for use in the treatment of a cancer associated with EGFR and to biomarkers that predict responsiveness to a LOX inhibitor.

BACKGROUND

LOX (protein-6-lysine-oxidase; EC 1.4.3.13) is an extracellular enzyme that catalyses oxidative deamination of the primary amines of lysine and hydroxylysine in proteins such as collagen and tropoelastin to generate peptidyl-[α]-aminoadipic-[δ]-semialdehyde, an aldehyde that spontaneously condenses to form inter- and intra-chain cross-links (Lucero and Kagan 2006). LOX regulates maturation of proteins in the extracellular matrix (ECM), thereby contributing to ECM tensile strength and function and so playing an important role in connective tissue remodelling. Other proteins have been reported as substrates for oxidation by LOX, such as basic fibroblast growth factor, PDGFR-β and other cationic proteins (Kagan and Li 2003, Li, Nugent et al. 2003, Lucero and Kagan 2006, Lucero, Ravid et al. 2008).

LOX is secreted as a precursor protein that is proteolytically processed by procollagen C-proteinases (bone morphogenetic protein 1—BMP-1) and mammalian tolloid-like protein (mTLL-1)(Uzel, Scott et al. 2001) to generate an 18 kDa pro-peptide and the 32 kDa active LOX enzyme (Lucero and Kagan 2006). The catalytic domain contains copper and a lysine-tyrosylquinone (LTQ) cofactor. LTQ is formed by post-translational oxidation of a catalytic site tyrosine (Tyr349), which then condenses onto a lysine, also within the catalytic site (Lys314), to form a stable covalent modification that is an essential part of the catalytic mechanism (Lucero and Kagan 2006) (Kagan and Li 2003).

LOX is part of a protein family consisting of five paralogues, LOX, LOX-like 1 [LOXL1], LOX-like 2 [LOXL2], LOX-like 3 [LOXL3] and LOX-like 4 [LOXL4]), all containing a conserved catalytic region. LOX enzymes play a crucial role in maintaining ECM stability, by initiating and regulating the crosslinking of collagens and elastin within the extracellular matrix (ECM). The activity of these enzymes is key to maintaining the normal tensile and elastic features of connective tissue of many organ systems within the body. LOX expression decreases during ageing indicating that its activity is especially important during development.

In addition to its role in tissue remodelling, LOX also plays a critical role in primary cancer and metastasis. Studies have shown that LOX plays a fundamental role in the growth of primary tumours in colorectal and lung cancer (Gao, Xiao et al. 2010, Baker, Cox et al. 2011) and glioblastoma (Mammoto, Jiang et al. 2013).

Expression of LOX is elevated in more than 70% of breast cancer patients with Estrogen Receptor negative disease, in 80% of head & neck cancer patients, in 33% of primary colorectal carcinomas (CRC) and 48% of metastatic tissues from patients with CRC (Baker, Cox et al. 2011), and in cirrhotic hepatocellular carcinoma (HCC) patients with a history of alcoholism (Huang, Ho et al. 2013). As discussed in more detail in the description, LOX is also overexpressed in numerous other cancers including lung, prostate and pancreatic cancers.

Elevated LOX expression is also associated with metastasis and decreased patient survival (Baker, Cox et al. 2011, Wilgus, Borczuk et al. 2011)

Other members of the LOX family have been implicated in proliferative diseases such as cancer. LOXL2 is another member of the LOX family that is involved in the cross-linking of extracellular collagens and elastin (Vadasz, Kessler et al. 2005) (Kim, Kim et al. 2010). In addition to conserved C-terminal region, the LOXL2 protein has scavenger receptor cysteine-rich regions that are commonly found in cell surface receptors and adhesion molecules, as well as a cytokine receptor-like domain.

LOXL2 expression has been found upregulated in breast, gastric, colon, esophageal, head and neck, lung and laryngeal carcinomas, as reviewed in Barker et al (Barker, Cox et al. 2012) and in renal cells carcinoma (Hase, Jingushi et al. 2014) (Nishikawa, Chiyomaru et al. 2015).

Studies have suggested that LOX and LOXL2 do not compensate one another, as manipulation of LOX expression did not affect LOXL2 levels in a colorectal cancer model (Baker, Cox et al. 2011). Thus while LOX and LOXL2 are involved in similar extra-cellular processes, it appears that they have distinct roles.

LOXL1 was found to be overexpressed in metastatic non-small cells lung cancer (NSCLC), and the metastatic phenotype can be reduced by inhibition with LOXL1 siRNA (Lee, Kim et al. 2011).

LOXL3 mRNA was expressed in Hs578T highly invasive breast cancer cells, but not in poorly invasive and non-metastatic breast cancer cells MCF7 and T47D (Kirschmann, Seftor et al. 2002). Overexpression of LOXL3 in MDCK epithelial cells induces an epithelial-mesenchymal transition (EMT) process, which is a key step in the progression of metastasis (Peinado, Del Carmen Iglesias-de la Cruz et al. 2005).

In a study on the mRNA levels of LOXL4 in head and neck squamous cell carcinomas, high expression of LOXL4 gene was detected in 71% of all carcinomas and only in 9% of the healthy mucosa samples, indicating that LOXL4 may serve as a selective molecular marker in primary and metastatic head and neck carcinoma (Scola and Gorogh 2010). Up-regulation of LOXL4 was demonstrated in invasive HNC and revealed a significant correlation between LOXL4 expression and local lymph node metastases and higher tumour stages (Goeroegh, Weise et al. 2007). LOXL4 promotes metastasis in gastric cancer (Li, Zhao et al. 2015). LOXL4 together with LOXL2 has been found to be required for metastatic niche formation in a breast orthotopic mouse model (Wong, Gilkes et al. 2011).

LOX and LOXL are implicated in fibrotic diseases, such as liver fibrosis, lung fibrosis, kidney fibrosis, cardiac fibrosis, myelofibrosis and schleroderma. Both LOX and LOXL are highly expressed in fibrotic areas, in surrounding myofibroblasts and in serum of patients with fibrotic conditions (Kagan 1994) (Kim, Peyrol et al. 1999) (Siegel, Chen et al. 1978) (Jourdan-Le Saux, Gleyzal et al. 1994) (Murawaki, Kusakabe et al. 1991).

LOX is also implicated in cardiovascular disease. As discussed in the detailed description of the invention, LOX inhibition may prove beneficial in the treatment or prevention of cardiovascular conditions, including hypertensive heart disease, heart failure, cardiac hypertrophy and atherosclerosis.

LOX is associated with the amyloid-beta (Aβ) related pathological hallmarks (such as cerebral amyloid angiopathy and senile plaques) of both Alzheimer's disease (AD) and hereditary cerebral hemorrhage with amyloidosis of the Dutch type (HCHWA-D) pathogenesis (Wilhelmus, Bol et al. 2013). LOX activity is increased in the hippocampal samples of Alzheimer's disease and also in non-Alzheimer's dementia (Gilad, Kagan et al. 2005). LOX is increased at the site of brain injury (Gilad, Kagan et al. 2001) and spinal cord injury and its inhibition lead to accelerated functional recovery in an unilateral spinal cord dissection model (Gilad and Gilad 2001).

LOXLs are implicated in pulmonary diseases. LOXL2 and LOXL3 are likely to have a role in Primary Alveolar Proteinosis (PAP) since both are expressed in PAP tissue, but not normal lung tissue (Neufeld and Brekhman 2009).

LOX inhibition may be beneficial in the treatment of various ocular conditions. Inhibition of LOX or LOXL2 prevents neovascularization and fibrosis following laser-induced choroidal neovascularization (CNV). Therefore LOX and LOXL inhibitors can be useful in the treatment of conditions characterized by neovascularization, such as age-related macular degeneration (AMD), diabetic retinopathy and retinopathy of prematurity (Stalmans, Marshall et al. 2010).

LOX is implicated in inflammatory conditions and may be useful in the treatment of conditions including, but not limited to acute respiratory distress syndrome (ARDS) (Mambetsariev, Tian et al. 2014).

LOX is the main isoenzyme expressed in human adipose tissue and that its expression is strongly upregulated in samples from obese patients. β-aminopropionitrile reduces body weight gain and improves the metabolic profile in diet-induced obesity in rats (Miana, Galan et al. 2015) and reduces local adipose tissue inflammation (Halberg, Khan et al. 2009).

LOX is upregulated in endometriosis and may be implicated in the establishment and progression of endometriotic lesions (Ruiz, Dutil et al. 2011) (Dentillo, Meola et al. 2010).

Certain LOX inhibitors are known. These include β-aminopropionitrile (BAPN), haloamines, 1,2-diamines, allyl and propargyl amines, hydrazines, semicarbazide and thiolactones, benzylamines, mercaptopyridine and pyridazinone compounds (Pinnell and Martin 1968) (Tang, Simpson et al. 1984) (Palfreyman, McDonald et al. 1989) (Sayre 2007) (Carrington, Bird et al. 1984) (Levene, Sharman et al. 1992) (Liu, Nellaiappan et al. 1997) (Williamson and Kagan 1987) (Anderson, Bartlett et al. 2007) (Schohe-Loop, Burchardt et al. 2003) (Burchardt 2006, Aslam, Miele et al. 2015). However, in general these compounds are either non-selective, lack potency or are unsuitable for use in patients. It is believed that the only LOX inhibitor which has progressed to clinical trials in humans is BAPN. However, it is believed that this compound has not been used clinically since 1978. More recent LOX and LOXL2 inhibitors have been described: LOX inhibitors containing hydrazine and hydrazide groups (Burke et al, 2017); LOXL2 inhibitors: derivatives of haloallylamine (Chang et al, 2017), pyridines (Rowbottom et al, 2016a; Rowbottom et al, 2016b), pyrimidines (Rowbottom & Hutchinson, 2017a) and chromenones (Rowbottom & Hutchinson, 2017b).

There is therefore a need for new LOX inhibitors.

BRIEF SUMMARY OF THE DISCLOSURE

In accordance with the present inventions there is provided a compound of the formula I, or a pharmaceutically acceptable salt thereof:

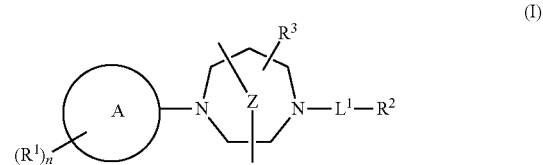

(I)

wherein
ring A is selected from a 3- to 10-membered carbocyclic ring system or a 3- to 10-membered heterocyclic ring system including 1, 2 or 3 heteroatoms selected from N, O or S;
$R^1$ is selected from hydrogen, halo, —CN, —NO$_2$, —OR$^{41}$, —NR$^{41}$R$^{42}$, —SR$^{41}$, —C(O)R$^{41}$, —C(O)OR$^{41}$, —OC(O)R$^{41}$, —O(CR$^{43}$R$^{44}$)$_o$OR$^{41}$, —C(O)NR$^{41}$R$^{42}$, —NR$^{41}$C(O)R$^{43}$, —NR$^{41}$C(O)NR$^{41}$R$^{42}$, —OC(O)NR$^{41}$R$^{42}$, —NR$^{41}$C(O)OR$^{42}$, —SO$_2$NR$^{41}$R$^{42}$, —NR$^{41}$SO$_2$R$^{42}$, —SO$_2$R$^{41}$, optionally substituted C$_{1-6}$ alkyl, optionally substituted C$_{1-6}$ haloalkyl, optionally substituted C$_{2-6}$ alkenyl, optionally substituted C$_{2-6}$ alkynyl, optionally substituted C$_{3-6}$ cycloalkyl, optionally substituted 3- to 7-membered heterocyclyl including 1, 2 or 3 heteroatoms selected from N, O or S, optionally substituted aryl, optionally substituted 5- to 10-membered heteroaryl including 1, 2 or 3 heteroatoms selected from N, O or S;
is selected from 1 to 6
$R^{41}$ and $R^{42}$ are each independently selected from H, optionally substituted C$_{1-6}$ alkyl, C$_{1-6}$ haloalkyl, C$_{2-6}$ alkenyl, C$_{2-6}$ alkynyl, C$_{3-6}$ cycloalkyl, 3- to 7-membered heterocyclyl including 1, 2 or 3 heteroatoms selected from N, O or S, 6-membered aryl, 3- to 7-membered heteroaryl including 1, 2 or 3 heteroatoms selected from N, O or S, or $R^{41}$ and $R^{42}$ together with the nitrogen atom to which they are attached form a 3- to 7-membered heterocyclyl including 1, 2 or 3 heteroatoms selected from N, O or S, wherein when C$_{1-6}$ alkyl is substituted it is substituted with SR$^{43}$, SO$_2$R$^{43}$, NR$^{43}$R$^{44}$ and OR$^{43}$;
$R^{43}$ and $R^{44}$ are each independently selected from H, halo, C$_{1-6}$ alkyl, C$_{1-6}$ haloalkyl, C$_{2-6}$ alkenyl, C$_{2-6}$ alkynyl, C$_{3-6}$ cycloalkyl, 3- to 7-membered heterocyclyl including 1, 2 or 3 heteroatoms selected from N, O or S, aryl, heteroaryl including 1, 2 or 3 heteroatoms selected from N, O or S, or $R^{41}$ and $R^{42}$ together with the nitrogen atom to which they are attached form a 4- to 6-membered heterocyclyl including 1, 2 or 3 heteroatoms selected from N, O or S;

n is 1, 2, 3 or 4;

the group

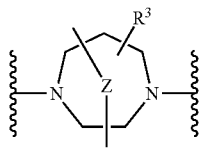

is selected from:

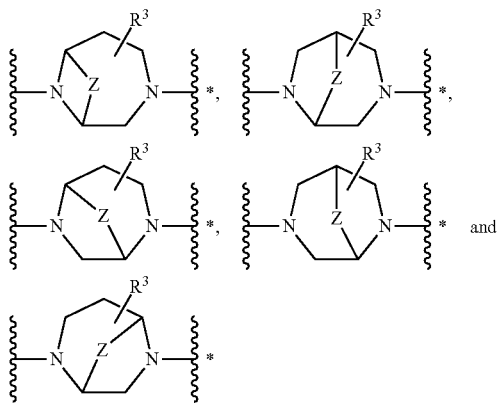

indicates the point of attachment to -$L^1$-$R^2$;

Z is —(C$R^a R^b$)$_m$—, —(C$R^a R^b$)$_p$(C$R^c R^d$)$_q$—;

each $R^a$, $R^b$, $R^c$ and $R^d$ is independently selected from H and $C_{1-4}$ alkyl, or $R^a$ and $R^b$ or $R^c$ and $R^d$ together with the carbon atom to which they are attached form a 3- to 7-membered heterocyclyl including 1, 2 or 3 heteroatoms selected from N, O or S or a $C_{3-6}$-cycloalkyl, provided that at least one of $R^a$ or $R^b$ or $R^c$ or $R^d$ is not H;

m is 1, 2, 3 or 4;

p is 1, 2 or 3;

q is 1, 2 or 3;

$L^1$ is selected from a bond, —C(O)—, —C(O)O—, —C(O)N$R^{45}$—, —C(O)N$R^{45}$N$R^{46}$—, —C(S)—, —C(S)N$R^{45}$—, —S(O)$_2$—, —S(O)$_2$N$R^{45}$—, —C(=N$R^{45}$)—, —C(=N—CN)N$R^{45}$— and —C(=N$R^{45}$)N$R^{46}$—, —C(O)(C$R^{47}R^{48}$)$_r$—, —C(O)N$R^{46}$(C$R^{47}R^{48}$)$_r$—, —S(O)$_2$(C$R^{47}R^{48}$)$_r$—, —(C$R^{47}R^{48}$)$_r$—;

r is 1, 2, 3 or 4;

each of $R^{45}$ and $R^{46}$, is independently selected at each occurrence from H, optionally substituted $C_{1-6}$ alkyl, optionally substituted $C_{1-6}$ haloalkyl, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkenyl, optionally substituted 3- to 6-membered heterocyclyl including 1, 2 or 3 heteroatoms selected from N, O or S, optionally substituted aryl and optionally substituted heteroaryl including 1, 2 or 3 heteroatoms selected from N, O or S;

each of $R^{47}$ and $R^{48}$ is independently selected at each occurrence from H, halo, —O$R^{45}$, optionally substituted $C_{1-6}$ alkyl, optionally substituted $C_{1-6}$ haloalkyl, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkenyl, optionally substituted 3- to 6-membered heterocyclyl including 1, 2 or 3 heteroatoms selected from N, O or S, optionally substituted aryl and optionally substituted heteroaryl including 1, 2 or 3 heteroatoms selected from N, O or S, or $R^{47}$ and $R^{48}$ together with the carbon atom to which they are attached form a $C_{3-6}$-cycloalkyl;

$R^2$ is selected from H, CN, OH, —N$R^{B1}R^{B2}$, halo, optionally substituted $C_{1-6}$ alkyl, $C_{1-6}$ haloalkyl, $C_{2-6}$ alkenyl, optionally substituted $C_{2-6}$ alkynyl, $C_{3-6}$ cycloalkyl, $C_{3-6}$ cycloalkenyl, optionally substituted 3- to 7-membered heterocyclyl including 1, 2 or 3 heteroatoms selected from N, O or S, optionally substituted aryl and optionally substituted 5- to 10-membered heteroaryl including 1, 2 or 3 heteroatoms selected from N, O or S, provided that when $L^1$ is a bond, $R^2$ is not H;

each of $R^{B1}$ and $R^{B2}$ is independently selected at each occurrence from H, optionally substituted $C_{1-6}$ alkyl, or optionally substituted $C_{1-6}$ haloalkyl and $R^3$ is selected from H, unsubstituted $C_{1-6}$ alkyl, $C_{1-6}$ alkyl substituted with O$R^{C1}$, or $C_{1-6}$ alkyl substituted with N$R^{C1}R^{C2}$, wherein $R^{C1}$ and $R^{C2}$ is independently selected at each occurrence from H or $C_{1-6}$ alkyl.

In an embodiment, $R^1$ is H only when A is a bicyclic ring system.

In embodiments, when a group is substituted, substituents are independently selected at each occurrence from: halo, —CN, —NO$_2$, —O$R^{41}$, —N$R^{41}R^{42}$, —S$R^{41}$, —C(O)$R^{41}$, —C(O)O$R^{41}$, —OC(O)$R^{41}$, —O(C$R^{41}R^{42}$)$_m$O$R^{43}$, —C(O)N$R^{41}R^{42}$, —N$R^{41}$C(O)$R^{42}$, —SO$_2R^{43}$, —SO$_2$N$R^{41}R^{42}$, —N$R^{41}$SO$_2R^{42}$, $C_{1-6}$ alkyl, $C_{1-6}$ haloalkyl, $C_{2-6}$ alkenyl, $C_{2-6}$ alkynyl, =O, =S, =N$R^{41}$, $C_{3-6}$ cycloalkyl, aryl and 3- to 6-membered heterocyclyl including 1, 2 or 3 heteroatoms selected from N, O and S.

In embodiments, the group

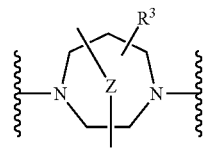

is selected from:

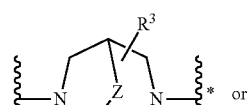 or

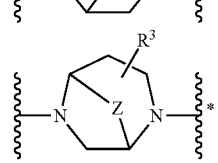

or wherein * indicates the point of attachment to -$L^1$-$R^2$.

In embodiments, $R^3$ is H and the group:

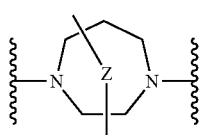
is selected from:
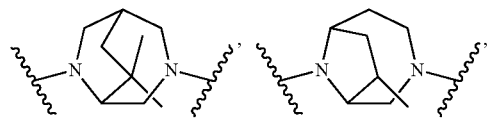
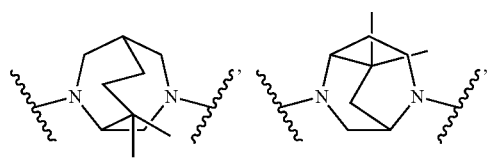
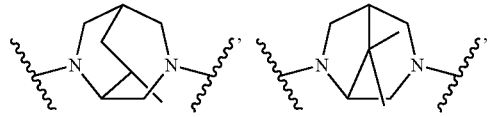
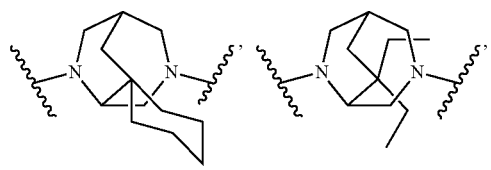
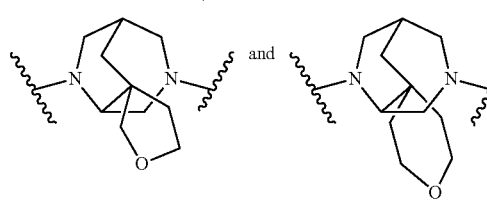
In embodiments, R³ is H and the group
is selected from:
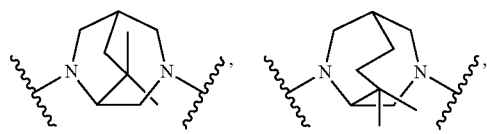
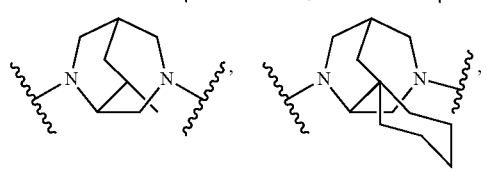
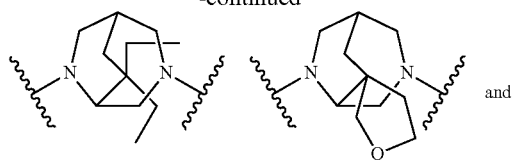
In embodiments, R³ is H and the group
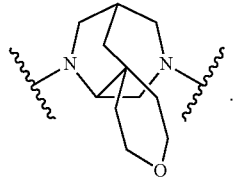 is 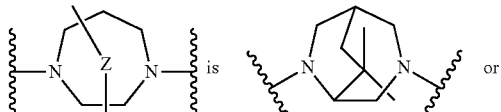 or
In embodiments, R³ is H and the group
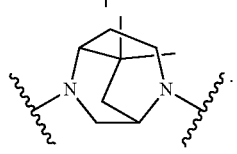
is selected from
In embodiments, the group:
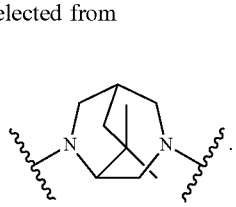
is selected from one of the groups below where the group is substituted with R³:
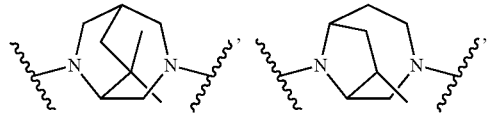

-continued

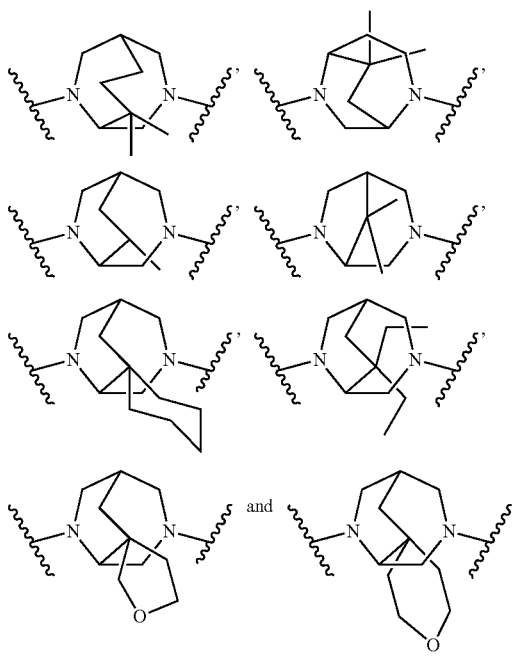

In embodiments, the group

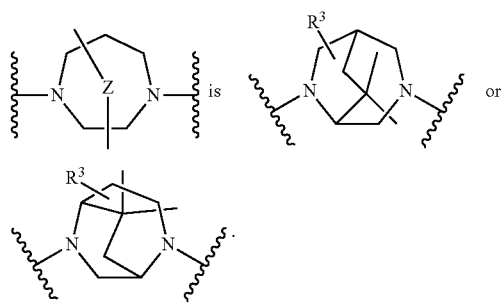

In embodiments, the group

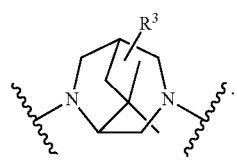

is selected from

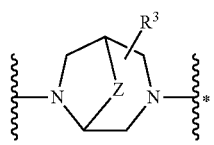

In embodiments, the group

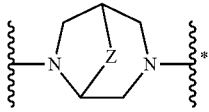

is selected from one of the groups below where the group is substituted with $R^3$:

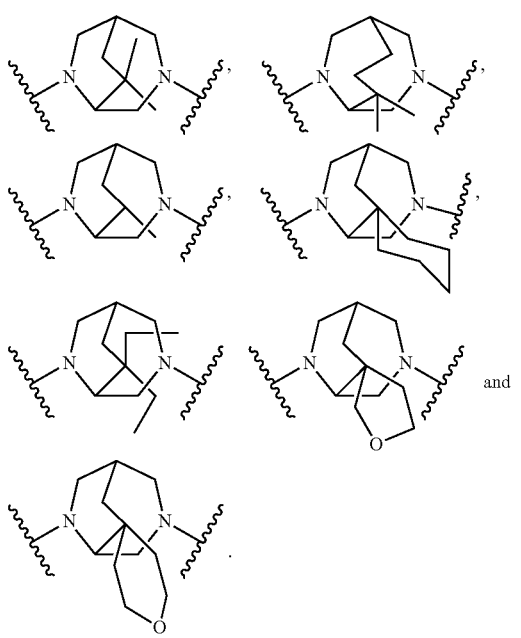

$R^3$ is substituted on a ring that comprises a bridging Z group. As the skilled person would appreciate, $R^3$ can be attached to any of the atoms in the ring on which $R^3$ is substituted. In embodiments, $R^3$ is not substituted at the atoms where the bridging Z group is attached to the ring. This is applicable where the bridging group is Z or any other embodiment of Z. Accordingly, in embodiments, $R^3$ is not substituted on the group

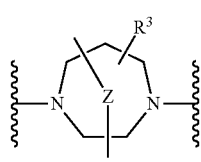

at a carbon on which the bridge portion —Z— is attached.

In embodiments, the group

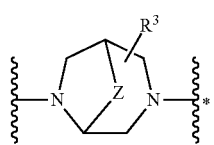

is selected from:

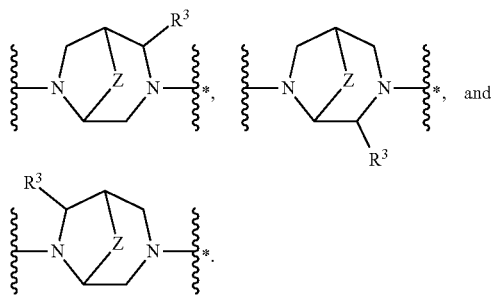

In embodiments, the group

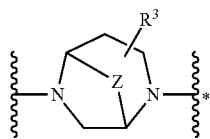

is selected from:

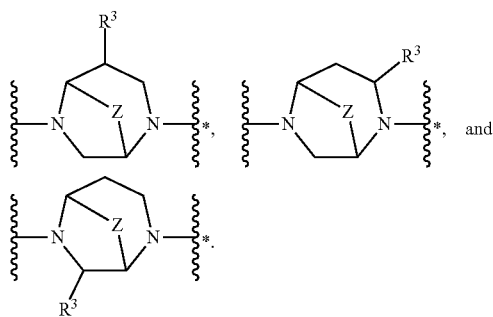

In embodiments, a compound of formula (I) is a compound according to formula (II):

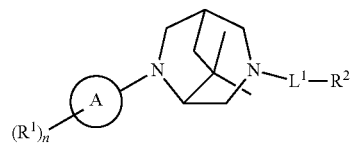

(II)

In embodiments A is selected from a 3- to 10-membered cycloalkyl ring, 3- to 10-membered unsaturated cycloalkyl ring, 6- to 10-membered aryl ring, 3- to 10-membered heterocycloalkyl ring, 3- to 10-membered unsaturated heterocycloalkyl ring, or 5- to 10-membered heteroaryl ring, wherein the heterocycloalkyl, unsaturated heterocycloalkyl, or heteroaryl rings include 1, 2 or 3 heteroatoms selected from N, O or S.

In embodiments A is selected from a 6- to 10-membered aryl ring, or a 5 to 10-membered heteroaryl ring including 1, 2 or 3 heteroatoms selected from N, O or S.

In embodiments, ring A is selected from cyclohexyl, phenyl, naphthyl, tetralin, pyrrole, furan, tetrahydrofuran, pyran, tetrahydropyran, thiophene, pyrazole, imidazole, oxazole, thiazole, isothiozole, triazole, oxadiazole, furazan, thiadiazole, pyridine, pyrimidine, pyrazine, indolizine, indole, indoline, isoindole, isoindoline, azaindole, azaisoindole, benzofuran, isobenzofuran, benzodioxolane, benzodioxane, benzothiophene, isobenzothiophene, benzothiazole, benzisothiazole, benzoxazole, benzisoxazole, imidazopyridine, imidazopyrimidine, indazole, azaindazole, benzimidazole, quinoline, isoquinoline and purine.

In embodiments, ring A is selected from phenyl, naphthyl, pyridine, pyrimidine, benzimidazole, indazole and quinoline.

In embodiments, ring A is selected from cyclohexyl, phenyl, naphthyl, pyridine, pyrimidine, benzimidazole, indazole, benzodioxane and quinoline.

In embodiments, ring A is selected from phenyl, benzodioxane, purine, indazole, thiophene, furan, pyrrole, pyridine, quinoline, isoquinoline, pyrimidine or cyclohexyl.

In embodiments, ring A is phenyl, pyridine or pyrimidine.
In embodiments, ring A is phenyl.

In embodiments, a compound of formula (I) is a compound according to formula (IIIa), (IIIb), (IIIc) or (IIId):

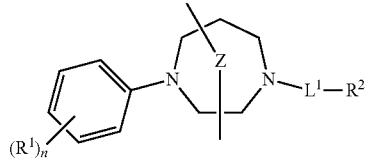

(IIIa)

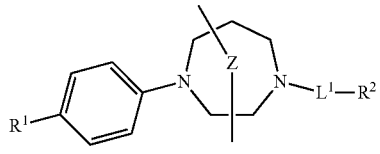

(IIIb)

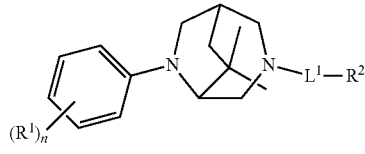

(IIIc)

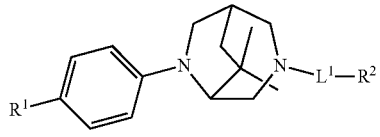

(IIId)

In embodiments, a compound of formula (I) is a compound according to formula (IVa), (IVb), (IVc) or (IVd):

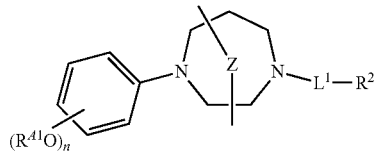

(IVa)

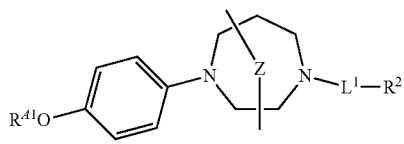

(IVb)

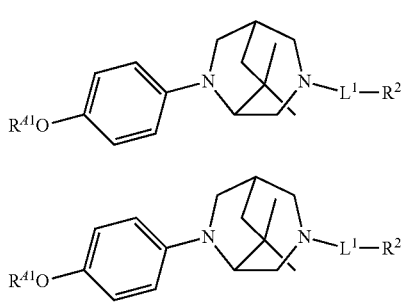

In embodiments, R¹ is independently selected at each occurrence from halo, CN, OR$^{A1}$, C(O)R$^{A1}$, —NR$^{A1}$R$^{A2}$, —SR$^{A1}$, optionally substituted C$_{1-6}$ alkyl and optionally substituted 4 to 7 membered heterocyclyl.

In embodiments, R¹ is independently selected at each occurrence from F, Cl, Br, CN, OH, OCH$_3$, OCH$_2$CH$_3$, OCH$_2$CH$_2$OMe, —O-pyridyl, C(O)H, C(O)CH$_3$, C(O)CH$_2$CH$_3$, —N(Me)CH$_2$CH$_2$S(O)$_2$Me, SCH$_2$CH$_2$OH, SCH$_2$CH$_3$, optionally substituted methyl, optionally substituted ethyl, optionally substituted propyl, optionally substituted butyl, optionally substituted pyrrolidine, optionally substituted tetrahydrofuran, optionally substituted tetrahydrothiophene, optionally substituted pyrazolidine, optionally substituted imidazolidine, optionally substituted dioxolane, optionally substituted thiazolidine, optionally substituted isoxazolidine, optionally substituted piperidine, optionally substituted piperazine, optionally substituted morpholine, optionally substituted dioxane, optionally substituted thiomorpholine and optionally substituted oxathiane.

In embodiments, R¹ is independently selected at each occurrence from halo, CN, OR$^{A1}$, C(O)R$^{A1}$ and optionally substituted methyl, optionally substituted ethyl, optionally substituted propyl, optionally substituted butyl, optionally substituted piperidine, optionally substituted morpholine, optionally substituted piperazine, optionally substituted thiomorpholine and optionally substituted piperazine.

In embodiments, R¹ is independently selected at each occurrence from F, Cl, Br, CN, OH, OCH$_3$, OCH$_2$CH$_3$, C(O)H, C(O)CH$_3$, OCH$_2$CH$_2$OMe, O-pyridyl, —N(Me)CH$_2$CH$_2$S(O)$_2$Me, SCH$_2$CH$_2$OH, optionally substituted methyl, optionally substituted ethyl, optionally substituted propyl, optionally substituted butyl, optionally substituted piperidine, optionally substituted morpholine, optionally substituted thiomorpholine and optionally substituted piperazine.

In embodiments, R¹ is independently selected at each occurrence from F, Cl, Br, CN, OH, OCH$_3$, OCH$_2$CH$_3$, C(O)H, C(O)CH$_3$, OCH$_2$CH$_2$OMe, O-pyridyl, —N(Me)CH$_2$CH$_2$S(O)$_2$Me, SCH$_2$CH$_2$OH, optionally substituted methyl, optionally substituted ethyl, optionally substituted propyl, optionally substituted butyl, optionally substituted piperidine, optionally substituted morpholine, optionally substituted thiomorpholine and optionally substituted piperazine; when R¹ is substituted it is substituted with 1 to 3 substituents independently selected from halo, CN, OH, —C(O)H, —C(O)Me, methyl, ethyl, iso-propyl, OCH$_3$, =O, SO$_2$CH$_3$.

In embodiments, R¹ is independently selected at each occurrence from F, Cl, Br, CN, OH, OCH$_3$, OCH$_2$CH$_3$, C(O)H, C(O)CH$_3$, OCH$_2$CH$_2$OMe, O-pyridyl, —N(Me)CH$_2$CH$_2$S(O)$_2$Me, SCH$_2$CH$_2$OH, methyl, ethyl, propyl, butyl, piperidine, morpholine, thiomorpholine and piperazine, piperidine substituted with two F, thiomorpholine substituted with two =O, and piperazine substituted with —SO$_2$CH$_3$.

In embodiments n is 1 or 2, preferably 1.

In embodiments R¹ is ethoxy or optionally substituted 6-membered heterocycloalkyl, for example R¹ may be ethoxy, optionally substituted piperidine, optionally substituted morpholine, optionally substituted thiomorpholine and optionally substituted piperazine. Preferably R¹ is thiomorpholine dioxide, morpholine, sulfonylpiperazine, difluoropiperidine or ethoxy. R¹ may be thiomorpholine dioxide.

In embodiments R¹ is ethoxy, —N(Me)CH$_2$CH$_2$S(O)$_2$Me, or optionally substituted 6-membered heterocycloalkyl, for example R¹ may be ethoxy, —N(Me)CH$_2$CH$_2$S(O)$_2$Me, optionally substituted piperidine, optionally substituted morpholine, optionally substituted thiomorpholine and optionally substituted piperazine; L¹ is selected from a bond, —C(O)—, —C(O)NH—, —C(O)NR$^{A6}$(CR$^{A7}$R$^{A8}$)$_r$—, and —(CR$^{A7}$R$^{A8}$)$_r$—; and R² is selected from —NHCH$_2$CH$_2$OH, —CH$_2$CH$_2$OH, thiomorpholine dioxide, morpholine or methylsulfonyl piperazine.

In embodiments R¹ is ethoxy or optionally substituted 6-membered heterocycloalkyl, for example R¹ may be ethoxy, optionally substituted piperidine, optionally substituted morpholine, optionally substituted thiomorpholine and optionally substituted piperazine; L¹ is selected from a bond, —C(O)NH—, —C(O)NR$^{A6}$(CR$^{A7}$R$^{A8}$)$_r$—, and —(CR$^{A7}$R$^{A8}$)$_r$—; and R² is selected from —CH$_2$CH$_2$OH, thiomorpholine dioxide, or morpholine.

Preferably R¹ is thiomorpholine dioxide, morpholine, methyl sulfonylpiperazine, difluoropiperidine or ethoxy; L¹ is selected from a bond, —C(O)NH—, —C(O)NR$^{A6}$(CR$^{A7}$R$^{A8}$)$_r$—, and —(CR$^{A7}$R$^{A8}$)$_r$—; and R² is selected from —CH$_2$CH$_2$OH, thiomorpholine dioxide, or morpholine.

In embodiments, R¹ is independently selected at each occurrence from fluoro, chloro, bromo, C(O)H, OCH$_3$, OCH$_2$CH$_3$, OCH$_2$CH$_2$OCH$_3$, and —N(Me)CH$_2$CH$_2$S(O)$_2$Me.

In embodiments, R¹ is independently selected at each occurrence from fluoro, chloro, bromo, C(O)H, OCH$_3$, OCH$_2$CH$_3$ and OCH$_2$CH$_2$OCH$_3$.

In embodiments, R¹ is independently selected at each occurrence from OCH$_3$, OCH$_2$CH$_3$ and OCH$_2$CH$_2$OCH$_3$.

In embodiments, R¹ is optionally substituted 3- to 7-membered heterocyclyl including 1, 2 or 3 heteroatoms selected from N, O or S.

In embodiments, R¹ is optionally substituted 6 membered heterocyclyl including 1, 2 or 3 heteroatoms selected from N, O or S.

In embodiments, R¹ is optionally substituted 6 membered heterocyclyl including 1 or 2 heteroatoms selected from N, O or S.

In embodiments, R¹ is 6 membered heterocyclyl including 1, 2 or 3 heteroatoms selected from N, O or S substituted with 1 or 2 oxo or halo groups.

In embodiments, R¹ is 6 membered heterocyclyl including 1 or 2 heteroatoms selected from N, O or S substituted with 1 or 2 oxo or halo groups.

In embodiments, R¹ is SR$^{A1}$.
In embodiments, R¹ is OR$^{A1}$.
In embodiments, R$^{A1}$ is optionally substituted C$_{1-6}$ alkyl.
In embodiments, R$^{A1}$ is optionally substituted ethyl.
In embodiments, R$^{A1}$ is ethyl.
In embodiments, R$^{A1}$ is ethyl substituted with OCH$_3$.
In embodiments, R$^{A1}$ is ethyl substituted with OH.

In embodiments, R[1] is a substituent that is located in the para position relative to the

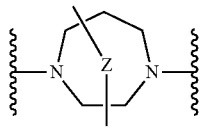

group on ring A.

In embodiments, R[1] is a substituent that is located in the meta position relative to the

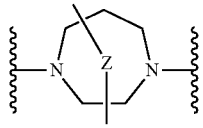

group on ring A.

In embodiments, R[1] is independently selected at each occurrence from F, Cl, Br, CN, OH, OCH$_3$, OCH$_2$CH$_3$, C(O)H, C(O)CH$_3$, C(O)CH$_2$CH$_3$, —N(Me)CH$_2$CH$_2$S(O)$_2$Me, optionally substituted methyl, optionally substituted ethyl, optionally substituted propyl, optionally substituted butyl, optionally substituted pyrrolidine, optionally substituted tetrahydrofuran, optionally substituted tetrahydrothiophene, optionally substituted pyrazolidine, optionally substituted imidazolidine, optionally substituted dioxolane, optionally substituted thiazolidine, optionally substituted isoxazolidine, optionally substituted piperidine, optionally substituted piperazine, optionally substituted morpholine, optionally substituted dioxane, optionally substituted thiomorpholine and optionally substituted oxathiane and is substituted in the para position relative to the

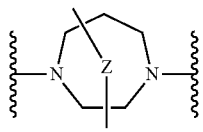

group on ring A.

In embodiments, when R[1] is substituted it is substituted with 1 to 3 substituents independently selected from halo, CN, OH, —C(O)H, —C(O)Me, methyl, ethyl, iso-propyl, OCH$_3$, =O and SO$_2$CH$_3$.

In embodiments, when R[1] is substituted it is substituted with 1 to 3 substituents independently selected from halo, CN, OH, OCH$_3$, =O and SO$_2$CH$_3$.

In embodiments, R$^{A1}$ and R$^{A2}$ are selected from H, optionally substituted C$_{1-6}$ alkyl and heteroaryl including 1, 2 or 3 heteroatoms selected from N, O or S. When substituted R$^{A1}$ and R$^{A2}$ may be substituted with —SO$_2$R$^{A3}$.

In embodiments, R$^{A1}$ and R$^{A2}$ are selected from H, methyl, ethyl, propyl, butyl, CH$_2$CH$_2$S(O)$_2$Me and pyridine.

In embodiments, n is 1, 2 or 3.

In embodiments, Z is —(CR$^a$R$^b$)$_p$(CR$^c$R$^d$)$_q$—.

In embodiments, Z is —(CR$^a$R$^b$)$_p$(CR$^c$R$^d$)$_q$— wherein each of R$^a$, R$^b$, R$^c$ and R$^d$ are independently selected from H and C$_{1-4}$ alkyl, provided that at least one of R$^a$ or R$^b$ or R$^c$ or R$^d$ is not H.

In embodiments, Z is —(CR$^a$R$^b$)$_p$(CR$^c$R$^d$)$_q$— wherein each of R$^a$, R$^b$, R$^c$ and R$^d$ are independently selected from H, methyl, ethyl, propyl and butyl, provided that at least one of R$^a$ or R$^b$ or R$^c$ or R$^d$ is not H.

In embodiments, Z is —(CR$^a$R$^b$)$_p$(CR$^c$R$^d$)$_q$— wherein each of R$^a$, R$^b$, R$^c$ and R$^d$ are independently selected from H and C$_{1-4}$ alkyl, or R$^a$ and R$^b$ or R$^c$ and R$^d$ together with the carbon atom to which they are attached from a 3- to 6-membered heterocyclyl including 1, 2 or 3 heteroatoms selected from N, O or S or C$_{3-6}$-cycloalkyl, provided that at least one of R$^a$ or R$^b$ or R$^c$ or R$^d$ is not H.

In embodiments, Z is —(CR$^a$R$^b$)$_p$(CR$^c$R$^d$)$_q$— wherein each of R$^a$, R$^b$, R$^c$ and R$^d$ are independently selected from H and C$_{1-4}$ alkyl, or R$^a$ and R$^b$ or R$^c$ and R$^d$ together with the carbon atom to which they are attached form a ring selected from: cyclopropane, cyclobutane, cyclopentane, cyclohexane, aziridine, oxirane, thirane, azetidine, oxelane, thietane, tetrahydrofuran, tetrahydrothiophene, pyrazolidine, imidazolidine, dioxolane, thiazolidine, isoxalidine, tetrahydropyran, piperidine, piperazine, morpholine, dioxane, thiomorpholine, oxathiane and dithiane, provided that at least one of R$^a$ or R$^b$ or R$^c$ or R$^d$ is not H.

In embodiments, Z is —(CR$^a$R$^b$)$_p$(CR$^c$R$^d$)$_q$— wherein each of R$^a$, R$^b$, R$^c$ and R$^d$ are independently selected from H, methyl, ethyl, propyl, butyl, or R$^a$ and R$^b$ or R$^c$ and R$^d$ together with the carbon atom to which they are attached from cyclohexane or tetrahydropyran, provided that at least one of R$^a$ or R$^b$ or R$^c$ or R$^d$ is not H.

In embodiments, L$^1$ is selected from a bond, —SO$_2$—, —C(O)—, —C(O)NR$^{A5}$— and —C(O)NR$^{A6}$(CR$^{A7}$R$^{A8}$)$_r$—.

In embodiments, L$^1$ is selected from —C(O)NR$^{A5}$—, wherein R$^{A5}$ is selected from H and optionally substituted C$_{1-6}$ alkyl. For example, the optional substituent is independently selected from halo, CN, OH, —C(O)H, —C(O)Me, methyl, ethyl, iso-propyl, OCH$_3$, =O and SO$_2$CH$_3$.

In embodiments, L$^1$ is selected from a bond, —SO$_2$—, —C(O)—, —C(O)NH— and —C(O)NH(CH$_2$)$_r$—.

In embodiments, L$^1$ is selected from —C(O)— or —C(O)NH—.

In embodiments, L$^1$ is selected from —C(O)NH—.

In embodiments, a compound of formula (I) is a compound according to formula (Va) or (Vb):

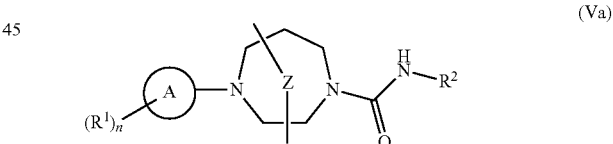

(Va)

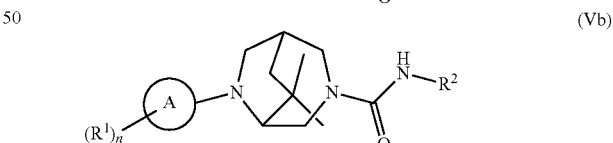

(Vb)

In embodiments, a compound of formula (I) is a compound according to formula (VIa) or (VIb):

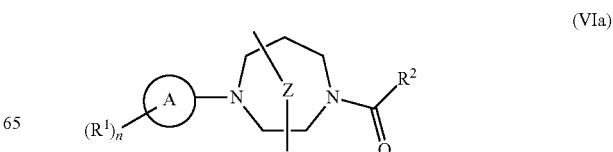

(VIa)

-continued

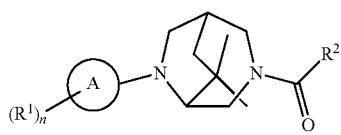
(VIb)

In embodiments, a compound of formula (I) is a compound according to formula (VIIa), (VIIb), (VIIc) or (VIId):

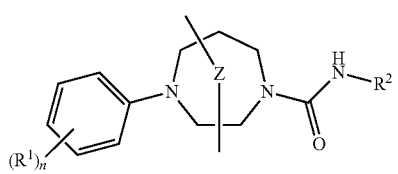
(VIIa)

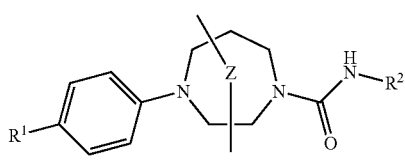
(VIIb)

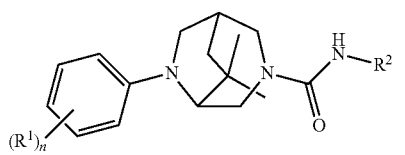
(VIIc)

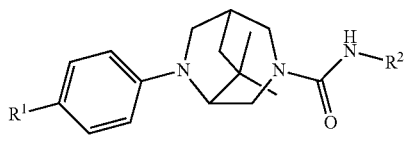
(VIId)

In embodiments according to formulae (VIIa), (VIIb), (VIIc) or (VIId), $R^1$ is optionally substituted 6 membered heterocyclyl including 1, 2 or 3 heteroatoms selected from N, O or S.

In embodiments according to formulae (VIIa), (VIIb), (VIIc) or (VIId), $R^1$ is optionally substituted 6 membered heterocyclyl including 1 or 2 heteroatoms selected from N, O or S.

In embodiments according to formulae (VIIa), (VIIb), (VIIc) or (VIId), $R^1$ is 6 membered heterocyclyl including 1 or 2 heteroatoms selected from N, O or S substituted with 1 or 2 oxo, halo or $SO_2CH_3$ groups.

In embodiments according to formulae (VIIa), (VIIb), (VIIc) or (VIId), $R^1$ is $OR^{41}$.

In embodiments according to formulae (VIIa), (VIIb), (VIIc) or (VIId), $R^1$ is $OR^{41}$, wherein $R^{41}$ is optionally substituted $C_{1-6}$ alkyl.

In embodiments according to formulae (VIIa), (VIIb), (VIIc) or (VIId), $R^1$ is $OR^{41}$, wherein $R^{41}$ is optionally substituted ethyl.

In embodiments, a compound of formula (I) is a compound according to formula (VIIIa), (VIIIb), (VIIIc) or (VIIId):

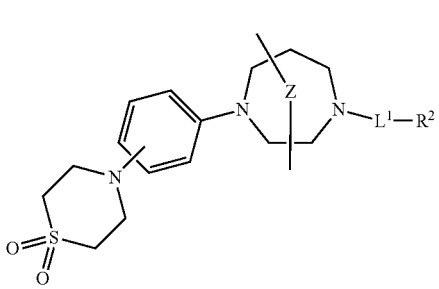
(VIIIa)

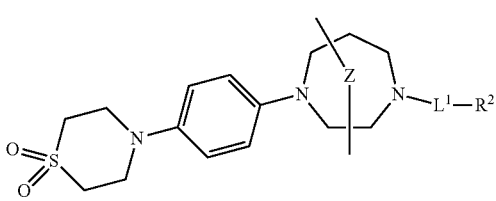
(VIIIb)

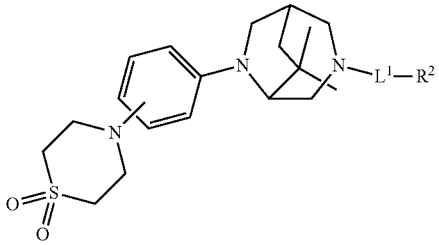
(VIIIc)

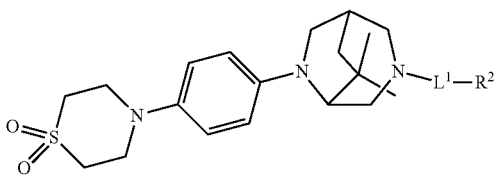
(VIIId)

In embodiments, a compound of formula (I) is a compound according to formula (IXa), (IXb), (IXc) or (IXd):

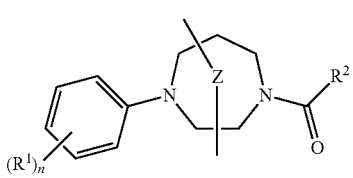
(IXa)

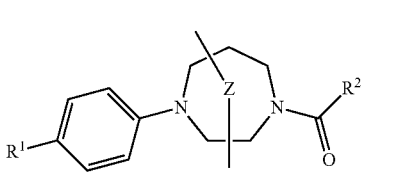
(IXb)

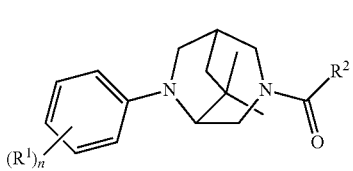
(IXc)

-continued

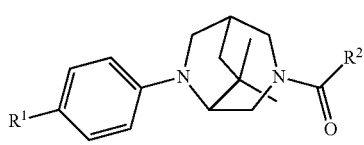
(IXd)

In embodiments, a compound of formula (I) is a compound according to formula (Xa) or (Xb):

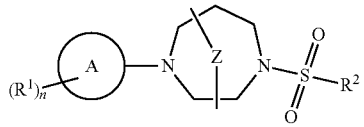
(Xa)

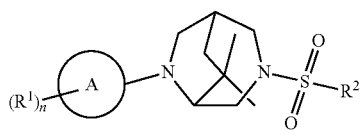
(Xb)

In embodiments, a compound of formula (I) is a compound according to formula (XIa), (XIb), (XIc) or (XId):

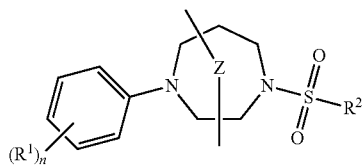
(XIa)

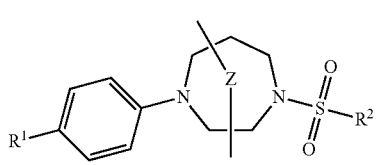
(XIb)

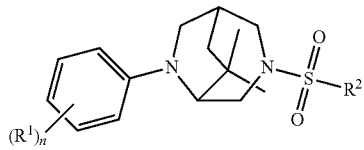
(XIc)

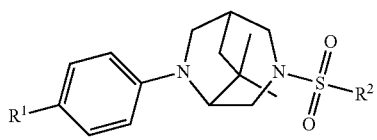
(XId)

In embodiments according to formulae (XIa), (XIb), (XIc) or (XId), $R^1$ is $OR^{A1}$.

In embodiments according to formulae (XIa), (XIb), (XIc) or (XId), $R^1$ is $OR^{A1}$, wherein $R^{A1}$ is optionally substituted $C_{1-6}$ alkyl.

In embodiments according to formulae (XIa), (XIb), (XIc) or (XId), $R^1$ is $OR^{A1}$ wherein $R^{A1}$ is optionally substituted ethyl.

In embodiments, a compound of formula (I) is a compound according to formula (XIIa), (XIIb), (XIIc), (XIId), (XIIe) or (XIIf) wherein $L^1$ is a bond:

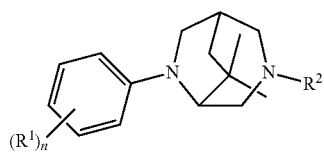
(XIIa)

(XIIb)

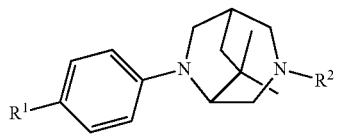

(XIIc)

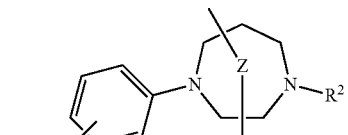

(XIId)

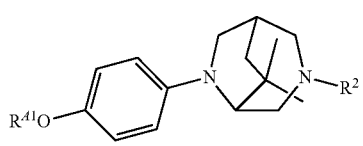

(XIIe)

(XIIf)

In embodiments according to formulae (XIIa) or (XIIb), $R^1$ is $OR^{A1}$.

In embodiments according to formulae (XIIa) or (XIIb), $R^1$ is $OR^{A1}$, wherein $R^{A1}$ is optionally substituted $C_{1-6}$ alkyl.

In embodiments according to formulae (XIIc) or (XIId), $R^{A1}$ is optionally substituted $C_{1-6}$ alkyl.

In embodiments according to formulae (XIIa) or (XIIb), $R^1$ is $OR^{A1}$ wherein $R^{A1}$ is optionally substituted ethyl.

In embodiments according to formulae (XIIc) or (XIId), $R^{A1}$ is optionally substituted ethyl.

In embodiments, $R^2$ is selected from H, CN, OH, —$NR^{B1}R^{B2}$, halo, optionally substituted $C_{1-6}$ alkyl, optionally substituted $C_{2-6}$ alkynyl, optionally substituted 3- to 6-membered heterocyclyl, optionally substituted aryl and optionally substituted heteroaryl including 1, 2 or 3 heteroatoms selected from N, O or S.

In embodiments $R^{B1}$ and $R^{B2}$ are independently selected at each occurrence from H and optionally substituted $C_{1-6}$ alkyl, wherein, when $R^{B1}$ and $R^{B2}$ are substituted, it is substituted with 1 to 3 substituents independently selected at each occurrence from: halo, —CN, —$NO_2$, —$OR^{A1}$, —$NR^{A1}R^{A2}$, —$SR^{A1}$, —C(O)$R^{A1}$, —C(O)O$R^{A1}$, —OC(O)

$R^{A1}$, —O(CR$^{A1}$R$^{A2}$)$_m$OR$^{A3}$, —C(O)NR$^{A1}$R$^{A2}$, —NR$^{A1}$C(O)R$^{A2}$, —SO$_2$R$^{A3}$, —SO$_2$NR$^{A1}$R$^{A2}$, NR$^{A1}$SO$_2$R$^{A2}$, $C_{1-6}$ alkyl, $C_{1-6}$ haloalkyl, $C_{2-6}$ alkenyl, $C_{2-6}$ alkynyl, =O, =S, =NR$^{A1}$. Optionally, R$^{B1}$ and R$^{B2}$ are substituted with 1 to 3 substituents independently selected at each occurrence from: halo, —CN, —OR$^{A1}$, —NR$^{A1}$R$^{A2}$, $C_{1-6}$ alkyl, $C_{1-6}$ haloalkyl, =O, =S, or =NR$^{A1}$.

In embodiments R$^{B1}$ is H and R$^{B2}$ is selected from H, unsubstituted $C_{1-6}$ alkyl, $C_{1-6}$ alkyl substituted with OH, $C_{1-6}$ alkyl substituted with NH$_2$, $C_{1-6}$ alkyl substituted with OH and =NH, $C_{1-6}$ alkyl substituted with NH$_2$ and =NH.

In embodiments, $R^2$ is selected from H, CN, OH, F, Cl, Br, —NR$^{B1}$R$^{B2}$, optionally substituted methyl, optionally substituted ethyl, optionally substituted propyl, optionally substituted butyl, optionally substituted pentyl, optionally substituted hexyl, optionally substituted phenyl, optionally substituted aziridine, optionally substituted oxirane, optionally substituted thirane, optionally substituted azetidine, optionally substituted oxelane, optionally substituted thietane, optionally substituted pyrrolidine, optionally substituted tetrahydrofuran, optionally substituted tetrahydrothiophene, optionally substituted pyrazolidine, optionally substituted imidazolidine, optionally substituted dioxolane, optionally substituted thiazolidine, optionally substituted isoxalidine, optionally substituted tetrahydropyran, optionally substituted dihydro-oxazole, optionally substituted piperidine, optionally substituted piperazine, optionally substituted morpholine, optionally substituted dioxane, optionally substituted thiomorpholine, optionally substituted thiane, optionally substituted oxathiane, optionally substituted dithiane, optionally substituted pyrrole, optionally substituted furan, optionally substituted thiophene, optionally substituted pyrazole, optionally substituted imidazole, optionally substituted oxazole, optionally substituted thiazole, optionally substituted isothiazole, optionally substituted triazole, optionally substituted oxadiazole, optionally substituted furazan, optionally substituted thiadiazole, optionally substituted pyridine, optionally substituted pyridazine, optionally substituted pyrimidine, optionally substituted thiane and optionally substituted pyrazine, wherein R$^{B1}$ is H and R$^{B2}$ is selected from H, unsubstituted $C_{1-6}$ alkyl, $C_{1-6}$ alkyl substituted with OH, $C_{1-6}$ alkyl substituted with NH$_2$, $C_{1-6}$ alkyl substituted with OH and =NH, $C_{1-6}$ alkyl substituted with NH$_2$ and =NH.

In embodiments $R^2$ is selected from H, CN, OH, F, Cl, —NR$^{B1}$R$^{B2}$, optionally substituted methyl, optionally substituted ethyl, optionally substituted propyl, optionally substituted butyl, optionally substituted pentyl, optionally substituted hexyl, optionally substituted tetrahydropyran, optionally substituted thiomorpholine, optionally substituted morpholine, optionally substituted thiane, optionally substituted phenyl, optionally substituted pyrazole, optionally substituted imidazole, optionally substituted pyrrolidine, optionally substituted piperidine, optionally substituted piperazine, and optionally substituted pyridine, wherein R$^{B1}$ is H and R$^{B2}$ is selected from H, unsubstituted $C_{1-6}$ alkyl, $C_{1-6}$ alkyl substituted with OH, $C_{1-6}$ alkyl substituted with NH$_2$, $C_{1-6}$ alkyl substituted with OH and =NH, $C_{1-6}$ alkyl substituted with NH$_2$ and =NH.

In embodiments, when $R^2$ is substituted it is substituted with 1 to 3 substituents selected at each occurrence from: halo, —CN, —NO$_2$, —OR$^{A1}$, —NR$^{A1}$R$^{A2}$, —SR$^{A1}$, —C(O)R$^{A1}$, —C(O)OR$^{A1}$, —OC(O)R$^{A1}$, —O(CR$^{A1}$R$^{A2}$)$_m$OR$^{A3}$, —C(O)NR$^{A1}$R$^{A2}$, —NR$^{A1}$C(O)R$^{A2}$, —SO$_2$R$^{A3}$, —SO$_2$NR$^{A1}$R$^{A2}$, —NR$^{A1}$SO$_2$R$^{A2}$, $C_{1-6}$ alkyl, $C_{1-6}$ haloalkyl, $C_{2-6}$ alkenyl, $C_{2-6}$ alkynyl, =O, =S, =NR$^{A1}$, $C_{3-6}$ cycloalkyl, aryl and 3- to 6-membered heterocyclyl including 1, 2 or 3 heteroatoms selected from N, O and S.

In embodiments, when $R^2$ is substituted it is substituted with 1 to 3 substituents selected at each occurrence from: halo, —CN, —OR$^{A1}$, —NR$^{A1}$C(O)R$^{A2}$, —SO$_2$R$^{A3}$, $C_{1-6}$ alkyl, $C_{1-6}$ haloalkyl, =O, $C_{3-6}$ cycloalkyl, aryl and 3- to 6-membered heterocyclyl (e.g heterocycloalkyl or heteroaryl) including 1, 2 or 3 heteroatoms selected from N, O and S.

In embodiments, when $R^2$ is substituted it is substituted with 1 to 3 substituents selected each occurrence from: halo, —CN, —OR$^{A1}$, —NR$^{A1}$C(O)R$^{A2}$, —SO$_2$R$^{A3}$, =O, 3- to 6-membered heterocycloalkyl including 1, 2 or 3 heteroatoms selected from N, O and S.

In embodiments, when $R^2$ is substituted it is substituted with 1 to 3 substituents selected from halo, CN, $C_{1-6}$ alkyl, pyrrolidinyl, —NHC(O)Me, =O, OH, OCH$_3$ and SO$_2$CH$_3$.

In embodiments, when $R^2$ is substituted it is substituted with 1 to 3 substituents selected from CN, =O, 3- to 6-membered heterocyclyl, OH and $C_{1-6}$ alkyl.

In embodiments, when $R^2$ is substituted it is substituted with 1 to 3 substituents selected from CN, =O, 5-membered heterocyclyl, OH and methyl.

In embodiments $R^2$ is selected from H, CN, OH, F, Cl, Br, —NR$^{B1}$R$^{B2}$, optionally substituted methyl, optionally substituted ethyl, optionally substituted propyl, optionally substituted butyl, optionally substituted pentyl, optionally substituted hexyl, optionally substituted tetrahydropyran, optionally substituted thiomorpholine, optionally substituted morpholine, optionally substituted thiane, optionally substituted phenyl, optionally substituted pyrazole, optionally substituted imidazole, optionally substituted pyrrolidine, optionally substituted piperidine, optionally substituted piperazine, and optionally substituted pyridine; when $R^2$ is substituted it is substituted with 1 to 3 substituents selected from halo, CN, $C_{1-6}$ alkyl, =O, OH, OCH$_3$ and SO$_2$CH$_3$ and wherein R$^{B1}$ is H and R$^{B2}$ is selected from H, unsubstituted $C_{1-6}$ alkyl, $C_{1-6}$ alkyl substituted with OH, $C_{1-6}$ alkyl substituted with NH$_2$, $C_{1-6}$ alkyl substituted with OH and =NH, $C_{1-6}$ alkyl substituted with NH$_2$ and =NH.

In embodiments, $R^2$ is —NR$^{B1}$R$^{B2}$, wherein R$^{B1}$ and R$^{B2}$ is selected from H and optionally substituted $C_{1-6}$ alkyl.

In embodiments, $R^2$ is —NR$^{B1}$R$^{B2}$, wherein R$^{B1}$ and R$^{B2}$ is selected from H and $C_{1-6}$ alkyl optionally substituted with OH, CN and SO$_2$CH$_3$.

In embodiments, $R^2$ is —NR$^{B1}$R$^{B2}$, wherein R$^{B1}$ and R$^{B2}$ is selected from H, $C_{1-6}$ alkyl and $C_{1-6}$ alkyl substituted with OH.

In embodiments, $R^2$ is —NR$^{B1}$R$^{B2}$, wherein R$^{B1}$ and R$^{B2}$ is selected from H and $C_{1-6}$ alkyl substituted with OH.

In embodiments, $R^2$ is —NR$^{B1}$R$^{B2}$, wherein R$^{B1}$ and R$^{B2}$ is selected from H and ethyl substituted with OH.

In embodiments, $R^2$ is optionally substituted $C_{1-6}$ alkyl.

In embodiments, $R^2$ is unsubstituted $C_{1-6}$ alkyl.

In embodiments, $R^2$ is substituted $C_{1-6}$ alkyl.

In embodiments, $R^2$ is optionally substituted propyl.

In embodiments, $R^2$ is optionally substituted ethyl.

In embodiments, $R^2$ is optionally substituted methyl.

In embodiments, $R^2$ is $C_{1-6}$ alkyl substituted with —OR$^{A1}$.

In embodiments, $R^2$ is $C_{1-6}$ alkyl substituted with OH.

In embodiments, $R^2$ is ethyl substituted with OH.

In embodiments, $R^2$ is $C_{1-6}$ alkyl substituted with CN.

In embodiments, $R^2$ is ethyl substituted with CN.

In embodiments, $R^2$ is propyl substituted with CN.

In embodiments, $R^2$ is $C_{1-6}$ alkyl substituted with SO$_2$R$^{A3}$.

In embodiments, $R^2$ is ethyl substituted with SO$_2$CH$_3$.

In embodiments, R² is optionally substituted 3- to 6-membered heterocyclyl including 1, 2 or 3 heteroatoms selected from N, O or S.

In embodiments, R² is unsubstituted 3- to 6-membered heterocyclyl including 1, 2 or 3 heteroatoms selected from N, O or S.

In embodiments, R² is substituted 3- to 6-membered heterocyclyl including 1, 2 or 3 heteroatoms selected from N, O or S.

In embodiments, R² is optionally substituted 5- to 6-membered heterocyclyl including 1, 2 or 3 heteroatoms selected from N, O or S.

In embodiments, R² is unsubstituted 5- to 6-membered heterocyclyl including 1, 2 or 3 heteroatoms selected from N, O or S.

In embodiments, R² is substituted 5- to 6-membered heterocyclyl including 1, 2 or 3 heteroatoms selected from N, O or S.

In embodiments, R² is optionally substituted 6-membered heterocyclyl including 1, 2 or 3 heteroatoms selected from N, O or S.

In embodiments, R² is unsubstituted 6-membered heterocyclyl including 1, 2 or 3 heteroatoms selected from N, O or S.

In embodiments, R² is substituted 6-membered heterocyclyl including 1, 2 or 3 heteroatoms selected from N, O or S.

In embodiments, R² is substituted 3- to 6-membered heterocyclyl including 1, 2 or 3 heteroatoms selected from N, O or S and is substituted with 1 to 3 substituents selected from CN, =O, 3- to 6-membered heterocyclyl, OH and $C_{1-6}$ alkyl.

In embodiments, R² is optionally substituted heteroaryl including 1, 2 or 3 heteroatoms selected from N, O or S.

In embodiments, R² is unsubstituted heteroaryl including 1, 2 or 3 heteroatoms selected from N, O or S.

In embodiments, R² is substituted heteroaryl including 1, 2 or 3 heteroatoms selected from N, O or S.

In embodiments, R² is unsubstituted pyridyl.

In embodiments, R² is $C_{1-6}$ alkyl substituted with 3- to 6-membered heterocyclyl including 1, 2 or 3 heteroatoms selected from N, O or S.

In embodiments, R² is $C_{1-6}$ alkyl substituted with 6-membered heterocyclyl including 1, 2 or 3 heteroatoms selected from N, O or S.

In embodiments, R² is ethyl substituted with 6-membered heterocyclyl.

In embodiments, R² is ethyl substituted with pyridyl.

In embodiments, R² is ethyl substituted with imidazole.

In embodiments, R² is optionally substituted aryl.

In embodiments, R² is unsubstituted aryl.

In embodiments, R² is substituted aryl.

In embodiments, R² is phenyl.

In embodiments, R² is phenyl substituted with $OR^{41}$.

In embodiments, R² is phenyl substituted with $OCH_3$.

In embodiments, R² is phenyl substituted with halo.

In embodiments, R² is phenyl substituted with F.

In embodiments R² is thiomorpholinedioxide.

In embodiments, a compound of formula (I) is a compound according to formula (XIIIa) or (XIIIb):

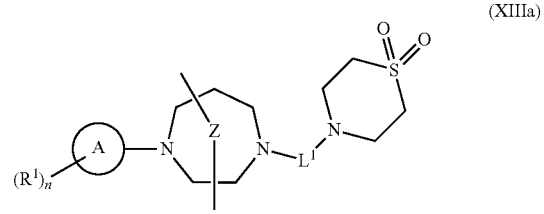

(XIIIa)

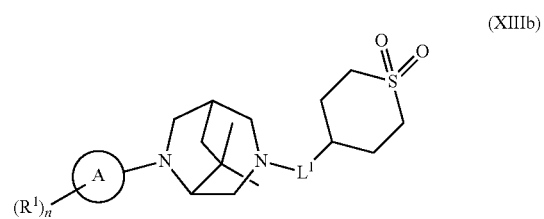

(XIIIb)

In embodiments, a compound of formula (I) is a compound of formula (XIVa), (XIVb), (XIVc) or (XIVd):

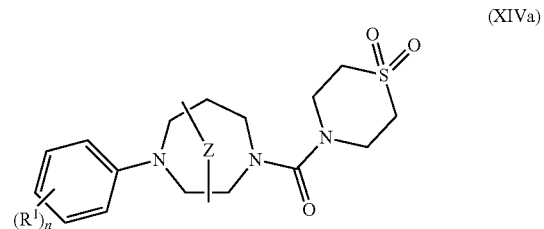

(XIVa)

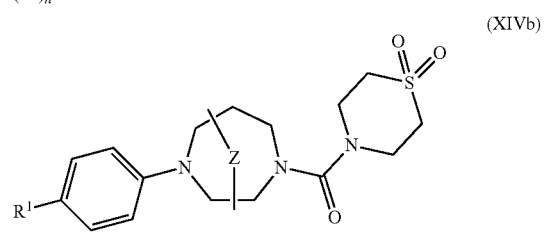

(XIVb)

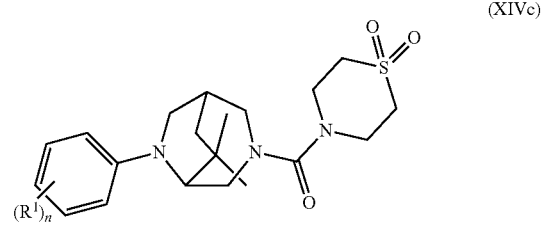

(XIVc)

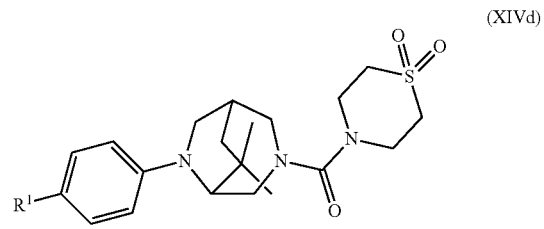

(XIVd)

In embodiments

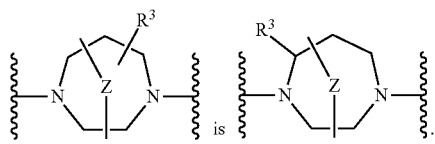

In embodiments R³ is substituted at the position shown above in any embodiment of the homopiperazine ring.

In embodiments R³ is H and consequently R³ can be considered to be absent.

In embodiments R³ is selected from: H, —CH$_2$OH, —CH$_3$, and —CH$_2$OMe.

In embodiments, ring A is selected from phenyl, naphthyl, pyrrole, furan, thiophene, pyrazole, imidazole, oxazole, thiazole, isothiazole, triazole, oxadiazole, furazan, thiadiazole, pyridine, pyrimidine, pyrazine, indole, isoindole, benzofuran, isobenzofuran, benzothiophene, isobenzothiophene, benzodioxane, indazole, benzimidazole, quinoline and isoquinoline; and R¹ is independently selected at each occurrence from halo, CN, OR$^{A1}$, C(O)R$^{A1}$, —NR$^{A1}$R$^{A2}$, —SR$^{A1}$, optionally substituted C$_{1-6}$ alkyl and optionally substituted 3 to 7 membered heterocyclyl.

In embodiments, ring A is selected from phenyl, naphthyl, pyrrole, furan, thiophene, pyrazole, imidazole, oxazole, thiazole, isothiazole, triazole, oxadiazole, furazan, thiadiazole, pyridine, pyrimidine, pyrazine, indole, isoindole, benzofuran, isobenzofuran, benzothiophene, isobenzothiophene, benzodioxane, indazole, benzimidazole, quinoline and isoquinoline; and R¹ is independently selected at each occurrence from F, C, Br, CN, OH, OCH$_3$, OCH$_2$CH$_3$, OCH$_2$CH$_2$OMe, —O-pyridyl, C(O)H, C(O)CH$_3$, C(O)CH$_2$CH$_3$, SCH$_2$CH$_2$OH, —N(Me)CH$_2$CH$_2$SO$_2$Me, SCH$_2$CH$_3$, optionally substituted methyl, optionally substituted ethyl, optionally substituted propyl, optionally substituted butyl, optionally substituted pyrrolidine, optionally substituted tetrahydrofuran, optionally substituted tetrahydrothiophene, optionally substituted pyrazolidine, optionally substituted imidazolidine, optionally substituted dioxolane, optionally substituted thiazolidine, optionally substituted isoxazolidine, optionally substituted piperidine, optionally substituted piperazine, optionally substituted morpholine, optionally substituted dioxane, optionally substituted thiomorpholine and optionally substituted oxathiane.

In embodiments, ring A is selected from phenyl, naphthyl, pyrrole, furan, thiophene, pyrazole, imidazole, oxazole, thiazole, isothiazole, triazole, oxadiazole, furazan, thiadiazole, pyridine, pyrimidine, pyrazine, indole, isoindole, benzofuran, isobenzofuran, benzothiophene, isobenzothiophene, benzodioxane, indazole, benzimidazole, quinoline and isoquinoline; and R¹ is independently selected at each occurrence from F, C, Br, CN, OH, OCH$_3$, OCH$_2$CH$_3$, C(O)H, C(O)CH$_3$, OCH$_2$CH$_2$OMe, —O-pyridyl, SCH$_2$CH$_2$OH, —N(Me)CH$_2$CH$_2$SO$_2$Me, optionally substituted methyl, optionally substituted ethyl, optionally substituted propyl, optionally substituted butyl, optionally substituted piperidine, optionally substituted morpholine, optionally substituted thiomorpholine and optionally substituted piperazine; when R¹ is substituted it is substituted with 1 to 3 substituents independently selected from halo, CN, OH, OCH$_3$, =O and SO$_2$CH$_3$.

In embodiments, ring A is selected from phenyl, naphthyl, pyrrole, furan, thiophene, pyrazole, imidazole, oxazole, thiazole, isothiazole, triazole, oxadiazole, furazan, thiadiazole, pyridine, pyrimidine, pyrazine, indole, isoindole, benzofuran, isobenzofuran, benzothiophene, isobenzothiophene, indazole, benzimidazole, quinoline and isoquinoline; R¹ is independently selected at each occurrence from halo, CN, OR$^{A1}$, C(O)R$^{A1}$, —NR$^{A1}$R$^{A2}$, —SR$^{A1}$, optionally substituted C$_{1-6}$ alkyl and optionally substituted 4 to 7 membered heterocyclyl; and n is 1, 2 or 3.

In embodiments, ring A is selected from phenyl, naphthyl, pyrrole, furan, thiophene, pyrazole, imidazole, oxazole, thiazole, isothiazole, triazole, oxadiazole, furazan, thiadiazole, pyridine, pyrimidine, pyrazine, indole, isoindole, benzofuran, isobenzofuran, benzothiophene, isobenzothiophene, indazole, benzimidazole, quinoline and isoquinoline; R¹ is independently selected at each occurrence from halo, CN, OR$^{A1}$, C(O)R$^{A1}$, —NR$^{A1}$R$^{A2}$, —SR$^{A1}$, optionally substituted C$_{1-6}$ alkyl and optionally substituted 4 to 7 membered heterocyclyl; n is 1, 2 or 3; and Z is —(CR$^a$R$^b$)$_p$(CR$^c$R$^d$)$_q$—.

In embodiments, ring A is selected from phenyl, naphthyl, pyrrole, furan, thiophene, pyrazole, imidazole, oxazole, thiazole, isothiazole, triazole, oxadiazole, furazan, thiadiazole, pyridine, pyrimidine, pyrazine, indole, isoindole, benzofuran, isobenzofuran, benzothiophene, isobenzothiophene, indazole, benzimidazole, quinoline and isoquinoline; R¹ is independently selected at each occurrence from halo, CN, OR$^{A1}$, C(O)R$^{A1}$, —NR$^{A1}$R$^{A2}$, —SR$^{A1}$, optionally substituted C$_{1-6}$ alkyl and optionally substituted 4 to 7 membered heterocyclyl; n is 1, 2 or 3; Z is —(CR$^a$R$^b$)$_p$(CR$^c$R$^d$)$_q$— wherein each of R$^a$, R$^b$, R$^c$ and R$^d$ are independently selected from H or C$_{1-6}$ alkyl or R$^a$ and R$^b$ or R$^c$ and R$^d$ together with the carbon atom to which they are attached form a C$_{3-6}$-cycloalkyl, provided that at least one of R$^a$ or R$^b$ or R$^c$ or R$^d$ is not H; and L¹ is selected from a bond, —SO$_2$—, —C(O)— and —C(O)NR$^{A5}$—.

In embodiments, Z is —(CR$^a$R$^b$)$_p$(CR$^c$R$^d$)$_q$— wherein each of R$^a$, R$^b$, R$^c$ and R$^d$ are independently selected from H or C$_{1-6}$ alkyl or R$^a$ and R$^b$ or R$^c$ and R$^d$ together with the carbon atom to which they are attached form a C$_{3-6}$-cycloalkyl, provided that at least one of R$^a$ or R$^b$ or R$^c$ or R$^d$ is not H, and L¹ is selected from a bond, —SO$_2$—, —C(O)— and —C(O)NR$^{A5}$—.

In embodiments, Z is —(CR$^a$R$^b$)$_p$(CR$^c$R$^d$)$_q$— wherein each of R$^a$, R$^b$, R$^c$ and R$^d$ are independently selected from H or C$_{1-6}$ alkyl or R$^a$ and R$^b$ or R$^c$ and R$^d$ together with the carbon atom to which they are attached form a C$_{3-6}$-cycloalkyl, provided that at least one of R$^a$ or R$^b$ or R$^C$ or R$^d$ is not H, and L¹ is selected from a bond, —SO$_2$—, —C(O)— and —C(O)NR$^{A5}$— and R² is selected from optionally substituted C$_{1-6}$ alkyl, optionally substituted C$_{2-6}$ alkynyl, optionally substituted 3- to 6-membered heterocyclyl, optionally substituted aryl and optionally substituted heteroaryl including 1, 2 or 3 heteroatoms selected from N, O or S.

In embodiments, Z is —(CR$^a$R$^b$)$_p$(CR$^c$R$^d$)$_q$— wherein each of R$^a$, R$^b$, R$^c$ and R$^d$ are independently selected from H or C$_{1-6}$ alkyl or R$^a$ and R$^b$ or R$^c$ and R$^d$ together with the carbon atom to which they are attached form a C$_{3-6}$-cycloalkyl, provided that at least one of R$^a$ or R$^b$ or R$^c$ or R$^d$ is not H, and L¹ is selected from a bond, —SO$_2$—, —C(O)— and —C(O)NR$^{A5}$— and R² is selected from optionally substituted methyl, optionally substituted ethyl, optionally substituted propyl, optionally substituted butyl, optionally substituted pentyl, optionally substituted hexyl, optionally substituted phenyl, optionally substituted aziridine, optionally substituted oxirane, optionally substituted thirane, optionally substituted azetidine, optionally substituted oxelane, optionally substituted thietane, optionally substituted pyrrolidine, optionally substituted tetrahydrofuran, optionally substituted dihydro-oxazole optionally substituted tetrahydrothiophene, optionally substituted pyrazolidine, optionally substituted imidazolidine, optionally substituted dioxolane, optionally substituted thiazolidine, optionally substituted isoxalidine, optionally substituted tetrahydropyran, optionally substituted piperidine, optionally substituted piperazine, optionally substituted thiane, optionally substituted morpholine, optionally substituted dioxane, optionally substituted thiomorpholine, optionally substituted oxathiane, optionally substituted dithiane, optionally substituted pyrrole, optionally substituted furan, optionally substituted thiophene, optionally substituted pyrazole, optionally substituted imidazole, optionally substituted oxazole, optionally substituted thiazole, optionally substituted isothiazole, optionally substituted triazole, optionally substituted oxadiazole, optionally substituted furazan, optionally substituted thiadoazole, optionally substituted pyridine, optionally substituted pyridazine, optionally substituted pyrimidine, optionally substituted thiane and optionally substituted pyrazine.

In embodiments, ring A is phenyl or pyridine and $L^1$ is —C(O)— or —C(O)NH—.

In embodiments, ring A is phenyl; $R^1$ is substituted in the para position relative to the

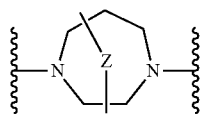

group on ring A and $R^1$ is independently selected at each occurrence from halo, CN, $OR^{41}$, $C(O)R^{41}$ and optionally substituted methyl, optionally substituted ethyl, optionally substituted propyl, optionally substituted butyl, optionally substituted piperidine, optionally substituted morpholine, optionally substituted thiomorpholine and optionally substituted piperazine.

In embodiments, ring A is pyridine or pyrimidine and $R^1$ is independently selected at each occurrence from halo, CN, $OR^{41}$, $C(O)R^{41}$ and optionally substituted methyl, optionally substituted ethyl, optionally substituted propyl, optionally substituted butyl, optionally substituted piperidine, optionally substituted morpholine, optionally substituted thiomorpholine and optionally substituted piperazine.

In embodiments, ring A is selected from phenyl, pyridine or pyrimidine and $R^1$ is independently selected at each occurrence from Br, F, Cl, CN, OH, $OCH_3$, $OCH_2CH_3$, C(O)H, $C(O)CH_3$, —N(Me)$CH_2CH_2SO_2$Me, optionally substituted methyl, optionally substituted ethyl, optionally substituted propyl, optionally substituted butyl, optionally substituted piperidine, optionally substituted morpholine, optionally substituted thiomorpholine and optionally substituted piperazine; when $R^1$ is substituted it is substituted with 1 to 3 substituents independently selected from halo, CN, OH, $OCH_3$, =O, $SO_2CH_3$.

In embodiments, ring A is selected from phenyl, pyridine or pyrimidine and $R^1$ is independently selected at each occurrence from Br, F, Cl, CN, OH, $OCH_3$, $OCH_2CH_3$, C(O)H, $C(O)CH_3$, —N(Me)$CH_2CH_2SO_2$Me, optionally substituted methyl, optionally substituted ethyl, optionally substituted propyl, optionally substituted butyl, optionally substituted piperidine, optionally substituted morpholine, optionally substituted thiomorpholine and optionally substituted piperazine; when $R^1$ is substituted it is substituted with 1 to 3 substituents independently selected from halo, CN, OH, $OCH_3$, =O and $SO_2CH_3$; and the group

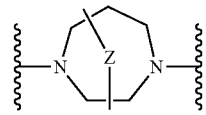

is selected from:

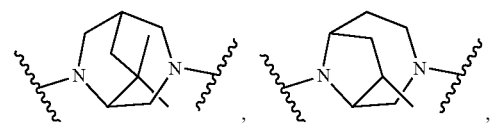

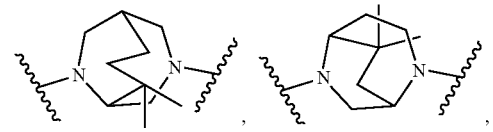

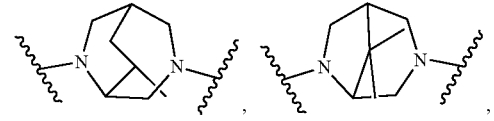

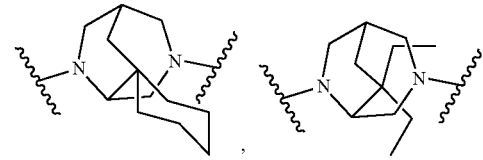

and

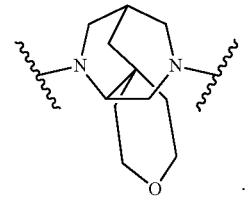

In embodiments, ring A is selected from phenyl, pyridine or pyrimidine and $R^1$ is independently selected at each occurrence from F, Cl, CN, OH, $OCH_3$, $OCH_2CH_3$, C(O)H, $C(O)CH_3$, optionally substituted methyl, optionally substituted ethyl, optionally substituted propyl, optionally substituted butyl, optionally substituted piperidine, optionally substituted morpholine, optionally substituted thiomorpholine and optionally substituted piperazine; when $R^1$ is substituted it is substituted with 1 to 3 substituents independently selected from halo, CN, OH, $OCH_3$, =O and $SO_2CH_3$; and $L^1$ is —C(O)— or —C(O)NH—.

In embodiments, the group:

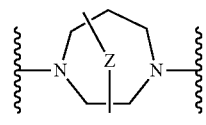

is selected from:

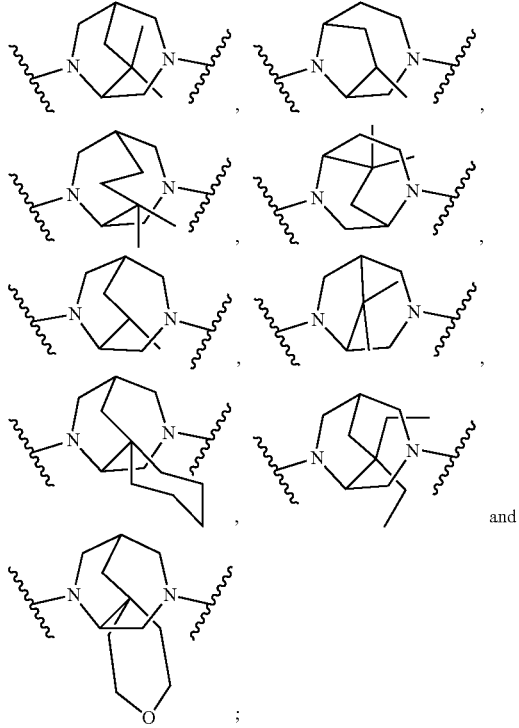

$L^1$ is selected from bond, $SO_2$, —C(O)— and —C(O)NH and ring A is phenyl, pyridine or pyrimidine.

In embodiments, $L^1$ is selected from a bond, —$SO_2$—, —C(O)—, —C(O)NH— —C(O)(CR$^{A7}$R$^{A8}$)$_r$, —C(O)NR$^{A6}$ (CR$^{A7}$R$^{A8}$)$_r$—, —S(O)$_2$(CR$^{A7}$R$^{A8}$)$_r$—, and —(CR$^{A7}$R$^{A8}$)$_r$— and $R^2$ is selected from H, CN, OH, fluoro, choro, optionally substituted methyl, optionally substituted ethyl, optionally substituted propyl, optionally substituted butyl, optionally substituted pentyl, optionally substituted hexyl, optionally substituted tetrahydropyran, optionally substituted thiomorpholine, optionally substituted morpholine, optionally substituted thiane, optionally substituted phenyl, optionally substituted pyrazole, optionally substituted imidazole, optionally substituted pyrrolidine, optionally substituted piperidine and optionally substituted pyridine; when $R^2$ is substituted it is substituted with 1 to 3 substituents selected from halo, CN, C$_{1-6}$ alkyl, =O, OH, OCH$_3$ and SO$_2$CH$_3$.

In embodiments, the group

is selected from:

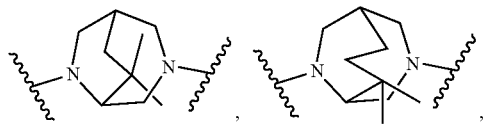

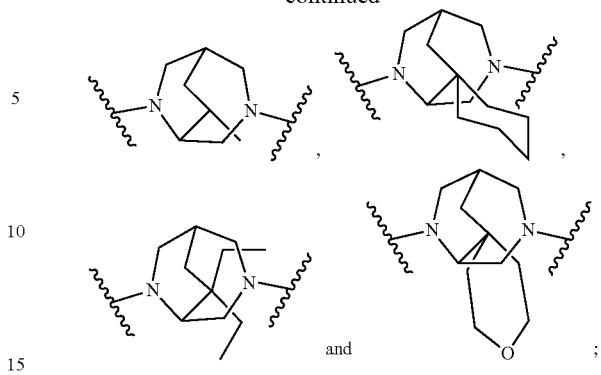

and

;

$L^1$ is selected from a bond, —$SO_2$—, —C(O)—, —C(O)NH—, C(O)(CR$^{A7}$R$^{A8}$)$_r$—, —C(O)NR$^{A6}$(CR$^{A7}$R$^{A8}$)$_r$—, —S(O)$_2$(CR$^{A7}$R$^{A8}$)$_r$—, and —(CR$^{A7}$R$^{A8}$)$_r$— and $R^2$ is selected from H, CN, OH, fluoro, choro, optionally substituted methyl, optionally substituted ethyl, optionally substituted propyl, optionally substituted butyl, optionally substituted pentyl, optionally substituted hexyl, optionally substituted tetrahydropyran, optionally substituted thiomorpholine, optionally substituted morpholine, optionally substituted thiane, optionally substituted phenyl, optionally substituted pyrazole, optionally substituted imidazole, optionally substituted pyrrolidine, optionally substituted piperidine and optionally substituted pyridine; when $R^2$ is substituted it is substituted with 1 to 3 substituents selected from halo, CN, C$_{1-6}$ alkyl, =O, OH, OCH$_3$, SO$_2$CH$_3$.

In embodiments, the group

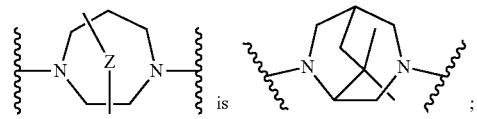

$L^1$ is selected from a bond, —$SO_2$—, —C(O)—, —C(O)NH—, C(O)(CR$^{A7}$R$^{A8}$)$_r$—, —C(O)NR$^{A6}$(CR$^{A7}$R$^{A8}$)$_r$—, —S(O)$_2$(CR$^{A7}$R$^{AB}$)$_r$—, and —(CR$^{A7}$R$^{A8}$)$_r$— and $R^2$ is selected from H, CN, OH, —NR$^{B1}$R$^{B2}$, fluoro, choro, optionally substituted methyl, optionally substituted ethyl, optionally substituted propyl, optionally substituted butyl, optionally substituted pentyl, optionally substituted hexyl, optionally substituted tetrahydropyran, optionally substituted thiomorpholine, optionally substituted morpholine, optionally substituted thiane, optionally substituted phenyl, optionally substituted pyrazole, optionally substituted imidazole, optionally substituted pyrrolidine, optionally substituted piperidine and optionally substituted pyridine; when $R^2$ is substituted it is substituted with 1 to 3 substituents selected from halo, CN, C$_{1-6}$ alkyl, pyrrolidinyl, —NHC(O)Me, =O, OH, OCH$_3$, SO$_2$CH$_3$.

In embodiments, the group

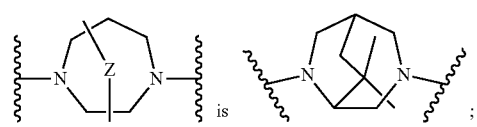

$L^1$ is selected from a —C(O)—, —C(O)NH—, C(O)(CR$^{A7}$R$^{A8}$)$_r$—, —C(O)NR$^{A6}$(CR$^{A7}$R$^{A8}$)$_r$—, —S(O)$_2$ $(CR^{A7}R^{A8})_r$—, and —$(CR^{A7}R^{A8})_r$— and $R^2$ is selected from H, CN, OH, —$NR^{B1}R^{B2}$, fluoro, choro, optionally substituted methyl, optionally substituted ethyl, optionally substituted propyl, optionally substituted butyl, optionally substituted pentyl, optionally substituted hexyl, optionally substituted tetrahydropyran, optionally substituted thiomorpholine, optionally substituted morpholine, optionally substituted thiane, optionally substituted phenyl, optionally substituted pyrazole, optionally substituted imidazole, optionally substituted pyrrolidine, optionally substituted piperidine and optionally substituted pyridine; when $R^2$ is substituted it is substituted with 1 to 3 substituents selected from halo, CN, $C_{1-6}$ alkyl, pyrrolidinyl, —NHC(O)Me, =O, OH, $OCH_3$, $SO_2CH_3$.

In an embodiment the compound of formula (I) is a compound selected from:

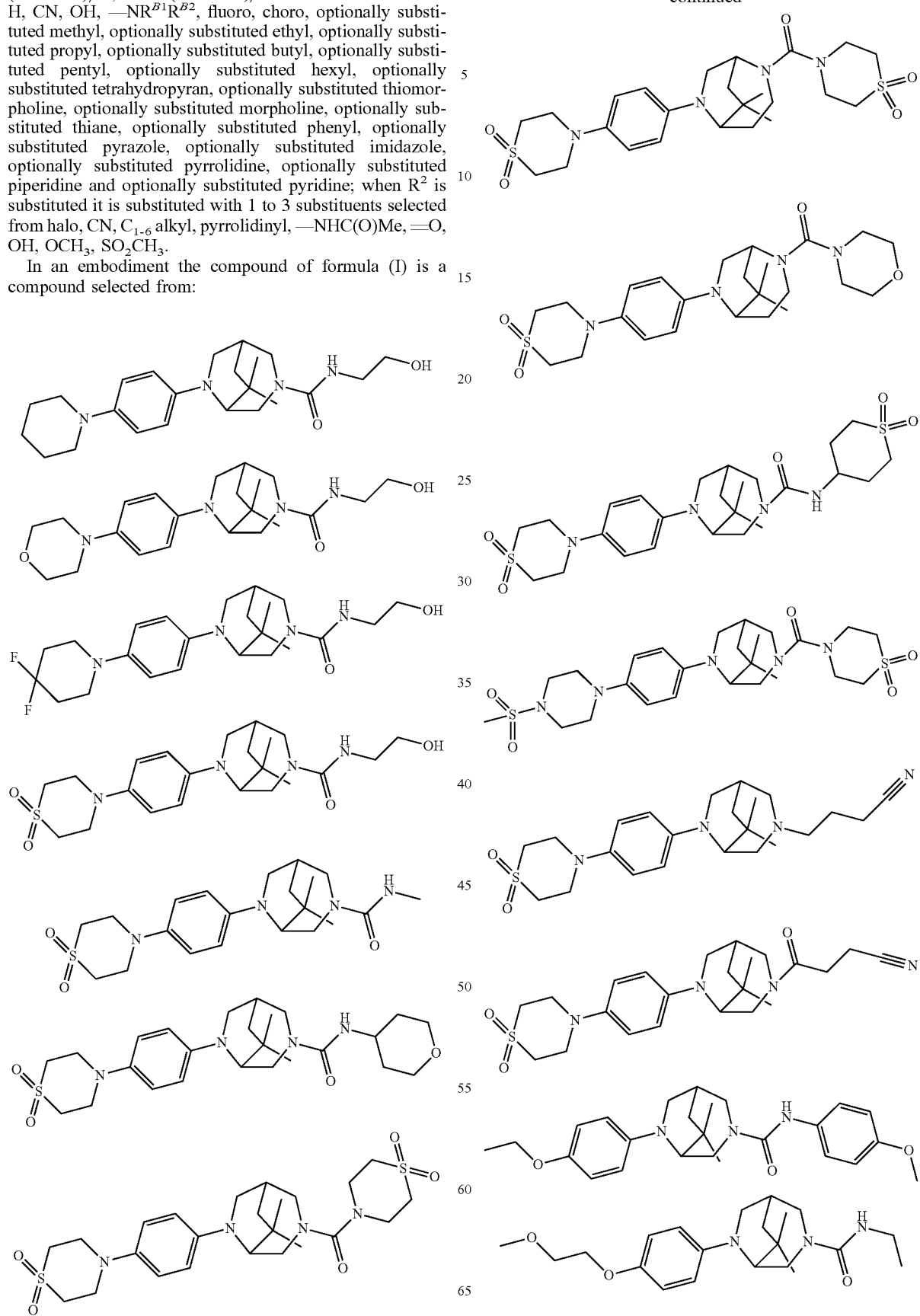

-continued

-continued
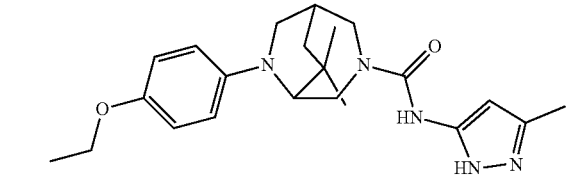
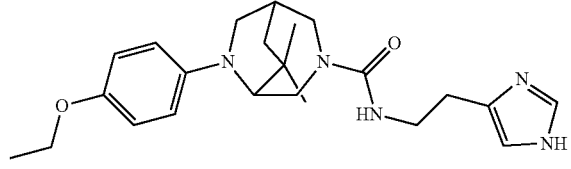
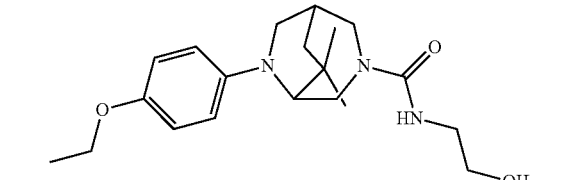
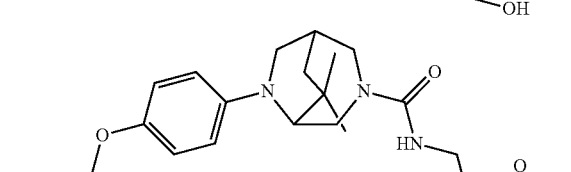
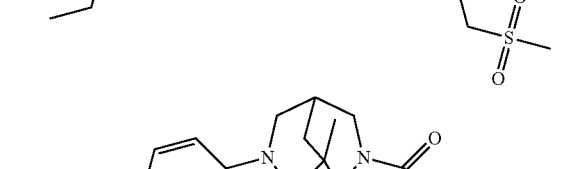
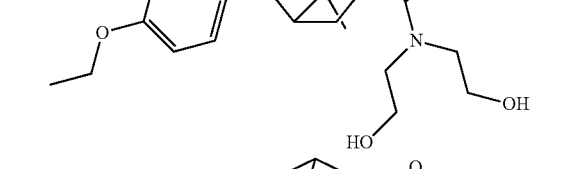
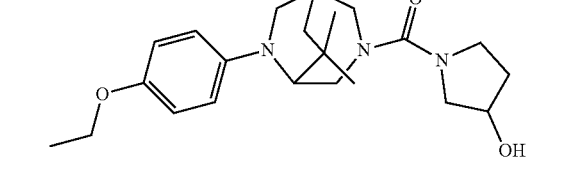
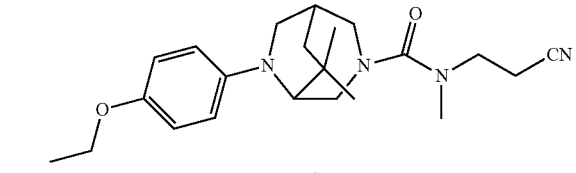
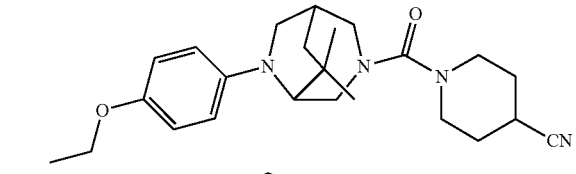
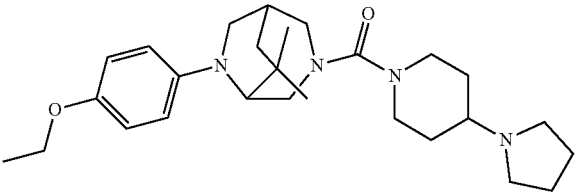
-continued
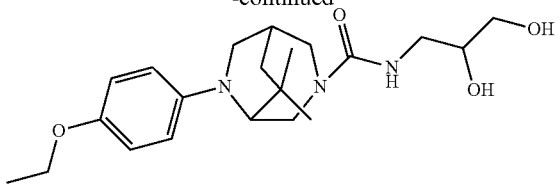
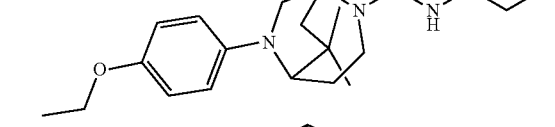
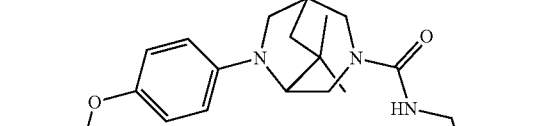
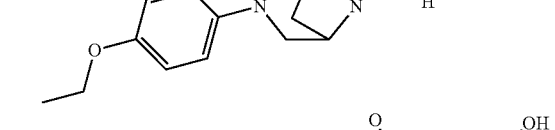
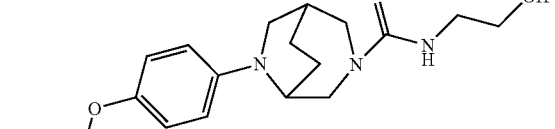
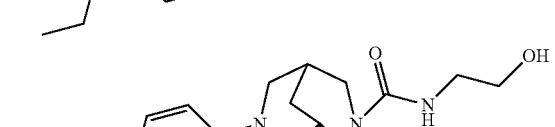
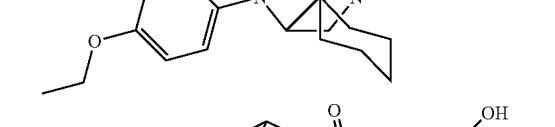
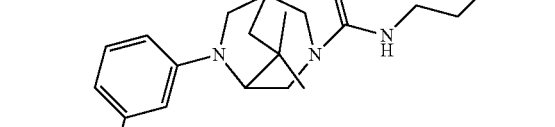
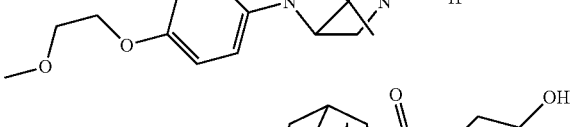
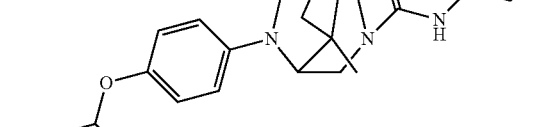

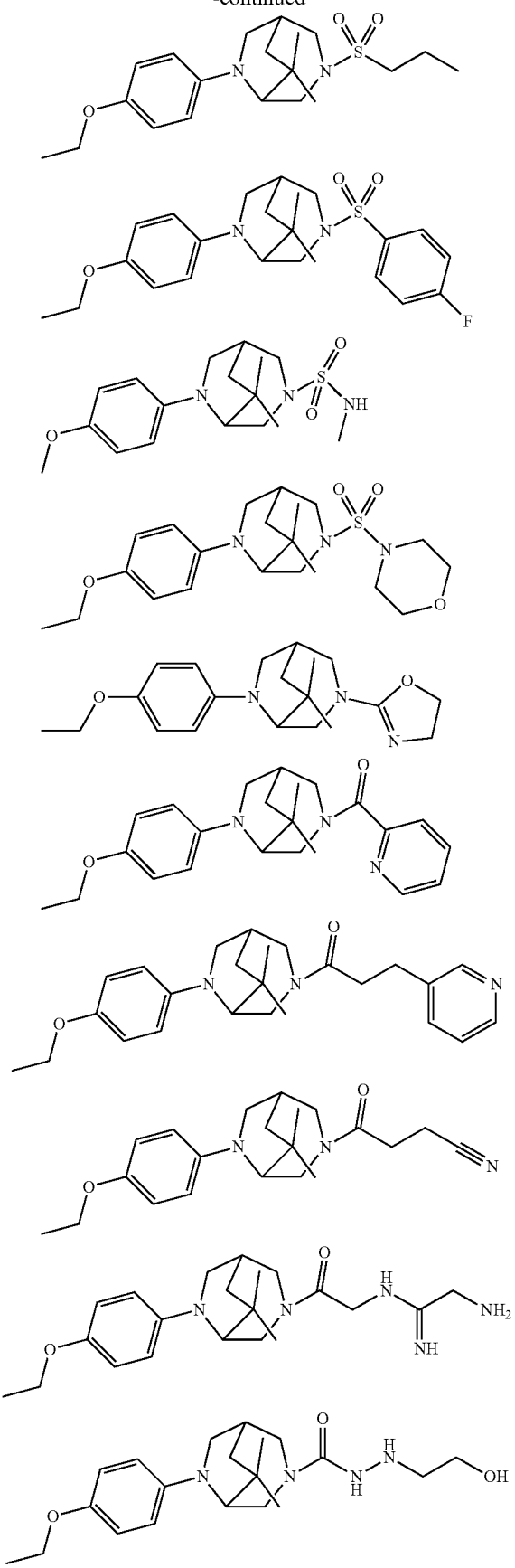
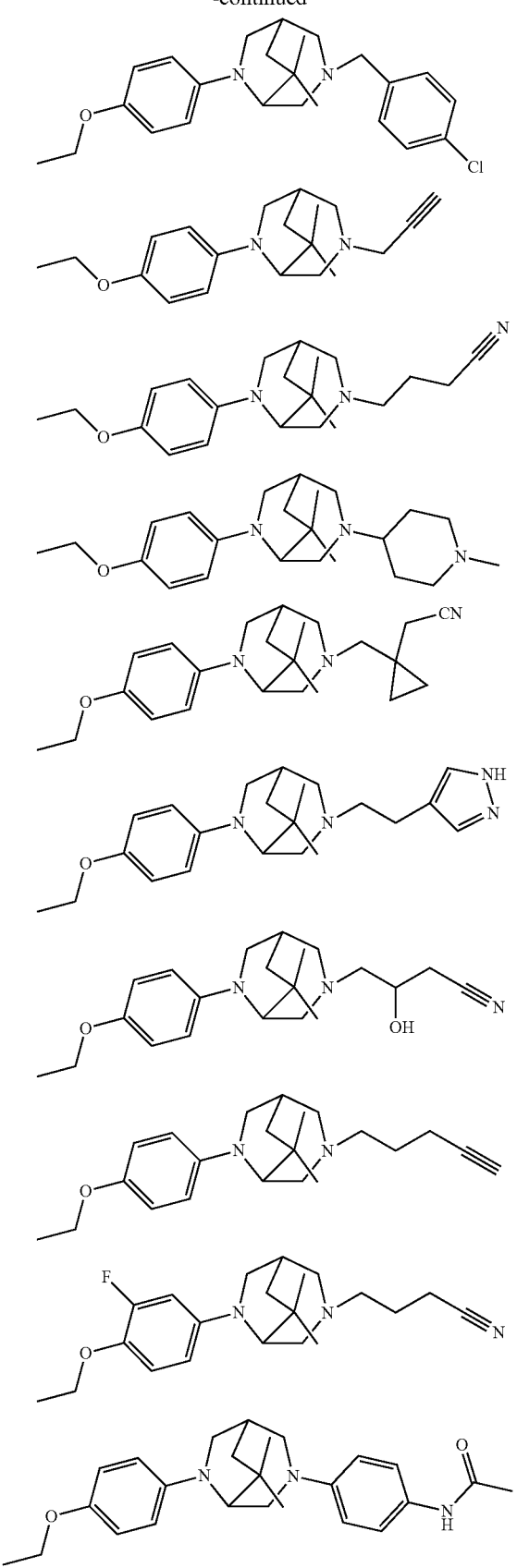

37
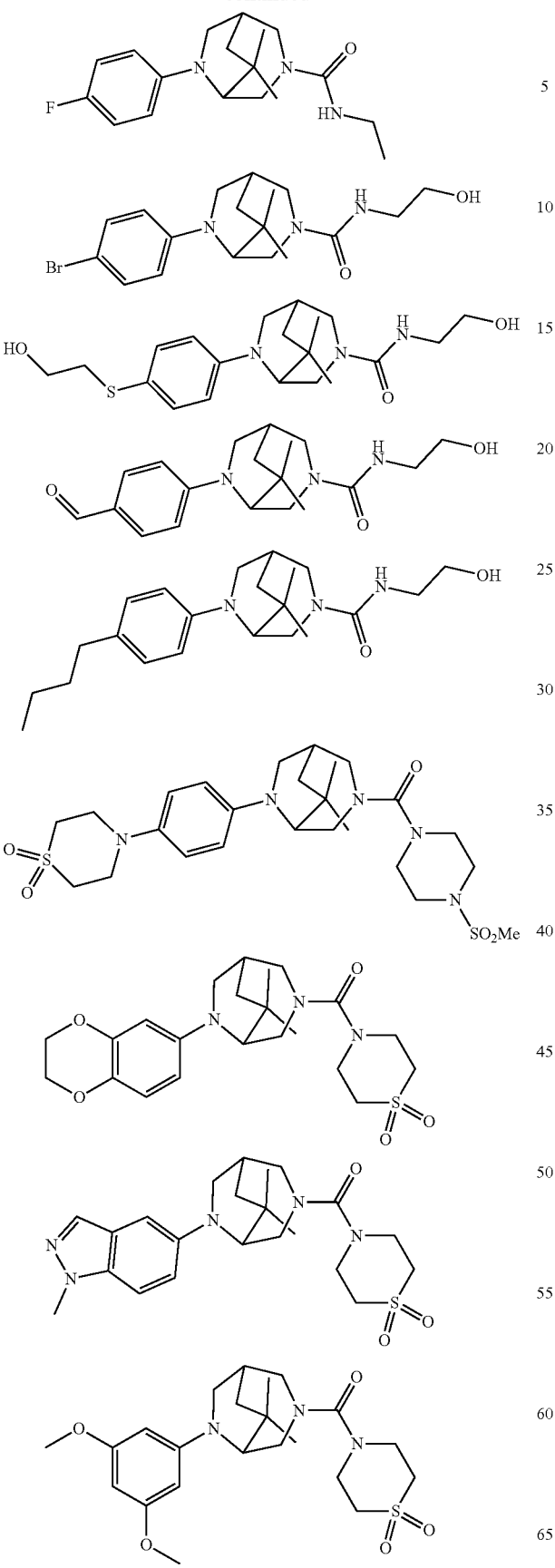
38
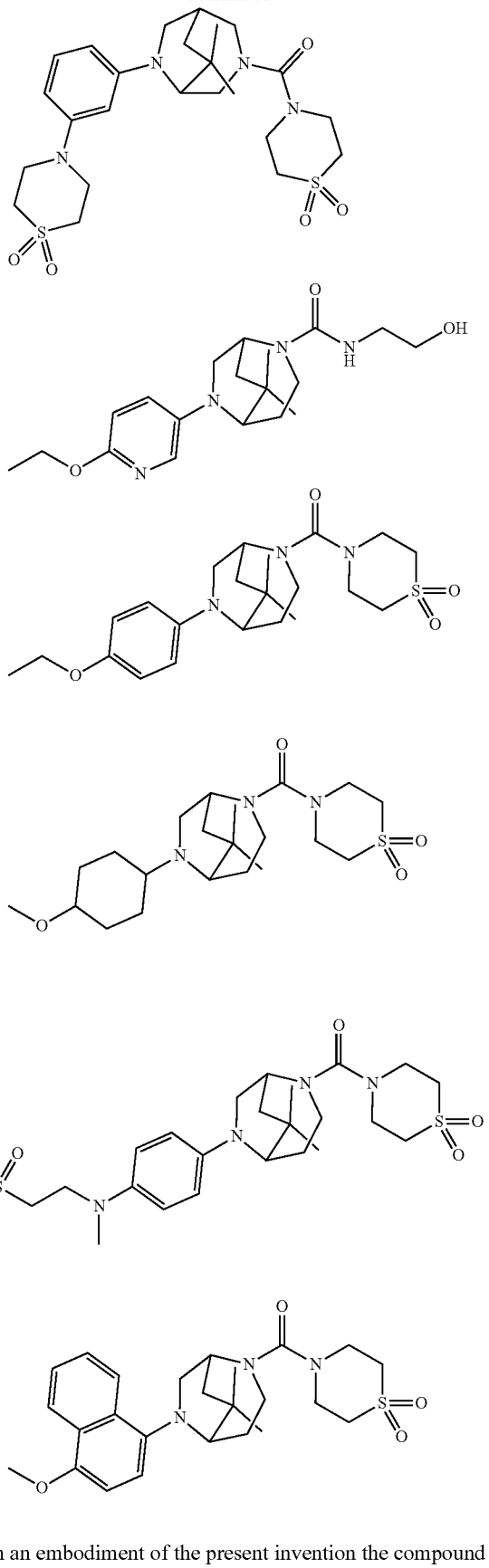
In an embodiment of the present invention the compound of formula (I) may be a compound selected from:

39
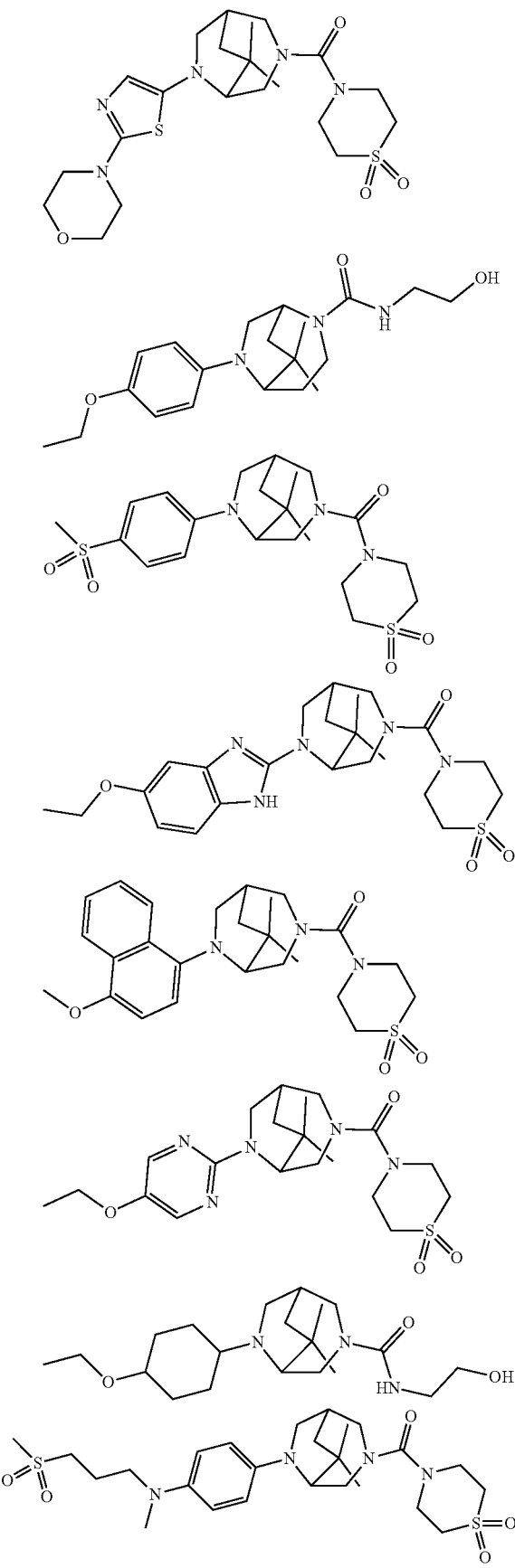
40
-continued
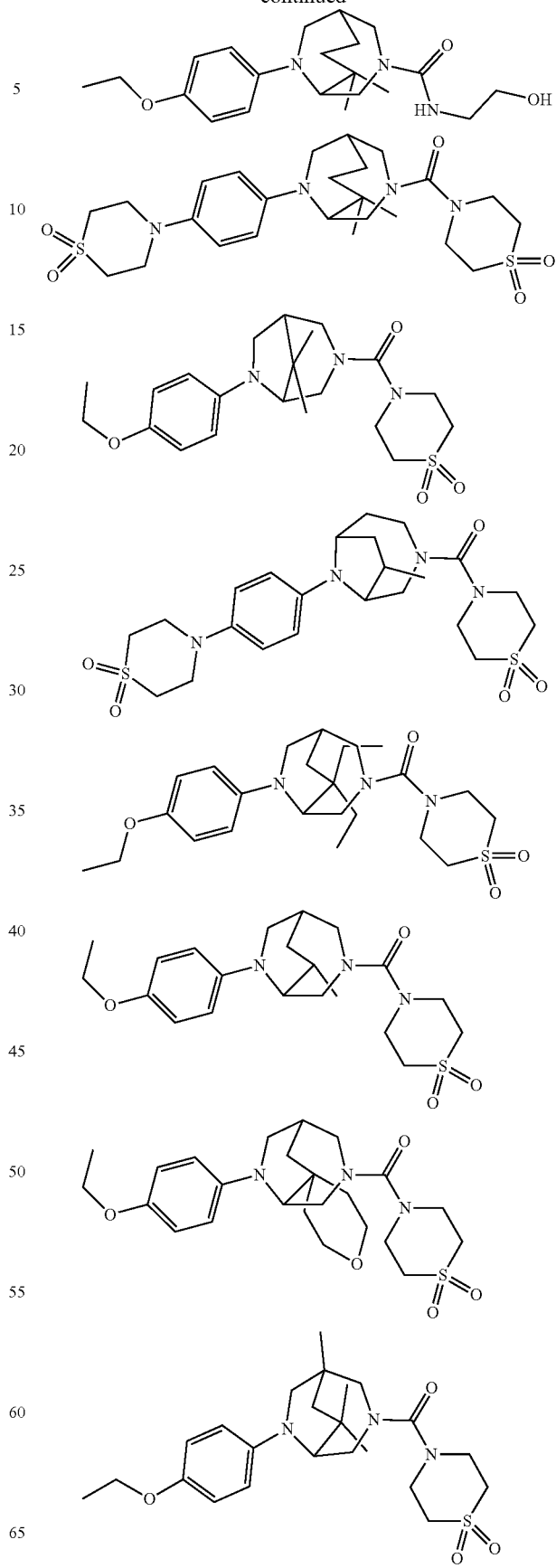

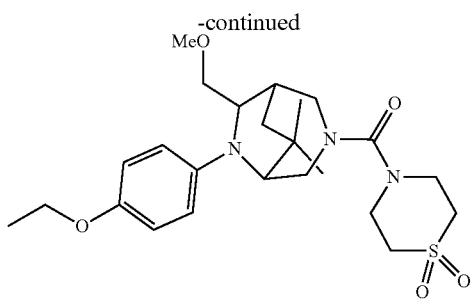

DETAILED DESCRIPTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_{1-4}$ alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_1$-$C_4$ alkoxy. Other substituents for the alkyl group may alternatively be used.

The term "$C_{1-6}$ haloalkyl", e.g. "$C_{1-4}$ haloalkyl", refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{3-6}$ cycloalkyl" includes a saturated hydrocarbon ring system containing 3, 4, 5 or 6 carbon atoms. For example, the "$C_3$-$C_6$ cycloalkyl" may be cyclopropyl, cyclobutyl, cyclopentyl, cyclohexyl, bicycle[2.1.1]hexane or bicycle[1.1.1]pentane.

The term "heterocyclyl", "heterocyclic" or "heterocycle" includes a non-aromatic saturated or partially saturated monocyclic or fused, bridged, or spiro bicyclic heterocyclic ring system(s). Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

The term "bridged ring systems" includes ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-Diaza-bicyclo[2.2.1]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

"Heterocyclyl-$C_{m-n}$ alkyl" includes a heterocyclyl group covalently attached to a $C_{m-n}$ alkylene group, both of which are defined herein.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl-$C_{m-n}$ alkyl-" includes a heteroaryl group covalently attached to a $C_{m-n}$ alkylene group, both of which are defined herein. Examples of heteroaralkyl groups include pyridin-3-ylmethyl and the like.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

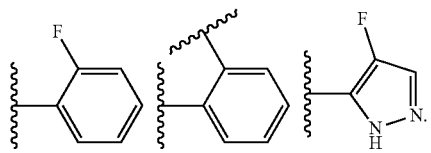

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

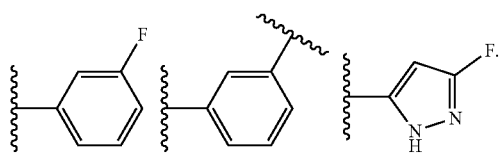

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

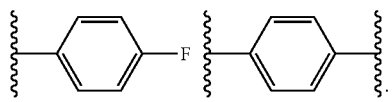

The term "acyl" includes an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:
  (i) by reacting the compound of the invention with the desired acid or base;
  (ii) by removing an acid- or base-labile protecting group from a suitable precursor of the compound of the invention or by ring-opening a suitable cyclic precursor, for example, a lactone or lactam, using the desired acid or base; or
  (iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess LOX inhibitory activity.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{18}$F and the like. The radionuclide that is used will depend on the specific application of that radio-labelled derivative. For example, for in vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

It is also to be understood that certain compounds of the invention may exist in solvated as well as unsolvated forms such as, for example, hydrated forms. It is to be understood that the invention encompasses all such solvated forms that possess LOX inhibitory activity.

It is also to be understood that certain compounds of the invention may exhibit polymorphism, and that the invention encompasses all such forms that possess LOX inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

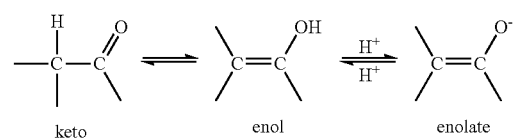

keto    enol    enolate

The in vivo effects of a compound of the invention may be exerted in part by one or more metabolites that are formed within the human or animal body after administration of a compound of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Further information on the preparation of the compounds of the invention is provided in the Examples section. The general reaction schemes and specific methods described in the Examples form a further aspect of the invention.

The resultant compound of the invention from the processes defined above can be isolated and purified using techniques well known in the art.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The processes defined herein may further comprise the step of subjecting the compound of the invention to a salt exchange, particularly in situations where the compound of the invention is formed as a mixture of different salt forms. The salt exchange suitably comprises immobilising the compound of the invention on a suitable solid support or resin, and eluting the compounds with an appropriate acid to yield a single salt of the compound of the invention.

In a further aspect of the invention, there is provided a compound of the invention obtainable by any one of the processes defined herein.

Certain of the intermediates described in the reaction schemes above and in the Examples herein are novel. Such novel intermediates, or a salt thereof, particularly a pharmaceutically acceptable salt thereof, form a further aspect of the invention.

Pharmaceutical Compositions

In accordance with another aspect, the present invention provides a pharmaceutical formulation comprising a compound of the invention, or a pharmaceutically acceptable salt thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to symptomatically relieve in a warm-blooded animal, particularly a human the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Suitably the compound of the invention is adminstered orally, for example in the form of a tablet, or capsule dosage form. The daily dose administered orally may be, for example a total daily dose selected from 1 mg to 2000 mg, 5 mg to 2000 mg, 5 mg to 1500 mg, 10 mg to 750 mg or 25 mg to 500 mg. Typically, unit dosage forms will contain about 0.5 mg to 0.5 g of a compound of this invention.

Therapeutic Uses and Applications

In accordance with another aspect, the present invention provides a compound of the invention, or a pharmaceutically acceptable salt thereof, for use as a medicament.

A further aspect of the invention provides a compound of the invention, or a pharmaceutically acceptable salt thereof, for use in the treatment of a disease or medical condition mediated by LOX.

Also provided is the use of a compound of the invention, or a pharmaceutically acceptable salt thereof in the manufacture of a medicament for the treatment of a disease or medical condition mediated by LOX.

Also provided is a method of treating a disease or medical condition mediated by LOX in a subject in need thereof, the method comprising administering to the subject an effective amount of a compound of the invention, or a pharmaceutically acceptable salt thereof.

Unless stated otherwise reference to the treatment of a disease or medical condition mediated by LOX is intended to encompass diseases or medical conditions mediated by any one of LOX, LOXL1, LOXL2, LOXL3 or LOXL4.

In the following sections of the application reference is made to a compound of the invention, or a pharmaceutically acceptable salt for use in the treatment of certain diseases or conditions. It is to be understood that any reference herein to a compound for a particular use is also intended to be a reference to (i) the use of the compound of the invention, or pharmaceutically acceptable salt thereof, in the manufacture of a medicament for the treatment of that disease or condition; and (ii) a method of treating the disease or condition in a subject, the method comprising administering to the subject a therapeutically effective amount of the compound of the invention, or pharmaceutically acceptable salt thereof.

The disease of medical condition mediated by LOX may be any of the diseases or medical conditions listed in this application.

As discussed in the background to the invention the role of the LOX family of may have distinct roles in diseases such as cancer. Accordingly the selective inhibition of a LOX may be advantageous. In one embodiment there is provided a compound of the invention, or pharmaceutically acceptable salt thereof, for use in the selective inhibition of LOX, LOXL1, LOXL2, LOXL3 or LOXL4. In other embodiments it may be advantageous to inhibit two or more members of the LOX family. Accordingly in another embodiment there is provided a compound of the invention, or pharmaceutically acceptable salt thereof, for use in the inhibition of two or more members of the LOX family selected from LOX, LOXL1, LOXL2, LOXL3 or LOXL4.

Proliferative Diseases—LOX and Cancer

A further aspect of the invention provides a compound of the invention, or pharmaceutically acceptable salt thereof, for use in the treatment of a proliferative disease. The proliferative disease may be malignant or non-malignant.

As mentioned in the Background to the invention, LOX plays a critical role in primary cancer and metastasis. Evidence supporting this role of LOX in primary tumour growth and metastasis is described below.

Studies have shown that LOX plays a fundamental role in the growth of primary tumours in colorectal and lung cancer (Gao, Xiao et al. 2010, Baker, Cox et al. 2011) and glioblastoma (Mammoto, Jiang et al. 2013). PDAC KRAS$^{mut}$/p53$^{wt}$ cells (which endogenously express low levels of LOX) were engineered to express high levels of human LOX. In murine allograft models using these cells primary tumour growth is increased significantly (Miller, Morton et al. 2015). Lysyl oxidase activity participates in primary tumor growth in a transgenic mouse model of aggressive pancreatic ductal adenocarcinoma (PDAC) by directly impacting the senescence stability (Wiel, Augert et al. 2013).

Expression of LOX is elevated in more than 70% of breast cancer patients with Estrogen Receptor negative disease, in 80% of head & neck cancer patients, in 33% of primary colorectal carcinomas (CRC) and 48% of metastatic tissues from patients with CRC (Baker, Cox et al. 2011), and in cirrhotic HCC patients with a history of alcoholism (Huang, Ho et al. 2013). LOX is also overexpressed in lung adenocarcinoma (Wilgus, Borczuk et al. 2011), LKB1-mutant lung cancer(Gao, Xiao et al. 2010), aggressive prostate adenocarcinoma (Stewart, Gray et al. 2008), uveal melanoma (Abourbih, Di Cesare et al. 2010), oral and oropharyngeal squamous carcinoma (Albinger-Hegyi, Stoeckli et al. 2010), thyroid cancer (Boufraqech, Nilubol et al. 2015), clear cell renal cell carcinoma (Vitalba et al, 2016), myeloproliferative neoplasms, especially myelofibrosis (Papadantonakis, Matsuura et al. 2012, Tadmor, Bejar et al. 2013) and pancreatic cancer (Sansom 2012, Miller, Morton et al. 2015).

Lysyl-Oxidase-Like Isoforms and Cancer

LOXL2 is another member of the LOX family that is involved in the cross-linking of extracellular collagens and elastin (Vadasz, Kessler et al. 2005) (Kim, Kim et al. 2010). In addition to conserved C-terminal region, the LOXL2 protein has scavenger receptor cysteine-rich regions that are commonly found in cell surface receptors and adhesion molecules, as well as a cytokine receptor-like domain.

LOXL2 expression has been found upregulated in breast, gastric, colon, esophageal, head and neck, lung and laryngeal carcinomas, as reviewed in Barker et al (Barker, Cox et al. 2012) and in renal cells carcinoma (Hase, Jingushi et al. 2014) (Nishikawa, Chiyomaru et al. 2015). High LOXL2 expression has been associated with poor prognosis in patients with squamous cell carcinoma, laryngeal, oesophagus and breast cancer, increased metastases in colon and breast cancer, as well as drug resistance in pancreatic cancer cells—reviewed in Barker et al (Barker, Cox et al. 2012). Additionally, it has been shown that LOXL2 up-regulation increases the invasiveness of otherwise non-invasive breast cancer cells (Akiri, Sabo et al. 2003). Furthermore, LOXL2 and LOXL4 are required for metastatic niche formation in a breast orthotopic mouse model (Wong et al, 2011). LOXL2 expression is associated with lymph node metastasis, histological grades and poor prognosis in cholangiocarcinoma, and knockdown of LOXL2 reduces invasion and metastasis (Xu, Li et al. 2014). HCC metastasis relies on LOXL2, which is overexpressed in tumor tissues and sera of HCC patients (Wong, Tse et al. 2014).

LOXL2 transcription is regulated by HIF-1 and upregulation of LOXL2 in hypoxia has been shown to downregulate E-cadherin leading to epithelial to mesenchymal transition (EMT) (Schietke, Warnecke et al. 2010) which is a key step in tumour progression, invasion and metastasis. This is in agreement with other reports where LOXL2 was shown to be involved in both EMT and tumour progression in murine squamous and spindle cell carcinomas (Fong, Dietzsch et al. 2007) (Moreno-Bueno, Salvador et al. 2011). LOXL2 expression is positively associated in CRC (Offenberg, Brunner et al. 2008). LOXL2 has also been linked to Src kinase/focal adhesion kinase (Src/FAK) pathway activation, and this appears to be the major pathway where secreted LOXL2 induces gastric tumour cell invasion and metastasis (Peng, Ran et al. 2009).

In certain cancers such as basal-like breast carcinoma and larynx squamous cell carcinoma perinuclear expression of LOXL2 is a marker of tumour aggressiveness and poor prognostic (Moreno-Bueno, Salvador et al. 2011) (Peinado, Moreno-Bueno et al. 2008).

Barry-Hamilton et al. reported that LOXL2 antibody treatment significantly reduces bone metastases from intracardiac injection of breast carcinoma cells (Barry-Hamilton, Spangler et al. 2010). In addition, Barker et al have provided preclinical evidence that LOXL2 inhibition is highly effective against spontaneous lung, liver and bone metastases of mammary carcinoma cells (Barker, Chang et al. 2011). Therefore, LOXL2 also represents a promising therapeutic target for the treatment of primary and metastatic cancer.

As mentioned in the Background to the Invention it is thought that although LOX and LOXL2 are involved in similar extra-cellular processes, it appears that they have distinct roles.

Other members of the LOX family, LOXL1, LOXL3 and LOXL3 are also implicated in proliferative conditions including cancer (see Background to the Invention).

Accordingly in one embodiment there is provided a compound of the invention, or pharmaceutically acceptable salt thereof for use in the treatment of a cancer. In one embodiment the cancer is non-metastatic. Accordingly the compound of the invention, or a pharmaceutically acceptable salt thereof may be for use in the treatment of a primary tumour in a subject.

The Role of LOX in Cancer Metastasis

Elevated LOX expression is associated with metastasis and decreased patient survival (Baker, Cox et al. 2011, Wilgus, Borczuk et al. 2011) Increased LOX expression is associated with disease grade, increased distant metastasis and lower overall survival in breast cancer patients with oestrogen receptor (ER)-negative tumours (Erler, Bennewith et al. 2006), in head & neck cancer patients (Albinger-Hegyi, Stoeckli et al. 2010, Toustrup, Sorensen et al. 2011), gastric cancer (Kasashima, Yashiro et al. 2015), hepatocellular carcinoma (Zhu, Huang et al. 2015), non-small cells lung cancer (Liu, Ping et al. 2014) and astrocytomas (da Silva, Uno et al. 2015), laryngeal cancer (Se, 2017). LOX expression is a determinant of poor survival in pancreatic cancer (Miller, Morton et al. 2015). Inhibition of LOX eliminates metastasis in mice with orthotopically grown human breast cancer (Erler, Bennewith et al. 2006) and inhibits tumour angiogenesis in a human colorectal cancer model (Baker, Bird et al. 2013).

A polyclonal antibody that was raised against LOX and shown to inhibit its enzymatic activity, was able to block the metastatic spread of tumour cells to the lungs and livers of recipient mice in an orthotopic model of metastatic human breast cancer (Erler et al, 2006). Suppression of LOX expression using shRNA blocks metastatic spread of the breast cancer cells and that BAPN, the non-selective small molecule inhibitor of LOX can block metastatic tumour growth of these cells in mice (Erler et al, 2006). Furthermore, inhibition of tumour-secreted LOX by genetic (shRNA), antibody (Ab) or the irreversible non-selective small molecule inhibitor BAPN, significantly reduced invasion and metastasis of orthotopic human breast tumours or circulating human breast cancer cells (Bondareva, Downey et al. 2009, Erler, Bennewith et al. 2009, Levental, Yu et al. 2009), CRC (Baker, Cox et al. 2011), HCC (Huang, Ho et al. 2013), LKB1-mutant lung adenocarcinoma (Gao, Xiao et al. 2010), anaplastic thyroid cancer (Boufraqech, Nilubol et al. 2015) and PDAC in mice (Sansom 2012; Miller, Morton et al. 2015). High expression of LOX in primary breast tumours leads to osteolytic lesion formation; silencing or inhibition of LOX activity abrogates tumour-driven bone metastases (Cox, Rumney et al. 2015). LOX inhibition with BAPN and new inhibitor CCT365623 significantly reduce metastatic lung tumour burden in a mouse model of spontaneous breast cancer that metastasizes to the lungs (Tang et al, 2017).

LOX family members (especially LOX and LOXL2) play a critical role in the metastatic spread of cancer cells (Erler, Bennewith et al. 2006, Bondareva, Downey et al. 2009, Erler, Bennewith et al. 2009, Levental, Yu et al. 2009, Gao, Xiao et al. 2010). In response to hypoxia (a condition that occurs due to inadequate blood supply when solid tumours exceed about 1 $cm^3$ in size), cancer cells produce and secrete LOX into the circulation (Erler, Bennewith et al. 2009).

LOX regulates invasion of cancer cells in vitro. Thus, cancer cells expressing high levels of LOX show increased ability to invade 3D collagen I and Matrigel matrices (Kirschmann, Seftor et al. 2002) (Erler, Bennewith et al. 2006). Furthermore, experimental over-expression of LOX enhances invasion of cancer cells, whereas genetic knockdown of LOX using RNA interference (RNAi; with both short hairpin RNA [shRNA] or small interfering RNA [siRNA]) or antisense technology) inhibits the in vitro invasion activity of cancer cells (Kirschmann, Seftor et al. 2002) (Erler, Bennewith et al. 2006). Similarly, a non-selective small molecule inhibitor of LOX, beta-aminopropionitrile (BAPN) also blocks the in vitro invasion activity of several human cancer cell lines (Kirschmann, Seftor et al. 2002) (Erler, Bennewith et al. 2006). LOX enhances hypoxia-induced invasion and migration in cervical cancer cells mediated by the EMT which can be inhibited by BAPN (Yang, Li et al. 2013). These studies implicate LOX in the invasive behaviour of cancer cells.

One of the critical functions of LOX appears to be to act remotely to pre-condition the niche at future sites of metastasis. Tumour cell metastasis is facilitated by these "premetastatic niches" formed in destination organs using invading bone marrow-derived dendritic cells (BMDCs). This "nest-building" activity is initiated when LOX becomes deposited at discreet sites in the target organ (Erler, Bennewith et al. 2009). Studies have shown that bone marrow derived cell recruitment is an essential step in niche conditioning and metastatic spread of cancer (Kaplan et al, 2005). This mechanism underlines the importance of LOX for the invasive activity of cancer cells and for the earliest stages of metastasis, when the cancer cells first migrate out of the primary tumour. It has been shown that BMDCs and LOX co-localise in human metastatic tissue, and inhibition of LOX can prevent BMDC recruitment and metastasis in models of breast cancer metastasis (Erler, Bennewith et al. 2009).

In addition to its roles in the early phases of metastasis, there is evidence that LOX is necessary to maintain the growth of the cancer cells once they arrive at the new metastatic sites because inhibition of LOX causes regression of these lesions, even after the development of metastatic disease (Erler, Bennewith et al. 2006) (Erler, Bennewith et al. 2009) (Bondareva, Downey et al. 2009). It was shown that although depletion of LOX does not affect tumour cell proliferation on plastic, it suppresses their growth in recombinant basement membrane (Matrigel) matrices (Erler, Bennewith et al. 2006). Furthermore, cancer cells do not colonise the lungs efficiently when LOX is inhibited by shRNA (Erler et al, 2006) and it was found that metastatic lung tumours regress when mice are treated with LOX neutralising antibodies (Erler, Bennewith et al. 2006). Notably, the colonisation of the lung by human breast cancer cells was enhanced when the cells were co-injected with conditioned medium from cells expressing LOX, but this was blocked if the mice were treated with conditioned medium in the presence of BAPN or a LOX antibody (Erler, Bennewith et al. 2009). These findings demonstrate a requirement for tumour-secreted LOX to maintain metastatic growth.

LOX is essential for phosphorylation of the focal adhesion kinase (FAK) downstream of integrin signalling (Erler, Bennewith et al. 2006). FAK is a tyrosine kinase that interacts with several signalling molecules and is critical for cell survival (van Nimwegen and van de Water 2007). LOX-mediated collagen cross-linking results in increased tissue stiffness and activation of the FAK/SRC signalling in in vitro and in vivo models of CRC. Cells expressing high levels of enzymatically active LOX have an increased capacity to proliferate, invade and metastasise. Thus LOX have both cell-dependent and cell-autonomous roles in metastatic tumour growth at several levels: enhances the ability of cancer cells to invade locally, possibly by enhancing migration away from the primary site; conditions the future metastatic sites in preparation for the arrival of the BMDCs and then tumour cells; supports the survival/proliferation of the cancer cells once they colonise the niche.

Host response to tumour surgery can promote further lung metastases in a mechanism mediated by LOX. Blocking LOX activity reduces the risk of lung metastases following surgery (Chen, 2017).

Accordingly the compound of the invention, or a pharmaceutically acceptable salt thereof may be for use in the treatment of metastatic cancer in a subject.

In another embodiment of the invention there is provided a compound of the invention, or a pharmaceutically acceptable salt thereof may be for use as an inhibitor of the motility of tumour cells. In another embodiment the compound of the invention, or a pharmaceutically acceptable salt thereof may be for use as an inhibitor of the dissemination and invasiveness of mammalian cancer cells leading to inhibition of metastatic tumour growth. In particular a compound of the invention, or a pharmaceutically acceptable salt thereof may be for use as an anti-invasive agent for use in the containment and/or treatment of solid tumour disease. In another embodiment a compound of the invention, or a pharmaceutically acceptable salt thereof may be for use in the prevention or inhibition of cancer metastasis.

LOX Family, Fibroblasts and Stroma

Cancer associated fibroblasts are recruited by cancer cells recruit fibroblasts through various growth factors and cytokines and form a myofibroblastic microenvironment that promotes cancer growth, survival, local invasion and metastasis (Karagiannis, Poutahidis et al. 2012). Persistent presence of myofibroblasts in cancer contributes to desmoplasia, a cancer-specific type of fibrosis. Desmoplasia and increased fibrosis have been associated with progression of several cancers such as breast, pancreatic, colorectal, gastric and hepatocellular (Barker, Cox et al. 2012). Desmoplasia is also an intrinsic mechanism of resistance to immunotherapy in stromally-rich tumours (Zhao and Subramanian, 2017). LOX and LOX family members have an essential role in extracellular matrix remodelling and desmoplasia (Levental, 2009; Xiao, 2012). Lysyl oxidase family members expression, either secreted by cancer cells or by activated fibroblasts, has been found associated with tumour ECM, tumour stroma or tumour-associated vasculature of several cancers, such as colorectal, pancreatic, breast, laryngeal, endometrial, testicular, hepatocellular, renal (reviewed in Barker et al (Barker, Cox et al. 2012)), gastric cancer (Kasashima, Yashiro et al. 2014), and to be involved in their progression and metastasis (Akiri, Sabo et al. 2003, Barry-Hamilton, Spangler et al. 2010, Barker, Bird et al. 2013) (Pickup, Laklai et al. 2013). Expression of LOXL4 is enhanced in keratocystic odontogenic tumors (KCOT) stromal tissues and primary KCOT stromal fibroblasts (Jiang, Sima et al. 2014)

In one embodiment there is provided a compound of the invention, or a pharmaceutically acceptable salt thereof for use in the treatment of desmoplasia.

As discussed herein, the compound of the invention, or a pharmaceutically acceptable salt thereof may be for use in the treatment of a cancer, which may be non-metastatic or metastatic and which may be a solid tumour or a haematological ("liquid") cancer selected from, for example:

(1) Carcinoma, including for example tumours derived from stratified squamous epithelia (squamous cell carcinomas) and tumours arising within organs or glands (adenocarcinomas). Examples include breast, colon, lung, prostate, ovary. esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumor), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma and non-small cell carcinoma of the lung, lung adenocarcinoma, squamous cell carcinoma, large cell carcinoma, bronchioloalveolar carcinoma, and mesothelioma), neuroendocrine tumors (including but not limited to carcinoids of the gastrointestinal tract, breast, and other organs), adrenocortical carcinoma, thyroid carcinoma, pancreatic carcinoma (including, but not limited to, pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors), breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumor including serous tumor, endometrioid tumor and mucinous cystadenocarcinoma, sex-cord-stromal tumor), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumors, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumor), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumors), testicular carcinoma, osteogenic carcinoma, epithelial carcinoma, sarcomatoid carcinoma, nasopharyngeal carcinoma, laryngeal carcinoma; oral and oropharyngeal squamous carcinoma;

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumor (mixed connective tissue types) and other soft tissue sarcomas;

(3) Myeloma and multiple myeloma;

(4) Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis.

(5) Lymphomas, including: Hodgkin and Non-Hodgkin lymphomas;

(6) Solid tumors of the nervous system including medulloblastoma, craniopharyngioma, ependymoma, pinealoma, hemangioblastoma, acoustic neuroma, oligodendroglioma, meningioma, neuroblastoma and schwannoma;

(7) Melanoma, uveal melanoma and retinoblastoma; and (8) Mixed Types, including, e.g., adenosquamous carcinoma, mixed mesodermal tumor, carcinosarcoma or teratocarcinoma.

In a particular embodiment a compound of the invention, or a pharmaceutically acceptable salt thereof may be for use in the treatment of a cancer selected from pancreatic, colorectal, breast and lung cancer.

A compound of the invention, or a pharmaceutically acceptable salt thereof the invention may be for use in the treatment of a benign proliferative disease. The benign disease may be a benign tumour, for example hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas. The benign condition may be endometriosis or a keratocystic odontogenic tumor.

Fibrotic Diseases

As discussed in the Background to the invention, LOX and LOXL are implicated in fibrotic diseases. Accordingly a compound of the invention or a pharmaceutically acceptable salt thereof may be for use in the treatment of a fibrotic disorder. The fibrotic disorder may be a disorder characterised by excess fibrosis, e.g., an excess of fibrous connective tissue in a tissue or organ, e.g., triggered by a reparative or reactive process, e.g., in response to injury (e.g., scarring, healing) or excess fibrotic tissue arising from a single cell line (e.g., fibroma).

LOX has been implicated in the pathogenesis of renal fibrosis and its inhibition with the alleviation of the symptoms (Di Donato, Ghiggeri et al. 1997, Haase 2009, Chen, Lin et al. 2015). Hyperuricemia results in hypertension, intrarenal vascular disease, and renal injury and is associated with increased expression of lysyl oxidase (LOX) and fibronectin in kidneys (Yang, Wang et al. 2010). Increased LOX activity has been linked to delayed graft failure after renal transplant, potentially due to increased local fibrosis (Zhi, 2017)

Similar involvement of LOX or LOXL2 in the pathology of disease and reduction in symptoms has been demonstrated for lung fibrosis (Barry-Hamilton, Spangler et al. 2010) (Haase 2009, Cox, Bird et al. 2013, Chien, Richards et al. 2014).

LOX and LOXL2 are involved in liver fibrosis (Kagan 1994, Marshall and Smith 2011) (Ricard-Blum, Bresson-Hadni et al. 1996) (Smith and Van Vlasselaer 2011) (Georges, Hui et al. 2007), liver cirrhosis (the last stage of liver fibrosis) (Kagan 1994) and related diseases such as Wilson's disease and primary biliary cirrhosis (Vadasz, Kessler et al. 2005). Therapeutic indications for LOX family inhibitors (such as simtuzumab, a humanized LOXL2 antibody) included a number of fibrotic conditions: myelofibrosis (Primary myelofibrosis, Post Polycythemia Vera or Post Essential Thrombocythemia Myelofibrosis), idiopathic pulmonary fibrosis (IPF), liver fibrosis due to non-alcoholic steatohepatitis (NASH), HIV and/or Hepatitis C-infection or primary sclerosing cholangitis (PSC) and compensated liver cirrhosis due to NASH. Levels of lysyl oxidase are increased in patients with scleroderma and systemic sclerosis (Chanoki, Ishii et al. 1995) (Rimar, Rosner et al. 2014).

LOX inhibitors assist in collagen remodeling and re-establishment of collagen architecture in human Dupuytren's, keloid and scar fibroblasts (Priyanka, 2016).

The fibrotic disorder may be any of those discussed in the above three paragraphs. In one embodiment the compound of the invention or a pharmaceutically acceptable salt thereof may be for use in the treatment of a fibrotic disorder selected from:

(i) a fibrotic condition affecting the lungs, for example pulmonary fibrosis secondary to cystic fibrosis; idiopathic pulmonary fibrosis; coal worker's progressive massive fibrosis; cryptogenic fibrosing alveolitis, chronic fibrosing interstitial pneumonia, interstitial lung disease (ILD), diffuse parenchymal lung disease (DPLD), emphysema and chronic obstructive pulmonary disease (COPD), or chronic asthma; or (ii) a fibrotic condition affecting the liver, for example cirrhosis, and associated conditions such as chronic viral hepatitis B or C, Wilson's disease, non-alcoholic fatty liver disease (NAFLD), alcoholic steatohepatitis (ASH), non-alcoholic steatohepatitis (NASH), primary biliary cirrhosis (PBC), biliary cirrhosis or autoimmune hepatitis; or (iii) a fibrotic condition affecting the kidneys, for example diabetic nephropathy, vesicoureteral reflux, tubulointerstitial renal fibrosis; glomerulonephritis or glomerular nephritis, including focal segmental glomerulosclerosis and membranous glomerulonephritis or mesangiocapillary glomerular nephritis;

(iv) a fibrotic condition affecting the heart or vascular system, for example endomyocardial fibrosis; old myocardial infarction; atrial fibrosis; congestive heart failure, cardiomyopathy, hypertensive heart disease (HHD), hypertension (for example pulmonary hypertension) and fibrosis associated with hypertension, atherosclerosis, restenosis (e.g. coronary, carotid, and cerebral lesions), and heart disease associated with cardiac ischemic events; or
(v) a fibrotic condition affecting the mediastinum, for example mediastinal fibrosis; or
(vi) a fibrotic condition affecting bone, for example myelofibrosis, including primary myelofibrosis, post polycythemia vera or post essential thrombocythemia myelofibrosis; or
(vii) a fibrotic condition affecting the retroperitoneum, for example retroperitoneal fibrosis skin; or
(viii) a fibrotic condition affecting the skin, for example nephrogenic systemic fibrosis, keloid formation and scarring, systemic sclerosis or scleroderma; or
(ix) a fibrotic condition affecting the GI tract, for example a fibrotic intestinal disorder, inflammatory bowel disease, ulcertative colitis or Crohn's disease; or
(x) a fibrotic condition affecting connective tissue, for example arthrofibrosis; or capsulitis; or
(xi) a fibrotic condition affecting the eye, for example ocular fibrosis following surgery or pseudoexfoliation syndrome glaucoma.

LOX Family, Angiogenesis and Vasculature Permeability

Angiogenesis, the formation of new blood vessels, is essential for tumor growth and progression.

LOX and LOXL2 are key players in promoting angiogenesis in a number of tumour models, such as colorectal (Baker, Bird et al. 2013), ovarian, lung cancer (Zaffryar-Eilot, Marshall et al. 2013), melanoma (Osawa, Ohga et al. 2013), glioblastoma (Mammoto, Jiang et al. 2013). LOX is overexpressed in tumour endothelial cells (Osawa, Ohga et al. 2013). Increased LOX tumour expression is associated with increased VEGF expression (Mammoto, Jiang et al. 2013), (Baker, Bird et al. 2013).

Additionally, LOXL2 inhibition led to the normalisation of vasculature and increased tumour perfusion in ovarian xenograft and lung allograft mice models (Zaffryar-Eilot, Marshall et al. 2013).

Excessive angiogenesis is involved in a number of diseases in addition to cancer discussed above. LOX mediates vascular permeability by modulating the stiffness of the endothelial barrier. Abnormal vascular permeability, such as present in diseases such as pulmonary edema and acute respiratory distress syndrome (ARDS) or endotoxin-induced lung injury can be normalised by LOX inhibition (Mammoto, Mammoto et al. 2013) (Ingber and Mammoto 2014).

Accordingly a compound of the invention or a pharmaceutically acceptable salt thereof may be for use as an anti-angiogenic agent. A compound of the invention or a pharmaceutically acceptable salt thereof may be for use in vascular normalisation.

In one embodiment a compound of the invention or a pharmaceutically acceptable salt thereof may be for use in the treatment is treatment of pulmonary embolism, emphysema, pleural effusion, pulmonary oedema, brain swelling, plural effusion, pericardial effusion and ascites.

In one embodiment a compound of the invention or a pharmaceutically acceptable salt thereof may be for use in the treatment is treatment of ischemia; ischemic stroke, ischemic heart disease, cerebral infarct, peripheral vascular disease, elephantiasis, lymphatic obstruction.

In one embodiment, the treatment is treatment of age-related macular degeneration (AMD), diabetic retinopathy and retinopathy of prematurity.

Inflammatory Disorders

Exacerbated inflammation and lung barrier dysfunction are hallmarks of acute respiratory distress syndrome (ARDS), a condition with dangerously high rates of morbidity and mortality. Increased LOX activity has been associated with bacterial lipopolysaccharide (LPS) induced inflammation. Inhibition of LPS-induced ECM crosslinking and stiffening by LOX suppression reduced EC inflammatory activation and lung dysfunction. Thus LOX inhibitors can be useful for the treatment of ARDS (Mambetsariev, Tian et al. 2014). LOX and LOXL1 reduction and collagen crosslinking reduction have been associated with decreased inflammation in an Angiotensin II induced model of hypertension (Gonzalez, Rhaleb et al. 2014).

In an embodiment there is provided a compound of the invention, or a pharmaceutically acceptable salt thereof may be useful in the treatment of an inflammatory condition. The inflammatory condition may be any of those described herein. For example the compound of the invention, or a pharmaceutically acceptable salt thereof may be for use in the treatment of acute inflammation (e.g., mediated by an acute infection).

In an embodiment the compound of the invention, or a pharmaceutically acceptable salt thereof may be for use in the treatment of chronic inflammatory disease, for example a disease selected from inflammatory bowel diseases (e.g. Crohn's disease and ulcerative colitis), psoriasis, sarcoidosis, rheumatoid arthritis, osteoarthritis, psoriatic arthritis, Reiter's syndrome, traumatic arthritis, rubella arthritis, acute synovitis, gouty arthritis and spondylitis.

In an embodiment the compound of the invention, or a pharmaceutically acceptable salt thereof may be for use in the treatment of rheumatoid arthritis; osteoarthritis; psoriatic arthritis; Reiter's syndrome; traumatic arthritis; rubella arthritis; acute synovitis; gouty arthritis; or spondylitis; diabetes or gout.

In an embodiment the compound of the invention, or a pharmaceutically acceptable salt thereof may be for use in the treatment of psoriasis; eczema; sarcoidosis, allergic rhinitis; allergic conjunctivitis; asthma, acute respiratory distress syndrome, acute lung injury (ALI), acute respiratory distress syndrome (ARDS), endotoxin-induced lung injury, pulmonary inflammation, chronic obstructive pulmonary disease and systemic cachexia.

In an embodiment the compound of the invention, or a pharmaceutically acceptable salt thereof may be for use in the treatment of rheumatoid arthritis, osteoarthritis, psoriatic arthritis, Reiter's syndrome, traumatic arthritis, rubella arthritis, acute synovitis, gouty arthritis or spondylitis, diabetes or gout.

In an embodiment the compound of the invention, or a pharmaceutically acceptable salt thereof may be for use in the treatment of endotoxemia; toxic shock syndrome, inflammatory bowel disease, atherosclerosis, irritable bowel syndrome, Crohn's disease, ulcerative colitis, a bone resorption disease, osteoporosis, diabetes, reperfusion injury, graft versus host reaction, allograft rejection, sepsis, septic shock, endotoxic shock, Gram negative sepsis, glomerulonephritis, restenosis, vasculitis, or thrombosis.

In another embodiment the compound of the invention, or a pharmaceutically acceptable salt thereof may be for use in the treatment of polymyositis, systemic lupus or interstitial nephritis.

Cardiovascular Disease

Interrupting collagen crosslinking by LOX with BAPN treatment reduces myocardial fibrosis in a mouse model, which is useful as potential therapeutic targeting of collagen regulation and thereby age-related myocardial fibrosis (Rosin, Sopel et al. 2015). Increased expression of LOX is associated with myocardial fibrosis and cardiac dysfunction (Zibadi, Vazquez et al. 2010) (Gao, Xiao et al. 2010) (Lopez, Gonzalez et al. 2010). Left atrial myocardium of patients with atrial fibrillation express higher levels of lysyl oxidase and fibronectin expression as well as collagen crosslinking. Fibronectin upregulation is mediated by LOX in cardiac fibroblasts (Adam, Theobald et al. 2011). LOX inhibitors can be useful for the prevention of fibrotic atrial remodelling. Inhibition of LOX by using a blocking antibody reduced cardiac fibrosis and infarct expansion in a mouse model (Gonzalez-Santamaria, 2016).

Lysyl oxidases play a causal role in experimental pulmonary hypertension and inhibition with BAPN reduces the symptoms (Nave, Mizikova et al. 2014). LOX facilitate the formation of crosslinked and therefore insoluble collagen and the subsequent left ventricle stiffness and systolic dysfunction in patients with hypertensive heart disease (HHD) and heart failure (HF) of hypertensive origin (Lopez, Gonzalez et al. 2013) (Lopez, Querejeta et al. 2012). A role for LOXL1 has been suggested in cardiac hypertrophy and BAPN administration inhibits angiotensin II-induced cardiac hypertrophy in vivo (Ohmura, Yasukawa et al. 2012). LOX knockdown attenuates cardiac and vascular fibrosis in high fat diet induced obesity (Martinez-Martinez, 2016).

Lysyl oxidase inhibition has been proposed as a therapeutic method for decreasing or preventing recurrent restenosis (Nuthakki, Fleser et al. 2004) (Brasselet, Durand et al. 2005). Increased LOX activity has been observed in atherosclerosis (Kagan, Raghavan et al. 1981). LOX is overexpressed in other pathologies associated with increased thrombosis, such as myeloproliferative neoplasms, chronic kidney disease and arterial stenosis and enhances platelets aggregation (Shinobu et al, 2016).

Accordingly in an embodiment compound of the invention, or a pharmaceutically acceptable salt thereof may be for use in the treatment of a cardiovascular disease, for example any one of the diseases mentioned in this section, e.g. the treatment of atherosclerosis, myocardial fibrosis, prevention of fibrotic atrial remodelling, old myocardial infarction; congestive heart failure, cardiomyopathy, hypertensive heart disease (HHD), hypertension (for example pulmonary hypertension) and fibrosis associated with hypertension, restenosis (e.g. coronary, carotid, and cerebral lesions), and heart disease associated with cardiac ischemic events.

Neurological Conditions

As discussed in the Background to the Invention, LOX is associated with nurological conditions including Alzheimer's disease and other neurological conditions. Accordingly, in one embodiment there is provided a compound of the invention, or a pharmaceutically acceptable salt thereof may be for use in the treatment of a neurological condition mediated by LOX or LOXL. The neurological condition may be Alzheimer's disease (AD) and hereditary cerebral hemorrhage with amyloidosis of the Dutch type (HCHWA-D) or non-Alzheimer's dementia.

LOX is increased at the site of brain injury (Gilad, Kagan et al. 2001) and spinal cord injury and its inhibition lead to accelerated functional recovery in a unilateral spinal cord dissection model (Gilad and Gilad 2001). Accordingly a compound of the invention, or a pharmaceutically acceptable salt thereof may be for use in the treatment nerve damage, for example the promotion of nerve regrowth and/or recovery after spinal cord injury.

Pulmonary Diseases

LOXL2 and LOXL3 are likely to have a role in Primary Alveolar Proteinosis (PAP) since both are expressed in PAP tissue, but not normal lung tissue (Neufeld and Brekhman 2009). Excessive lysyl oxidase activity was linked to the pathologic pulmonary features of bronchopulmonary dysplasia (Kumarasamy, Schmitt et al. 2009). A compound of the invention, or a pharmaceutically acceptable salt thereof may be for use in the treatment of primary alveolar proteinosis (PAP) or bronchopulmonary dysplasia.

Eye Diseases

Increased LOXL2 levels have been associated with failure following glaucoma surgery and treatment with a LOXL2 antibody reduced pathological angiogenesis, inflammation, and ocular fibrosis (Park, Kim et al. 2014) (Van Bergen, Marshall et al. 2013) (Stalmans, Van Bergen et al. 2011). Expression of lysyl oxidase-type enzymes increases following laser-induced choroidal neovascularization (CNV) in a model of age-related macular degeneration (AMD), in parallel with fibrotic damage. Inhibition of LOX or LOXL2 prevents neovascularization and fibrosis following laser-induced CNV. Therefore LOX and LOXL inhibitors can be useful in the treatment of conditions characterized by neovascularization, such as age-related macular degeneration (AMD), diabetic retinopathy and retinopathy of prematurity (Stalmans, Marshall et al. 2010). LOXL1 expression is increased in the initial stages of abnormal fibrogenesis in pseudoexfoliation syndrome/glaucoma tissues (Zenkel, Krysta et al. 2011) (Schlotzer-Schrehardt, Pasutto et al. 2008).

A compound of the invention, or a pharmaceutically acceptable salt thereof may be for use in the treatment of an ocular condition mediated by LOX or a LOXL, for example any of the ocular conditions listed in the paragraph above.

Other Diseases

LOX is the main isoenzyme expressed in human adipose tissue and that its expression is strongly upregulated in samples from obese patients. β-aminopropionitrile reduces body weight gain and improves the metabolic profile in diet-induced obesity in rats (Miana, Galan et al. 2015) and reduces local adipose tissue inflammation (Halberg, Khan et al. 2009). In an embodiment a compound of the invention, or a pharmaceutically acceptable salt thereof may be for use in the treatment of obesity.

LOX has been suggested as a new therapeutic target in bacterial infections and subsequent fibrotic complications. LOX is upregulated in infections with *Staphylococcus Aureus* and inhibition with BAPN influences resulting abscesses morphology and collagenisation (Beerlage, Greb et al. 2013). LOX is implicated also in some parasitic diseases: LOX and LOXLs are upregulated in the early stages of liver granuloma development in schistosomiasis (Decitre, Gleyzal et al. 1998), and BAPN inhibition reduces the size of the granulomas and reduces the egg load in combination with antiparasitic drug PZQ compared to PZQ alone (Giboda, Zenka et al. 1992), In one embodiment, the compound is for use in the treatment of a bacterial infection, for example infection with *Staphylococcus Aureus*. The compound of the invention may be for use in the treatment or prevention of infection associated fibrosis, for example to prevent or inhibit abcess formation associated with the infection. The formation of abcesses can provide a favourable microenvironment for the bacteria to multiply. Inhibition of abcess formation may be beneficial in that it may provide enhanced exposure of the bacteria to antibiotics at the site of infection, because the shielding effect provided by the abcess would be reduced or eliminated. Thus combination treatments comprising a compound of the invention together with an antibiotic agent may provide an enhanced antibacterial effect. The compound of the invention may also be for use in the prevention or inhibition of tissue fibrosis following eradication of the infection and healing of the infection sites.

In one embodiment, the compound is for use in the treatment of a parasitic infection, for example schistosomiasis.

EGFR Mediated Conditions

Elevated levels of the epidermal growth factor receptor (EGFR), a growth-factor-receptor tyrosine kinase, and/or its ligands is observed in many cancer types and is involved in the promotion of tumour growth. EGFR inhibitors have been directed to a number of cancer types, including NSCLC, pancreatic cancer, squamous cells carcinoma, skin cancer, thyroid, colorectal, prostate, gastric, renal, breast, head & neck cancers, glioma, meningiomas, mesothelioma, cervical carcinomas epidermal carcinomas (reviewed in Bianco et al (Bianco, Gelardi et al. 2007)). Elevated EGFR was found to act as a strong indicator of poor prognosis in head and neck, ovarian, cervical, bladder and oesophageal cancers (Nicholson, Gee et al. 2001). EGFR inhibitors have also been proposed for the treatment of metastatic prostate cancer (Ree, Bratland et al. 2008), biliary cancer such as cholangiocarcinoma with a mutation in ERRFI1 (Borad, Carpten et al. 2014).

Blockade of the kinase activity of EGFR does not reach maximum therapeutic efficacy. LOX inhibitors reduce the level of surface EGFR suggesting the possibility that these compounds will have an effect on reducing EGFR activation (Tang et al, 2017).

EGFR inhibition has been targeted as treatment for a number of other diseases, such as prevention and treatment of obesity (Threadgill and Barrick 2007), treatment of Alzheimer's disease (Ma 2013), treatment of *Chlamydia* infection and related diseases (Tsang and Furdui 2015), treatment of viral diseases (Jung 2010), promotion of axon regeneration (He and Koprivica 2007), treatment of genetic skin disorders characterized by hyperkeratosis, keratinocyte hyperplasia, and/or ichthyosis (Alexandrescu 2009).

Given the role of LOX inhibition in modulating the surface EGFR levels and EGFR signalling, LOX inhibitors could be useful in the treatment of diseases which can be targeted by EGFR inhibition.

In an embodiment there is provided a compound of the invention, or a pharmaceutically acceptable salt thereof may be for use in the treatment of a disorder (e.g., a disease) that is ameliorated by the inhibition of EGFR. The EGFR mediated condition may be, for example, any of those listed in this section or elsewhere in the description. The compound of the invention, or a pharmaceutically acceptable salt thereof may be for use in the treatment of a cancer which over-expresses EGFR. The cancer over-expressing EGFR may be, for example NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers or a biliary cancer such as cholangiocarcinoma.

In one embodiment, the compound is for use in the treatment of a viral infection, for example Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus or cytomegalovirus.

In one embodiment, the compound is for use in the treatment of *Chlamydia* infection.

In one embodiment, the compound is for use in the treatment of a genetic skin disorder, for example a keratinization disorder is selected from among Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratoderma, erythrokeratodermia variabilis, verrucous epidermal nevi, *Pityriasis rubra* pilaris, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratoderma of Vohwinkel, Harlequin ichthyosis and Tay's syndrome.

LOX and EGFR

In one aspect, the present invention relates to a lysyl oxidase inhibitor for use in the treatment or prevention of a cancer associated with overexpression of EGFR.

In another aspect, the present invention relates to the use of a lysyl oxidase inhibitor in the manufacture of a medicament for the treatment or prevention of a cancer associated with overexpression of EGFR.

Suitably, in all aspects, the cancer may be selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, in all aspects, the lysyl oxidase inhibitor may be a compound of the present invention or a pharmaceutical composition of the present invention.

Suitably, in all aspects of the invention, the lysyl oxidase inhibitor of the invention may downregulate expression of MATN2 and/or activate SMAD2. Suitably, the lysyl oxidase inhibitor of the invention may downregulate expression of HTRA1. Optionally, in all aspects of the invention, the lysyl oxidase inhibitor of the invention may inhibit maturation of lysyl oxidase and/or inhibit the catalytic activity of lysyl oxidase. Suitably, the lysyl oxidase inhibitor of the invention may not inhibit MAO-A and/or MAO-B.

In a further aspect, the present invention relates to a method of treating or preventing cancer in a subject, said method comprising administering a therapeutically effective amount of a lysyl oxidase inhibitor of the invention to said subject, wherein said subject has a cancer associated with overexpression of EGFR.

Optionally, the method may comprise determining the level EGFR in a biological sample of said subject, and administering a lysyl oxidase inhibitor of the invention to said subject when the presence of EGFR is determined to be overexpressed in the biological sample.

Optionally, the method may further comprise the steps of determining the level of MATN2, pSMAD2 or HTRA1 or combinations thereof in a biological sample of said subject, and administering a lysyl oxidase inhibitor of the invention to said subject when:
  a) the level of MATN2 is greater than a reference sample; and/or
  b) the level of pSMAD2 is lower than a reference sample; and/or
  c) the level of HTRA1 is greater than a reference sample.

Optionally, said subject may have a cancer selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, in all aspects of the invention, the lysyl oxidase inhibitor of the invention may downregulate expression of MATN2 or HTRA1 and/or activate SMAD2. Optionally, in all aspects of the invention, the lysyl inhibitor of the invention may inhibit maturation of lysyl oxidase and/or inhibit the catalytic activity of lysyl oxidase. Suitably, the lysyl oxidase inhibitor of the invention may not inhibit MAO-A and/or MAO-B.

In another aspect, the present invention relates to a method of increasing the sensitivity rate (efficacy rate) of a lysyl oxidase inhibitor of the invention to treat cancer in a patient population said method comprising selecting a sub population which overexpresses an EGFR and/or MATN2 and/or HTRA1 biomarker. Optionally, said subgroup may underexpress pSMAD2.

In a further aspect, the present invention relates to a method of identifying a subject having increased likelihood of responsiveness or sensitivity to a lysyl oxidase inhibitor of the invention comprising:
  a) determining the level of one or more of EGFR, MATN2, and HTRA1 in a biological sample of the subject;
wherein increased levels EGFR, MATN2, HTRA1 or a combination thereof compared to a reference sample indicates an increased likelihood of responsiveness or sensitivity to a lysyl oxidase inhibitor in the subject.

In another aspect, the present invention relates to a method of identifying a subject having responsiveness or sensitivity to a lysyl oxidase inhibitor of the invention comprising:
  a) determining the level of one or more of EGFR, MATN2, and HTRA1 in a biological sample of the subject;
wherein increased levels one or more of EGFR, MATN2, and HTRA1 compared to a reference sample identifies the subject as having responsiveness or sensitivity to a lysyl oxidase inhibitor.

Optionally, in all methods of the invention, the methods may comprise a further step of administering a therapeutically effective amount of a lysyl oxidase inhibitor of the invention when the subject is identified as having increased likelihood of responsiveness of sensitivity to a lysyl oxidase inhibitor.

In a further aspect, the present invention relates to a method of determining a treatment regimen for a subject with cancer, comprising:
  a) determining the level one or more of EGFR, MATN2, and HTRA1 in a biological sample; and
  b) administering a treatment regimen comprising a therapeutically effective amount of a lysyl oxidase inhibitor of the invention, when levels one or more of EGFR, MATN2, and HTRA1 are elevated compared to a reference sample.

Biomarkers

The present invention therefore provides the possibility of a clinical test to predict response to LOX inhibition therapy, preferably prior to a subject commencing LOX inhibition therapy. Such a test will inform the clinician whether the patient is likely to respond to LOX inhibition therapy or not, and enable the clinician to commence alternative therapy if the patient is predicted to be unlikely to respond. This will benefit the patient by targeting their treatment with an appropriate therapy early, rather than relying on the current "trial and error" approach. Such a test will therefore enable better of targeting of LOX inhibition therapy to patients early in their disease, when maximum effect can be achieved, and may result in greater access to these drugs as they are used in a more cost-efficient manner.

The present invention is advantageous in enabling likely responders and non-responders to be identified, so that non-responders may be provided alternative treatment, and those who are not non-responders (and therefore may be a moderate or good responder) may be provided LOX inhibition therapy. As a result of the present invention, LOX inhibition therapies may therefore be used in a more targeted and cost-efficient manner.

For the purposes of the biomarker and stratification aspects disclosed herein a "LOX inhibitor" is an agent which is able to reduce the expression, reduce the catalytic activity or prevent maturation of LOX. Suitably the LOX inhibitor is a compound of the invention, or a pharmaceutically acceptable salt thereof.

Any suitable source of lysyl oxidase may be employed for the determination of LOX inhibition. The enzyme can be derived, isolated, or recombinantly produced from any source known in the art, including yeast, microbial, and mammalian, that will permit the generation of a suitable product that can generate a detectable reagent or will be biologically active in a suitable assay. In one embodiment, the lysyl oxidase is of human, bovine, or other mammalian origin. See, e.g., Williams, et al., Anal. Biochem. 113:336 (1985); Kirschmann et al., supra; Cancer Res. 62:4478-83 (2002); LOX may be obtained from Accession No. NP00238 (preprotein sequence); Accession No. NM02317 (DNA sequence). A functional fragment or a derivative of lysyl oxidase that still substantially retains its enzymatic activity catalyzing the oxidation of lysyl oxidase can also be used. The lysyl oxidase enzyme can sometimes be the pre-pro-protein, proprotein, the protein, or a biologically active fragment thereof.

The enzymatic activity of lysyl oxidase can be assessed by any suitable method. Exemplary methods of assessing lysyl oxidase activity include that of Trackman et al., Anal. Biochem. 113:336-342 (1981); Kagan, et al., Methods Enzymol. 82A:637-49 (1982); Palamakumbura et al., Anal. Biochem. 300:245-51 (2002); Albini et al., Cancer Res. 47: 3239-45 (1987); Kamath et al, Cancer Res. 61:5933-40 (2001); for example.

The enzymatic activity of the lysyl oxidase may be assessed by detecting and/or quantitating "lysyl oxidase byproducts," such as $H_2O_2$ production; collagen pyridinium residuesammonium production; aldehyde product production; lysyl oxidation, or deoxypyridinoline (Dpd). One may also detect and quantitate cellular invasive capacity in vitro; cellular adhesion and growth in vitro; and metastatic growth in vivo. In vivo models include, but are not limited to suitable syngeneic models, human tumor xenograft models, orthotopic models, metastatic models, transgenic models, and gene knockout models. See, e.g., Teicher, Tumors Models in Cancer Research (Humana Press 2001).

A compound is an inhibitor of lysyl oxidase expression or biological activity when the compound reduces the expression or activity or lysyl oxidase relative to that observed in the absence of the compound. In one embodiment, a compound is an inhibitor of lysyl oxidase when the compound reduces the incidence of metastasis relative to the observed in the absence of the compound and, in further testing, inhibits metastatic tumor growth.

The tumor inhibition can be quantified using any convenient method of measurement. For example, the incidence of metastasis can be assessed by examining relative dissemination (e.g., number of organ systems involved) and relative tumor burden in these sites. Metastatic growth can be ascertained by microscopic or macroscopic analysis, as appropriate. Tumor metastasis can be reduced by about 10%, 20%, 30%, 40%, 50%, 60%, 70%, 80%, 90%, 95% or greater.

In one embodiment, lysyl oxidase expression is assessed using promoter analysis. Any convenient system for promoter activity analysis can be employed. Typically, the reporter gene system allows promoter activity to be detected using the lysyl oxidase promoter attached to a reporter molecule such that promoter activity results in the expression of the reporter molecule. See, e.g., Ausubel et al., Current Protocols in Molecular Biology (John Wiley & Sons, current edition) at chapter 9.6.

Also, LOX may be inhibited by degradation of its mRNA. An approach to this form of gene regulation is described in Wilson et al. "Modulation of LDL receptor mRNA stability by phorbol esters in human liver cell culture models," Lipid Res. 38, 437-446 (1997).

The lysyl oxidase inhibitor compounds of the present invention may be used in the LOX inhibition therapy described herein.

The present invention provides an improved method for prediction of response to anti-LOX inhibition therapy, using biomarkers which could not have been predicted from the prior art as being indicative of a favourable response.

Throughout this section, the terms patient and subject are used interchangeably herein to refer to an individual for whom it is desirable to determine likely response to LOX inhibition therapy. Such an individual may have, or be predisposed to having, or expected to develop, cancer.

A biomarker as used herein is a biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. A biomarker may be a gene, exhibiting differential expression between responders and non-responders to LOX inhibition therapy. Expression of a biomarker gene (transcription and optionally translation) may be determined by measuring an expression product of the gene, referred to herein as a target molecule. A combination of two or more biomarkers may be referred to herein as a panel or a genetic signature which correlates with likely response to LOX inhibition therapy.

Predicting response means making a determination of the likely effect of treatment in a subject. Prediction typically means an assessment made prior to commencing the relevant treatment, although it is understood that a prediction of the likely response to a particular treatment may be made whilst a subject is receiving an alternative treatment. Predicting response to therapy, within the scope of the present invention may also include making an assessment of likely continued response to LOX inhibition therapy. Therefore, prediction of response may include a determination of likely response during a course of LOX inhibition therapy.

A sample may be selected from the group comprising tissue sample, such as a biopsy sample; and a body fluid sample. A body fluid sample may be a blood sample. A blood sample may be a peripheral blood sample. It may be a whole blood sample, or cellular extract thereof. In one embodiment, preferably the sample is a tissue sample.

The level of a target molecule herein refers to a measure of the amount of a target molecule in a sample. The level may be based upon a measure of one type of target molecule indicative of expression specific for a particular biomarker (i.e. DNA, RNA or protein). The level may alternatively be based upon a measure of a combination of two or more types of target molecule indicative of expression specific for a particular biomarker (i.e. two or more of DNA, RNA and protein). The level of a target molecule may be expressed as a direct measure of the amount of target molecule (for example concentration (mg/vol sample) or RPKM).

Elevated level means an increase in level (i.e. amount) of a target molecule compared to the level of the same target molecule in a subject who does not have cancer. An elevated level includes any statistically significant increase compared to the control. The level of a target molecule indicative of expression of a biomarker in a subject which does not have cancer or a disease associated with overexpression of EGFR may be referred to as a reference value or baseline value.

The elevated level of the target molecule representative of gene expression may be assessed by comparing the amount of the target molecule present in the patient sample under investigation with a reference value indicative of the amount of the target molecule in a control sample.

References herein to the "same" level of target molecule or biomarker expression indicate that the biomarker expression of the sample is identical to the reference or baseline value. References herein to a "similar" level of target molecule or biomarker expression indicate that the biomarker expression of the sample is not identical to the reference or baseline value but the difference between them is not statistically significant i.e. the levels have comparable quantities.

Suitable control samples for determination of a reference value or baseline value may be derived from individuals without a disease associated with overexpression of EGFR and without cancer. A control sample may be age matched with the patient undergoing investigation. Reference values or baseline value may be obtained from suitable individuals and used as a general reference value for multiple analysis.

Favourable response to LOX inhibition therapy may include, without limitation, treatment or prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms. Thus, favourable response to LOX inhibition therapy includes delay or reduction of proliferation of tumour growth and/or delay of metastasis.

Target molecules as used herein may be selected from the group consisting of: a biomarker protein; and nucleic acid encoding the biomarker protein. The nucleic acid may be DNA or RNA. In an embodiment the nucleic acid is mRNA. Reference herein to a target molecule may include one type of biological molecule (i.e. DNA or RNA or protein) or a combination of two or more types of such biological molecules, all indicative of the expression of the same biomarker.

A binding partner may be selected from the group comprising: complementary nucleic acids; aptamers; receptors, antibodies or antibody fragments. By a specific binding partner is meant a binding partner capable of binding to at least one such target molecule in a manner that can be distinguished from non-specific binding to molecules that are not target molecules. A suitable distinction may, for example, be based on distinguishable differences in the magnitude of such binding.

One aspect of the present invention may make use of one or more target molecules, each target molecule being indicative of the expression of a different biomarker selected from the group consisting of: EGFR, MATN2, HTRA1 and pSMAD2. This aspect of the invention may make use of two or more or three or more, target molecules, each being indicative of the expression of a different biomarker selected from the group consisting of: EGFR, MATN2, HTRA1 and pSMAD2.

In an embodiment, the present invention may make use of a target molecule indicative of the expression of EGFR.

In an embodiment, the present invention may make use of a target molecule indicative of the expression of MATN2.

In an embodiment, the present invention may make use of two or more target molecules or three or more biomarkers, each being indicative of the expression of a different biomarker. For example, wherein the biomarkers are EGFR and MATN2; MATN2 and pSMAD2 or EGFR and pSMAD2.

Therefore, the present invention identifies an expression signature which identifies subjects who are unlikely to respond or are likely to respond to LOX inhibition therapy. In an embodiment, the signature is characterized by an up regulation of MATN2, an upregulation of EGFR, an upregulation of homotrimeric HTRA1, a down regulation of pSMAD2 or a combination thereof.

A method of increasing the sensitivity (efficacy) rate, or identifying increased likelihood of response to LOX inhibitors in accordance with the present invention will preferably be carried out in vitro, but it will be appreciated that a method of the invention may also be carried out in vivo.

A level of a target molecule may be investigated using a binding partner for the target molecule. A binding partner may be specific for a target molecule. In the context of the present invention, a binding partner specific to a target molecule will be capable of binding to at least one such target molecule in a manner that can be distinguished from non-specific binding to molecules that are not target molecules. A suitable distinction may, for example, be based on distinguishable differences in the magnitude of such binding.

Reference to a protein target may include precursors or variants produced on translation of the transcripts produced when the gene is expressed. Therefore, where a protein undergoes modification between first translation and its mature form, the precursor and/or the mature protein may be used as suitable target molecules. As above, techniques by which protein target molecules may be preserved within a patient sample, thus facilitating its detection, will be well known to those skilled in the art. A protein target may be found within a cell of a patient sample, or may be secreted or released from the cell.

In embodiments of the present invention where the target molecule is a protein, a binding partner may be used to determine the level of the protein in a sample obtained from the subject. A suitable binding partner may be is selected from the group consisting of: aptamers; receptors, and antibodies or antibody fragments. Suitable methods for determining the level of a protein in a sample are available in the art. For example, in certain embodiments of the methods or devices of the invention the binding partner is an antibody, or antibody fragment, and the detection of the target molecules utilises an immunological method. In certain embodiments of the methods or devices, the immunological method may be an enzyme-linked immunosorbent assay (ELISA) including variants such as sandwich ELISAs; radioimmuno assays (RIA). In other embodiments an immunological method may utilise a lateral flow device. Other suitable techniques may include multiplex assays such as Luminex or proteomic MRM or fluorescence activated cell sorting (FACS); chemiluminescence.

In certain embodiments, a binding partner may be labelled, for example using a reporter moiety such as a fluorophore, chromogenic substrate or chromogenic enzyme. Where it is desired that the invention will make use of reporter moieties, the reporter moieties may be directly attached to the binding partners. Examples of such embodiments include those utilising labelled antibodies. Alternatively, the reporter moieties may be attached to reporter molecules that interact with the binding partners. Examples of such embodiments include those utilising antibodies indirectly attached to a reporter moiety by means of biotin/avidin complex.

In embodiments where the target molecule is a nucleic acid, binding partners may be complementary nucleic acids and aptamers, for example provided in a microarray or chip. Methods for determining the level of a nucleic acid target molecule in a sample are available in the art. In an embodiment, a suitable target molecule representative of gene expression may comprise an RNA transcript translatable to yield a protein. mRNA of this sort will typically be found within a patient sample. In particular, the transcriptome of white blood cells, for example neutrophils, of a patient sample have been found to provide a biomarker signature with improved sensitivity and specificity for determining non-responders and/or good responders to anti-TNF therapy, and the use of mRNA and in particular the transcriptome may represent a preferred embodiment. Use of mRNA as the target molecule has advantages in that the assays for detecting mRNA (such as quantitative rtPCR or the like) tend to be cheaper than methods for detecting protein (such as ELISAs). mRNA assays can be more readily multiplexed, allowing for high throughput analysis; nucleic acids generally show greater stability than their protein counterparts; and processing of the sample to obtain and amplify nucleic acid is generally simpler than for protein.

Techniques by which mRNA may be collected, purified and amplified as necessary, are well known to those skilled in the art. In an embodiment, the present invention may make use of transcriptome analysis for determining biomarker expression. Suitable techniques for determining the level of RNA in a sample, for example by transcriptome analysis, may include hybridization techniques, for example by detecting binding to a nucleic acid library, quantitative PCR, and high throughput sequencing including tag based sequencing such as SAGE (serial analysis of gene expression) and RNA-seq.

The above examples are non-limiting, and the methods of the invention may make use of any appropriate assay by which the presence or elevated levels of a requisite target molecule may be detected. It will be appreciated that suitable assays may be determined with reference to the nature of the target molecule to be detected and/or the nature of the patient sample to be used.

Multiple samples may be processed simultaneously, sequentially or separately. Multiple samples may be processed simultaneously, for example in a high throughput method.

Suitably, the present invention may also provide kits for carrying out the stratification or biomarker methods disclosed herein. Such kits may contain compounds by which the presence or elevated levels of a requisite target molecule may be detected, such as antibodies to one or more biomarkers of the present invention. Optionally, the kit may further comprise one or more of a set of instructions for use, a chart providing reference or baseline values for at least the biomarker to de detected using the kits; and reagents.

Once the amounts or concentrations of the target molecules in the patient sample have been determined, this information may be used as the basis of an assessment of the predicted response to LOX inhibition therapy, which may, in turn, be used to suggest a suitable course of treatment for the patient. The assessment may be qualitative or quantitative.

An elevated level of a biomarker may include at least 10%, 15, 20, 30, 40, 50, 60, 70, 80, 90 or 100% or more increase compared to the baseline or reference value level. In one embodiment, an elevated level may be 1 fold or more difference relative to the baseline or reference value, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges there between. In one embodiment, the higher level is between a 1 and 15 fold difference relative to the baseline level, such as between a 1.5 and 12 fold difference relative to the baseline level. In a further embodiment, the higher level is between a 1 and 7 fold difference relative to the baseline level. It is appreciated that elevation levels may differ from the same biomarker depending on the target molecule being used. Where nucleic acid and protein target molecules are used for any particular biomarker, an elevated level may be expressed individually for a target molecule, or may be expressed as a sum or average of the target molecules.

The invention may produce a quantitative output, based upon elevation values for a biomarker or a sum or biomarkers. Alternatively, the invention may provide a qualitative output, based on likely response, for example yes/no; elevated; non-elevated; responder/non-responder; good, moderate or low based on EULAR criteria, etc. Where the levels of two or more target molecules are determined, a composite score may be determined, which may be compared to a composite score of reference values for the same target molecules.

In certain embodiments the methods or devices of the invention may further involve investigating physiological measurements of the patient.

In a further embodiment, there is provided a method for treating a subject having cancer, wherein it was previously determined (or previously estimated) that the cancer is associated with overexpression of EGFR compared to a reference value, the method comprising administering an therapeutically effective amount of a LOX Inhibitor of the invention to the subject.

In a further embodiment, there is provided a method for treating a subject having cancer, wherein it was previously determined (or previously estimated) that a target molecule indicative of expression of MATN2 is increased in a sample from the subject compared to a reference value, the method comprising administering an therapeutically effective amount of a LOX Inhibitor of the invention to the subject.

In a further embodiment, there is provided a method for treating a subject having cancer, wherein it was previously determined (or previously estimated) that a target molecule indicative of expression of homotrimeric HTRA1 is increased in a sample from the subject compared to a reference value, the method comprising administering an therapeutically effective amount of a LOX Inhibitor of the invention to the subject.

In a further embodiment, there is provided a method for treating a subject having cancer, wherein it was previously determined (or previously estimated) that a target molecule indicative of expression of pSMAD2 is decreased in a sample from the subject compared to a reference value, the method comprising administering an therapeutically effective amount of a LOX Inhibitor of the invention to the subject.

LOX inhibitors can disrupt EGFR membrane localisation, block EGFR signalling and, thereby, suppress tumour growth in cancers associated with overexpression of EGFR. As such, LOX inhibitors will have particular utility in the treatment of cancers associated with overexpression of EGFR.

In one aspect, the present invention relates to a lysyl oxidase inhibitor of the invention for use in the treatment or prevention of a cancer associated with overexpression of EGFR.

In another aspect, the present invention relates to the use of a lysyl oxidase inhibitor of the invention in the manufacture of a medicament for the treatment or prevention of a cancer associated with overexpression of EGFR.

In a further aspect, the present invention relates to a method of treating or preventing cancer in a subject, said method comprising administering a therapeutically effective amount of a lysyl oxidase inhibitor of the invention to said subject, wherein said subject has a cancer or has a predisposition for a cancer associated with overexpression of EGFR.

Optionally, the method may comprise determining the level EGFR in a biological sample of said subject, and administering a lysyl oxidase inhibitor of the invention to said subject when the presence of EGFR is determined to be overexpressed in the biological sample.

By "EGFR overexpression" it is meant the presence of increased copies of the EGFR gene or increased EPGR protein (preferably at the surface) in or on a cancer cell compared to a non-cancerous cell of the same tissue type. Thus, in one embodiment overexpression may be defined as at least a two-fold amplification of the EGFR gene, as determined by fluorescent in-situ hybridization (FISH), or as a positive staining using anti-EGFR antibodies in an immunohistochemistry (IHC) assay. In addition or in the alternative, overexpression may be measured by the fraction of cell membrane labelled with a specific antibody; thus overexpression of EGFR may be defined as at least 1% or at least 2% or at least 3% membranous staining and 1+(or 2+ or 3+) intensity, or at least 10% membranous staining. Furthermore, cells may be classified as cells that do not express, or have undetectable levels of EGFR, cells expressing low levels of EGFR (about 1000 to about 100,00 receptors/cell), medium levels of EGFR (about 10,000 to about 100,000 receptors/cell) and cells expressing high levels of EGFR (about $1 \times 10^6$ or more receptors/cell). Therefore, the cancer susceptible to treatment using a LOX inhibitor of the present invention are cancers characterized by two-fold or greater amplification of the EGFR gene, positive (1+, 2+, or 3+)

IHC assay, at least 1%, or at least 10% membranous staining, medium or high levels of EGFR and preferably cancer cells characterized by high levels of EGFR. Suitably, overexpression may be determined using anti-EGFR antibodies (preferably anti-HER1) in an immunohistochemistry (IHC) assay.

Optionally, the method may further comprise the steps of determining the level of MATN2, pSMAD2 or both MATN2 and pSMAD2 in a biological sample of said subject, and administering a lysyl oxidase inhibitor of the invention to said subject when:
  a) the level of MATN2 is greater than a reference sample;
  b) the level of pSMAD2 is lower than a reference sample; or
  c) the level of MATN2 is greater than a reference sample and the level of pSMAD2 is lower than a reference sample.

Suitably, the cancer may be selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Optionally, in all aspects of the invention, the lysyl oxidase inhibitor may inhibit maturation of lysyl oxidase and/or inhibit the catalytic activity of lysyl oxidase. Suitably, the lysyl oxidase inhibitor may not inhibit MAO-A and/or MAO-B. Suitably, inhibition of MAO-A and/or MAO-B may be determined using the in vitro oxidase-A/-B activity assay as described in the Examples. Suitably, the lysyl oxidase inhibitor may not inhibit DAO and/or hERG.

In another aspect, the present invention relates to a method of increasing the sensitivity rate (efficacy rate) of a lysyl oxidase inhibitor of the invention to treat cancer in a patient population said method comprising selecting a sub population which overexpresses an EGFR and, optionally overexpresses MATN2 and/or HTRA1. Optionally, said subgroup may also exhibit reduced expression of pSMAD2.

By "increased likelihood of responsiveness or sensitivity to a LOX inhibitor" it is meant a higher prediction of a favourable effects associated with LOX inhibition therapy.

In a further aspect, the present invention relates to a method of determining a treatment regimen for a subject with cancer, comprising:
  a) determining the level of EGFR (and optionally MATN2 or HTRA1) in a biological sample; and
  b) administering a treatment regimen comprising a therapeutically effective amount of a lysyl oxidase inhibitor of the invention, when levels of EGFR (and optionally increased MATN2 and/or HTRA1) are elevated compared to a reference sample.

MATN2

Matrilin2 (MATN2) is a secreted protein with 10 EGF-like repeats (Wagener, R. et al. The matrilins—adaptor proteins in the extracellular matrix. FEBS Lett 579, 3323-3329, doi:10.1016/j.febslet.2005.03.018 (2005)). A protein sequence of human MATN2 may be obtained from uniprot (Universal protein resource) reference 000339-1.

Advantageously, the present invention has surprisingly shown that recombinant human MATN2 increase the levels of EGFR at the surface of the cell and thus MATN2 strongly enhances EGF-induced EGFR activation. Without wishing to be bound by theory, it is believed that MATN2 binding traps EGFR at the cell surface to present it to EGF for activation.

It has been surprisingly found that LOX inhibitors can downregulate expression of MATN2 which leads to increased internalisation of EGFR. Accordingly, the LOX inhibitors of the invention may have particular utility in the treatment of cancers having elevated levels of MATN2 compared to a reference sample.

Suitably, levels of MATN2 may be determined using immunofluorescence using a commercially available anti-human MATN2 antibody (e.g. from R&D). For example, the sample may be subjected to incubation with primary anti-MATN2 antibodies followed by fluorescence secondary antibodies (such as those available from Life Technologies) and then the levels determined using confocal imaging. An identical procedure is carried out on a reference sample so that it can be determined if MATN2 levels are increased.

Thus, MATN2 (optionally in combination with EGFR) may be used as a biomarker to predict responsiveness or sensitivity of a patient suffering from cancer to treatment with a lysyl oxidase inhibitor of the invention. Optionally, one or more further biomarkers may be used such as pSMAD2.

In another aspect, the present invention relates to a method of increasing the sensitivity rate (efficacy rate) of a lysyl oxidase inhibitor of the invention to treat cancer in a patient population said method comprising selecting a sub population which has enhanced expression of MATN2. Optionally, said subgroup may also exhibit reduced expression of pSMAD2.

In a further aspect, the present invention relates to a method of identifying a subject having increased likelihood of responsiveness or sensitivity to a lysyl oxidase inhibitor of the invention comprising:
  a) determining the level of MATN2 in a biological sample of the subject;
wherein increased levels MATN2 compared to a reference sample indicates an increased likelihood of responsiveness or sensitivity to a lysyl oxidase inhibitor in the subject.

In another aspect, the present invention relates to a method of identifying a subject having responsiveness or sensitivity to a lysyl oxidase inhibitor of the invention comprising:
  a) determining the level of MATN2 in a biological sample of the subject;
wherein increased levels MATN2 compared to a reference sample identifies the subject as having responsiveness or sensitivity to a lysyl oxidase inhibitor of the invention.

Optionally, in all methods of the invention, the methods may comprise a further step of administering a therapeutically effective amount of a lysyl oxidase inhibitor when the subject is identified has have increased likelihood of responsiveness of sensitivity to a lysyl oxidase inhibitor.

In a further aspect, the present invention relates to a method of determining a treatment regimen for a subject with cancer, comprising:
  a) determining the level of MATN2 in a biological sample; and
  b) administering a treatment regimen comprising a therapeutically effective amount of a lysyl oxidase inhibitor, when levels MATN2 are elevated compared to a reference sample.

SMAD2

Smad proteins are signal transducers and transcriptional modulators that mediate multiple signaling pathways. SMAD2 mediates the signal of the transforming growth factor (TGF)-beta, and thus regulates multiple cellular processes, such as cell proliferation, apoptosis, and differentiation. This protein is recruited to the TGF-beta receptors through its interaction with the Smad anchor for receptor activation (SARA) protein. In response to TGF-beta signal, this protein is phosphorylated by the TGF-beta receptors. A human protein sequence may be obtained from uniprot (Universal protein resource) reference Q15796.

The present invention has surprisingly found strong activation of SMAD2 in LOX deficient cells and that TGFβ1 downregulates MATN2 mRNA. Without wishing to be bound by theory, it is believed that LOX inhibitors may activate SMAD2 which will lead to the downregulation of MATN2. Accordingly, activation of SMAD2 (which may be measured by upregulation of phospho-SMAD2 (pSMAD2)) will lead to a reduction of EGFR at the cell surface. Thus, SMAD2 may be used as a biomarker to determine response to treatment with a LOX inhibitor.

Suitably, levels of pSMAD2 may be determined using an anti-pSMAD2 antibody (such as those commercially available from Millipore).

HTRA1

HTRA1 is a secreted serine protease known to block TGF31 signalling by cleaving mature TGF31. A protein sequence for HTRA1 may be obtained from uniprot (Universal protein resource) reference Q92743 version 1.

Advantageously, the present invention has surprisingly shown that LOX depletion reduces the levels of extracellular homotrimeric HTRA1, the active form of this enzyme and HTRA1 suppresses SMAD2 activation and rescues MATN2 expression in LOX depleted cells. Without wishing to be bound by theory, it is believed that reducing HTRA1 will activate SMAD2 causing a reduction in the expression of MATN2 mRNA. As the present invention has shown MATN2 binding traps EGFR at the cell surface to present it to EGF for activation, it is believed that elevated protein stability of HTRA1 will indicate an increased likelihood of response to treatment with a LOX inhibitor. Hence, HTRA1 may be used as a biomarker.

Accordingly, the LOX inhibitors may have particular utility in the treatment of cancers having elevated levels of HTRA1 compared to a reference sample.

Suitably, levels of HTRA1 may be determined using immunofluorescence using a commercially available anti-human HTRA1 antibody (anti-human HTRA1 antibody, R&D). For example, the sample may be subjected to incubation with primary anti-HTRA1 antibodies followed by fluorescence secondary antibodies (such as those available from Life Technologies) and then the levels determined using confocal imaging. An identical procedure is carried out on a reference sample so that it can be determined if HTRA1 levels are increased.

In a further aspect, the present invention relates to a method of determining a treatment regimen for a subject with cancer, comprising:
a) determining the level of HTRA1 in a biological sample; and
b) administering a treatment regimen comprising a therapeutically effective amount of a lysyl oxidase inhibitor, when levels HTRA1 are elevated compared to a reference sample.

In Vitro Methods

The present invention also provides in vitro methods of internalising EGFR or reducing EGFR expression in a cell, said method comprising the step of contacting the cell with a LOX inhibitor of the invention.

In another aspect, the present invention further comprises an in vitro method of downregulating MATN2 expression in a cell, comprising the step of contacting the cell with a LOX inhibitor of the invention.

In a further aspect, the present invention also provides upregulating pSMAD2 in a cell comprising contacting a cell with a LOX inhibitor of the invention.

Suitably, in all aspects, the cell may be a cell-line, preferably a mammalian cell line.

Suitably, the cell may be a cancer cell, preferably a cancer cell associated with overexpression of EGFR.

Combination Therapies e.g. for the Treatment of Cancer

LOX inhibition can be a useful method for improving the efficacy of other drugs or addressing resistance to drug treatment through a number of mechanisms. Specific inhibition of LOX with siRNA can induce apoptosis of laryngeal cancer Hep-2 cells and enhance the sensitivity of Hep-2 cells to chemotherapeutic drugs such as cisplatin (Dong, Lu et al. 2014) and to radiation (Dong, Xin et al. 2014). LOX-expression and secretion is increased in response to ionizing radiation (IR) and hypoxia, suggesting that LOX may contribute towards an IR-induced migratory phenotype in sublethally-irradiated tumor cells and tumor progression; therefore LOX inhibitors can be used in combination with radiotherapy to reduce side effects in surrounding tissues receiving a reduced radiation dose (Shen, Sharma et al. 2014). LOX and LOXL2 inhibition can alter vascular permeability or normalise vasculature in a tumour environment, which can enhance the delivery or effectiveness of drugs (Ingber and Mammoto 2014) (Marshall, Spangler et al. 2012), for example improved efficacy of treatment in ovarian xenograft and lung allograft mice models with chemotherapeutic agents such as taxol (Zaffryar-Eilot, Marshall et al. 2013). Pharmacological inhibition of lysyl oxidases improved drug delivery and reversed the negative effect of VEGF ablation on drug delivery and therapeutic response in anti-VEGF-resistant tumors (Roehrig et al, 2017). The extracellular matrix has been proposed to have an important role in the resistance to chemotherapeutics. It has been shown that inhibition of LOX for cells grown in collagen (as a surrogate of ECM) reverses their collagen-dependent increased resistance to chemotherapeutics such as erlotinib, cisplatin or methotrexate (Smith and Holzer 2010). Drug diffusion and efficacy is reduced by the enzymatic action of LOX and LOXLs on the ECM in a 3D cell culture (not in 2D) and sensitivity to doxorubicin and paclitaxel can be restored by inhibition with BAPN (Schuetze, Roehrig et al. 2015). LOX inhibition synergized with gemcitabine to kill tumors and significantly prolonged tumor-free survival in a pancreatic mouse model. This was associated with stromal alterations and increased infiltration of macrophages and neutrophils into tumors. Therefore, targeting LOX could improve outcome in surgically resectable disease (Miller, Morton et al. 2015).

The compounds of the invention may be used alone to provide a therapeutic effect. The compounds of the invention may also be used in combination with one or more additional anti-tumour agent and/or radiotherapy.

Such chemotherapy may include one or more of the following categories of anti-cancer agents:
(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, leucovorin, cytosine arabinoside, floxuridine, cytarabine, 6-mercaptopurine, 6-thioguanine, fludarabine phosphate, pentostatine, and gemcitabine and hydroxyurea, and trifluridine with trifluracil); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors; eribulin); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™) nabpaclitaxel, docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939; and belinostat, panobinostat); trabectedin;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, cyclophosphamide, ifosamide, and droloxafine; and abiraterone, Enzalutamide; analogues of somatostatin such as lanreotide;

(iii) anti-invasion agents, for example dasatinib and bosutinib (SKI-606), and metalloproteinase inhibitors, inhibitors of urokinase plasminogen activator receptor function or antibodies to Heparanase:

(iv) inhibitors of growth factor function: for example such inhibitors include growth factor antibodies and growth factor receptor antibodies, for example the anti-erbB2 antibody trastuzumab [Herceptin™], the anti-HER2 antibody pertuzumab; the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of fibroblasts growth factor receptor family, such as ponatinib, nintedanib, lenvatinib, dovitinib, lucitanib, danusertinib, brivatinib, erdafitinib, PD173074, PD-166866, AZD4547, BGJ398, LY2874455, TAS-120, ARQ 087, BLU9931, DEBIO 1347, FGF401, BAY-1163877, FIIN-2, H3B-6527, PRN1371, BLU554, S49076, SU5416, SU6668, ENMD-2076, GP-369, IMCA1, PRO-001, R3mab; antibodies that block FGF ligand binding (ligand traps), such as FP-1039; antibodies that hinder FGFR dimerization such as MFGR1877S; antibody-drug conjugates targeting the FGFR family, such as BAY1187982; inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, sorafenib, tipifarnib and lonafarnib, vemurafenib, dabrafenib), inhibitors of cell signalling through MEK (such as trametinib, cobirnetinib) and/or AKT kinases, c-kit inhibitors, abl kinase inhibitors such as ponatinib, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors or CDK4/CDK6 inhibitors such as palbociclib; CCR2, CCR4 or CCR6 antagonists; mTOR kinase inhibitors such as Everolimus; Janus kinase family inhibitors such as ruxolitinib; Brunton's tyrosine kinase inhibitors such as Ibrutinib; anaplastic lymphoma kinase—ALK—such as ceritinib, crizotinib, aiectinib; c-Met kinase inhibitors such as cabozantinib; hedgehog signalling pathway inhibitors such as vismodegib, sonidegib; and RAF kinase inhibitors such as BAL3833 or other RAF inhibitors described in WO2006043090, WO2009077766, WO2011092469 or WO2015075483;

(v) antiangiogenic agents such as those which inhibit the effects of vascular endothelial growth factor, [for example the anti-vascular endothelial cell growth factor antibody bevacizumab (Avastin™) anti-VEGF2 antibody ramucirumab; recombinant fusion protein ziv-aflibercept]; thalidomide; pomalidomide; lenalidomide; and for example, a VEGF receptor tyrosine kinase inhibitor such as regorafenib, vandetanib, vatalanib, sunitinib, axitinib and pazopanib and lenvatinib;

(vi) gene therapy approaches, including for example approaches to replace aberrant genes such as aberrant p53 or aberrant BRCA1 or BRCA2; oncolytic viruses such as talimogene laherparepvec;

(vii) immunotherapy approaches, including for example antibody therapy such as denosumab, obinutuzumab, blinatomumab, dinutuximab idarucizumab, daratumumab, necitumumab, elotuzumab, olaratumab, alemtuzumab, rituximab, ibritumomab tiuxetan (Zevalin®) and ofatumumab; interferons such as interferon α, peginterferon alpha-2b; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab, pembrolizumab, atezolizumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab); antibody-drug conjugates such as Brentuximab vedotin, trastuzumao emtansine.

(viii) cytotoxic agents for example fludaribine (fludara), cladribine, pentostatin (Nipent™);

(ix) targeted therapies, for example PI3K inhibitors, for example idelalisib and perifosine; SMAC (second mitochondriaderived activator of caspases) mimetics, also known as Inhibitor of Apoptosis Proteins (IAP) antagonists (IAP antagonists). These agents act to supress IAPs, for example XIAP, cIAP1 and cIAP2, and thereby re-establish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Burnham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, ixazomib, carfilzomib, marizomib (NPI-0052), and MLN9708; and DNA repair inhibitors such as Olaparib, rucaparib; antiapoptotic BCL proteins family inhibitors such as venetoclax.

(xii) chimeric antigen receptors, anticancer vaccines and arginase inhibitors.

The additional anti-tumour agent may be a single agent or one or more of the additional agents listed herein.

Particular anti-cancer agents which may be used together with a compound of the invention include for example:

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the compound of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention there is provided a compound of the invention as defined hereinbefore and an additional anti-cancer agent as defined hereinbefore, for use in the conjoint treatment of cancer.

According to a further aspect of the invention there is provided a pharmaceutical product comprising a compound of the invention as defined hereinbefore and an additional anti-cancer agent as defined hereinbefore for the conjoint treatment of cancer.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with an additional anti-cancer agent as defined hereinbefore.

According to a further aspect of the invention there is provided a compound of the invention, or a pharmaceutically acceptable salt thereof for use simultaneously, sequentially or separately with an additional anti-cancer agent as defined hereinbefore, in the treatment of a cancer.

The compound of the invention may also be used be used in combination with radiotherapy. Suitable radiotherapy treatments include, for example X-ray therapy, proton beam therapy or electron beam therapies. Radiotherapy may also encompass the use of radionuclide agents, for example $^{131}$I, $^{32}$P, $^{90}$Y, $^{89}$Sr, $^{153}$Sm or $^{223}$Ra. Such radionuclide therapies are well known and commercially available.

According to a further aspect of the invention there is provided a compound of the invention, or a pharmaceutically acceptable salt thereof as defined hereinbefore for use in the treatment of cancer conjointly with radiotherapy.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with radiotherapy.

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl or trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

I. General Method for the Preparation of Bridged Piperidin-4-Ones Derivatives

Method A

A solution of the aniline (1 to 1.2 eq.), 2-cyclohexen-1-one (1.6 to 2.5 eq.), L- or D-proline (0.3 eq.) and 37% aqueous formaldehyde (1 eq.) in dimethylsulfoxide (1 to 2.5 M) was stirred at rt or 50° C. for up to 24 hours. After cooling to room temperature, the mixture was diluted with ethyl acetate then washed with water and brine. The organic phase was dried over anhydrous magnesium sulfate, filtered and evaporated under reduced pressure. The resulting residue was purified by silica gel chromatography using a gradient of ethyl acetate in cyclohexane or in some cases by recrystallisation from cyclohexane. The product was obtained pure or in some cases contaminated with 2-cyclohexen-1-one. In the latter case, it was used in the next step without further purification.

Intermediate:

(1R,4S)-7,7-dimethyl-2-(4-morpholinophenyl)-2-azabicyclo[2.2.2]octan-5-one (A-1)

Using the general method A, a solution of 4-morpholinoaniline (1 g, 5.6 mmol), 4,4-dimethyl-2-cylohexen-1-one (982 μL, 7.47 mmol), L-proline (161 mg, 1.4 mmol) and 37% aqueous formaldehyde (349 μL, 4.67 mmol) in dimethylsulfoxide (10 mL) was stirred at 50° C. for 24 h. After work-up and silica gel column chromatography (1R,4S)-7,7-dimethyl-2-(4-morpholinophenyl)-2-azabicyclo[2.2.2]octan-5-one (889 mg, 50%) was obtained. $^1$H NMR (500 MHz, MeOD-d$_4$) δ 6.97-6.92 (m, 2H), 6.73-6.68 (m, 2H), 3.92 (t, 1H, J=2.9 Hz), 3.85-3.81 (m, 4H), 3.53-3.42 (m, 2H), 3.03-2.96 (m, 4H), 2.71 (dd, 1H, J=19.0, 3.3 Hz), 2.53 (p, 1H, J=2.8 Hz), 2.42 (dd, 1H, J=19.0, 3.3 Hz), 1.82 (dd, 1H, J=13.8, 3.2 Hz), 1.74 (d, 1H, J=13.8 Hz), 1.10 (s, 3H), 1.07 (s, 3H). HRMS calculated for $C_{19}H_{27}N_2O_2$ [M+H]+ 315.2028; found 315.2118.

The following intermediate compounds were prepared by the aforementioned methodology, using the appropriately substituted reagent. The requisite starting materials were commercially available, described in the literature or readily synthesized by one skilled in the art of organic synthesis without undue experimentation.

| Cpd | Structure | Name | Analytical Data |
| --- | --- | --- | --- |
| A-2 | 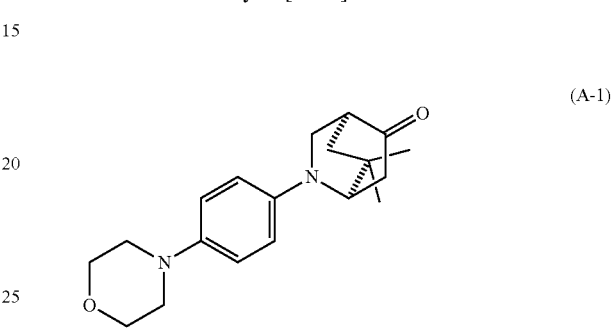 | (1R,4S)-2-(4-(4,4-difluoropiperidin-1-yl)phenyl)-7,7-dimethyl-2-azabicyclo[2.2.2]octan-5-one | HRMS calculated for C20H27N2OF2 [M + H]+ 349.2047; found 349.2114 |

| Cpd | Name | Analytical Data |
|---|---|---|
| A-3 | (1R,4S)-2-(4-(1,1-dioxidothiomorpholino)phenyl)-7,7-dimethyl-2-azabicyclo[2.2.2]octan-5-one | 1H NMR (500 MHz, CDCl3) δ 6.93 (d, 2H, J = 8.7 Hz), 6.63 (d, 2H, J = 8.7 Hz), 3.79 (t, 1H, J = 2.8 Hz), 3.62 (t, 4H, J = 5.2 Hz), 3.53-3.44 (m, 2H), 3.15 (t, 4H, J = 5.3 Hz), 2.75-2.62 (m, 2H), 2.49-2.43 (m, 1H), 1.78 (d, 2H, J = 3.0 Hz, 2H), 1.10 (s, 3H), 1.09 (s, 3H). HRMS calculated for C19H27N2O3S [M + H]+ 363.1698; found 363.1803. |
| A-4 | (1S,4R)-2-(4-(1,1-dioxidothiomorpholino)phenyl)-7,7-dimethyl-2-azabicyclo[2.2.2]octan-5-one | 1H NMR (500 MHz, DMSO-d6) δ 6.92 (d, 2H, J = 8.4 Hz), 6.65 (d, 2H, J = 8.6 Hz), 3.91 (s, 1H), 3.55-3.45 (m, 4H), 3.40-3.33 (m, 2H), 3.17-3.11 (m, 4H), 2.63 (d, 1H, J = 18.8 Hz), 2.51 (pseudo s, 1H), 2.36-2.28 (m, 1H), 1.70 (dd, 1H, J = 13.7 and 3.2 Hz), 1.63 (dd, 1H, J = 13.8 and 2.5 Hz), 1.03 (s, 3H), 0.97 (s, 3H). HRMS calculated for C19H27N2O3S [M + H]+ 363.1664; found 363.1731. |
| A-5 | (1R,4S)-2-(4-methoxyphenyl)-7,7-dimethyl-2-azabicyclo[2.2.2]octan-5-one | 1H NMR (500 MHz, CDCl3) δ 6.91-6.83 (m, 2H), 6.65-6.58 (m, 2H), 3.79-3.75 (m, 1H), 3.77 (s, 3H), 3.49 (d, J = 1.6 Hz, 2H), 2.73-2.66 (m, 1H), 2.63 (p, J = 2.8 Hz, 1H), 2.48 (dd, J = 18.8, 3.3 Hz, 1H), 1.77 (t, J = 8.1 Hz, 2H), 1.11 (s, 3H), 1.09 (s, 3H). |
| A-6 | (1R,4S)-2-(4-ethoxyphenyl)-7,7-dimethyl-2-azabicyclo[2.2.2]octan-5-one | 1H NMR (500 MHz, CDCl3) δ 6.90-6.76 (m, 2H), 6.69-6.50 (m, 2H), 3.97 (q, J = 7.0 Hz, 2H), 3.75 (t, J = 2.7 Hz, 1H), 3.53-3.40 (m, 2H), 2.68 (dd, J = 18.9, 2.1 Hz, 1H), 2.62 (p, J = 2.8 Hz, 1H), 2.47 (dd, J = 18.9, 3.2 Hz, 1H), 1.77 (d, J = 3.0 Hz, 2H), 1.38 (t, J = 7.0 Hz, 3H), 1.09 (s, 3H), 1.08 (s, 3H). |
| A-7 | (1S,4R)-2-(4-ethoxyphenyl)-7,7-dimethyl-2-azabicyclo[2.2.2]octan-5-one | 1H NMR data as for A-6 |
| A-8 | (1R,4S)-2-(4-ethoxyphenyl)-2-azaspiro[bicyclo[2.2.2]octane-7,1'-cyclohexan]-5-one | Used without purification |

-continued

| Cpd | Structure | Name | Analytical Data |
| --- | --- | --- | --- |
| A-9 | 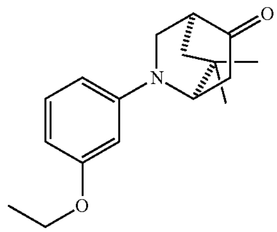 [SMILES: CCOc1cccc(N2C[C@@H]3CC(C)(C)[C@H]2CC3=O)c1] | (1R,4S)-2-(3-ethoxyphenyl)-7,7-dimethyl-2-azabicyclo[2.2.2]octan-5-one | Used without purification |
| A-10 | 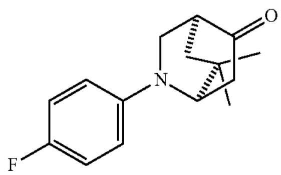 [SMILES: CC1(C)C[C@H]2CN(c3ccc(F)cc3)[C@@H]1CC2=O] | (1R,4S)-2-(4-fluorophenyl)-7,7-dimethyl-2-azabicyclo[2.2.2]octan-5-one | 1H NMR (500 MHz, CDCl3) δ 6.99-6.85 (m, 2H), 6.62-6.52 (m, 2H), 3.77 (t, J = 2.8 Hz, 1H), 3.55-3.38 (m, 2H), 2.70 (dd, J = 18.9, 2.1 Hz, 1H), 2.64 (p, J = 2.8 Hz, 1H), 2.47 (dd, J = 15.4, 3.5 Hz, 1H), 1.77 (d, J = 3.0 Hz, 2H), 1.09 (s, 3H), 1.08 (s, 3H). |
| A-11 | 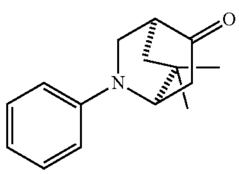 [SMILES: CC1(C)C[C@H]2CN(c3ccccc3)[C@@H]1CC2=O] | (1R,4S)-7,7-dimethyl-2-phenyl-2-azabicyclo[2.2.2]octan-5-one | 1H NMR (500 MHz, CDCl3) δ 7.34-7.27 (m, 2H), 6.78-6.70 (m, 3H), 3.93 (t, J = 2.8 Hz, 1H), 3.62-3.51 (m, 2H), 2.80-2.69 (m, 2H), 2.57-2.48 (m, 1H), 1.83 (d, J = 2.5 Hz, 2H), 1.15 (s, 3H), 1.14 (s, 3H). LRMS (ESI) m/z 230 (M + H)+. |
| A-12 | 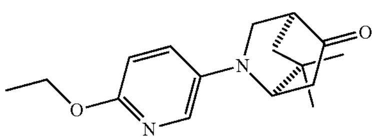 [SMILES: CCOc1ccc(N2C[C@@H]3CC(C)(C)[C@H]2CC3=O)cn1] | (1R,4S)-2-(6-ethoxypyridin-3-yl)-7,7-dimethyl-2-azabicyclo[2.2.2]octan-5-one | 1H NMR (500 MHz, Chloroform-d) δ 7.58 (d, J = 3.2 Hz, 1H), 7.05 (dd, J = 9.0, 3.2 Hz, 1H), 6.67 (d, J = 8.9 Hz, 1H), 4.28 (q, J = 7.1 Hz, 2H), 3.71 (t, J = 2.9 Hz, 1H), 3.56-3.42 (m, 2H), 2.76-2.62 (m, 2H), 2.49 (dd, J = 18.9, 3.3 Hz, 1H), 1.79 (app. d, J = 3.1 Hz, 2H), 1.38 (t, J = 7.0 Hz, 3H), 1.10 (s, 3H), 1.09 (s, 3H). MS (ES+) m/z = 275 [M + H]+. |

II. General Methods for the Preparation of Bridged Homopiperazinone Derivatives.

Method B (Schmidt Reaction)

To a stirred solution of the bridged piperidin-4-one (1 eq.) in concentrated sulfuric acid (0.4 to 1 M) at 0° C. sodium azide (1.5 to 2.5 eq.) was added carefully. The reaction mixture was stirred at 0° C. or allowed to warm to room temperature after 30 mins and stirred for 30 mins to 2 hrs at room temperature. The mixture was then cooled to 0° C., diluted with ice, made basic by the cautious addition of sodium hydroxide pellets (or a 3M aqueous solution of sodium hydroxide) and extracted with dichloromethane (or ethyl acetate). The combined organic layers were dried over anhydrous magnesium sulfate, filtered and evaporated under reduced pressure. The resulting residue was purified by silica gel column chromatography using a gradient of methanol in ethyl acetate (or a gradient of ethyl acetate in cyclohexane or a gradient of ethyl acetate in dichloromethane) to give the two separate regioisomers. In some cases, the regioisomers could not be separated and were used in the next step as a mixture.

Intermediate:

(1S,5S)-9,9-dimethyl-6-(4-morpholinophenyl)-3,6-diazabicyclo[3.2.2]nonan-2-one; and (1S,5R)-9,9-dimethyl-6-(4-morpholinophenyl)-2,6-diazabicyclo[3.2.2]nonan-3-one

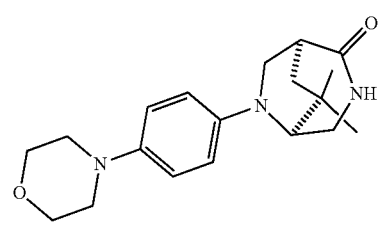

(B1a)

-continued

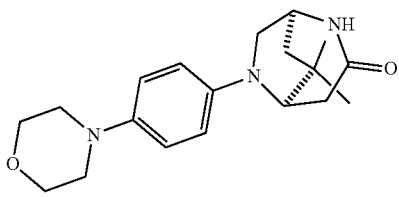
(B1b)

Using method B, a solution of (1R,4S)-7,7-dimethyl-2-(4-morpholinophenyl)-2-azabicyclo[2.2.2]octan-5-one (885 mg, 2.89 mmol) in concentrated sulfuric acid (17 mL) was reacted with sodium azide (365 mg, 5.62 mmol). After work-up and silica gel column chromatography, 260.6 mg of (1S,5S)-9,9-dimethyl-6-(4-morpholinophenyl)-3,6-diazabicyclo[3.2.2]nonan-2-one (27%) and 145.6 mg of (1S,5R)-9,9-dimethyl-6-(4-morpholinophenyl)-2,6-diazabicyclo[3.2.2]nonan-3-one (17%) were obtained.

(1S,5S)-9,9-dimethyl-6-(4-morpholinophenyl)-3,6-diazabicyclo[3.2.2]nonan-2-one (B1a) $^1$H NMR (500 MHz, MeOD-d$_4$) δ 7.01-6.96 (m, 2H), 6.79-6.74 (m, 2H), 3.88-3.81 (m, 5H), 3.55 (dd, 1H, J=13.5, 3.1 Hz), 3.51-3.42 (m, 2H), 3.39-3.34 (m, 1H), 3.05-2.99 (m, 4H), 2.85-2.80 (m, 1H), 1.92-1.88 (m, 1H), 1.71 (dd, 1H, J=14.3, 5.8 Hz), 1.21 (s, 3H), 1.09 (s, 3H). HRMS calculated for C$_{19}$H$_{28}$N$_3$O$_2$ [M+H]$^+$ 330.2137; found 330.2187.

(1S,5R)-9,9-dimethyl-6-(4-morpholinophenyl)-2,6-diazabicyclo[3.2.2]nonan-3-one (B1b) $^1$H NMR (500 MHz, MeOD-d$_4$) δ 6.99-6.94 (m, 2H), 6.76-6.71 (m, 2H), 3.86-3.81 (m, 4H), 3.68-3.62 (m, 2H), 3.54 (dd, 1H, J=11.0, 4.1 Hz), 3.45-3.41 (m, 1H), 3.03-2.99 (m, 4H), 2.83 (dd, 1H, J=18.7, 3.2 Hz), 2.74-2.67 (m, 1H), 1.92-1.88 (m, 1H), 1.76 (dd, 1H, J=14.4, 5.0 Hz), 1.17 (s, 3H), 1.06 (s, 3H). HRMS calculated for C$_{19}$H$_{28}$N$_3$O$_2$ [M+H]$^+$ 330.2137; found 330.2176.

The following intermediate compounds were prepared by the aforementioned methodology, using the appropriately substituted reagent.

| Cpd | Structure | Name | Analytical Data |
|---|---|---|---|
| B2a | 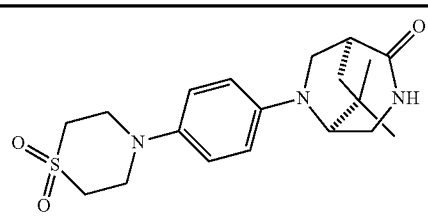 | (1S,5S)-6-(4-(1,1-dioxidothiomorpholino)phenyl)-9,9-dimethyl-3,6-diazabicyclo [3.2.2]nonan-2-one | $^1$H NMR (500 MHz, DMSO-d$_6$) δ 7.14 (br s, 1H), 6.96-6.90 (m, 2H), 6.72-6.66 (m, 2H), 3.81-3.77 (m, 1H), 3.55-3.49 (m, 4H), 3.37-3.25 (m, 3H), 3.17-3.10 (m, 5H), 2.67-2.63 (m, 1H), 1.73 (d, 1H, J = 14.1 Hz), 1.54 (dd, 1H, J = 14.2 and 5.9 Hz), 1.11 (s, 3H), 0.98 (s, 3H). HRMS calculated for C$_{19}$H$_{28}$N$_3$O$_3$S [M + H]$^+$ 378.1807; found 378.1868. |
| B2b | 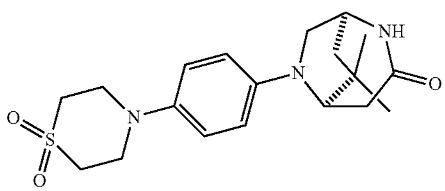 [SMILES: CC1(C)C[C@H]2CN(c3ccc(N4CCS(=O)(=O)CC4)cc3)[C@@H]1CC(=O)N2] | (1S,5R)-6-(4-(1,1-dioxidothiomorpholino)phenyl)-9,9-dimethyl-2,6-diazabicyclo[3.2.2]nonan-3-one | $^1$H NMR (500 MHz, CDCl$_3$) δ 6.93 (d, 2H, J = 8.5 Hz), 6.64 (d, 2H, J = 8.5 Hz), 3.72-3.58 (m, 5H), 3.52 (t, 1H, J = 3.6 Hz), 3.51-3.46 (m, 2H), 3.15 (t, 4H, J = 5.3 Hz), 2.82 (2× dd, 2H, J = 18.5 and 3.7 Hz), 1.95 (d, 1H, J = 14.4 Hz), 1.72 (dd, 1H, J = 14.3 and 5.1 Hz), 1.18 (s, 3H), 1.06 (s, 3H). HRMS calculated for C$_{19}$H$_{28}$N$_3$O$_3$S [M + H]$^+$, 378.1807; found 378.1867. |
| B3a | 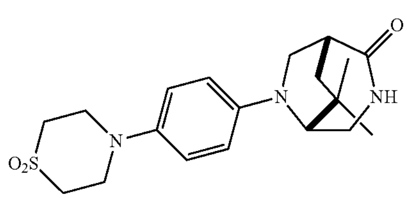 [SMILES: CC1(C)C[C@@H]2CN(c3ccc(N4CCS(=O)(=O)CC4)cc3)[C@H]1CNC2=O] | (1R,5R)-6-(4-(1,1-dioxidothiomorpholino)phenyl)-9,9-dimethyl-3,6-diazabicyclo [3.2.2]nonan-2-one | $^1$H NMR (500 MHz, DMSO-d$_6$) δ 7.14 (br s, 1H), 6.95-6.91 (m, 2H), 6.71-6.66 (m, 2H), 3.79 (t, 1H, J = 3 Hz), 3.55-3.50 (m, 4H), 3.36-3.26 (m, 3H), 3.17-3.09 (m, 5H), 2.67-2.63 (m, 1H), 1.75-1.70 (m, 1H), 1.54 (dd, 1H, J = 14.1 and 6.0 Hz), 1.11 (s, 3H), 0.98 (s, 3H). HRMS calculated for C$_{19}$H$_{28}$N$_3$O$_3$S [M + H]$^+$ 378.1848; found 378.1851. |
| B3b | 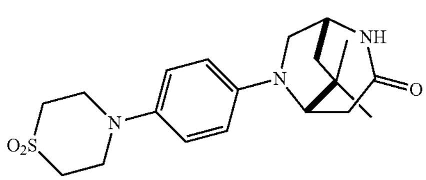 [SMILES: CC1(C)C[C@@H]2CN(c3ccc(N4CCS(=O)(=O)CC4)cc3)[C@H]1CC(=O)N2] | (1R,5S)-6-(4-(1,1-dioxidothiomorpholino)phenyl)-9,9-dimethyl-2,6-diazabicyclo[3.2.2]nonan-3-one | $^1$H NMR (500 MHz, DMSO-d$_6$) δ 8.00 (d, 1H, J = 7.3 Hz), 6.95-6.91 (m, 2H), 6.67-6.62 (m, 2H), 3.56-3.45 (m, 6H), 3.41 (dd, 1H, J = 11 and 3.9 Hz), 3.25-3.20 (m, 1H), 3.17-3.12 (m, 4H), 2.64 (dd, 1H, J = 18.4 and 3.1 Hz), 2.46 (dd, 1H, J = 18.4 and 4.3 Hz), 1.75-1.69 (m, 1H), 1.64 (dd, 1H, J = 14.2 and 5.1 Hz), 1.08 (s, 3H), 0.95 (s, 3H). HRMS calculated for C$_{19}$H$_{28}$N$_3$O$_3$S [M + H]$^+$ 378.1845; found 378.1851. |
| B4a | 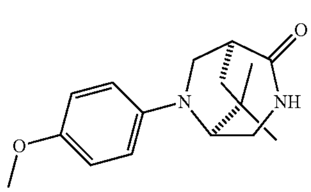 [SMILES: COc1ccc(N2C[C@@H]3CC(C)(C)[C@H]2CNC3=O)cc1] | (1S,5S)-6-(4-methoxyphenyl)-9,9-dimethyl-3,6-diazabicyclo[3.2.2]nonan-2-one | $^1$H NMR (500 MHz, CDCl$_3$) δ 6.93-6.76 (m, 2H), 6.71-6.56 (m, 2H), 5.98 (s, 1H), 3.75 (s, 3H), 3.72-3.61 (m, 1H), 3.55 (dt, J = 9.3 and 1.5 Hz, 1H), 3.49 (dt, J = 12.7 and 2.8 Hz, 1H), 3.43 (ddd, J = 12.7, 3.0 and 1.8 Hz, 1H), 3.37 (dd, J = 10.8 and 4.9 Hz, 1H), 2.96-2.82 (m, 1H), 1.94 (dt, J = 14.3 and 1.8 Hz, 1H), 1.65 (dd, J = 14.3 and 5.9 Hz, 1H), 1.19 (s, 3H), 1.10 (s, 3H). HRMS |

-continued

| Cpd | Structure | Name | Analytical Data |
|---|---|---|---|
| | | | calculated for $C_{16}H_{22}N_2NaO_2$ [M + Na]$^+$ 297.1573; found 297.1563 |
| B4b | 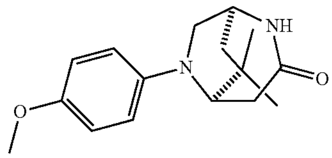 [SMILES: COc1ccc(N2C[C@@H]3CC(C)(C)[C@H]2CC(=O)N3)cc1] | (1S,5R)-6-(4-methoxyphenyl)-9,9-dimethyl-2,6-diazabicyclo[3.2.2]nonan-3-one | $^1$H NMR (500 MHz, CDCl$_3$) δ 7.16 (d, J = 7.1 Hz, 1H), 6.93-6.81 (m, 2H), 6.70-6.57 (m, 2H), 3.76 (s, 3H), 3.62-3.55 (m, 1H), 3.54-3.41 (m, 3H), 2.90-2.69 (m, 2H), 1.97-1.85 (m, 1H), 1.70 (dd, J = 14.3 and 4.9 Hz, 1H), 1.16 (s, 3H), 1.07 (s, 3H). HRMS calculated for $C_{16}H_{22}N_2NaO_2$ [M + Na]$^+$ 297.1573; found 297.1562 |
| B5a | 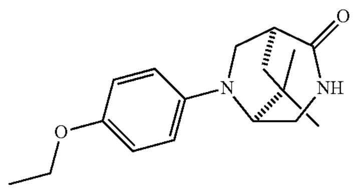 [SMILES: CCOc1ccc(N2C[C@@H]3CC(C)(C)[C@H]2CNC3=O)cc1] | (1S,5S)-6-(4-ethoxyphenyl)-9,9-dimethyl-3,6-diazabicyclo[3.2.2]nonan-2-one | $^1$H NMR (500 MHz, CDCl$_3$) δ 6.88-6.82 (m, 2H), 6.68-6.61 (m, 2H), 5.48 (s, 1H), 3.97 (q, J = 7.0 Hz, 2H), 3.67 (s, 1H), 3.55 (dt, J = 10.8 and 1.7 Hz, 1H), 3.49 (dt, J = 12.6 and 2.8 Hz, 1H), 3.44 (ddd, J = 12.6, 3.1 and 1.8 Hz, 1H), 3.38 (dd, J = 10.8 and 4.9 Hz, 1H), 2.93-2.87 (m, 1H), 1.95 (dt, J = 14.3 and 1.8 Hz, 1H), 1.65 (dd, J = 14.3 and 5.9 Hz, 1H), 1.38 (t, J = 7.0 Hz, 3H), 1.19 (s, 3H), 1.10 (s, 3H). HRMS calculated for $C_{17}H_{25}N_2O_2$ [M + H]$^+$ 289.1911; found 289.1911. |
| B5b | 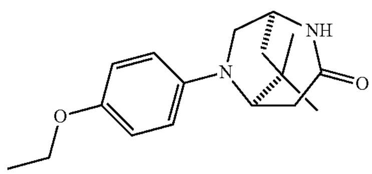 [SMILES: CCOc1ccc(N2C[C@@H]3CC(C)(C)[C@H]2CC(=O)N3)cc1] | (1S,5R)-6-(4-ethoxyphenyl)-9,9-dimethyl-2,6-diazabicyclo[3.2.2]nonan-3-one | $^1$H NMR (500 MHz, CDCl$_3$) δ 7.19 (t, J = 9.6 Hz, 1H), 6.91-6.82 (m, 2H), 6.68-6.51 (m, 2H), 3.97 (q, J = 7.0 Hz, 2H), 3.65-3.54 (m, 1H), 3.53-3.43 (m, 3H), 2.90-2.72 (m, 2H), 1.92 (d, J = 14.2 Hz, 1H), 1.69 (dd, J = 14.3 and 4.9 Hz, 1H), 1.37 (t, J = 7.0 Hz, 3H), 1.16 (s, 3H), 1.06 (s, 3H). HRMS calculated for $C_{17}H_{24}N_2NaO_2$ [M + Na]$^+$ 311.7300; found 311.1721 |
| B6a | 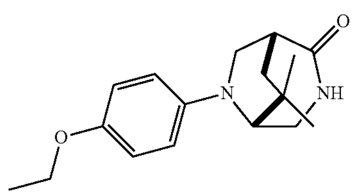 [SMILES: CCOc1ccc(N2C[C@H]3CC(C)(C)[C@@H]2CNC3=O)cc1] | (1R,5R)-6-(4-ethoxyphenyl)-9,9-dimethyl-3,6-diazabicyclo[3.2.2]nonan-2-one | As B5a |
| B6b | 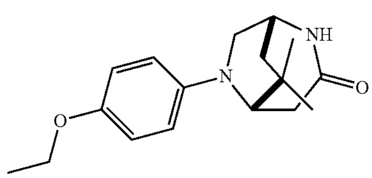 [SMILES: CCOc1ccc(N2C[C@H]3CC(C)(C)[C@@H]2CC(=O)N3)cc1] | (1R,5S)-6-(4-ethoxyphenyl)-9,9-dimethyl-2,6-diazabicyclo[3.2.2]nonan-3-one | As B5b |
| B7 | 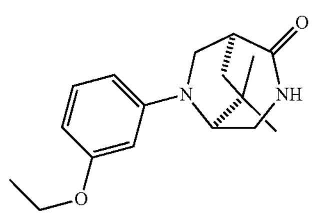 [SMILES: CCOc1cccc(N2C[C@@H]3CC(C)(C)[C@H]2CNC3=O)c1] | (1S,5S)-6-(3-ethoxyphenyl)-9,9-dimethyl-3,6-diazabicyclo[3.2.2]nonan-2-one | 1H NMR (500 MHz, CDCl3) δ 7.17 (t, J = 8.2 Hz, 1H), 6.32 (td, J = 8.0 and 2.2 Hz, 2H), 6.25 (t, J = 2.3 Hz, 1H), 5.39 (br s, 1H), 4.04 (q, J = 7.0 Hz, 2H), 3.76 (m, 1H), 3.60 (m, 1H), 3.53 (dt, J = 12.6 and 2.6 Hz, 1H), 3.46 (ddd, J = 12.6, 3.2 and 1.9 Hz, 1H), 3.41 (dd, J = 11.0 and 4.6 Hz, 1H), 2.93 (m, 1H), 1.97 (m, 1H), 1.67 (dd, J = 14.4 and 6.1 Hz, 1H), 1.42 (t, J = 7.0 Hz, 3H), 1.20 (s, 3H), 1.09 (s, 3H). HRMS calculated for C17H25N2O2 [M + H]+ 289.1911; found 289.1900. |
| B8a | 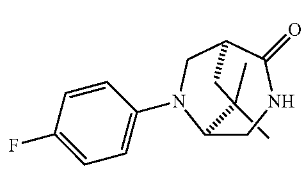 [SMILES: CC1(C)C[C@H]2CN(c3ccc(F)cc3)[C@@H]1CNC2=O] | (1S,5S)-6-(4-fluorophenyl)-9,9-dimethyl-3,6-diazabicyclo[3.2.2]nonan-2-one | 1H NMR (500 MHz, CDCl3) δ 7.01-6.85 (m, 2H), 6.69-6.48 (m, 2H), 5.75 (s, 1H), 3.68 (s, 1H), 3.57-3.50 (m, 2H), 3.43 (ddd, J = 12.7, 3.2 and 1.8 Hz, 1H), 3.38 (dd, J = 10.8 and 4.8 Hz, 1H), 2.98-2.81 (m, 1H), 1.96 (dt, J = 14.4 and 1.8 Hz, 1H), 1.66 (dd, J = 14.4 and |

| Cpd | Structure | Name | Analytical Data |
|---|---|---|---|
| | | | 6.0 Hz, 1H), 1.20 (s, 3H), 1.09 (s, 3H). HRMS calculated for C15H20FN2O [M + H]+ 263.1554; found 263.1557. |
| B8b | 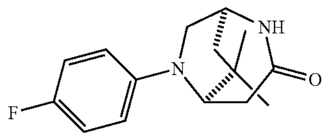 [SMILES: CC1(C)C[C@H]2CN(c3ccc(F)cc3)[C@@H]1CC(=O)N2] | (1S,5R)-6-(4-fluorophenyl)-9,9-dimethyl-2,6-diazabicyclo[3.2.2]nonan-3-one | 1H NMR (500 MHz, CDCl3) δ 7.34 (d, J = 7.1 Hz, 1H), 7.02-6.90 (m, 2H), 6.65-6.49 (m, 2H), 3.65-3.56 (m, 1H), 3.50 (t, J = 3.7 Hz, 1H), 3.47-3.41 (m, 2H), 2.82 (qd, J = 18.6 and 3.7 Hz, 2H), 1.94 (d, J = 14.4 Hz, 1H), 1.71 (dd, J = 14.4 and 5.1 Hz, 1H), 1.17 (s, 3H), 1.05 (s, 3H). HRMS calculated for C15H20FN2O [M + H]+ 263.1554; found 263.1557. |
| B9a | 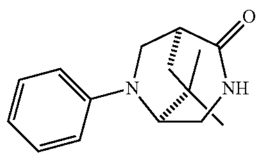 [SMILES: CC1(C)C[C@H]2CN(c3ccccc3)[C@@H]1CNC2=O] | (1S,5S)-9,9-dimethyl-6-phenyl-3,6-diazabicyclo[3.2.2]nonan-2-one | 1H NMR (500 MHz, CDCl3) δ 7.33-7.25 (m, 2H), 6.77-6.69 (m, 3H), 5.50 (s, 1H), 3.80 (m, 1H), 3.61 (dt, J = 11.0 and 2.0 Hz, 1H), 3.55 (dt, J = 12.6 and 2.7 Hz, 1H), 3.47 (ddd, J = 12.6, 3.4 and 1.9 Hz, 1H), 3.43 (dd, J = 11.0 and 4.7 Hz, 1H), 2.94 (m, 1H), 1.98 (dt, J = 14.3 and 1.9 Hz, 1H), 1.68 (dd, J = 14.4 and 6.1 Hz, 1H), 1.22 (s, 3H), 1.10 (s, 3H). LRMS (ESI) m/z 245 (M + H)+. |
| B9b | 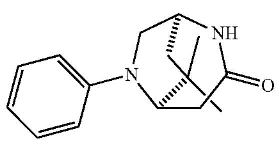 [SMILES: CC1(C)C[C@H]2CN(c3ccccc3)[C@@H]1CC(=O)N2] | (1S,5R)-9,9-dimethyl-6-phenyl-2,6-diazabicyclo[3.2.2]nonan-3-one | 1H NMR (500 MHz, CDCl3) δ 7.52 (br, 1H), 7.30-7.22 (m, 2H), 6.75-6.66 (m, 3H), 3.64-3.57 (m, 2H), 3.55-3.45 (m, 2H), 2.87 (dd, J = 18.6 and 3.2 Hz, 1H), 2.81 (dd, J = 18.6 and 4.2 Hz, 1H), 1.95 (dt, J = 14.3 and 2.2 Hz, 1H), 1.72 (dd, J = 14.4 and 5.2 Hz, 1H), 1.18 (s, 3H), 1.05 (s, 3H). LRMS (ESI) m/z 245 (M + H)+. |

Intermediate:

(1S,5S)-6-(4-(4,4-difluoropiperidin-1-yl)phenyl)-9,9-dimethyl-3,6-diazabicyclo[3.2.2]nonan-2-one; and (1 S,5R)-6-(4-(4,4-difluoropiperidin-1-yl)phenyl)-9,9-dimethyl-2,6-diazabicyclo[3.2.2]nonan-3-one (B10a)

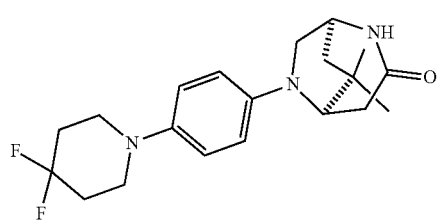

(B10b)

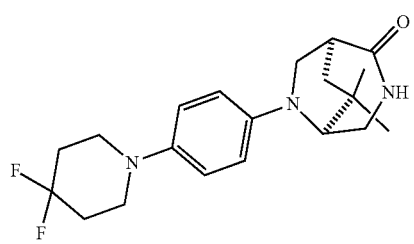

Using method B, a solution of (1R,4S)-2-(4-(4,4-difluoropiperidin-1-yl)phenyl)-7,7-dimethyl-2-azabicyclo[2.2.2]octan-5-one (329.6 mg, 0.946 mmol) in concentrated sulfuric acid (25 mL) was reacted with sodium azide (123 mg, 1.89 mmol). After work-up and silica gel column chromatography, 129 mg of a mixture of (1 S,5S)-6-(4-(4,4-difluoropiperidin-1-yl)phenyl)-9,9-dimethyl-3,6-diazabicyclo[3.2.2]nonan-2-one and (1S,5R)-6-(4-(4,4-difluoropiperidin-1-yl)phenyl)-9,9-dimethyl-2,6-diazabicyclo[3.2.2]nonan-3-one (38%) were obtained and used in the next step without further purification. HRMS calculated for $C_{20}H_{28}N_3OF_2$ $[M+H]^+$ 364.2156; found 364.2110.

Method C (Beckmann Reaction)

A mixture of the bridged piperidin-4-one (1 eq.), the hydrochloride acid salt of hydroxylamine (5 eq.), triethylamine (5 eq.), methanol (2 M) and dichloromethane (2 M) was stirred at 50° C. for 16 h. After cooling to room temperature, the reaction mixture was diluted with dichloromethane, washed with a 1:1 water/brine, dried over anhydrous magnesium sulfate, filtered and evaporated under reduced pressure. The intermediate oxime was dissolved in tetrahydrofuran (1 M) and cooled to 0° C. Thionyl chloride (1.2 eq.) was added and the reaction mixture was stirred at 0° C. for 1 h then quenched with a saturated aqueous solution of sodium bicarbonate and diluted with ethyl acetate. After separation of the two layers, the organic phase was washed two more times with a saturated aqueous solution of sodium bicarbonate, dried over anhydrous magnesium sulfate, filtered and evaporated under reduced pressure. The resulting residue was purified by silica gel column chromatography using a gradient of ethyl acetate in cyclohexane or a gradient of methanol in ethyl acetate.

Intermediate:

(1S,5S)-9-(4-ethoxyphenyl)-3,9-diazaspiro[bicyclo[3.2.2]nonane-6,1'-cyclohexan]-2-one; and (1S,5R)-9-(4-ethoxyphenyl)-2,9-diazaspiro[bicyclo[3.2.2]nonane-6,1'-cyclohexan]-3-one (C1a)

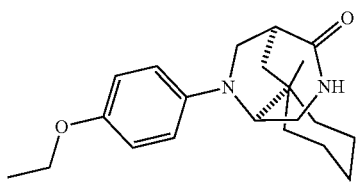

Using method C, a mixture (1R,4S)-2-(4-ethoxyphenyl)-2-azaspiro[bicyclo[2.2.2]octane-7,1'-cyclohexan]-5-one (3.23 g, 10.3 mmol), hydroxylamine hydrochloride (3.58 g, 51.5 mmol), triethylamine (7.19 mL, 51.5 mmol), methanol (70 mL) and dichloromethane (35 mL) was stirred at room temperature for 3 h. DCM (100 mL) was added. After work-up, the intermediate oxime dissolved in tetrahydrofuran (103 mL) was reacted at 0° C. with thionyl chloride (903 µL, 12.4 mmol) for 2 h. After work-up and silica gel column chromatography, 285 mg of (1 S,5S)-9-(4-ethoxyphenyl)-3,9-diazaspiro[bicyclo[3.2.2]nonane-6,1'-cyclohexan]-2-one (9%) and 457 mg of (1S,5R)-9-(4-ethoxyphenyl)-2,9-diazaspiro[bicyclo[3.2.2]nonane-6,1'-cyclohexan]-3-one (14%) were obtained.

(1S,5S)-9-(4-ethoxyphenyl)-3,9-diazaspiro[bicyclo[3.2.2]nonane-6,1'-cyclohexan]-2-one. H NMR (500 MHz, CDCl$_3$) δ 6.90-6.80 (m, 2H), 6.67-6.59 (m, 2H), 5.97 (br, 1H), 3.98 (q, J=7.0 Hz, 2H), 3.81 (br, 1H), 3.56 (m, 1H), 3.50 (dt, J=12.6, 2.7 Hz, 1H), 3.42 (ddd, J=12.7, 3.0, 1.7 Hz, 1H), 3.36 (dd, J=10.8, 4.8 Hz, 1H), 2.91 (m, 1H), 1.92 (m, 1H), 1.69-1.23 (m, 14H).

(1S,5R)-9-(4-ethoxyphenyl)-2,9-diazaspiro[bicyclo[3.2.2]nonane-6,1'-cyclohexan]-3-one. H N M R (500 MHz, CDCl$_3$) δ 6.99 (d, J=7.3 Hz, 1H), 6.89-6.83 (m, 2H), 6.65-6.59 (m, 2H), 3.98 (q, J=7.0 Hz, 2H), 3.69-3.60 (m, 2H), 3.53-3.43 (m, 2H), 2.83 (dd, J=18.6, 3.4 Hz, 1H), 2.78 (dd, J=18.6, 4.0 Hz, 1H), 1.91 (d, J=14.4 Hz, 1H), 1.70 (dd, J=14.4, 5.0 Hz, 1H), 1.64-1.17 (m, 13H).

The following intermediate compounds were prepared by the aforementioned methodology, using the appropriately substituted reagent.

| Cpd | Structure | Name | Analytical Data |
|---|---|---|---|
| C-2 | 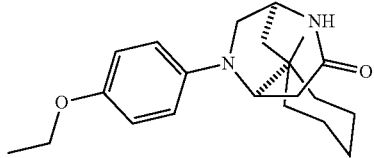 | (1S,5R)-6-(6-ethoxypyridin-3-yl)-9,9-dimethyl-2,6-diazabicyclo[3.2.2]nonan-3-one | $^1$H NMR (500 MHz, Chloroform-d) δ 7.59 (d, J = 3.2 Hz, 1H), 7.50 (br, 1H), 7.04 (dd, J = 9.0, 3.2 Hz, 1H), 6.67 (d, J = 9.0 Hz, 1H), 4.27 (q, J = 7.1 Hz, 2H), 3.62 (m, 1H), 3.50-3.37 (m, 3H), 2.84 (dd, J = 18.6, 3.3 Hz, 1H), 2.76 (dd, J = 18.6, 4.1 Hz, 1H), 1.94 (d, J = 14.3 Hz, 1H), 1.71 (dd, J = 14.3, 4.9 Hz, 1H), 1.37 (t, J = 7.1 Hz, 3H), 1.17 (s, 3H), 1.07 (s, 3H). MS (ES$^+$) m/z = 290 [M + H]$^+$. |

-continued (C1b)

Method D (Photochemical Rearrangement of Oxaziridines Using Continuous Flow Chemistry)

In a first step, to a mixture of ketone A1a (1 eq.) in anhydrous dichloromethane (or toluene) (0.05 to 0.5 M) and molecular sieves (3 to 4 Å, 0.5 to 15 g) was added benzylamine (1 to 1.1 eq.) followed by para-toluene sulfonic acid (hydrate form) or acetic acid (catalytic amount) or no acid catalyst. The reaction mixture was allowed to stand at room temperature for 4 to 48 h then filtered through glass wool to remove the molecular sieves. The solution containing the imine was cooled (−78° C. to 0° C.) and a solution of meta-chloroperbenzoic acid (1 to 1.7 eq.) in anhydrous dichloromethane (or toluene) (0.1 to 0.7 M) added dropwise. The reaction was stirred at this temperature until completion then quenched with an aqueous solution of sodium thiosulfate and an aqueous solution of metal carbonate or metal hydrogen carbonate (10% to saturated) and water. The phases were separated and the organic phase extracted with dichloromethane (or toluene). The combined organic phases were washed successively with 10% aqueous metal hydrogen carbonate solution, brine, dried over anhydrous magnesium sulphate, filtered and evaporated under reduced pressure. The resulting residue was purified by silica gel column chromatography using a gradient of ethyl acetate in cyclohexane affording the oxaziridine as a mixture of diastereoisomers (9:1 to 1:1). Alternatively the major oxaziridine diastereoisomer may be recrystallised from a suitable solvent system such as ether/hexane.

In a second step, photochemical rearrangement of the oxaziridine was achieved under continuous flow conditions. A solution of the oxaziridine in cyclohexane (or acetonitrile or ether) (0.5 to 6 g·L$^{−1}$) was thoroughly degassed with nitrogen (or argon) then pumped (flow rate: 0.2 mL/min to 10 mL/min) through UV-transparent tubing (Fluorinated Ethylene Propylene tubing is preferred) including a section irradiated with a broad-spectrum UV or UV-C light source, and then collected at the outlet. Continuous operation demonstrated mass flow rates of up to 8 g per day. The solvent was evaporated under vacuum and recycled affording a mixture of regioisomers of bridged homopiperazinones in ratios of 5.9:1 to 9:1. The resulting residue was purified by silica gel chromatography using a gradient of ethyl acetate in cyclohexane.

Intermediate:

(1S,5S)-3-benzyl-6-(4-ethoxyphenyl)-9,9-dimethyl-3,6-diazabicyclo[3.2.2]nonan-2-one; and (1S,5R)-2-benzyl-6-(4-ethoxyphenyl)-9,9-dimethyl-2,6-diazabicyclo[3.2.2]nonan-3-one

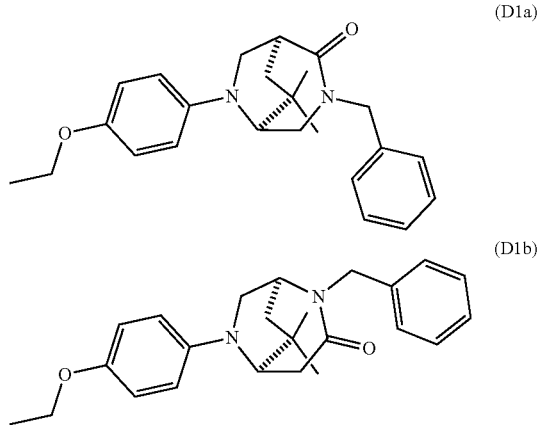

(D1a)

(D1b)

Using method D, in a first step, a mixture of (1R,4S)-2-(4-ethoxyphenyl)-7,7-dimethyl-2-azabicyclo[2.2.2]octan-5-one (3.00 g, 11.0 mmol) and 4 Å molecular sieves (7 g) in anhydrous dichloromethane (35 mL) was reacted at room temperature for 6 hours with benzylamine (1.20 mL, 11.0 mmol) and TsOH·H$_2$O (10 mg, catalytic amount). After filtration, the imine solution was cooled to −10° C. and reacted with a solution of mCPBA (4.18 g, 18.7 mmol) in dichloromethane (35 mL) at −10° C. for 45 min then allowed to warm to room temperature. After work-up and silica gel column chromatography, 2.87 g of (1 S,4R)-2'-benzyl-5-(4-ethoxyphenyl)-8,8-dimethyl-5-azaspiro[bicyclo[2.2.2]octane-2,3'-[1,2]oxaziridine] (69%) as a mixture of diastereoisomers.

(1S,2R,4R)-2'-Benzyl-5-(4-ethoxyphenyl)-8,8-dimethyl-5-azaspiro[bicyclo[2.2.2]octane-2,3'-[1,2]oxaziridine] (Major isomer). $^1$H NMR (500 MHz, CDCl$_3$) δ 7.43 (d, J=7.3 Hz, 2H), 7.37 (t, J=7.3 Hz, 2H), 7.31 (t, J=7.3 Hz, 1H), 6.85 (d, J=9.1 Hz, 2H), 6.60 (d, J=9.1 Hz, 2H), 3.98 (q, J=6.9 Hz, 2H), 3.90 (app q, J=15.1 Hz, 2H), 3.58 (t, J=2.5 Hz, 1H), 3.51 (dt, J=10.9, 2.5 Hz, 1H), 3.26 (dt, J=9.8, 2.2 Hz, 1H), 2.61 (dd, J=15.5, 2.2 Hz, 1H), 2.26 (dd, J=15.5, 3.5 Hz, 1H), 1.67 (t, J=2.5 Hz, 1H), 1.60-1.57 (m, 2H), 1.39 (t, J=6.9 Hz, 3H), 0.98 (s, 3H), 0.89 (s, 3H). HRMS calculated for C$_{24}$H$_{31}$N$_2$O$_2$ [M+H]$^+$ 379.2307; found 379.2302.

(1S,2S,4R)-2'-benzyl-5-(4-ethoxyphenyl)-8,8-dimethyl-5-azaspiro[bicyclo[2.2.2]octane-2,3'-[1,2]oxaziridine] (Minor isomer). $^1$H NMR (500 MHz, CDCl$_3$) δ 7.44 (d, J=7.3 Hz, 2H), 7.38 (t, J=7.3 Hz, 2H), 7.31 (t, J=7.3 Hz, 1H), 6.86 (d, J=9.1 Hz, 2H), 6.61 (d, J=9.1 Hz, 2H), 3.98 (q, J=6.9 Hz, 2H), 3.92 (d, J=14.2 Hz, 1H), 3.71 (d, J=14.2 Hz, 1H), 3.62 (t, J=2.8 Hz, 1H), 3.38-3.34 (m, 2H), 2.42 (dq, J=15.5, 3.2 Hz, 2H), 1.83 (dq, J=13.6, 1.9 Hz, 1H), 1.72 (t, J=2.5 Hz, 1H), 1.53 (dt, J=13.6, 2.5 Hz, 1H), 1.39 (t, J=6.9 Hz, 3H), 1.18 (s, 3H), 1.08 (s, 3H). HRMS calculated for C$_{24}$H$_{31}$N$_2$O$_2$ [M+H]$^+$ 379.2307; found 379.2302.

In a second step, the photochemical rearrangement of the diastereomeric oxaziridine mixture was achieved under continuous flow conditions. A solution of (1 S,4R)-2'-benzyl-5-(4-ethoxyphenyl)-8,8-dimethyl-5-azaspiro[bicyclo[2.2.2]octane-2,3'-[1,2]oxaziridine] (1.20 g, 3.17 mmol) in cyclohexane (368 mL) was degassed with argon for 30 min then pumped through FEP tubing (total length 15.00 m; internal diameter: 760 μm; volume: 6800 μL) including a section irradiated with a Phillips TUV 4W UV-C bulb (λ$_{max}$=254 nm, photochemical path length=5.10 m, average residence time: 185 s) via a HPLC pump (flow rate: 0.75 mL/min) and collected at the outlet. After evaporation under reduced pressure and silica gel column chromatography, 854 mg of (1 S,5S)-3-Benzyl-6-(4-ethoxyphenyl)-9,9-dimethyl-3,6-diazabicyclo[3.2.2]nonan-2-one (71%) and 150 mg of (1 S,5R)-2-Benzyl-6-(4-ethoxyphenyl)-9,9-dimethyl-2,6-diazabicyclo[3.2.2]nonan-3-one (12%) were obtained.

(1S,5S)-3-Benzyl-6-(4-ethoxyphenyl)-9,9-dimethyl-3,6-diazabicyclo[3.2.2]nonan-2-one. $^1$H NMR (500 MHz, CDCl$_3$) δ 7.32-7.24 (m, 5H), 6.86 (d, J=8.8 Hz, 2H), 6.65 (d, J=9.1 Hz, 2H), 4.82 (d, J=14.5 Hz, 1H), 4.26 (d, J=14.5 Hz, 1H), 3.99 (q, J=6.9 Hz, 2H), 3.62 (t, J=3.2 Hz, 1H), 3.58 (d, J=10.7 Hz, 1H), 3.41 (dd, J=5.4, 10.7 Hz, 1H), 3.37 (d, J=3.5 Hz, 2H), 3.17-3.15 (m, 1H), 1.95 (d, J=14.2 Hz, 1H), 1.68 (dd, J=5.7, 14.2 Hz, 1H), 1.39 (t, J=6.9 Hz, 3H), 1.07 (s, 3H), 0.94 (s, 3H). HRMS calculated for C$_{24}$H$_{31}$N$_2$O$_2$ [M+H]$^+$ 379.2380; found 379.2364.

(1S,5R)-2-Benzyl-6-(4-ethoxyphenyl)-9,9-dimethyl-2,6-diazabicyclo[3.2.2]nonan-3-one. $^1$H NMR (500 MHz, CDCl$_3$) δ 7.36-7.30 (m, 5H), 6.85 (d, J=9.1 Hz, 2H), 6.63 (d, J=9.1 Hz, 2H), 4.80 (d, J=14.8 Hz, 1H), 4.53 (d, J=14.8 Hz, 1H), 3.99 (q, J=7.3 Hz, 2H), 3.66-3.64 (m, 1H), 3.51 (t, J=3.8 Hz, 1H), 3.43-3.39 (m, 1H), 3.31 (d, J=11.4 Hz, 1H), 2.93 (dq, J=4.1, 12.9 Hz, 2H), 1.70 (dt, J=2.2, 14.2 Hz, 1H), 1.55 (dd, J=4.7, 14.5 Hz, 1H), 1.39 (t, J=6.9 Hz, 3H), 1.11 (s, 3H), 1.07 (s, 3H). HRMS calculated for C$_{24}$H$_{31}$N$_2$O$_2$ [M+H]$^+$ 379.2380; found 379.2364.

III. General Methods for the Reduction of Bridged Homopiperazinones Derivatives.

Method E

To a solution of the bridged homopiperazinone (1 eq.) in anhydrous tetrahydrofuran (0.3 to 1 M) was added dropwise at 0° C. a solution of lithium aluminium hydride in tetrahydrofuran (1.0 M or 2.0 M, 2 to 6 eq.) or solid lithium aluminium hydride (4 to 6 eq.). The mixture was stirred at reflux for 3 to 24 hours then cooled to room temperature and water (0.05 mL per mmol of lithium aluminium hydride), a 2.0 M aqueous solution of sodium hydroxide (0.1 mL per mmol of lithium aluminium hydride), and again water (0.1 mL per mmol of lithium aluminium hydride) were added. The mixture was stirred for 30 min at room temperature, diluted with ethyl acetate, dried over anhydrous magnesium sulfate, filtered and concentrated under reduced pressure to give the bridged homopiperazine derivative. This material was used in the next step without further purification or purified further by silica gel column chromatography using a gradient of ethanol (or methanol) in dichloromethane (optionally with addition of 1 M aqueous solution of ammonia).

Intermediate:

4-(4-((1R,5S)-9,9-dimethyl-3,6-diazabicyclo[3.2.2]nonan-6-yl)phenyl)morpholine (E1)

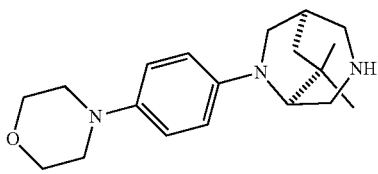 [SMILES: CC1(C)C[C@@H]2CNC[C@H]1N(c1ccc(N3CCOCC3)cc1)C2]

Using method E, a solution of (1S,5S)-9,9-dimethyl-6-(4-morpholinophenyl)-3,6-diazabicyclo[3.2.2]nonan-2-one (250 mg, 0.76 mmol) in anhydrous tetrahydrofuran (7.6 mL) was reacted with a 2.0 M solution of lithium aluminium hydride in tetrahydrofuran (2.2 mL). After work-up, 282 mg of contaminated 4-(4-((1R,5S)-9,9-dimethyl-3,6-diazabicyclo[3.2.2]nonan-6-yl)phenyl)morpholine was obtained. This material was used in the next step without further purification. HRMS calculated for $C_{19}H_{30}N_3O$ [M+H]$^+$ 316.2344; found 316.2315.

The following intermediate compounds were prepared by the aforementioned methodology, using the appropriately substituted reagent.

| Cpd | Structure | Name | Analytical Data |
| --- | --- | --- | --- |
| E-2 | 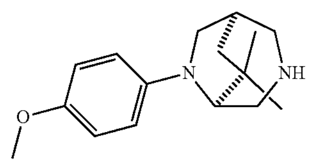 [SMILES: COc1ccc(N2C[C@H]3CNC[C@@H]2C(C)(C)C3)cc1] | (1R,5S)-6-(4-methoxyphenyl)-9,9-dimethyl-3,6-diazabicyclo[3.2.2]nonane | $^1$H NMR (500 MHz, CDCl$_3$) δ 6.88-6.81 (m, 2H), 6.60-6.52 (m, 2H), 3.76 (s, 3H), 3.32-3.26 (m, 2H), 3.23 (dd, J = 13.4 and 3.8 Hz, 1H), 3.13 (dt, J = 10.2 and 2.5 Hz, 1H), 3.07 (dd, J = 13.4 and 6.6 Hz, 1H), 2.87 (dd, J = 13.4 and 2.1 Hz, 1H), 2.84 (dd, J = 13.4 and 0.9 Hz, 1H), 2.33-2.28 (m, 1H), 1.70 (d, J = 13.8 Hz, 2H), 1.47 (dd, J = 13.8 and 6.6 Hz, 1H), 1.15 (s, 3H), 0.88 (s, 3H). HRMS calculated for $C_{16}H_{25}N_2O$ [M + H]$^+$ 261.1961; found 261.1961. |
| E-3 | 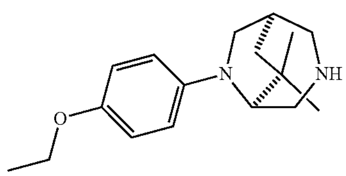 [SMILES: CCOc1ccc(N2C[C@H]3CNC[C@@H]2C(C)(C)C3)cc1] | (1R,5S)-6-(4-ethoxyphenyl)-9,9-dimethyl-3,6-diazabicyclo[3.2.2]nonane | $^1$H NMR (500 MHz, CDCl$_3$) δ 6.85 (d, J = 9.1 Hz, 2H), 6.56 (d, J = 9.1 Hz, 2H), 3.98 (q, J = 6.9 Hz, 2H), 3.32-3.31 (m, 1H), 3.29 (dd, J = 10.1 and 2.1 Hz, 1H), 3.24 (app dd, J = 13.6 and 3.8 Hz, 1H), 3.14 (dt, J = 10.1 and 2.8 Hz, 1H), 3.10-3.06 (m, 1H), 2.88 (dd, J = 13.2 and 2.1 Hz, 1H), 2.84 (d, J = 13.6 Hz, 1H), 2.32-2.20 (m, 1H), 1.77 (br s, 1H) 1.71 (d, J = 13.6 Hz, 1H), 1.49-1.45 (m, 1H), 1.38 (t, J = 6.9 Hz, 3H), 1.15 (s, 3H), 0.89 (s, 3H). HRMS calculated for $C_{17}H_{27}N_2O$ [M + H]$^+$ 275.2118; found 275.2119. |
| E-4 | 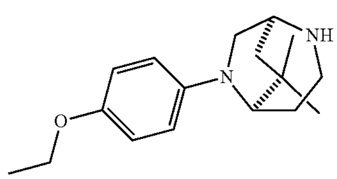 [SMILES: CCOc1ccc(N2C[C@@H]3CC(C)(C)[C@H]2CCN3)cc1] | (1S,5R)-6-(4-ethoxyphenyl)-9,9-dimethyl-2,6-diazabicyclo[3.2.2]nonane | Used without purification |
| E-5 | 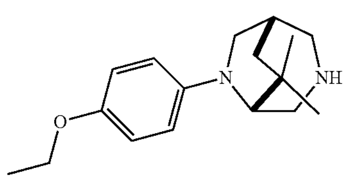 [SMILES: CCOc1ccc(N2C[C@@H]3CNC[C@H]2C(C)(C)C3)cc1] | (1S,5R)-6-(4-ethoxyphenyl)-9,9-dimethyl-3,6-diazabicyclo[3.2.2]nonane | HRMS calculated for $C_{17}H_{27}N_2O$ [M + H]$^+$ 275.2118; found 275.2115. |
| E-6 | 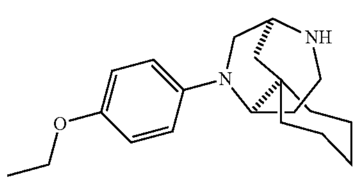 [SMILES: CCOc1ccc(N2C[C@@H]3CC4(CCCCC4)[C@H]2CCN3)cc1] | (1S,5R)-9-(4-ethoxyphenyl)-2,9-diazaspiro[bicyclo[3.2.2]nonane-6,1'-cyclohexane] | $^1$H NMR (500 MHz, CDCl$_3$) δ 6.84 (d, J = 9.0 Hz, 2H), 6.55 (d, J = 9.1 Hz, 2H), 3.96 (q, J = 7.0 Hz, 2H), 3.69-3.57 (m, 2H), 3.31-3.18 (m, 2H), 3.00 (ddd, J = 13.9, 9.3 and 4.8 Hz, 1H), 2.85 (dt, J = 13.6 and 5.2 Hz, 1H), 2.02 (m, 1H), 1.85 (m, 1H), 1.78-1.60 (m, 3H), 1.60-1.47 (m, 2H), 1.46-1.19 (m, 10H), 1.11 (m, 1H). |

| Cpd | Structure | Name | Analytical Data |
|---|---|---|---|
| E-7 | 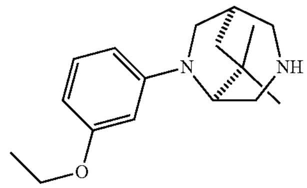 [SMILES: CCOc1cccc(N2C[C@H]3CNC[C@@H]2C(C)(C)C3)c1] | (1R,5S)-6-(3-ethoxyphenyl)-9,9-dimethyl-3,6-diazabicyclo[3.2.2]nonane | $^1$H NMR (500 MHz, Chloroform-d) δ 7.14 (t, J = 8.2 Hz, 1H), 6.27-6.24 (m, 2H), 6.18 (t, J = 2.3 Hz, 1H), 4.04 (q, J = 7.0 Hz, 2H), 3.39 (m, 1H), 3.33-3.26 (m, 2H), 3.21-3.14 (m, 2H), 2.94 (dd, J = 13.5, 1.9 Hz, 1H), 2.87 (d, J = 13.6 Hz, 1H), 2.77 (br, 1H), 2.35 (m, 1H), 1.79 (d, J = 14.0 Hz, 1H), 1.51 (dd, J = 14.0, 6.7 Hz, 1H), 1.41 (t, J = 7.0 Hz, 3H), 1.18 (s, 3H), 0.90 (s, 3H). HRMS calculated for $C_{17}H_{27}N_2O$ [M + H]$^+$ 275.2118; found 275.2157. |
| E-8 | 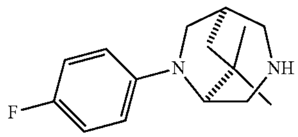 [SMILES: CC1(C)C[C@@H]2CNC[C@H]1N(c1ccc(F)cc1)C2] | (1R,5S)-6-(4-fluorophenyl)-9,9-dimethyl-3,6-diazabicyclo[3.2.2]nonane | $^1$H NMR (500 MHz, CDCl3) δ 7.00-6.83 (m, 2H), 6.57-6.37 (m, 2H), 3.31-3.29 (m, 1H), 3.28-3.21 (m, 2H), 3.16-2.95 (m, 2H), 2.84 (dt, J = 14.0 and 7.2 Hz, 2H), 2.32 (td, J = 6.6 and 3.3 Hz, 1H), 1.70 (d, J = 13.8 Hz, 1H), 1.47 (dd, J = 13.8 and 6.6 Hz, 1H), 1.15 (s, 3H), 0.87 (s, 3H). HRMS calculated for C15H22FN2 [M + H]+ 249.1762; found 249.176 |
| E-9 | 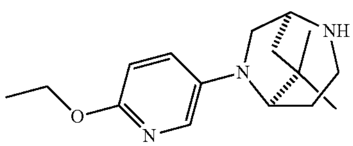 [SMILES: CCOc1ccc(N2C[C@@H]3CC(C)(C)[C@H]2CCN3)cn1] | (1S,5R)-6-(6-ethoxypyridin-3-yl)-9,9-dimethyl-2,6-diazabicyclo[3.2.2]nonane | Used without purification |

Intermediate:

(1R,5S)-6-(4-(4,4-difluoropiperidin-1-yl)phenyl)-9,9-dimethyl-3,6-diazabicyclo[3.2.2]nonane and (1S,5R)-6-(4-(4,4-difluoropiperidin-1-yl)phenyl)-9,9-dimethyl-2,6-diazabicyclo[3.2.2]nonane (E9)—Used as Mixture

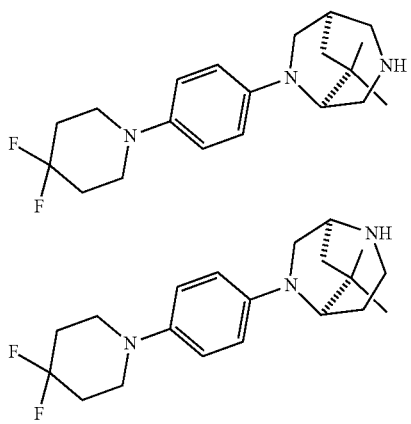

Using method E, a mixture of (1S,5S)-6-(4-(4,4-difluoropiperidin-1-yl)phenyl)-9,9-dimethyl-3,6-diazabicyclo[3.2.2]nonan-2-one and (1S,5R)-6-(4-(4,4-difluoropiperidin-1-yl)phenyl)-9,9-dimethyl-2,6-diazabicyclo[3.2.2]nonan-3-one (198 mg, 0.544 mmol) in anhydrous tetrahydrofuran (4 mL) was reacted with a 1.0 M solution of lithium aluminium hydride in tetrahydrofuran (2.72 mL). After work-up, 115 mg of a mixture of (1R,5S)-6-(4-(4,4-difluoropiperidin-1-yl)phenyl)-9,9-dimethyl-3,6-diazabicyclo[3.2.2]nonane and (1S,5R)-6-(4-(4,4-difluoropiperidin-1-yl)phenyl)-9,9-dimethyl-2,6-diazabicyclo[3.2.2]nonane was obtained. This material was used in the next step without further purification. HRMS calculated for $C_{20}H_{30}N_3F_2$ [M+H]$^+$ 350.2363; found 350.2440.

Alternative Method for Intermediate (E-3)

Alternatively, (1R,5S)-6-(4-ethoxyphenyl)-9,9-dimethyl-3,6-diazabicyclo[3.2.2]nonane can be prepared by reduction of the bridged homopiperazinone obtained following photochemical rearrangement of oxaziridines in continuous flow) In a first step, using method E, a solution of (1S,5S)-3-Benzyl-6-(4-ethoxyphenyl)-9,9-dimethyl-3,6-diazabicyclo[3.2.2]nonan-2-one (105 mg, 0.28 mmol) in tetrahydrofuran (5 mL) was reacted with a 1.0 M solution of lithium aluminium hydride in tetrahydrofuran (1.83 mL, 1.83 mmol) at reflux for 30 min. After work-up, 98 mg of (1R,5S)-3-benzyl-6-(4-ethoxyphenyl)-9,9-dimethyl-3,6-diazabicyclo[3.2.2]nonane (97%) were obtained and used in the next step without further purification.

$^1$H NMR (500 MHz, CDCl$_3$) δ 7.38-7.33 (m, 4H), 7.30-7.27 (m, 1H), 6.88 (d, J=9.1 Hz, 2H), 6.56 (d, J=9.1 Hz, 2H), 4.01 (q, J=6.9 Hz, 2H), 3.58 (d, J=12.9 Hz, 1H), 3.50 (d, J=12.9 Hz, 1H), 3.31 (d, J=5.0 Hz, 1H), 3.28 (dd, J=10.1 and 2.5 Hz, 1H), 3.16-3.10 (m, 2H), 3.05-3.01 (m, 1H), 2.38 (d, J=11.4 Hz, 1H), 2.33-2.31 (m, 1H), 2.23 (d, J=11.7 Hz, 1H), 2.00 (d, J=12.9 Hz, 1H), 1.41 (t, J=6.9 Hz, 3H), 1.37-1.33 (m, 1H), 1.22 (s, 3H), 0.86 (s, 3H). HRMS calculated for $C_{24}H_{33}N_2O$ [M+H]$^+$ 365.2587; found 365.2590.

In a second step, to a solution of (1R,5S)-3-benzyl-6-(4-ethoxyphenyl)-9,9-dimethyl-3,6-diazabicyclo[3.2.2]nonane (98 mg, 0.27 mmol) in 2,2,2-trifluoroethanol (5 mL) were added 1,4,-cyclohexadiene (255 μL, 2.70 mmol) followed by palladium on carbon (10% w/w, 10 mg, 10 wt %). The solution was degassed with nitrogen then heated at reflux for 36 h. After cooling down to room temperature, the reaction mixture was filtered through a celite pad then concentrated under reduced pressure to give 54 mg of (1R,5S)-6-(4-ethoxyphenyl)-9,9-dimethyl-3,6-diazabicyclo[3.2.2]nonane (73%). Analyical data in table E, entry 3.
Intermediate:

(1R,5S)-6-(4-(2-methoxyethoxy)phenyl)-9,9-dimethyl-3,6-diazabicyclo[3.2.2]nonane—E10

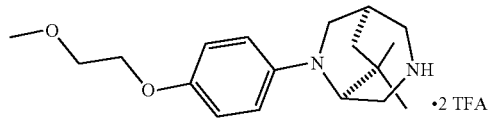 [SMILES: COCCOc1ccc(N2C[C@H]3CNC[C@@H]2C(C)(C)C3)cc1]

In the first step, to a stirred solution of (1R,5S)-6-(4-ethoxyphenyl)-9,9-dimethyl-3,6-diazabicyclo[3.2.2]nonane (4.31 g, 15.72 mmol) in dichloromethane (25 mL) at 0° C. was added dropwise a 1.0 M solution of boron tribromide in dichloromethane (39.29 mL, 39.29 mmol). The reaction mixture was stirred for 3h at 0° C. then quenched with a saturated aqueous solution of sodium hydrogen carbonate (15 mL). Di-tert-butyl dicarbonate (3.60 g, 16.50 mmol) was added and the mixture stirred at room temperature for 6 h. Upon completion, the phases were separated and the aqueous phase was extracted with dichloromethane. The combined organic extracts were washed with brine, dried over anhydrous magnesium sulfate, filtered and evaporated under reduced pressure. The resulting residue was purified by silica gel column chromatography using a gradient of ethyl acetate in cyclohexane to give 4.74 g of tert-butyl (1S,5S)-6-(4-hydroxyphenyl)-9,9-dimethyl-3,6-diazabicyclo[3.2.2]nonane-3-carboxylate (87%).

$^1$H NMR (500 MHz, CDCl$_3$) δ 6.79 (br s, 2H), 6.51 (br s, 2H), 4.95 (br s, 1H), 4.51-4.21 (m, 2H), 3.48-2.98 (m, 3H), 2.88 (d, J=13.9 Hz, 1H), 2.44 (m, 1H), 1.54 (t, J=12.0 Hz, 1H), 1.47 (s, 9H), 1.42 (dd, J=13.9 and 6.3 Hz, 2H), 1.06 (s, 3H), 0.88 (s, 3H). HRMS calculated for C$_{20}$H$_{31}$N$_2$O$_3$ [M+H]$^+$ 347.2329; found 347.2313.

In the second step, 2-chloroethyl methyl ether (796 μL, 8.71 mmol) was added to a mixture of tert-butyl-(1S,5S)-6-(4-hydroxyphenyl)-9,9-dimethyl-3,6-diazabicyclo[3.2.2]nonane-3-carboxylate (1.00 g, 2.90 mmol) and cesium carbonate (2.84 g, 8.71 mmol). The reaction mixture was heated to 95° C. under microwave irradiation for 2.5 h. After cooling down to room temperature, the mixture was filtered and the filtrate concentrated under reduced pressure. The resulting residue was purified by silica gel column chromatography using a gradient of ethyl acetate in cyclohexane to give 1.01 g of tert-butyl (1S,5S)-6-(4-(2-methoxyethoxy)phenyl)-9,9-dimethyl-3,6-diazabicyclo[3.2.2]nonane-3-carboxylate (86%).

$^1$H NMR (500 MHz, CDCl$_3$) δ 6.88 (d, J=8.8 Hz, 2H), 6.55 (d, J=8.8 Hz, 2H), 4.48-4.21 (m, 2H), 4.06 (t, J=4.9 Hz, 2H), 3.72 (t, J=4.9 Hz, 2H), 3.44 (s, 3H), 3.41-3.35 (m, 1H), 3.27 (dd, J=10.4 and 1.9 Hz, 1H), 3.18-3.09 (m, 1H), 2.87 (d, J=13.9 Hz, 1H), 2.45 (m, 1H), 1.54 (t, J=13.9 Hz, 1H), 1.46 (s, 9H), 1.44-1.40 (m, 2H), 1.06 (s, 3H), 0.87 (s, 3H). HRMS calculated for C$_{23}$H$_{37}$N$_2$O$_4$ [M+H]$^+$ 405.2748; found 405.2763.

In a third step, a solution of tert-butyl-(1S,5S)-6-(4-(2-methoxyethoxy)phenyl)-9,9-dimethyl-3,6-diazabicyclo[3.2.2]nonane-3-carboxylate (600 mg, 1.48 mmol) in a mixture of dichloromethane (7 mL) and trifluoroacetic acid (7 mL) was stirred at room temperature for 4 h, then the solvents were evaporated under reduced pressure to give (1R,5S)-6-(4-(2-methoxyethoxy)phenyl)-9,9-dimethyl-3,6-diazabicyclo[3.2.2]nonane as a trifluoroacetate salt which was used without further purification. HRMS calculated for C18H28N2O2 [M+H]$^+$ 305.2229; found 305.2226.

Intermediate:

(1R,5S)-9,9-dimethyl-6-(4-(pyridin-2-yloxy)phenyl)-3,6-diazabicyclo[3.2.2]nonane—E11

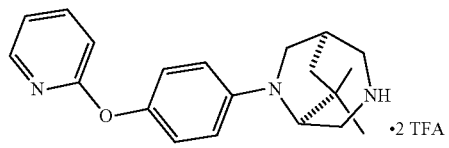 [SMILES: CC1(C)C[C@@H]2CNC[C@H]1N(c1ccc(Oc3ccccn3)cc1)C2]

To a mixture of tert-butyl (1S,5S)-6-(4-hydroxyphenyl)-9,9-dimethyl-3,6-diazabicyclo[3.2.2]nonane-3-carboxylate (257 mg, 0.74 mmol), 2-bromopyridine (107 μL, 1.11 mmol), picolinic acid (37 mg, 0.30 mmol) and cesium carbonate (604 mg, 1.85 mmol) in dimethylformamide was added copper(I) iodide (28 mg, 0.15 mmol) The reaction mixture was heated to 100° C. under microwave irradiation for 3.5 h. After cooling to room temperature, the mixture was filtered and the filtrate diluted with water and extracted with ethyl acetate. The combined organic phases were washed with water and brine, dried over anhydrous magnesium sulfate, filtered and concentrated under reduced pressure. The resulting residue was purified by silica gel column chromatography using a gradient of ethyl acetate in cyclohexane to give 172 mg of tert-butyl-(1S,5S)-9,9-dimethyl-6-(4-(pyridin-2-yloxy)phenyl)-3,6-diazabicyclo[3.2.2]nonane-3-carboxylate (55%).

$^1$H NMR (500 MHz, CDCl$_3$) δ 8.22-8.18 (m, 1H), 7.66-7.61 (m, 1H), 7.03 (d, J=9.2 Hz, 2H), 6.95-6.92 (m, 1H), 6.85 (d, J=8.5 Hz, 1H), 6.63 (d, J=9.2 Hz, 2H), 4.53-4.24 (m, 2H), 3.47-3.43 (m, 1H), 3.31 (dd, J=10.4 and 1.9 Hz, 1H), 3.24-2.97 (m, 2H), 2.85 (d, J=13.6 Hz, 1H), 2.46 (br s, 1H), 1.56 (t, J=13.9 Hz, 1H), 1.49 (s, 9H), 1.45-1.42 (m, 1H), 1.08 (s, 3H), 0.91 (s, 3H). HRMS calculated for C$_{21}$H$_{26}$N$_3$O$_3$ [M-tBu+2H]$^+$368.1974; found 368.1977.

In a second step, a solution of tert-butyl-(1S,5S)-9,9-dimethyl-6-(4-(pyridin-2-yloxy)phenyl)-3,6-diazabicyclo[3.2.2]nonane-3-carboxylate (172 mg, 0.41 mmol) in a mixture of dichloromethane (5 mL) and trifluoroacetic acid (5 mL) was stirred at room temperature for 4 h, then the solvents were evaporated under reduced pressure to give (1R,5S)-9,9-dimethyl-6-(4-(pyridin-2-yloxy)phenyl)-3,6-diazabicyclo[3.2.2]nonane as a trifluoroacetate salt which was used without further purification. HRMS calculated for C$_{20}$H$_{26}$N$_3$O [M+H]$^+$ 324.2076; found 324.2075.

Intermediate:

(1R,5S)-6-(4-ethoxy-3-fluorophenyl)-9,9-dimethyl-3,6-diazabicyclo[3.2.2]nonane (E-12)

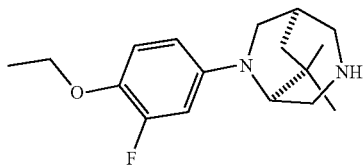 [SMILES: CCOc1ccc(N2C[C@H]3CNC[C@@H]2C(C)(C)C3)cc1F]

To a stirred solution of (1R,5S)-6-(4-ethoxyphenyl)-9,9-dimethyl-3,6-diazabicyclo[3.2.2]nonane (195 mg, 0.71 mmol) in acetonitrile (15 mL) at 0° C. was added Selectfluor (529 mg, 1.49 mmol). The reaction mixture was stirred at 0° C. for 1 hour, then allowed to warm to room temperature for a further 1.5 hour, quenched with a saturated aqueous solution of sodium thiosulfate (2 mL) and concentrated under reduced pressure. Dichloromethane (15 mL) and water (10 mL) were added, the phases separated and the organic phase washed with water, brine, and concentrated under reduced pressure to give 197 mg of a crude containing (1R,5S)-6-(4-ethoxy-3-fluorophenyl)-9,9-dimethyl-3,6-diazabicyclo[3.2.2]nonane. This residue was used in the next step without further purification. HRMS calculated for $C_{17}H_{26}N_2OF$ [M+H]$^+$ 293.2029; found 293.2026.

Method F

To a solution of the bridged homopiperazinone (1 eq.) in anhydrous tetrahydrofuran (0.5 M) was added dropwise at 0° C. borane-tetrahydrofuran complex (1.0 M) (5 eq.). The mixture was stirred at reflux temperature for 1 to 5 days then quenched with ethanol (or diethylamine) (large excess) and stirred again at reflux temperature for 1 day. After cooling to room temperature, the mixture was concentrated under reduced pressure to give a crude product. This material was used in the next step without further purification.

Intermediate:

4-(4-((1R,5S)-9,9-dimethyl-3,6-diazabicyclo[3.2.2]nonan-6-yl)phenyl) thiomorpholine-1,1-dioxide (F-1)

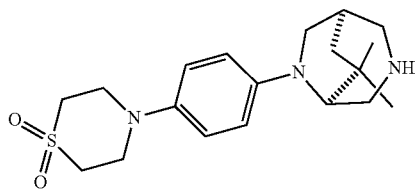 [SMILES: CC1(C)C[C@@H]2CNC[C@H]1N(c1ccc(N3CCS(=O)(=O)CC3)cc1)C2]

Using method F, a solution of (1S,5S)-6-(4-(1,1-dioxido-thiomorpholino)phenyl)-9,9-dimethyl-3,6-diazabicyclo[3.2.2]nonan-2-one (375.0 mg, 0.993 mmol) in anhydrous tetrahydrofuran (10 mL) was reacted with a 1.0 M borane.tetrahydrofuran complex (4.96 mL). After work-up, a crude containing 4-(4-((1R,5S)-9,9-dimethyl-3,6-diazabicyclo[3.2.2]nonan-6-yl)phenyl) thiomorpholine-1,1-dioxide was obtained and used in the next step without further purification. HRMS calculated for $C_{19}H_{30}N_3O_2S$ [M+H]$^+$ 364.2014; found 364.2112.

Intermediate:

4-(4-((1R,5S)-9,9-dimethyl-2,6-diazabicyclo[3.2.2]nonan-6-yl)phenyl) thiomorpholine-1,1-dioxide (F-2)

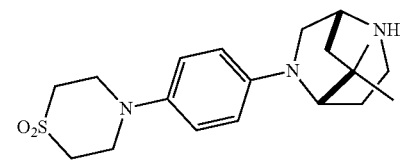 [SMILES: CC1(C)C[C@@H]2CN(c3ccc(N4CCS(=O)(=O)CC4)cc3)[C@H]1CCN2]

Using method F, a solution of (1R,5S)-6-(4-(1,1-dioxido-thiomorpholino)phenyl)-9,9-dimethyl-2,6-diazabicyclo[3.2.2]nonan-3-one (100 mg, 0.265 mmol) in anhydrous tetrahydrofuran (2 mL) was reacted with a 1.0 M borane-tetrahydrofuran complex (1.32 mL). After work-up, a crude containing 4-(4-((1R,5S)-9,9-dimethyl-2,6-diazabicyclo[3.2.2]nonan-6-yl)phenyl) thiomorpholine-1,1-dioxide was obtained and used in the next step without further purification. HRMS calculated for $C_{19}H_{30}N_3O_2S$ [M+H]$^+$ 364.2059; found 364.2053.

IV. General Methods for the Synthesis of Compounds with Urea Linker

Method G

To a solution of the bridged homopiperazine derivative (1 eq.) in dichloromethane (or tetrahydrofuran) (0.25 to 1 M) was added triethylamine (1 to 5 eq.) and the isocyanate (1 to 1.5 eq.). The reaction mixture was stirred at room temperature for 2 to 72 hours then concentrated under reduced pressure. The resulting residue was purified by silica gel column chromatography using a gradient of methanol in ethyl acetate (or a gradient of ethyl acetate in cyclohexane). In some examples, the crude was purified by preparative HPLC using a gradient of methanol (10 to 100%) in water (+0.1% of triethylamine or formic acid in each solvent) or by both a silica gel column chromatography and a preparative HPLC.

Example 1

(1S,5S)-6-(4-ethoxyphenyl)-N-(4-methoxyphenyl)-9,9-dimethyl-3,6-diazabicyclo[3.2.2]nonane-3-carboxamide

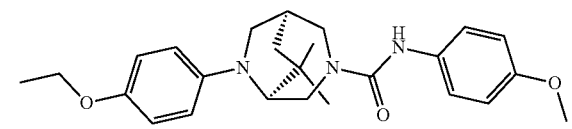 [SMILES: CCOc1ccc(N2C[C@H]3CN(C(=O)Nc4ccc(OC)cc4)C[C@@H]2C(C)(C)C3)cc1]

Using method G, a solution of (1R,5S)-6-(4-ethoxyphenyl)-9,9-dimethyl-3,6-diazabicyclo[3.2.2]nonane (80 mg, 0.3 mmol) in tetrahydrofuran (3 mL) was reacted with p-methoxyphenylisocyanate (60 µL, 0.45 mmol). After work-up and silica gel column chromatography, 50 mg of (1S,5S)-6-(4-ethoxyphenyl)-N-(4-methoxyphenyl)-9,9-dimethyl-3,6-diazabicyclo[3.2.2]nonane-3-carboxamide (39%) were obtained.

$^1$H NMR (500 MHz, DMSO-d$_6$) δ 8.36 (s, 1H), 7.33-7.27 (d, J=9.1 Hz, 2H), 6.84-6.77 (m, 4H), 6.59 (d, J=9.2 Hz, 2H), 4.36 (m, 2H), 3.96-3.86 (q, J=7.0 Hz, 2H), 3.71 (s, 3H), 3.51 (d, J=4.0 Hz, 1H), 3.22-3.09 (m, 2H), 2.97 (d, J=13.2 Hz, 1H), 2.86 (d, J=13.8 Hz, 1H), 2.49 (t, 1H), 1.54 (d, J=13.6 Hz, 1H), 1.41-1.33 (m, 1H), 1.28 (t, J=7.0 Hz, 3H), 0.99 (s, 3H), 0.81 (s, 3H). HRMS calculated for $C_{25}H_{33}N_3O_3$ [M+H]$^+$ 424.5558; found 424.5142.

Example 2

(1 S,5S)—N-ethyl-6-(4-fluorophenyl)-9,9-dimethyl-3,6-diazabicyclo[3.2.2]nonane-3-carboxamide

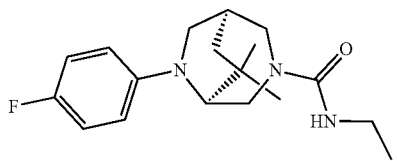 [SMILES: CCNC(=O)N1C[C@@H]2CN(c3ccc(F)cc3)[C@H](C1)C(C)(C)C2]

Using method G, a solution of (1R,5S)-6-(4-fluorophenyl)-9,9-dimethyl-3,6-diazabicyclo[3.2.2]nonane (45 mg, 0.18 mmol) in a mixture of dichloromethane (3 mL) and triethylamine (25 µL, 0.18 mmol) was reacted with ethyl isocyanate (14 µL, 0.18 mmol). After work-up and silica gel column chromatography, 46 mg of (1 S,5S)—N-ethyl-6-(4-fluorophenyl)-9,9-dimethyl-3,6-diazabicyclo[3.2.2]nonane-3-carboxamide (80%) were obtained.

$^1$H NMR (500 MHz, CDCl$_3$) δ 7.02-6.81 (m, 2H), 6.59-6.41 (m, 2H), 4.45 (s, 1H), 4.26 (dd, J=13.4 and 8.2 Hz, 1H), 4.09 (ddd, J=12.7, 4.3 and 1.4 Hz, 1H), 3.41 (d, J=3.9 Hz, 1H), 3.37-3.20 (m, 3H), 3.18-3.13 (m, 1H), 3.11 (dd, J=12.7 and 1.2 Hz, 1H), 2.90 (d, J=13.6 Hz, 1H), 2.49 (t, J=7.1 Hz, 1H), 1.62 (d, J=13.7 Hz, 1H), 1.42 (dd, J=13.7 and 6.5 Hz, 1H), 1.13 (t, J=7.2 Hz, 3H), 1.05 (s, 3H), 0.87 (s, 3H). HRMS calculated for $C_{18}H_{26}N_3FNaO$ [M+Na]$^+$ 342.1952; found 342.1955

Example 3

(1S,5S)—N-ethyl-6-(4-(2-methoxyethoxy)phenyl)-9,9-dimethyl-3,6-diazabicyclo[3.2.2]nonane-3-carboxamide

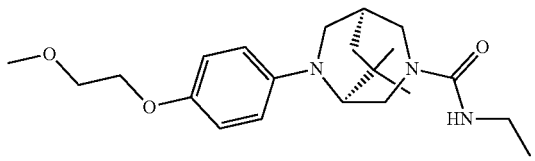 [SMILES: CCNC(=O)N1C[C@@H]2CN(c3ccc(OCCOC)cc3)[C@H](C1)C(C)(C)C2]

In a first step, a solution of (1R,5S)-6-(4-ethoxyphenyl)-9,9-dimethyl-3,6-diazabicyclo[3.2.2]nonane (100 mg, 0.37 mmol) in dichloromethane was reacted with a 1 M solution of boron tribromide in dichloromethane (1 mL, 1 mmol) at room temperature for 3 hours. The reaction mixture was diluted with ethyl acetate, cooled to 0° C., slowly quenched with water, then extracted with ethyl acetate. The combined organic phases were dried over anhydrous magnesium sulfate, filtered and evaporated under reduced pressure to give 50 mg of 4-((1R,5S)-9,9-dimethyl-3,6-diazabicyclo[3.2.2]nonan-6-yl)phenol. This residue was used in the next step without further purification.

$^1$H NMR (500 MHz, CDCl3) δ 8.61 (bs, 1H), 8.42 (bs, 1H), 6.68-6.66 (m, 2H), 6.60-6.55 (m, 2H), 3.59 (bd, 1H), 3.19 (m, 1H), 1.84 (m, 1H), 1.70 (d, J=10.1 Hz, 1h), 1.58 (dd, 2H), 1.52 (m, 1H), 1.32-1.22 (m, 1H), 1.18 (t, 1H), 1.09 (s, 3H), 0.80 (s, 3H). HRMS calculated for $C_{15}H_{23}N_2O$ [M+H]$^+$ 247.1810; found 247.1848.

In a second step, using method G, a solution of 4-((1R, 5S)-9,9-dimethyl-3,6-diazabicyclo[3.2.2]nonan-6-yl)phenol (50 mg, 0.2 mmol) in dimethyl sulfoxide (2 mL) was reacted with N-ethyl isocyanate (30 uL, 0.4 mmol) at rt overnight. The reaction mixture was then diluted with water and extracted with ethyl acetate. The combined organic phases were dried over anhydrous magnesium sulfate, filtered and evaporated under reduced pressure to give 20 mg of (1 S,5S)—N-ethyl-6-(4-hydroxyphenyl)-9,9-dimethyl-3,6-diazabicyclo[3.2.2]nonane-3-carboxamide. This residue was used in the next step without further purification.

$^1$H NMR (500 MHz, CDCl$_3$) δ 8.40 (s, 1H), 6.61 (m, 2H), 6.45 (m, 2H), 6.41 (t, J=5.4 Hz, 1H), 4.24-4.21 (m, 1H), 4.16 (dd, J=13.7 and 8.3 Hz, 1H), 3.38 (d, J=4.2 Hz, 1H), 3.13 (dd, J=10.2 and 2.4 Hz, 1H), 3.08-3.00 (m, 3H), 2.80 (dd, J=13.3 and 1.2 Hz, 1H), 2.71 (d, J=13.8 Hz, 1H), 2.40 (br s, 1H), 1.44-1.39 (m, 1H), 1.32-1.25 (m, 1H), 0.99 (t, J=7.1 Hz, 3H), 0.94 (s, 3H), 0.77 (s, 3H). HRMS calculated for $C_{18}H_{27}N_3O_2$ [M+H]$^+$ 318.2182; found 318.2162.

In a third step, to a solution of (1S,5S)—N-ethyl-6-(4-hydroxyphenyl)-9,9-dimethyl-3,6-diazabicyclo[3.2.2] nonane-3-carboxamide (60 mg, 0.2 mmol) in a mixture of tetrahydrofuran (2 mL) and dimethylformamide (1 mL) were added sodium hydride (60% in mineral oil, 26 mg, 0.65 mmol) then after 10 mins, bromoethyl methyl ether (40 mg, 0.3 mmol). The reaction mixture was stirred at room temperature overnight then diluted with water and extracted with ethyl acetate. The combined organic layers were dried over anhydrous magnesium sulfate, filtered and evaporated under reduced pressure. The resulting residue was purified by silica gel column chromatography to give (1 S,5S)—N-ethyl-6-(4-(2-methoxyethoxy)phenyl)-9,9-dimethyl-3,6-diazabicyclo[3.2.2]nonane-3-carboxamide (8 mg, 10%).

$^1$H NMR (500 MHz, CDCl3) δ 6.95-6.85 (m, 2H), 6.62-6.53 (m, 2H), 4.42 (s, 1H), 4.29 (dd, J=13.4 and 8.2 Hz, 1H), 4.08 (dt, J=8.2 and 3.5 Hz, 3H), 3.79-3.69 (m, 2H), 3.46 (s, 3H), 3.44 (d, J=3.9 Hz, 1H), 3.35-3.25 (m, 3H), 3.16 (t, J=12.8 Hz, 2H), 2.93 (d, J=13.5 Hz, 1H), 2.51 (t, J=6.9 Hz, 1H), 1.64 (d, J=13.6 Hz, 1H), 1.44 (dd, J=13.7 and 6.4 Hz, 1H), 1.16 (t, J=7.2 Hz, 3H), 1.08 (s, 3H), 0.90 (s, 3H). HRMS calculated for $C_{21}H_{33}N_3O_3$ [M+H]$^+$ 376.2600; found 376.2575.

Method H

To a solution of the bridged homopiperazine derivative (1 eq.) in a mixture of dichloromethane (or chloroform) (0.5 to 2 M) and triethylamine (or N,N-diisopropylethylamine) (3 to 10 eq.) were added triphosgene (0.5 to 1.4 eq.). After 15 to 60 minutes of stirring at room temperature, the amine or hydrazine (5 to 25 eq.) was added. The reaction mixture was stirred at room temperature for 2 to 72 hours then washed with a 5% aqueous solution of ammonium chloride (or a saturated aqueous solution of sodium bicarbonate), water and brine, dried over anhydrous magnesium sulfate, filtered and evaporated to dryness. In one example, a 10% aqueous solution of citric acid was used to wash the organic phase prior to the wash with a basic aqueous solution. The resulting residue was purified by silica gel column chromatography using a gradient of methanol in ethyl acetate (or a gradient of ethyl acetate in dichloromethane or a gradient of acetone in dichloromethane). In some examples, the crude product was purified by preparative HPLC using a gradient of methanol (10 to 100%) in water (with 0.1% of diethyl amine or formic acid in each solvent) or by both a silica gel chromatography and a preparative HPLC.

Example 4

(1S,5S)—N-(2-hydroxyethyl)-9,9-dimethyl-6-(4-morpholinophenyl)-3,6-diazabicyclo[3.2.2]nonane-3-carboxamide

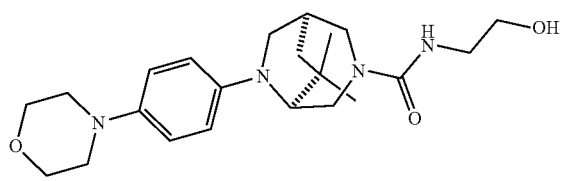 [SMILES: CC1(C)C[C@@H]2CN(C(=O)NCCO)C[C@H]1N(c1ccc(N3CCOCC3)cc1)C2]

Using method H, a solution of 4-(4-((1R,5S)-9,9-dimethyl-3,6-diazabicyclo[3.2.2]nonan-6-yl)phenyl)morpholine (262 mg, 0.83 mmol) in dichloromethane (8.3 mL) and triethylamine (1.16 mL, 8.30 mmol) was reacted with triphosgene (295 mg, 1.00 mmol) then 2-aminoethanol (496 µL, 8.30 mmol). After work-up and silica gel column chromatography, 260 mg of (1␣S,5S)—N-(2-hydroxyethyl)-9,9-dimethyl-6-(4-morpholinophenyl)-3,6-diazabicyclo [3.2.2]nonane-3-carboxamide (78%) was obtained. $^1$H NMR (500 MHz, MeOD-d$_4$) δ 7.00-6.90 (m, 2H), 6.70-6.60 (m, 2H), 4.31-4.19 (m, 2H), 3.83 (t, 4H, J=4.7 Hz), 3.62-3.56 (m, 3H), 3.32-3.26 (m, 4H), 3.11-2.89 (m, 6H), 2.53-2.47 (m, 1H), 1.59 (d, 1H, J=13.7 Hz), 1.46 (dd, 1H, J=13.7 and 6.5 Hz), 1.05 (s, 3H), 0.88 (s, 3H) HRMS calculated for $C_{22}H_{35}N_4O_3$ [M+H]$^+$ 403.2634; found 403.2676.

The following example compounds were prepared by the aforementioned methodology, using the appropriately substituted reagent.

| Example | Structure | Name | Analytical Data |
|---|---|---|---|
| 5 | 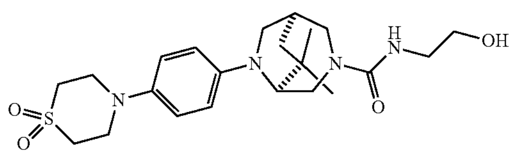 [SMILES: CC1(C)C[C@@H]2CN(C(=O)NCCO)C[C@H]1N(c1ccc(N3CCS(=O)(=O)CC3)cc1)C2] | (1S,5S)-6-(4-(1,1-dioxidothiomorpholino)phenyl)-N-(2-hydroxyethyl)-9,9-dimethyl-3,6-diazabicyclo[3.2.2]nonane-3-carboxamide | 1H NMR (500 MHz, DMSO-d6) δ 6.92 (d, 2H, J = 9.1 Hz), 6.57 (d, 2H, J = 9.1 Hz), 6.44 (t, 1H, J = 5.5 Hz), 4.60 (t, 1H, J = 5.4 Hz), 4.25 (ddd, 1H, J = 13.5, 4.8 and 1.9 Hz), 4.16 (dd, 1H, J = 13.7 and 8.1 Hz), 3.52-3.44 (m, 5H), 3.40-3.34 (m, 3H), 3.18-3.05 (m, 7H), 2.81 (d, 1H, J = 13.2 Hz), 2.73 (d, 1H, J = 13.8 Hz), 2.41 (q, 1H, J = 7.4 Hz), 1.43 (d, 1H, J = 13.5 Hz), 1.31 (dd, 1H, J = 13.5 and 6.4 Hz), 0.95 (s, 3H), 0.78 (s, 3H). HRMS calculated for C22H35N4O4S [M + H]+ 451.2334; found 451.2389. |
| 6 | 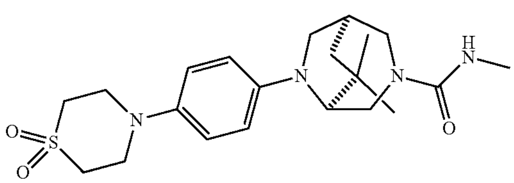 [SMILES: CNC(=O)N1C[C@@H]2CN(c3ccc(N4CCS(=O)(=O)CC4)cc3)[C@H](C1)C(C)(C)C2] | (1S,5S)-6-(4-(1,1-dioxidothiomorpholino)phenyl)-N,9,9-trimethyl-3,6-diazabicyclo[3.2.2]nonane-3-carboxamide | 1H NMR (500 MHz, DMSO-d6) δ 6.92 (m, 2H), 6.60-6.53 (m, 2H), 6.38 (q, 1H, J = 4.2 Hz), 4.23 (dd, 1H, J = 13.3 and 6.3 Hz), 4.15 (dd, 1H, J = 13.5 and 8.3 Hz), 3.53-3.44 (m, 5H), 3.19-3.11 (m, 6H), 2.80 (d, 1H, J = 13.2 Hz), 2.72 (d, 1H, J = 13.7 Hz), 2.56 (d, 1H, J = 4 Hz), 2.44-2.37 (m, 1H), 1.43 (d, 1H, J = 13.3 Hz), 1.32 (dd, 1H, J = 13.1 and 6.1 Hz), 0.95 (s, 3H), 0.78 (s, 3H). HRMS calculated for C21H33N4O3S [M + H]+ 421.2229; found 421.2228. |
| 7 | 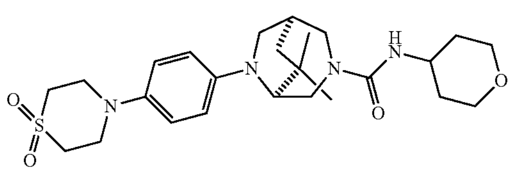 [SMILES: CC1(C)C[C@@H]2CN(C(=O)NC3CCOCC3)C[C@H]1N(c1ccc(N3CCS(=O)(=O)CC3)cc1)C2] | (1S,5S)-6-(4-(1,1-dioxidothiomorpholino)phenyl)-9,9-dimethyl-N-(tetrahydro-2H-pyran-4-yl)-3,6-diazabicyclo[3.2.2]nonane-3-carboxamide | 1H NMR (500 MHz, DMSO-d6) δ 6.96-6.89 (m, 2H), 6.60-6.52 (m, 2H), 6.22 (d, 1H, J = 7.6 Hz), 4.27 (dd, 1H, J = 13.7 and 4.5 Hz), 4.18 (dd, 1H, J = 13.8, 8.4 Hz), 3.85-3.78 (m, 2H), 3.68-3.58 (m, 1H), 3.52-3.47 (m, 4H), 3.45 (d, 1H, J = 4.3 Hz), 3.32-3.28 (m, 2H), 3.19-3.05 (m, 6H), 2.82 (d, 1H, J = 13.3 Hz), 2.72 (d, 1H, J = 13.8 Hz), 2.41 (t, 1H, J = 7.3 Hz), 1.70-1.60 (m, 2H), 1.50-1.28 (m, 4H), 0.95 (s, 3H), 0.78 (s, 3H). HRMS calculated for C25H39N4O4S [M + H]+ 491.2647; found 491.2763. |
| 8 | 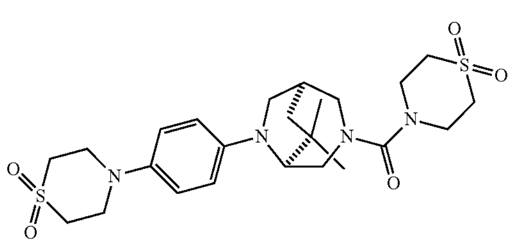 [SMILES: CC1(C)C[C@@H]2CN(C(=O)N3CCS(=O)(=O)CC3)C[C@H]1N(c1ccc(N3CCS(=O)(=O)CC3)cc1)C2] | (1,1-dioxidothiomorpholino)((1S,5S)-6-(4-(1,1-dioxidothiomorpholino)phenyl)-9,9-dimethyl-3,6-diazabicyclo[3.2.2]nonan-3-yl)methanone | 1H NMR (500 MHz, DMSO-d6) δ 6.96-6.90 (m, 2H), 6.63-6.53 (m, 2H), 4.12-4.04 (m, 1H), 3.99-3.92 (m, 1H), 3.54-3.41 (m, 9H), 3.26-3.02 (m, 11H), 2.84 (d, 1H, J = 13.6 Hz), 2.49-2.43 (m, 1H), 1.56 (d, 1H, J = 13.5 Hz), 1.31 (dd, 1H, J = 13.6 and 6.6 Hz), 0.93 (s, 3H), 0.79 (s, 3H). HRMS calculated for C24H37N4O5S2 [M + H]+ 525.2161; found 525.2154. |

| Example | Structure | Name | Analytical Data |
|---|---|---|---|
| 9 | 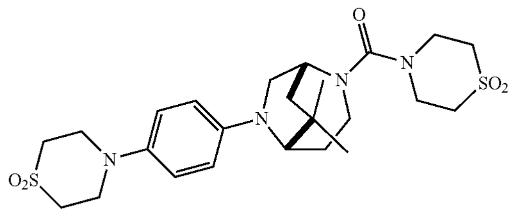 [SMILES: CC1(C)C[C@@H]2CN(c3ccc(N4CCS(=O)(=O)CC4)cc3)[C@H]1CCN2C(=O)N1CCS(=O)(=O)CC1] | (1,1-dioxidothiomorpholino)((1R,5S)-6-(4-(1,1-dioxidothiomorpholino)phenyl)-9,9-dimethyl-2,6-diazabicyclo[3.2.2]nonan-2-yl)methanone | 1H NMR (500 MHz, DMSO-d6) δ 6.93-6.89 (m, 2H), 6.58-6.53 (m, 2H), 4.23-4.17 (m, 1H), 3.56 (t, J = 3.7 Hz, 1H), 3.52-3.26 (m, 10H), 3.20-3.06 (m, 10H), 2.00-1.93 (m, 1H), 1.81-1.72 (m, 2H), 1.62 (dd, J = 15 and 6.5 Hz, 1H), 1.08 (s, 3H), 0.86 (s, 3H). HRMS calculated for C24H37N4O5S2 [M + H]+ 525.2205; found 525.2200. |
| 10 | 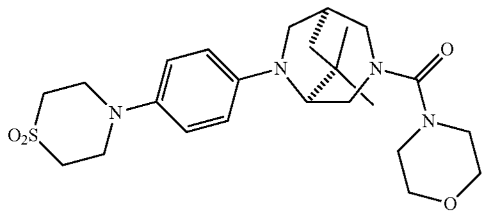 [SMILES: CC1(C)C[C@@H]2CN(C(=O)N3CCOCC3)C[C@H]1N(c1ccc(N3CCS(=O)(=O)CC3)cc1)C2] | ((1S,5S)-6-(4-(1,1-dioxidothiomorpholino)phenyl)-9,9-dimethyl-3,6-diazabicyclo[3.2.2]nonan-3-yl)(morpholino)methanone | 1H NMR (500 MHz, DMSO-d6) δ 6.94-6.90 (m, 2H), 6.63-6.58 (m, 2H), 4.15-4.07 (m, 1H), 3.98-3.92 (m, 1H), 3.57-3.44 (m, 9H), 3.19-3.05 (m, 11H), 2.77 (d, 1H, J = 13.5 Hz), 2.45 (t, J = 7.4 Hz, 1H), 1.58 (d, 1H, J = 13.6 Hz), 1.29 (dd, 1H, J = 13.6 and 6.5 Hz), 0.93 (s, 3H), 0.78 (s, 3H). HRMS calculated for C24H37N4O4S [M + H]+ 477.2536; found 477.2639. |
| 11 | 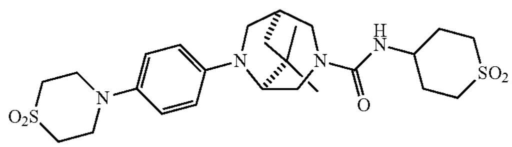 [SMILES: CC1(C)C[C@@H]2CN(C(=O)NC3CCS(=O)(=O)CC3)C[C@H]1N(c1ccc(N3CCS(=O)(=O)CC3)cc1)C2] | (1S,5S)-N-(1,1-dioxidotetrahydro-2H-thiopyran-4-yl)-6-(4-(1,1-dioxido thiomorpholino)phenyl)-9,9-dimethyl-3,6-diazabicyclo[3.2.2]nonane-3-carboxamide | 1H NMR (500 MHz, DMSO-d6) δ 6.92 (d, J = 8.7 Hz, 2H), 6.57 (d, J = 8.6 Hz, 2H), 6.38 (d, J = 7.7 Hz, 1H), 4.32-4.24 (m, 1H), 4.16 (dd, J = 14 and 8.0 Hz, 1H), 3.89-3.72 (m, 2H), 3.56-3.42 (m, 5H), 3.27-2.98 (m, 9H), 2.82 (d, J = 13.5 Hz, 1H), 2.74 (d, J = 13.8 Hz, 1H), 2.41 (t, J = 7.1 Hz, 1H), 2.09-1.86 (m, 4H), 1.41 (d, J = 13.5 Hz, 1H), 1.36-1.29 (m, 1H), 0.95 (s, 3H), 0.78 (s, 3H). HRMS calculated for C25H39N4O5S2 [M + H]+ 539.2362; found 539.2432. |
| 12 | 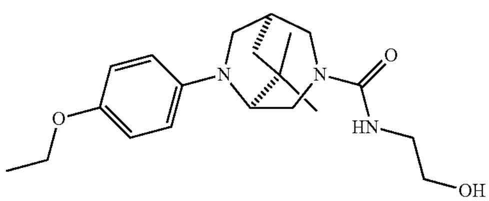 [SMILES: CCOc1ccc(N2C[C@H]3CN(C(=O)NCCO)C[C@@H]2C(C)(C)C3)cc1] | (1S,5S)-N-(2-hydroxyethyl)-6-(4-ethoxyphenyl)-9,9-dimethyl-3,6-diazabicyclo[3.2.2]nonane-3-carboxamide | 1H NMR (500 MHz, CDCl3) δ 6.84 (d, 2H, J = 9.1 Hz), 6.55 (d, 2H, J = 9.1 Hz), 5.06 (t, 1H, J = 5.4 Hz), 4.23 (dd, 1H, J = 13.4 and 8.0 Hz), 4.09 (dd, 1H, J = 12.6 and 3.3 Hz), 3.96 (q, 2H, J = 7.0 Hz), 3.72-3.66 (m, 2H), 3.51 (br s, 1H), 3.44-3.35 (m, 3H), 3.28 (dd, 1H, J = 10.2 and 2.3 Hz), 3.18-3.14 (m, 2H), 2.96 (d, 1H, J = 13.6 Hz), 2.48 (t, 1H, J = 6.8 Hz), 1.59 (d, 1H, J = 13.8 Hz), 1.43 (dd, 1H, J = 13.7 and 6.5 Hz), 1.37 (t, 3H, J = 7.0 Hz), 1.04 (s, 3H), 0.88 (s, 3H). HRMS calculated for C20H32N3O3 [M + H]+ 362.2438; found 362.2439. |
| 13 | 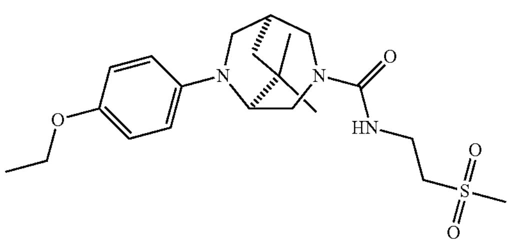 [SMILES: CCOc1ccc(N2C[C@H]3CN(C(=O)NCCS(C)(=O)=O)C[C@@H]2C(C)(C)C3)cc1] | (1S,5S)-6-(4-ethoxyphenyl)-9,9-dimethyl-N-(2-(methylsulfonyl)ethyl)-3,6-diazabicyclo[3.2.2]nonane-3-carboxamide | 1H NMR (500 MHz, CDCl3) δ 6.90-6.74 (m, 2H), 6.59-6.50 (m, 2H), 5.34 (t, J = 5.7 Hz, 1H), 4.17 (dd, J = 13.3, 7.9 Hz, 1H), 4.08 (d, J = 9.9 Hz, 1H), 3.97 (q, J = 7.0 Hz, 2H), 3.77 (dd, J = 11.5, 5.8 Hz, 2H), 3.43 (d, J = 3.3 Hz, 1H), 3.34-3.19 (m, 3H), 3.16 (dd, J = 12.7, 1.2 Hz, 2H), 2.99 (d, J = 13.6 Hz, 1H), 2.94 (s, 3H), 2.49 (t, J = 6.7 Hz, 1H), 1.59 (d, J = 13.8 Hz, 1H), 1.45 (dd, J = 13.5, 6.3 Hz, 1H), 1.37 (t, J = 7.0 Hz, 3H), 1.04 (s, 3H), 0.89 (s, 3H). HRMS calculated for C21H34N3O4S [M + H]+ 424.2265; found 424.2262. |
| 14 | 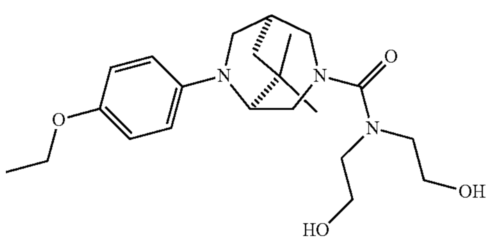 [SMILES: CCOc1ccc(N2C[C@H]3CN(C(=O)N(CCO)CCO)C[C@@H]2C(C)(C)C3)cc1] | (1S,5S)-6-(4-ethoxyphenyl)-N,N-bis(2-hydroxyethyl)-9,9-dimethyl-3,6-diazabicyclo[3.2.2]nonane-3-carboxamide | 1H NMR (500 MHz, CDCl3) δ 6.85 (d, J = 8.9 Hz, 2H), 6.57 (d, J = 9.0 Hz, 2H), 4.19 (dd, J = 13.4 and 7.7 Hz, 1H), 4.04 (d, J = 10.9 Hz, 1H), 3.96 (q, J = 6.9 Hz, 2H), 3.83 (s, 2H), 3.77-3.58 (m, 4H), 3.48-3.27 (m, 6H), 3.23 (d, J = 9.0 Hz, 1H), 3.16 (d, J = 9.8 Hz, 1H), 2.97 (d, J = 13.7 Hz, 1H), 2.50 (s, 1H), 1.75 (d, J = 13.8 Hz, 1H), 1.51-1.29 (m, 4H), 1.00 (s, 3H), 0.87 (s, 3H). HRMS calculated for C22H36N3O4 [M + H]+ 406.2700; found 406.2697. |

| Example | Name | Analytical Data |
|---|---|---|
| 15 | ((1S,5S)-6-(4-ethoxyphenyl)-9,9-dimethyl-3,6-diazabicyclo[3.2.2]nonan-3-yl)((S)-3-hydroxypyrrolidin-1-yl)methanone | 1H NMR (DMSO-d6, 500 MHz) δ 6.78 (d, 2H, J = 9.2 Hz), 6.58 (d, 2H, J = 9.2 Hz), 4.93 (d, 1H, J = 4.0 Hz), 4.17 (s 1H, J = 5.3 Hz), 4.03 (dd, 1H, J = 13.4 and 8.3 Hz), 3.97 (dd, 1H, J = 13.3 and 2.9 Hz), 3.90 (q, 2H, J = 7.0 Hz), 3.45 (d, 1H, J = 3.6 Hz), 3.39 (dt, 1H, J = 10.2 and 7.2 Hz), 3.29 (dd, 1H, J = 10.5 and 5.6 Hz), 3.23 (dt, 1H, J = 10.3 and 7.1 Hz), 3.17-3.11 (m, 2H), 3.08-3.03 (m, 2H), 2.81 (d, 1H, J = 13.5 Hz), 2.43 (t, 1H, J = 6.8 Hz), 1.86 (dq, 1H, J = 12.3 and 6.7 Hz), 1.68-1.59 (m, 2H), 1.31 (d, 1H, J = 6.5 Hz), 1.27 (t, 3H, J = 7.0 Hz), 0.97 (s, 3H), 0.77 (s, 3H). HRMS calculated for C22H34N3O3 [M + H]+ 388.2595; found 388.2594. |
| 16 | (1S,5S)-N-(2-cyanoethyl)-6-(4-ethoxyphenyl)-N,9,9-trimethyl-3,6-diazabicyclo[3.2.2]nonane-3-carboxamide | 1H NMR (CDCl3, 500 MHz) δ 6.85 (d, 2H, J = 8.6 Hz), 6.57 (br s, 2H), 4.20 (dd, 1H, J = 13.3 and 8.1 Hz), 4.02-3.90 (m, 3H), 3.60 (dt, 1H, J = 13.3 and 6.5 Hz), 3.43-3.30 (m, 2H), 3.24 (dt, 2H, J = 13.5 and 6.7 Hz), 2.92 (d, 1H, J = 13.7 Hz), 2.87 (s, 3H), 2.68-2.55 (m, 2H), 2.53-2.49 (m, 1H), 1.73 (d, 1H, J = 13.9 Hz), 1.66 (br s, 1H) 1.43-1.39 (m, 1H), 1.37 (t, 3H, J = 7.0 Hz), 1.01 (s, 3H), 0.88 (s, 3H). HRMS calculated for C22H33N4O2 [M + H]+ 385.2604; found 385.2577. |
| 17 | 1-((1S,5S)-6-(4-ethoxyphenyl)-9,9-dimethyl-3,6-diazabicyclo[3.2.2]nonane-3-carbonyl)piperidine-4-carbonitrile | 1H NMR (CDCl3, 500 MHz) δ 6.85 (d, 2H, J = 9.1 Hz), 6.56 (d, 2H, J = 9.1 Hz,), 4.24 (dd, 1H, J = 13.5 and 8.2 Hz), 3.97 (q, 2H, J = 7.0 Hz), 3.93 (ddd, 1H, J = 12.8, 4.1 and 1.8 Hz), 3.44-3.34 (m, 3H), 3.30 (dd, 1H, J = 12.8 and 1.2 Hz), 3.24 (dd, 1H, J = 10.1 and 2.0 Hz), 3.16-3.08 (m, 2H), 3.03-2.98 (m, 1H), 2.86 (d, 1H, J = 13.6 Hz), 2.81-2.76 (m, 1H), 2.51 (t, 1H, J = 6.9 Hz), 2.03-1.99 (m, 1H), 1.90 (q, 2H, J = 5.9 Hz), 1.82-1.75 (m, 1H), 1.70 (d, 1H, J = 13.8 Hz), 1.40-1.36 (m, 1H), 1.38 (t, 3H, J = 7.0 Hz), 0.95 (s, 3H), 0.87 (s, 3H). HRMS calculated for C24H35N4O2 [M + H]+ 411.2755; found 411.2782. |
| 18 | ((1S,5S)-6-(4-ethoxyphenyl)-9,9-dimethyl-3,6-diazabicyclo[3.2.2]nonan-3-yl)(4-(pyrrolidin-1-yl)piperidin-1-yl)methanone | 1H NMR (CDCl3, 500 MHz) δ 6.85 (d, 2H, J = 9.1 Hz), 6.56 (d, 2H, J = 9.1 Hz), 4.28 (dd, 1H, J = 13.6 and 8.3 Hz), 3.97 (q, 2H, J = 7.0 Hz), 3.98-3.95 (m, 1H), 3.58 (d, 1H, J = 13.1 Hz), 3.50 (d, 1H, J = 13.1Hz), 3.50 (d, 1H, J = 13.1 Hz), 3.33 (d, 1H, J = 3.8 Hz), 3.28 (d, 1H, J = 12.8 Hz), 3.22 (dd, 1H, J = 10.1 and 1.9 Hz), 3.12 (dt, 1H, J = 10.1 and 2.4 Hz), 2.82-2.75 (m, 2H), 2.69 (td, 2H, J = 12.9 and 2.2 Hz), 2.64-2.59 (m, 3H), 2.49 (t, 1H, J = 7.0 Hz), 2.19-2.11 (m, 1H), 1.99-1.91 (m, 2H), 1.84-1.80 (m, 4H), 1.72 (d, 1H, J = 13.8 Hz), 1.67-1.59 (m, 2H), 1.50-1.42 (m, 1H), 1.37 (t, 3H, J = 7.0 Hz), 1.39-1.33 (m, 1H), 0.94 (s, 3H), 0.85 (s, 3H). HRMS calculated for C27H43N4O2 [M + H]+ 455.3381; found 455.3433. |
| 19 | (1S,5S)-N-((R)-2,3-dihydroxypropyl)-6-(4-ethoxyphenyl)-9,9-dimethyl-3,6-diazabicyclo[3.2.2]nonane-3-carboxamide | 1H NMR (CDCl3, 500 MHz) δ 6.85 (d, 2H, J = 9.1 Hz), 6.55 (d, 2H, J = 9.1 Hz), 4.98 (t, 1H, J = 5.8 Hz), 4.18-4.10 (m, 2H), 3.97 (q, 2H, J = 7.0 Hz), 3.70 (q, 1H, J = 4.5 Hz), 3.55-3.53 (m, 2H), 3.50 (d, 1H, J = 4.7 Hz), 3.47-3.42 (m, 2H), 3.40-3.35 (m, 1H), 3.30-3.28 (m, 2H), 3.19-3.16 (m, 2H), 3.01 (d, 1H, J = 13.6 Hz), 2.49 (t, 1H, J = 6.6 Hz), 1.57 (d, 1H, J = 13.8 Hz), 1.46 (dd, 1H, J = 13.8, 6.5 Hz), 1.37 (t, 3H, J = 7.0 Hz), 1.05 (s, 3H), 0.89 (s, 3H). HRMS calculated for C21H34N3O4 [M + H]+ 392.2544; found 392.256. |

-continued

| Example | Structure | Name | Analytical Data |
|---|---|---|---|
| 20 | 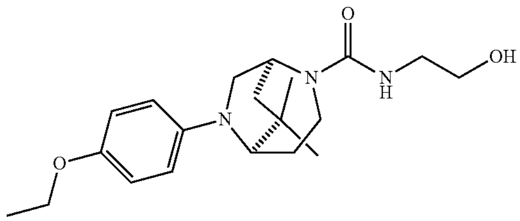 [SMILES: CCOc1ccc(N2C[C@@H]3CC(C)(C)[C@H]2CCN3C(=O)NCCO)cc1] | (1S,5R)-6-(4-ethoxyphenyl)-N-(2-hydroxyethyl)-9,9-dimethyl-2,6-diazabicyclo[3.2.2]nonane-2-carboxamide | 1H NMR (500 MHz, CDCl3) δ 6.91-6.76 (m, 2H), 6.58-6.47 (m, 2H), 4.86 (t, J = 5.4 Hz, 1H), 4.47 (s, 1H), 3.96 (q, J = 7.0 Hz, 2H), 3.68 (s, 2H), 3.58-3.43 (m, 3H), 3.43-3.30 (m, 4H), 3.25 (dd, J = 11.1 and 2.6 Hz, 1H), 2.06-1.97 (m, 1H), 1.97-1.88 (m, 1H), 1.79 (d, J = 15.0 Hz, 1H), 1.65 (dd, J = 15.0 and 6.0 Hz, 1H), 1.37 (t, J = 7.0 Hz, 3H), 1.11 (s, 3H), 0.95 (s, 3H). HRMS calculated for C20H32N3O3 [M + H]+ 362.2438; found 362.2437. |
| 21 | 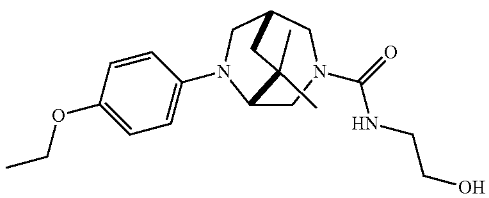 [SMILES: CCOc1ccc(N2C[C@@H]3CN(C(=O)NCCO)C[C@H]2C(C)(C)C3)cc1] | (1R,5R)-6-(4-ethoxyphenyl)-N-(2-hydroxyethyl)-9,9-dimethyl-3,6-diazabicyclo[3.2.2]nonane-3-carboxamide | 1H NMR (500 MHz, CDCl3) δ 6.91-6.72 (m, 2H), 6.63-6.46 (m, 2H), 4.95 (t, J = 5.3 Hz, 1H), 4.23 (dd, J = 13.2 and 8.1 Hz, 1H), 4.13-4.12 (m, 1H), 4.09 (dd, J = 12.6 and 3.4 Hz, 1H), 3.97 (q, J = 7.0 Hz, 2H), 3.77-3.64 (m, 2H), 3.48-3.32 (m, 3H), 3.31-3.25 (m, 2H), 3.21-3.11 (m, 2H), 2.97 (d, J = 13.6 Hz, 1H), 2.49 (t, J = 6.8 Hz, 1H), 1.60 (d, J = 13.8 Hz, 1H), 1.44 (dd, J = 13.7 and 6.5 Hz, 1H), 1.37 (t, J = 7.0 Hz, 3H), 1.05 (s, 3H), 0.89 (s, 3H). HRMS calculated for C20H32N3O3 [M + H]+ 362.2438; found 362.2437. |
| 22 | 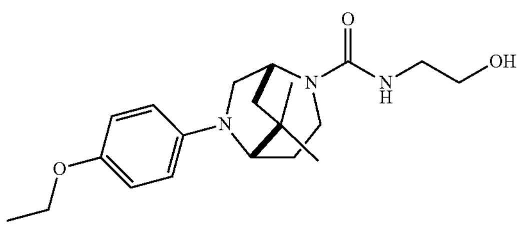 [SMILES: CCOc1ccc(N2C[C@H]3CC(C)(C)[C@@H]2CCN3C(=O)NCCO)cc1] | (1R,5S)-6-(4-ethoxyphenyl)-N-(2-hydroxyethyl)-9,9-dimethyl-2,6-diazabicyclo[3.2.2]nonane-2-carboxamide | 1H NMR (500 MHz, CDCl3) δ 6.91-6.76 (m, 2H), 6.65-6.40 (m, 2H), 4.84 (t, J = 5.4 Hz, 1H), 4.47 (s, 1H), 3.96 (q, J = 7.0 Hz, 2H), 3.68 (t, J = 4.7 Hz, 2H), 3.58-3.29 (m, 7H), 3.25 (dd, J = 11.1 and 2.6 Hz, 1H), 2.07-1.87 (m, 1H), 1.80 (d, J = 15.0 Hz, 1H), 1.65 (dd, J = 15.0 and 6.0 Hz, 2H), 1.37 (t, J = 7.0 Hz, 3H), 1.11 (s, 3H), 0.96 (s, 3H). HRMS calculated for C20H32N3O3 [M + H]+ 362.2438; found 362.2437. |
| 23 | 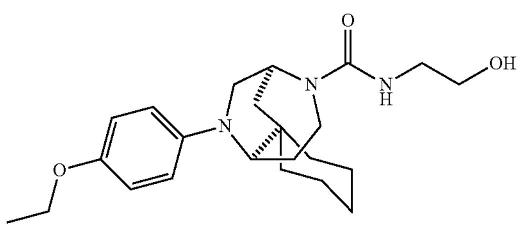 [SMILES: CCOc1ccc(N2C[C@@H]3CC4(CCCCC4)[C@H]2CCN3C(=O)NCCO)cc1] | (1S,5R)-6-(4-ethoxyphenyl)-N-(2-hydroxyethyl)-2,6-diazaspiro[bicyclo[3.2.2]nonane-9,1'-cyclohexane]-2-carboxamide | 1H NMR (500 MHz, CDCl3) δ 6.88-6.79 (m, 2H), 6.58-6.51 (m, 2H), 4.91 (br, 1H), 4.49 (br, 1H), 3.97 (q, J = 7.0 Hz, 2H), 3.76-3.64 (m, 3H), 3.51 (m, 1H), 3.43-3.31 (m, 4H), 3.22 (m, 1H), 2.01 (m, 1H), 1.90 (m, 1H), 1.76-1.66 (m, 2H), 1.61-1.10 (m, 14H). HRMS calculated for C23H36N3O3 [M + H]+ 402.2751; found 402.2747. |
| 24 | 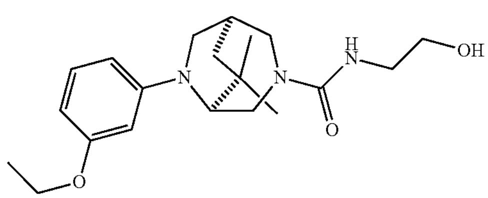 [SMILES: CCOc1cccc(N2C[C@H]3CN(C(=O)NCCO)C[C@@H]2C(C)(C)C3)c1] | (1S,5S)-6-(3-ethoxyphenyl)-N-(2-hydroxyethyl)-9,9-dimethyl-3,6-diazabicyclo[3.2.2]nonane-3-carboxamide | 1H NMR (500 MHz, CDCl3) δ 7.14 (t, J = 8.2 Hz, 1H), 6.29-6.23 (m, 2H), 6.18 (t, J = 2.4 Hz, 1H), 5.08 (br s, 1H), 4.24 (dd, J = 13.3 and 8.1 Hz, 1H), 4.12 - 4.06 (m, 1H), 4.03 (q, J = 7.0 Hz, 2H), 3.70 (q, J = 6.8 and 4.9 Hz, 2H), 3.54-3.34 (m, 4H), 3.29 (dd, J = 10.5 and 2.5 Hz, 1H), 3.21 (m, 1H), 3.17 (d, J = 12.9 Hz, 1H), 2.95 (d, J = 13.7 Hz, 1H), 2.48 (m, 1H), 1.62 (d, J = 13.8 Hz, 1H), 1.50-1.43 (m, 1H), 1.41 (t, J = 7.0 Hz, 3H), 1.06 (s, 3H), 0.90 (s, 3H). HRMS calculated for C20H32N3O3 [M + H]+ 362.2438; found 362.2434. |
| 25 | 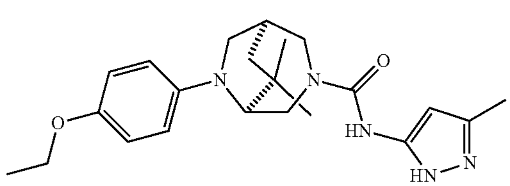 [SMILES: CCOc1ccc(N2C[C@H]3CN(C(=O)Nc4cc(C)n[nH]4)C[C@@H]2C(C)(C)C3)cc1] | (1S,5S)-6-(4-ethoxyphenyl)-9,9-dimethyl-N-(3-methyl-1H-pyrazol-5-yl)-3,6-diazabicyclo[3.2.2]nonane-3-carboxamide | 1H NMR (500 MHz, DMSO-d6) δ 6.79 (d, J = 9.1 Hz, 2H), 6.60 (d, J = 9.1 Hz, 2H), 5.80 (s, 1H), 5.76 (s, 1H), 5.18 (s, 1H), 4.66-4.51 (m, 1H), 4.43 (d, J = 14.0 Hz, 1H), 3.90 (q, J = 6.9 Hz, 2H), 3.53 (s, 1H), 3.45 (s, 1H), 3.23-3.04 (m, 2H), 2.97 (d, J = 13.4 Hz, 1H), 2.02 (s, 3H), 1.36 (dd, J = 13.7 and 6.4 Hz, 1H), 1.27 (t, J = 6.9 Hz, 3H), 1.18 (d, J = 7.1 Hz, 1H), 0.91 (s, 3H), 0.78 (s, 3H). HRMS calculated for C22H32N5O2 [M + H]+ 398.2551; found 398.2547. |

| Example | Structure | Name | Analytical Data |
|---|---|---|---|
| 26 | 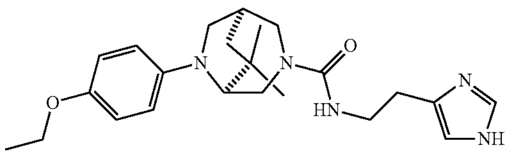 [SMILES: CCOc1ccc(N2C[C@H]3CN(C(=O)NCCc4c[nH]cn4)C[C@@H]2C(C)(C)C3)cc1] | (1S,5S)-N-(2-(1H-imidazol-4-yl)ethyl)-6-(4-ethoxyphenyl)-9,9-dimethyl-3,6-diazabicyclo[3.2.2]nonane-3-carboxamide | 1H NMR (500 MHz, DMSO) δ 11.79 (s, 1H), 7.50 (s, 1H), 6.78 (d, J = 9.0 Hz, 2H), 6.61 (t, J = 5.4 Hz, 1H), 6.55 (d, J = 9.1 Hz, 2H), 4.31-4.22 (m, 1H), 4.17 (dd, J = 13.6 and 8.1 Hz, 1H), 3.89 (q, J = 6.9 Hz, 2H), 3.48-3.40 (m, 1H), 3.27-3.19 (m, 2H), 3.15 (dd, J = 9.9 and 2.3 Hz, 1H), 3.06 (d, J = 10.3 Hz, 1H), 2.81 (d, J = 13.3 Hz, 1H), 2.73 (d, J = 13.8 Hz, 1H), 2.62 (t, J = 7.5 Hz, 2H), 2.40 (d, J = 8.0 Hz, 1H), 1.42 (d, J = 13.6 Hz, 1H), 1.31 (m, 1H), 1.27 (t, J = 6.9 Hz, 3H), 0.94 (s, 3H), 0.77 (s, 3H). HRMS calculated for C23H4N5O2 [M + H]+ 412.2713; found 412.2694. |
| 27 | 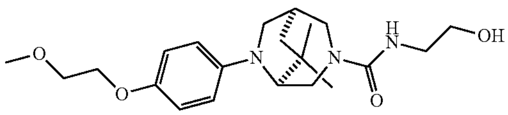 [SMILES: COCCOc1ccc(N2C[C@H]3CN(C(=O)NCCO)C[C@@H]2C(C)(C)C3)cc1] | (1S,5S)-N-(2-Hydroxyethyl)-6-(4-(2-methoxyethoxy)phenyl)-9,9-dimethyl-3,6-diazabicyclo[3.2.2]nonane-3-carboxamide | 1H NMR (500 MHz, CDCl3) δ 6.89 (d, J = 8.9 Hz, 2H), 6.56 (d, J = 8.9 Hz, 2H), 5.02 (t, J = 4.7 Hz, 1H), 4.24 (dd, J = 7.8 and 5.4 Hz, 1H), 4.11-4.06 (m, 3H), 3.73-3.69 (m, 4H), 3.45 (s, 3H), 3.44-3.35 (m, 4H), 3.29 (dd, J = 10.4 and 2.2 Hz, 1H), 3.17 (d, J = 12.0 Hz, 2H), 2.97 (d, J = 13.6 Hz, 1H), 2.49 (s, 1H), 1.74 (br s, 1H), 1.61 (d, J = 13.6 Hz, 1H), 1.45 (dd, J = 13.6 and 6.3 Hz, 1H), 1.05 (s, 3H), 0.89 (s, 3H). HRMS calculated for C21H34N3O4 [M + H]+ 392.2549; found 392.2537. |
| 28 | 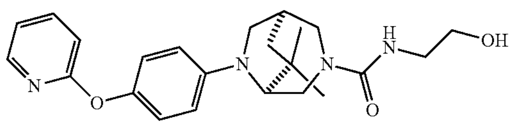 [SMILES: CC1(C)C[C@@H]2CN(C(=O)NCCO)C[C@H]1N(c1ccc(Oc3ccccn3)cc1)C2] | (1S,5S)-N-(2-hydroxyethyl)-9,9-dimethyl-6-(4-(pyridin-2-yloxy)phenyl)-3,6-diazabicyclo[3.2.2]nonane-3-carboxamide | 1H NMR (500 MHz, CDCl3) δ 8.19-8.16 (m, 1H), 7.68-7.62 (m, 1H), 7.04 (d, J = 9.1 Hz, 2H), 6.96-6.93 (m, 1H), 6.87 (d, J = 8.2 Hz, 1H), 6.64 (d, J = 9.1 Hz, 2H), 5.01 (t, J = 5.4 Hz, 1H), 4.17-4.12 (m, 1H), 4.06 (dd, J = 12.9 and 3.1 Hz, 1H), 3.70-3.65 (m, 2H), 3.50-3.31 (m, 5H), 3.23 (d, J = 12.9 Hz, 2H), 3.10 (d, J = 13.6 Hz, 1H), 2.51 (t, J = 6.3 Hz, 1H), 1.63 (d, J = 13.9 Hz, 1H), 1.49 (dd, J = 13.9 and 6.3 Hz, 1H), 1.09 (s, 3H), 0.94 (s, 3H). HRMS calculated for C23H31N4O3 [M + H]+ 411.2396; found 411.2395. |
| 29 | 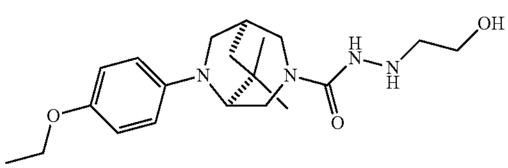 [SMILES: CCOc1ccc(N2C[C@H]3CN(C(=O)NNCCO)C[C@@H]2C(C)(C)C3)cc1] | 6-(4-ethoxyphenyl)-N'-(2-hydroxyethyl)-9,9-dimethyl-3,6-diazabicyclo[3.2.2]nonane-3-carbohydrazide | 1H NMR (CDCl3, 500 MHz) δ 6.85 (d, 2H, J = 9.1 Hz, ArH), 6.56 (d, 2H, J = 9.1 Hz, ArH), 4.33 (dd, 1H, J = 13.2, 8.3 Hz), 4.15-4.11 (m, 2H), 3.97 (q, 2H, J = 6.2 Hz, CH2CH3), 3.93-3.86 (m, 2H), 3.38 (d, 1H, J = 3.5 Hz), 3.32-3.24 (m, 3H), 3.17-3.13 (m, 1H), 3.10 (ddd, 1H, J = 14.1, 6.6, 2.7 Hz), 2.92 (d, 1H, J = 13.6 Hz), 2.52 (t, 1H, J = 6.8 Hz), 1.66-1.62 (m, 3H), 1.42 (dd, 1H, J = 14.0, 6.7 Hz), 1.37 (t, 3H, J = 7.0 Hz, CH2CH3), 0.99 (s, 3H, CH3), 0.88 (s, 3H, CH3) ppm; LCMS m/z 399.2354 found (M + Na)+, 399.2367 calculated for C20H32N4O3Na. |
| 59 | 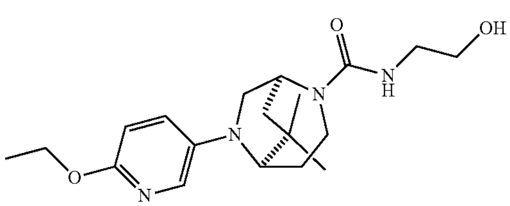 [SMILES: CCOc1ccc(N2C[C@@H]3CC(C)(C)[C@H]2CCN3C(=O)NCCO)cn1] | (1S,5R)-6-(6-ethoxypyridin-3-yl)-N-(2-hydroxyethyl)-9,9-dimethyl-2,6-diazabicyclo[3.2.2]nonane-2-carboxamide | 1H NMR (300 MHz, Chloroform-d) δ 7.51 (d, J = 3.0 Hz, 1H), 6.97 (dd, J = 9.1, 3.2 Hz, 1H), 6.64 (d, J = 9.0 Hz, 1H), 5.08 (t, J = 5.5 Hz, 1H), 4.49 (m, 1H), 4.24 (q, J = 7.0 Hz, 2H), 3.73-3.65 (m, 2H), 3.61-3.09 (m, 8H), 2.09-1.86 (m, 2H), 1.85-1.77 (m, 1H), 1.65 (dd, J = 15.1, 5.9 Hz, 1H), 1.36 (t, J = 7.1 Hz, 3H), 1.11 (s, 3H), 0.95 (s, 3H). LCMS (ES+) m/z = 363 ([M + H]+, 100). |

| Example | Structure | Name | Analytical Data |
|---|---|---|---|
| 60 | 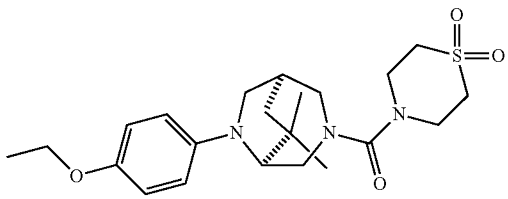 [SMILES: CCOc1ccc(N2C[C@H]3CN(C(=O)N4CCS(=O)(=O)CC4)C[C@@H]2C(C)(C)C3)cc1] | (1,1-dioxidothiomorpholino)((1S,5S)-6-(4-ethoxyphenyl)-9,9-dimethyl-3,6-diazabicyclo[3.2.2]nonan-3-yl)methanone | $^1$H NMR (500 MHz, Chloroform-d) δ 6.85 (d, J = 8.4 Hz, 2H), 6.57 (br s, 2H), 4.18 (dd, J = 13.3, 7.8 Hz, 1H), 3.98-3.92 (m, 3H), 3.77-3.72 (m, 2H), 3.65-3.59 (m, 2H), 3.42-3.36 (m, 2H), 3.29-3.12 (m, 4H), 3.00-2.94 (m, 3H), 2.53 (br s, 1H), 1.67 (d, J = 14.0 Hz, 1H), 1.44 (dd, J = 13.9, 6.5 Hz, 1H), 1.38 (t, J = 7.0 Hz, 3H), 0.96 (s, 3H), 0.89 (s, 3H) ppm. HRMS calculated for $C_{22}H_{34}N_3O_4S$ [M + H]$^+$ 436.2270; found 436.2252. |
| 61 | 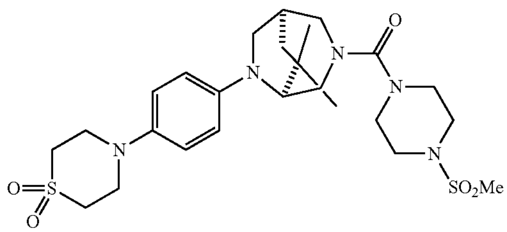 [SMILES: CC1(C)C[C@@H]2CN(C(=O)N3CCN(S(C)(=O)=O)CC3)C[C@H]1N(c1ccc(N3CCS(=O)(=O)CC3)cc1)C2] | ((1S,5S)-6-(4-(1,1-dioxidothiomorpholino)phenyl)-9,9-dimethyl-3,6-diazabicyclo[3.2.2]nonan-3-yl)(4-(methylsulfonyl)piperazin-1-yl)methanone | $^1$H NMR (500 MHz, Chloroform-d) δ 6.94 (d, J = 8.4 Hz, 2H), 6.60 (d, J = 8.4 Hz, 2H), 4.27 (dd, J = 13.7, 8.1 Hz, 1H), 3.99 (d, J = 12.8 Hz, 1H), 3.63 (s, 4H), 3.50-3.35 (m, 4H), 3.34-3.22 (m, 5H), 3.21-3.12 (m, 7H), 2.89 (d, J = 13.7 Hz, 1H), 2.80 (s, 3H), 2.55 (t, J = 6.6 Hz, 1H), 1.72 (d, J = 14.0 Hz, 1H), 1.43 (dd, J = 14.0, 6.6 Hz, 1H), 0.99 (s, 3H), 0.90 (s, 3H). HRMS calculated for $C_{25}H_{40}N_5O_5S_2$ [M + H]$^+$ 554.2471; found 554.2473. |

Example 30

(1S,5S)-6-(4-(4,4-difluoropiperidin-1-yl)phenyl)-N-(2-hydroxyethyl)-9,9-dimethyl-3,6-diazabicyclo[3.2.2]nonane-3-carboxamide

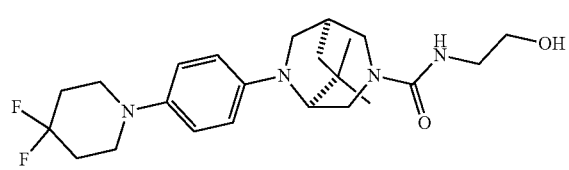 [SMILES: CC1(C)C[C@@H]2CN(C(=O)NCCO)C[C@H]1N(c1ccc(N3CCC(F)(F)CC3)cc1)C2]

Using method H, a mixture of (1R,5S)-6-(4-(4,4-difluoropiperidin-1-yl)phenyl)-9,9-dimethyl-3,6-diazabicyclo[3.2.2]nonane and (1 S,5R)-6-(4-(4,4-difluoropiperidin-1-yl)phenyl)-9,9-dimethyl-2,6-diazabicyclo[3.2.2]nonane (146.6 mg, 0.420 mmol) in dichloromethane (10 mL) and diisopropylethylamine (731 µL, 4.20 mmol) were reacted with triphosgene (124.6 mg, 0.420 mmol) then 2-aminoethanol (251 µL, 4.20 mmol). After work-up, silica gel column chromatography and preparative HPLC, 16.6 mg of (1 S,5S)-6-(4-(4,4-difluoropiperidin-1-yl)phenyl)-N-(2-hydroxyethyl)-9,9-dimethyl-3,6-diazabicyclo[3.2.2]nonane-3-carboxamide (9%) were obtained.

$^1$H NMR (500 MHz, DMSO-d$_6$) δ 6.92-6.86 (m, 2H), 6.58-6.53 (m, 2H), 6.45 (t, 1H, J=5.4 Hz), 4.29-4.22 (m, 1H), 4.17 (dd, 1H, J=13.9 and 8.2 Hz), 3.45 (d, 1H, J=4.4 Hz), 3.37 (t, 2H, J=6.3 Hz), 3.18-3.03 (m, 8H), 2.81 (d, 1H, J=13.7 Hz), 2.73 (d, 1H, J=13.7 Hz), 2.41 (t, 1H, J=7.2 Hz), 2.11-1.99 (m, 4H), 1.43 (d, 1H, J=13.4 Hz), 1.31 (dd, 1H, J=13.5 and 6.4 Hz), 0.95 (s, 3H), 0.78 (s, 3H). HRMS calculated for $C_{23}H_{35}N_4O_2F_2$[M+H]$^+$ 437.2683; found 437.2809.

Alternative Route Via Modification of Ring A tert-butyl (1S,5S)-6-(4-bromophenyl)-9,9-dimethyl-3,6-diazabicyclo[3.2.2]nonane-3-carboxylate—Intermediate F-2

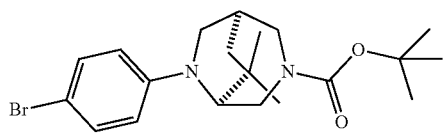 [SMILES: CC(C)(C)OC(=O)N1C[C@@H]2CN(c3ccc(Br)cc3)[C@H](C1)C(C)(C)C2]

In a first step, using method E, a solution of (1 S,5S)-9,9-dimethyl-6-phenyl-3,6-diazabicyclo[3.2.2]nonan-2-one (682 mg, 2.80 mmol) in tetrahydrofuran (11.1 mL) was reacted with a 1.0 M solution of lithium aluminium hydride (5.6 mL, 5.60 mmol). After work-up, the resulting residue was dissolved in a mixture of dichloromethane (14 mL) and triethylamine (779 µL, 5.59 mmol) and reacted with di-tert-butyl dicarbonate (834 µL, 3.63 mmol) at room temperature for 16 h. The reaction mixture was then diluted with dichloromethane (80 mL), washed with a 1 M aqueous solution of sodium hydroxide (100 mL), dried over anhydrous magnesium sulfate, filtered and concentrated under reduced pressure. The crude was purified by silica gel column chromatography to give 670 mg of tert-butyl (1 S,5S)-9,9-dimethyl-6-phenyl-3,6-diazabicyclo[3.2.2]nonane-3-carboxylate—intermediate F-1 (73%).

$^1$H NMR (500 MHz, CDCl$_3$) δ 7.29-7.20 (m, 2H), 6.73-6.61 (m, 3H), 4.57-4.24 (m, 2H), 3.48 (m, 1H), 3.31 (dd, J=10.6 and 2.6 Hz, 1H), 3.25-2.95 (m, 2H), 2.86 (d, J=13.8 Hz, 1H), 2.46 (m, 1H), 1.65-1.52 (m, 2H), 1.47 (br s, 9H), 1.08 (br s, 3H), 0.90 (s, 3H). LRMS (ESI) m/z 275 (M-tBu+2H)+.

In a second step, N-bromosuccinimide (207 mg, 1.16 mmol) was added to a solution of tert-butyl (1 S,5S)-9,9-dimethyl-6-phenyl-3,6-diazabicyclo[3.2.2]nonane-3-carboxylate (383 mg, 1.16 mmol) in tetrahydrofuran (5.8 mL). The reaction mixture was stirred at room temperature for 16 h then quenched with a saturated aqueous solution of sodium hydrosulfite (5 mL), stirred vigorously for 5 min and diluted with water (40 mL). The aqueous phase was extracted with dichloromethane (2×40 mL). The combined organic phase was dried over anhydrous magnesium sulfate, filtered and concentrated under reduced pressure. The crude was purified by silica gel column chromatography (using a 0 to 15% gradient of ethyl acetate in cyclohexane) to give tert-butyl (1S,5S)-6-(4-bromophenyl)-9,9-dimethyl-3,6-diazabicyclo[3.2.2]nonane-3-carboxylate as a colourless oil (433 mg, 91%).

$^1$H NMR (500 MHz, CDCl$_3$) δ 7.34-7.28 (m, 2H), 6.54-6.45 (m, 2H), 4.55-4.19 (m, 2H), 3.40 (m, 1H), 3.26 (dd, J=10.5 and 2.6 Hz, 1H), 3.19-2.93 (m, 2H), 2.86 (d, J=13.9 Hz, 1H), 2.46 (m, 1H), 1.69-1.42 (m, 11H), 1.08 (s, 2H), 0.88 (s, 3H). LRMS (ESI) m/z 353/355 (M-tBu+2H)+.

Method I. Buchwald Substitution of Haloaryl

A solution of tert-butyl (1S,5S)-6-(4-bromophenyl)-9,9-dimethyl-3,6-diazabicyclo[3.2.2]nonane-3-carboxylate (1 eq) in a mixture of tert-butanol and toluene (1:3 to 1:5, v/v) was reacted with palladium (II) acetate or Pd$_2$(dba)$_3$ (0.05 eq), X-Phos (0.1-0.2 eq) and sodium tert-butoxide (1-2 eq) is heated at 110° C. for 2-72 hrs. After cooling down to room temperature, the reaction mixture is filtered through a celite pad and concentrated under reduced pressure. Optionally, the resulting residue is dissolved in EtOAc and extracted with water and brine, dried over MgSO4, filtered and evaporated. The crude is purified by silica gel column chromatography using a gradient of ethyl acetate in cyclohexane or DCM, or a gradient of methanol in EtOAc.

The following intermediates have been obtained using method I tert-butyl (1S,5S)-6-(4-butylphenyl)-9,9-dimethyl-3,6-diazabicyclo[3.2.2]nonane-3-carboxylate—Intermediate F-6

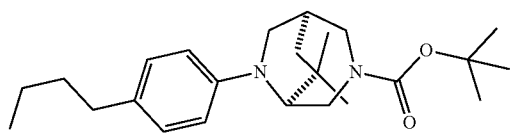

A solution of tert-butyl (1 S,5S)-6-(4-bromophenyl)-9,9-dimethyl-3,6-diazabicyclo[3.2.2]nonane-3-carboxylate (240 mg, 0.586 mmol), Pd$_2$dba$_3$ (27 mg, 5 mol %) and XPhos (56 mg, 20 mol %) in anhydrous toluene (5 mL) was degassed with nitrogen for 5 minutes. nBuLi (1.6 M in hexanes, 0.44 mL, 0.703 mmol) was then added drop-wise over 5 minutes with stirring at room temperature, before heating to 80° C., with stirring for 18 hours. The reaction mixture was then quenched with saturated aqueous NH$_4$Cl and separated between diethyl ether (40 mL) and aqueous NaHCO$_3$ (40 mL). The organic phase was washed with brine (40 mL), dried over anhydrous magnesium sulfate, filtered and concentrated to give the crude product, which was purified using flash column chromatography over silica (dry-loading onto basic alumina), eluting with 2-20% ethyl acetate/cyclohexane, to give tert-butyl (1 S,5S)-6-(4-butylphenyl)-9,9-dimethyl-3,6-diazabicyclo[3.2.2]nonane-3-carboxylate (138 mg, 61% yield) as a pale yellow oil. LCMS m/z 387.3006 found (M+H)+, $C_{24}H_{39}N_2O_2$.

| Cpd | Structure | Name | Analytical Data |
|---|---|---|---|
| F-3 | 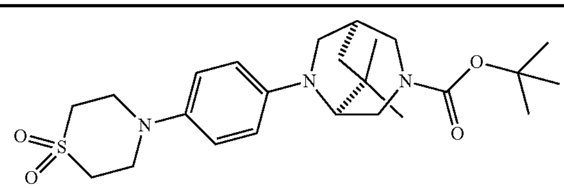 | tert-butyl (1S,5S)-6-(4-(1,1-dioxidothiomorpholino)phenyl)-9,9-dimethyl-3,6-diazabicyclo[3.2.2]nonane-3-carboxylate | HRMS calculated for $C_{24}H_{38}N_3O_4S$ [M + H-t-Bu]$^+$ 408.1957; found 408.2290. |
| F-4 | 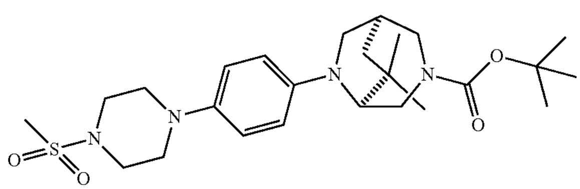 [SMILES: CC(C)(C)OC(=O)N1C[C@@H]2CN(c3ccc(N4CCN(S(C)(=O)=O)CC4)cc3)[C@H](C1)C(C)(C)C2] | (1R,5S)-6-(4-ethoxyphenyl)-9,9-dimethyl-3,6-diazabicyclo[3.2.2]nonane | $^1$H NMR (500 MHz, CDCl$_3$) δ 6.93 (d, J = 8.6 Hz, 2H), 6.60 (d, J = 8.6 Hz, 2H), 4.55-4.20 (m, 2H), 3.46-3.36 (m, 5H), 3.32-3.26 (m, 1H), 3.22-3.09 (m, 6H), 2.90-2.82 (m, 4H), 2.52-2.40 (m, 1H), 1.62-1.40 (m, 11H), 1.07 (s, 3H), 0.89 (s, 3H). HRMS calculated for $C_{25}H_{41}N_4O_4S$ [M + H]$^+$ 493.2849; found 408.2998 |
| F-5 | 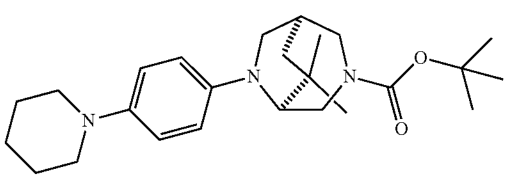 [SMILES: CC(C)(C)OC(=O)N1C[C@@H]2CN(c3ccc(N4CCCCC4)cc3)[C@H](C1)C(C)(C)C2] | tert-butyl (1S,5S)-9,9-dimethyl-6-(4-(piperidin-1-yl)phenyl)-3,6-diazabicyclo[3.2.2]nonane-3-carboxylate | LCMS m/z 414.3212 found (M + H)$^+$, $C_{25}H_{40}N_3O_2$. |
| F-6 | | tert-butyl (1S,5S)-9,9-dimethyl-6-(4-(methyl(2-(methylsulfonyl)ethyl)amino)phenyl)-3,6-diazabicyclo[3.2.2]nonane-3-carboxylate | HRMS calculated for $C_{24}H_{40}N_3O_4S$ [M + H]$^+$ 466.2740; found 466.2817. | tert-butyl (1 S,5S)-6-(4-((2-hydroxyethyl)thio)phenyl)-9,9-dimethyl-3,6-diazabicyclo[3.2.2]nonane-3-carboxylate—Intermediate F-7

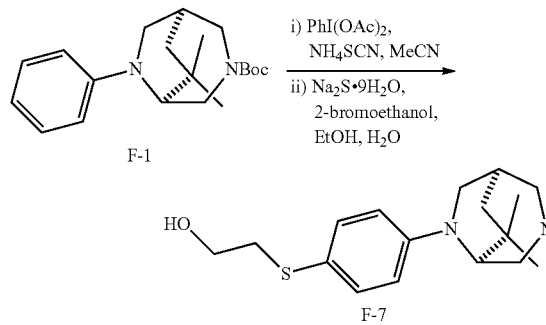

PhI(OAc)$_2$ (362 mg, 1.12 mmol) was added to a solution of tert-butyl (1S,5S)-9,9-dimethyl-6-phenyl-3,6-diazabicyclo[3.2.2]nonane-3-carboxylate (337 mg, 1.02 mmol) and NH$_4$SCN (233 mg, 3.06 mmol) in MeCN (10 mL). The reaction mixture was stirred at rt for 3 h and then diluted with H$_2$O (100 mL). The aqueous layer was extracted with DCM (3×80 mL). The combined organic layers was dried over MgSO$_4$ and filtered. The solvent was removed under reduced pressure and the crude was purified by chromatography (EtOAc/cyclohexane 0→25%) to afford tert-butyl (1 S,5S)-9,9-dimethyl-6-(4-thiocyanatophenyl)-3,6-diazabicyclo[3.2.2]nonane-3-carboxylate as a white foam (362 mg, 91%). $^1$H NMR (500 MHz, Chloroform-d) δ 7.50-7.39 (m, 2H), 6.69-6.60 (m, 2H), 4.60-4.21 (m, 2H), 3.47 (d, J=18.5 Hz, 1H), 3.31 (dd, J=10.8, 2.7 Hz, 1H), 3.24-2.81 (m, 3H), 2.48 (m, 1H), 1.65-1.57 (m, 1H), 1.51-1.40 (m, 10H), 1.10 (s, 3H), 0.90 (s, 3H). MS (ESI) m/z 410 [M+Na]$^+$.

A solution of Na$_2$S·9H$_2$O (223 mg, 0.929 mmol) in H$_2$O (0.5 mL) was added to a solution of tert-butyl (1 S,5S)-9,9-dimethyl-6-(4-thiocyanatophenyl)-3,6-diazabicyclo[3.2.2]nonane-3-carboxylate (360 mg, 0.929 mmol) and 2-bromoethanol (73 μL, 1.02 mmol) in EtOH (2.1 mL). The reaction mixture was stirred at 60° C. for 3 h. After cooling to rt, the mixture was diluted with H$_2$O (80 mL) and extracted with DCM (3×60 mL). The combined organic layers was washed with brine (100 mL), dried over MgSO$_4$ and filtered. The solvent was removed under reduced pressure and the crude was purified by chromatography (EtOAc/cyclohexane 0→50%) to afford tert-butyl (1 S,5S)-6-(4-((2-hydroxyethyl)thio)phenyl)-9,9-dimethyl-3,6-diazabicyclo[3.2.2]nonane-3-carboxylate as a colourless oil (73 mg, 19%). $^1$H NMR (500 MHz, Chloroform-d) δ 7.37-7.29 (m, 2H), 6.59-6.52 (m, 2H), 4.53-4.20 (m, 2H), 3.75-3.60 (m, 2H), 3.44 (m, 1H), 3.27 (dd, J=10.5, 2.6 Hz, 1H), 3.20-2.94 (m, 2H), 2.92 (t, J=5.9 Hz, 2H), 2.86 (d, J=14.0 Hz, 1H), 2.53-2.34 (m, 2H), 1.56 (t, J=13.6 Hz, 1H), 1.42 (s, 10H), 1.07 (s, 3H), 0.88 (s, 3H). MS (ESI) m/z 429 [M+Na]$^+$.

Method J. Boc Deprotection and Formation of Urea

In a first step, a suspension or solution of N-tert-butoxycarbonyl carbamate in a 4.0 M solution of hydrochloric acid with optional DCM co-solvent is stirred at room temperature for 0.5-2 hrs, then concentrated under reduced pressure. The residue is then converted to the desired urea using method H.

In an example, a suspension of tert-butyl (1S,5S)-6-(4-(1,1-dioxidothiomorpholino)phenyl)-9,9-dimethyl-3,6-diazabicyclo[3.2.2]nonane-3-carboxylate (F-3) (1.70 g, 3.67 mmol) in a 4.0 M solution of hydrochloric acid in dioxane (18 mL) was stirred at room temperature for 1 hrs, then concentrated under reduced pressure. The residue was then dissolved in a mixture of dichloromethane (24 mL) and N,N-diisopropylethylamine (2.4 mL, 13.8 mmol) and reacted with triphosgene (410 mg, 1.38 mmol) and thiomorpholine-1,1-dioxide (745.2 mg, 5.52 mmol). After work-up and silica gel column chromatography, 1.25 g of (1,1-dioxidothiomorpholino)((1 S,5S)-6-(4-(1,1-dioxidothiomorpholino)phenyl)-9,9-dimethyl-3,6-diazabicyclo[3.2.2]nonan-3-yl)methanone (86%) were obtained (Example 8).

The following example compounds were prepared by the aforementioned methodology, using the appropriately substituted reagent.

| Example | Structure | Name | Analytical Data |
|---|---|---|---|
| 31 | 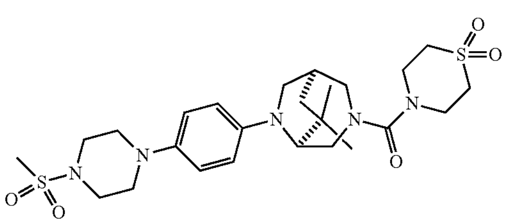 [SMILES: CC1(C)C[C@@H]2CN(C(=O)N3CCS(=O)(=O)CC3)C[C@H]1N(c1ccc(N3CCN(S(C)(=O)=O)CC3)cc1)C2] | ((1S,5S)-9,9-dimethyl-6-(4-(4-(methylsulfonyl)-1λ4-piperazin-1-yl)phenyl)-3,6-diazabicyclo[3.2.2]nonan-3-yl)(1,1-dioxido thiomorpholino) methanone | 1H NMR (500 MHz, DMSO-d6) δ 6.89-6.85 (m, 2H), 6.62-6.57 (m, 2H), 4.06 (dd, J = 13.6 and 7.9 Hz, 1H), 3.93 (dd, J = 13.5 and 4.1 Hz, 1H), 3.61-3.42 (m, 5H), 3.26-2.97 (m, 15H), 2.89 (s, 3H), 2.82 (d, J = 13.6 Hz, 1H), 2.48-2.42 (m, 1H), 1.57-1.51 (m, 1H), 1.34-1.27 (m, 1H), 0.91 (s, 3H), 0.77 (s, 3H). HRMS calculated for C$_{25}$H$_{40}$N$_5$O$_5$S$_2$ [M + H]$^+$ 554.2471; found 554.2481 |
| 32 | 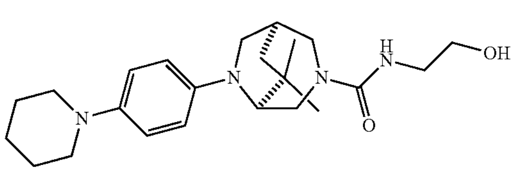 [SMILES: CC1(C)C[C@@H]2CN(C(=O)NCCO)C[C@H]1N(c1ccc(N3CCCCC3)cc1)C2] | (1S,5S)-N-(2-hydroxyethyl)-9,9-dimethyl-6-(4-(piperidin-1-yl)phenyl)-3,6-diazabicyclo[3.2.2]nonane-3-carboxamide | $^1$H NMR (CDCl$_3$, 500 MHz) δ 6.93 (d, 2H, J = 6.4 Hz), 6.57 (d, 2H, J = 6.4 Hz), 4.97 (t, 1H, J = 5.4 Hz), 4.22 (dd, 1H, J = 13.5, 7.9 Hz), 4.07 (d, 1H, J = 13.6 Hz), 3.73-3.66 (m, 2H), 3.46-3.34 (m, 3H), 3.32-3.25 (m, 1H), 3.20-3.14 (m, 2H), 3.00-2.94 (m, 4H), 2.56 (q, 1H, J = 7.2 Hz), 2.48 (t, 1H, J = 6.9 Hz), 1.74-1.69 (m, 4H), 1.60 (d, 1H, J = 13.7 Hz), 1.55-1.49 (m, 2H), 1.44 (dd, 1H, J = 13.7, 6.5 Hz), 1.07-1.03 (m, 4H), 0.89 (s, 3H). LCMS m/z 401.2888 found (M + H)$^+$, 401.2911 calculated for C$_{23}$H$_{37}$N$_4$O$_2$. |

-continued

| Example | Name | Analytical Data |
|---|---|---|
| 33 | (1S,5S)-6-(4-butylphenyl)-N-(2-hydroxyethyl)-9,9-dimethyl-3,6-diazabicyclo[3.2.2]nonane-3-carboxamide | $^1$H NMR (CDCl$_3$, 500 MHz) δ 7.06 (d, 2H, J = 8.7 Hz, ArH), 6.56 (d, 2H, J = 8.7 Hz, ArH), 4.94 (t, 1H, J = 5.0 Hz), 4.23 (dd, 1H, J = 13.5, 8.4 Hz), 4.11-4.06 (m, 1H), 3.72-3.68 (m, 2H), 3.48 (d, 1H, J = 3.5 Hz), 3.44-3.35 (m, 2H), 3.30 (dd, 1H, J = 10.3, 2.2 Hz), 3.22-3.16 (m, 2H), 2.96 (d, 1H, J = 13.6 Hz), 2.53-2.47 (m, 3H), 1.63-1.53 (m, 4H), 1.45 (dd, 1H, J = 13.7, 6.6 Hz), 1.39-1.32 (m, 2H), 1.06 (s, 3H), 0.92 (t, 3H, J = 7.4 Hz), 0.90 (s, 3H). LCMS m/z 374.2799 found (M + H)$^+$, 374.2802 calculated for C$_{22}$H$_{36}$N$_3$O$_2$ |
| 34 | (1S,5S)-N-(2-Hydroxyethyl)-6-(4-((2-hydroxyethyl)thio)phenyl)-9,9-dimethyl-3,6-diazabicyclo[3.2.2]nonane-3-carboxamide | (500 MHz, CDCl$_3$) δ 7.35 (d, J = 8.7 Hz, 2H), 6.57 (d, J = 8.8 Hz, 2H), 5.23 (br, 1H), 4.22 (dd, J = 13.8, 7.9 Hz, 1H), 4.14 (m, 1H), 3.73-3.62 (m, 4H), 3.48 (d, J = 4.2 Hz, 1H), 3.45-3.34 (m, 2H), 3.29 (dd, J = 10.6, 2.6 Hz, 1H), 3.22-3.12 (m, 2H), 2.99-2.90 (m, 3H), 2.65 (br, 1H), 2.50 (m, 1H), 2.33-1.86 (br, 1H), 1.62 (d, J = 13.8 Hz, 1H), 1.52-1.42 (m, 1H), 1.07 (s, 3H), 0.90 (s, 3H). HRMS (ESI) for C$_{20}$H$_{32}$N$_3$O$_3$S ([M + H]$^+$): Calculated 394.2164; Observed 394.2172. |
| 35 | (1S,5S)-6-(4-Bromophenyl)-N-(2-hydroxyethyl)-9,9-dimethyl-3,6-diazabicyclo[3.2.2]nonane-3-carboxamide | $^1$H NMR (500 MHz, CDCl$_3$) δ 7.34-7.29 (m, 2H), 6.58-6.43 (m, 2H), 5.17 (br, 1H), 4.25 (dd, J = 13.6, 8.0 Hz, 1H), 4.15 (dd, J = 13.8, 4.5 Hz, 1H), 3.74-3.64 (m, 2H), 3.52-3.36 (m, 3H), 3.27 (dd, J = 10.6, 2.5 Hz, 1H), 3.20-3.05 (m, 2H), 2.94 (d, J = 13.6 Hz, 1H), 2.50 (m, 1H), 1.62 (d, J = 13.8 Hz, 1H), 1.50-1.41 (m, 2H), 1.07 (s, 3H), 0.89 (s, 3H). HRMS (ESI) for C$_{18}$H$_{27}$BrN$_3$O$_2$ ([M + H]$^+$): Calculated 396.1281; Observed 396.1257. |
| 36 | (1S,5S)-N-(2-hydroxyethyl)-9,9-dimethyl-6-phenyl-3,6-diazabicyclo[3.2.2]nonane-3-carboxamide | 1H NMR (500 MHz, Acetone-d6) _ 7.20-7.12 (m, 2H), 6.71-6.65 (m, 2H), 6.59 (tt, J = 7.3, 1.1 Hz, 1H), 6.15 (t, J = 5.4 Hz, 1H), 4.46-4.28 (m, 2H), 3.60 (m, 1H), 3.56 (t, J = 5.5 Hz, 2H), 3.34-3.26 (m, 4H), 3.20 (dt, J = 10.4, 2.6 Hz, 1H), 3.02 (dd, J = 13.3, 1.3 Hz, 1H), 2.88 (d, J = 13.7 Hz, 1H), 2.50 (m, 1H), 1.61 (m, 1H), 1.42 (m, 1H), 1.06 (s, 3H), 0.85 (s, 3H). HRMS (ESI) for C18H28N3O2 ([M + H]+): Calculated 318.2176; Observed 318.2201. |
| 62 | ((1S,5S)-9,9-dimethyl-6-(4-(methyl(2-(methylsulfonyl)ethyl)amino)phenyl)-3,6-diazabicyclo[3.2.2]nonan-3-yl)(1,1-dioxidothiomorpholino)methanone | $^1$H NMR (500 MHz, Chloroform-d) δ 6.76 (br s, 2H), 6.61 (br s, 2H), 4.09 (dd, 1H, J = 13.3, 7.9 Hz), 3.95 (d, 1H, J = 8.8 Hz), 3.60-3.55 (m, 4H), 3.49-3.47 (m, 4H), 3.26-3.21 (m, 4H), 3.18-3.16 (m, 2H), 3.09-3.04 (m, 3H), 3.00 (s, 3H), 2.83 (d, 1H, J = 13.5 Hz), 2.73 (br s, 2H), 2.47-2.44 (m, 1H), 1.56 (d, 1H, J = 13.6 Hz), 1.31 (dd, 1H, J = 13.7, 6.4 Hz), 0.92 (s, 3H), 0.79 (s, 3H) ppm. HRMS calculated for C$_{24}$H$_{39}$N$_4$O$_5$S$_2$ [M + H]$^+$ 527.2356; found 527.2309. |

Example 37—(1 S,5S)-6-(4-Formylphenyl)-N-(2-hydroxyethyl)-9,9-dimethyl-3,6-diazabicyclo[3.2.2]nonane-3-carboxamide

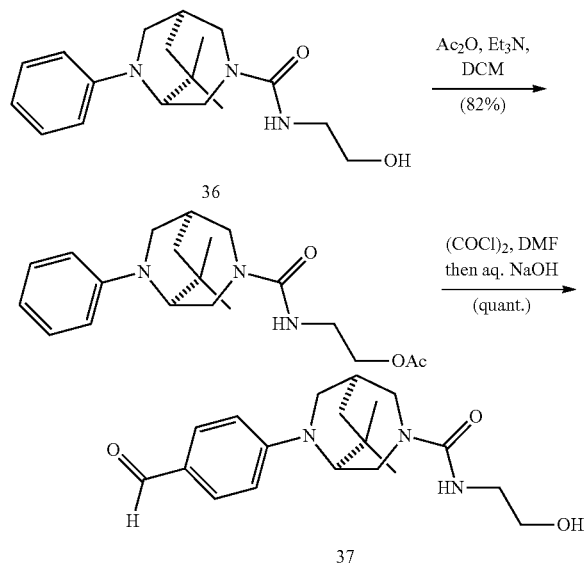

Ac$_2$O (447 μL, 4.73 mmol) was added to a solution of (1 S,5S)—N-(2-hydroxyethyl)-9,9-dimethyl-6-phenyl-3,6-diazabicyclo[3.2.2]nonane-3-carboxamide (1.0 g, 3.15 mmol) and in DCM (16 mL). The reaction mixture was stirred at rt for 16 h and then diluted with DCM (100 mL). The organic layer was washed with H$_2$O (100 mL), dried over MgSO$_4$ and filtered. The solvent was removed under reduced pressure and the crude was purified by chromatography (EtOAc/DCM 0→100%) to afford 2-((1 S,5S)-9,9-dimethyl-6-phenyl-3,6-diazabicyclo[3.2.2]nonane-3-carboxamido)ethyl acetate as a white foam (933 mg, 82%). $^1$H NMR (500 MHz, Chloroform-d) δ 7.28-7.22 (m, 2H), 6.70 (m, 1H), 6.67-6.62 (m, 2H), 4.91 (br, 1H), 4.29 (dd, J=13.4, 8.4 Hz, 1H), 4.25-4.16 (m, 2H), 4.09 (ddd, J=12.8, 4.6, 1.8 Hz, 1H), 3.61-3.42 (m, 3H), 3.32 (dd, J=10.5, 2.5 Hz, 1H), 3.22 (dt, J=10.5, 2.7 Hz, 1H), 3.16 (dd, J=12.9, 1.4 Hz, 1H), 2.91 (d, J=13.7 Hz, 1H), 2.52 (m, 1H), 2.08 (s, 3H), 1.62 (d, J=13.7 Hz, 1H), 1.46 (dd, J=13.7, 6.5 Hz, 1H), 1.06 (s, 3H), 0.91 (s, 3H). MS (ESI) m/z 360 [M+H]$^+$.

Oxalyl chloride (192 μL, 2.26 mmol) was added dropwise to a solution of 2-((1S,5S)-9,9-dimethyl-6-phenyl-3,6-diazabicyclo[3.2.2]nonane-3-carboxamido)ethyl acetate (203 mg, 0.565 mmol) in DMF (2.8 mL) at 0° C. The reaction mixture was stirred at rt for 3 h. 2 M NaOH (2.8 mL) was added and the mixture was stirred at rt for a further 16 h before it was diluted with EtOAc (40 mL). The organic layer was washed with H$_2$O (3×40 mL), dried over MgSO$_4$ and filtered. The solvent was removed under reduced pressure and the crude was purified by chromatography (THF/DCM 0→100%) to afford a white foam (238 mg, quant.). $^1$H NMR (500 MHz, Chloroform-d) δ 9.70 (s, 1H), 7.73 (d, J=8.6 Hz, 2H), 6.68 (d, J=8.6 Hz, 2H), 5.52 (br, 1H), 4.33-4.18 (m, 2H), 3.94 (m, 1H), 3.75-3.65 (m, 2H), 3.61 (d, J=4.3 Hz, 1H), 3.44-3.34 (m, 3H), 3.30 (d, J=11.2 Hz, 1H), 3.13 (d, J=13.3 Hz, 1H), 2.92 (d, J=13.7 Hz, 1H), 2.52 (m, 1H), 1.66 (d, J=13.9 Hz, 1H), 1.49 (dd, J=13.9, 6.6 Hz, 1H), 1.09 (s, 3H), 0.89 (s, 3H). $^{13}$C NMR (126 MHz, Chloroform-d) δ 190.43, 159.47, 153.75, 132.39, 125.55, 110.37, 63.22, 61.13, 50.53, 49.66, 47.90, 44.00, 35.59, 35.41, 31.99, 31.93, 28.82. HRMS (ESI) for C$_{19}$H$_{28}$N$_3$O$_3$ ([M+H]$^+$): Calculated 346.2130; Observed 346.2122.

Example 38

2-((1S,5S)-6-(4-ethoxyphenyl)-9,9-dimethyl-3,6-diazabicyclo[3.2.2]nonan-3-yl)-4,5-dihydrooxazole

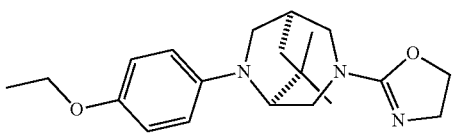 [SMILES: CCOc1ccc(N2C[C@H]3CN(C4=NCCO4)C[C@@H]2C(C)(C)C3)cc1]

Mesyl chloride (546 μL, 7.05 mmol) was added to a solution of (1 S,5S)—N-(2-hydroxyethyl)-6-(4-ethoxyphenyl)-9,9-dimethyl-3,6-diazabicyclo[3.2.2]nonane-3-carboxamide (Example 12) (1.70 g, 4.70 mmol) in a mixture of dichloromethane (16 mL) and triethylamine (9.40 mmol). The reaction mixture was stirred at room temperature for 1 hour then water (40 mL) was added and the aqueous phase extracted with dichloromethane (2×20 mL). The combined organic layers were dried over anhydrous magnesium sulfate, filtered and evaporated under reduced pressure. The resulting residue was dissolved in dimethylformamide (16 mL) and sodium methanesulfinate (930 mg, 7.74 mmol) was added. The mixture was stirred at 100° C. for 24 h. After cooling down to room temperature, ethyl acetate (50 mL) was added and the organic phase was washed with a 1:1 water/brine mixture (3×50 mL), dried over anhydrous magnesium sulfate, filtered and evaporated under reduced pressure. The resulting residue was purified by silica gel column chromatography using a gradient of acetone (5 to 100%) in cyclohexane to afford 432 mg of 2-((1 S,5S)-6-(4-ethoxyphenyl)-9,9-dimethyl-3,6-diazabicyclo[3.2.2]nonan-3-yl)-4,5-dihydrooxazole (27%).

$^1$H NMR (500 MHz, CDCl$_3$) δ 6.89-6.80 (m, 2H), 6.59-6.50 (m, 2H), 4.35-4.26 (m, 2H), 4.25-4.15 (m, 2H), 3.97 (q, J=7.0 Hz, 2H), 3.79 (t, J=8.5 Hz, 2H), 3.40 (d, J=4.2 Hz, 1H), 3.29 (dd, J=10.2, 2.3 Hz, 1H), 3.21-3.13 (m, 2H), 3.03 (d, J=13.6 Hz, 1H), 2.46 (m, 1H), 1.65 (d, J=13.7 Hz, 1H), 1.44 (dd, J=13.8, 6.5 Hz, 1H), 1.38 (t, J=7.0 Hz, 3H), 1.07 (s, 3H), 0.89 (s, 3H). HRMS calculated for C$_{20}$H$_{30}$N$_3$O$_2$ [M+H]$^+$ 344.2333; found 344.2335.

V. General Method for the Synthesis of Compounds with an N-Alkyl Linker

Method K

A mixture of the bridged homopiperazine derivative (1 eq.), the alkyl bromide (or chloride) (1 to 1.5 eq.) and cesium carbonate (or triethylamine, N,N-diisopropylethylamine or potassium carbonate) (1.5 to 5 eq.) in anhydrous acetonitrile (or dimethylformamide or tetrahydrofuran or dichloromethane) (0.2 to 1 M) was stirred at 90° C. under microwave irradiation (or at room temperature up to 80° C. without MW) for 3 to 4 hours (or for 12 to 96 hours without MW). After cooling down to room temperature, the reaction mixture was either filtered and evaporated under reduced pressure or diluted with dichloromethane (or ethyl acetate) and washed with water and brine. The combined organic layers were dried over anhydrous magnesium sulfate, filtered and evaporated under reduced pressure. In both cases, the resulting residue was purified by silica gel column chromatography using a gradient of methanol in ethyl acetate or a gradient of ethyl acetate in cyclohexane or a gradient of acetone in dichloromethane. In some examples, the crude product was purified by preparative HPLC using a gradient of methanol (10 to 100%) in water (with 0.1% of diethyl amine or formic acid in each solvent) or by both a silica gel column chromatography and a preparative HPLC. If desired, an acid salt may be prepared by treatment of this product with an acid, or anhydrous hydrogen halide solution followed by concentration under reduced pressure.

Example 39

4-((1R,5S)-6-(4-(1,1-dioxidothiomorpholino)phenyl)-9,9-dimethyl-3,6-diaza bicyclo[3.2.2]nonan-3-yl)butanenitrile (hydrochloric acid salt)

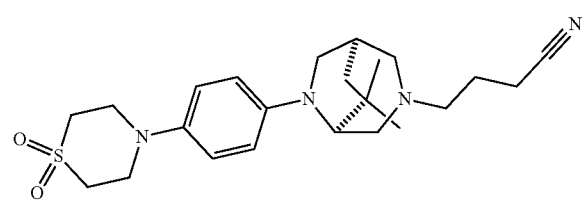 [SMILES: CC1(C)C[C@@H]2CN(CCCC#N)C[C@H]1N(c1ccc(N3CCS(=O)(=O)CC3)cc1)C2]

Using method K, a solution of 4-(4-((1R,5S)-9,9-dimethyl-3,6-diazabicyclo[3.2.2]nonan-6-yl)phenyl)thiomorpholine-1,1-dioxide (749 mg, 1.59 mmol) and bromobutyronitrile (159 µL, 1.59 mmol) in dimethylformamide (8 mL) was reacted with potassium carbonate (661 mg, 4.78 mmol). After work-up and silica gel column chromatography, the product was stirred in a 4.0 M solution of hydrogen chloride in dioxane (3.2 mL) for 1 hour at room temperature and concentrated under reduced pressure to give 441.4 mg of 4-((1R,5S)-6-(4-(1,1-dioxidothiomorpholino)phenyl)-9,9-dimethyl-3,6-diazabicyclo[3.2.2]nonan-3-yl)butanenitrile hydrochloric acid salt (51%) were obtained.

$^1$H NMR (500 MHz, MeOD-$d_4$) δ 6.97 (d, 2H, J=8.5 Hz), 6.59 (d, 2H, J=8.5 Hz), 3.61-3.54 (m, 4H), 3.40 (d, 1H, J=5.0 Hz), 3.29-3.23 (m, 1H), 3.22-3.09 (m, 6H), 3.08-3.01 (m, 1H), 2.56-2.48 (m, 3H), 2.47-2.41 (m, 1H), 2.40-2.34 (m, 1H), 2.29 (d, 1H, J=11.6 Hz), 2.19-2.14 (m, 1H), 1.94-1.73 (m, 3H), 1.37 (dd, 1H, J=13.1 and 6.4 Hz), 1.21 (s, 3H), 0.85 (s, 3H). HRMS calculated for $C_{23}H_{35}N_4O_2S$ [M+H]$^+$ 431.2436; found 431.2386.

The following example compounds were prepared by the aforementioned methodology, using the appropriately substituted reagent.

| Example | Structure | Name | Analytical Data |
|---|---|---|---|
| 40 | 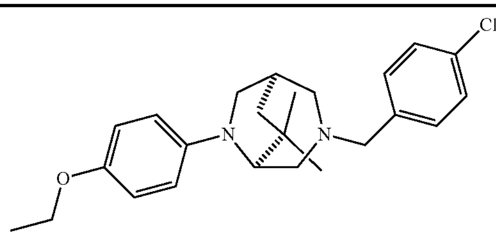 | (1R,5S)-3-(4-chlorobenzyl)-6-(4-ethoxyphenyl)-9,9-dimethyl-3,6-diazabicyclo[3.2.2]nonane | 1H NMR (500 MHz, CDCl3) δ 7.29 (m, 4H), 6.89-6.83 (m, 2H), 6.57-6.52 (m, 2H), 4.00 (q, J = 7.0 Hz, 2H), 3.54-3.43 (m, 2H), 3.33-3.25 (m, 2H), 3.16-3.06 (m, 2H), 3.03-2.95 (m, 1H), 2.36 (d, J = 11.3 Hz, 1H), 2.34-2.30 (br s, 1H), 2.22 (d, J = 11.6 Hz, 1H), 1.95 (dd, J = 12.9 and 1.8 Hz, 1H), 1.41 (t, J = 7.0 Hz, 3H), 1.35 (dd, J = 12.9 and 6.4 Hz, 1H), 1.19 (s, 3H), 0.88 (s, 3H). HRMS calculated C24H32ClN2O [M + H]+ 399.2203; found 399.2277. |
| 41 | 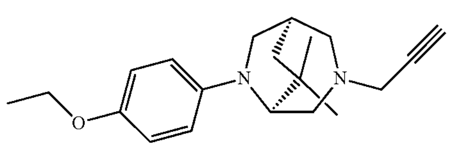 [SMILES: C#CCN1C[C@@H]2CN(c3ccc(OCC)cc3)[C@H](C1)C(C)(C)C2] | (1R,5S)-6-(4-ethoxyphenyl)-9,9-dimethyl-3-(prop-2-yn-1-yl)-3,6-diazabicyclo[3.2.2]nonane | 1H NMR (500 MHz, CDCl3) δ 6.92-6.79 (m, 2H), 6.62-6.49 (m, 2H), 3.99 (q, J = 7.0 Hz, 2H), 3.44-3.32 (m, 3H), 3.28 (dd, J = 10.0 and 2.5 Hz, 1H), 3.20-3.09 (m, 2H), 2.99-2.89 (m, 1H), 2.55 (dd, J = 22.8 and 11.4 Hz, 2H), 2.36 (t, J = 7.6 Hz, 1H), 2.19 (t, J = 2.4 Hz, 1H), 1.91 (d, J = 12.9 Hz, 1H), 1.40 (t, J = 7.0 Hz, 3H), 1.37-1.30 (m, 1H), 1.18 (s, 3H), 0.87 (s, 3H). HRMS calculated for C20H29N2O [M + H]+ 313.2280; found 313.2298. |
| 42 | 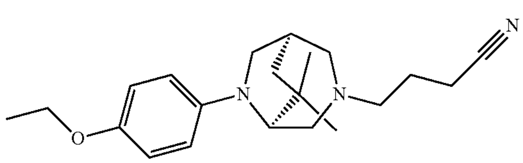 [SMILES: CCOc1ccc(N2C[C@H]3CN(CCCC#N)C[C@@H]2C(C)(C)C3)cc1] | 4-((1R,5S)-6-(4-ethoxyphenyl)-9,9-dimethyl-3,6-diazabicyclo[3.2.2]nonan-3-yl)butanenitrile | 1H NMR (500 MHz, CDCl3) δ 6.89-6.79 (m, 2H), 6.58-6.48 (m, 2H), 3.98 (q, J = 7.0 Hz, 2H), 3.32 (d, J = 4.9 Hz, 1H), 3.27 (dd, J = 10.0 and 2.4 Hz, 1H), 3.17-3.07 (m, 2H), 3.02-2.91 (m, 1H), 2.55-2.41 (m, 4H), 2.40-2.32 (m, 2H), 2.25-2.20 (m, 1H), 1.90-1.75 (m, 3H), 1.39 (t, J = 7.0 Hz, 3H), 1.38-1.33 (m, 1H), 1.17 (s, 3H), 0.87 (s, 3H). HRMS calculated for C21H32N3O [M + H]+ 342.2545; found 342.2532. |
| 43 | 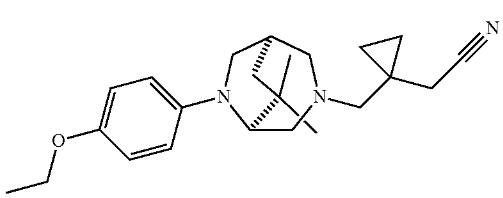 [SMILES: CCOc1ccc(N2C[C@H]3CN(CC4(CC#N)CC4)C[C@@H]2C(C)(C)C3)cc1] | 2-(1-(((1R,5S)-6-(4-ethoxyphenyl)-9,9-dimethyl-3,6-diazabicyclo[3.2.2]nonan-3-yl)methyl)cyclopropyl)acetonitrile | 1H NMR (500 MHz, DMSO-d6) δ 6.76 (d, J = 9.1 Hz, 2H), 6.51 (d, J = 9.1 Hz, 2H), 3.88 (q, J = 6.9 Hz, 2H), 3.36 (d, J = 4.8 Hz, 1H), 3.22-3.09 (m, 3H), 3.01 (dt, J = 10.2 and 2.5 Hz, 1H), 2.73 (d, J = 16.9 Hz, 1H), 2.66-2.63 (m, 1H), 2.43 (d, J = 16.9 Hz, 1H), 2.35 (br s, 1H), 2.18 (d, J = 11.6 Hz, 1H), 1.98 (d, J = 11.8 Hz, 1H), 1.85 (2 × d, J = 12.9 and 9.0 Hz, 2H), 1.32-1.28 (m, 4H), 1.18 (s, 3H), 0.78 (s, 3H), 0.61-0.56 (m, 1H), 0.51 (ddd, J = 9.4, 5.6 and 4.2 Hz, 1H), |

| Example | Structure | Name | Analytical Data |
|---|---|---|---|
| | | | 0.43 (ddd, J = 9.7, 5.6 and 4.2 Hz, 1H), 0.37-0.29 (m, 1H). HRMS calculated for C23H34N3O [M + H]+ 368.2702; found 368.2697. |
| 44 | 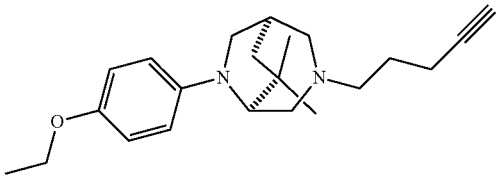 [SMILES: C#CCCCN1C[C@@H]2CN(c3ccc(OCC)cc3)[C@H](C1)C(C)(C)C2] | (1R,5S)-6-(4-ethoxyphenyl)-9,9-dimethyl-3-(pent-4-yn-1-yl)-3,6-diazabicyclo[3.2.2]nonane | 1H NMR (CDCl3, 500 MHz) δ 6.83 (d, 2H, J = 9.1 Hz), 6.52 (d, 2H, J = 9.1 Hz), 3.96 (q, 2H, J = 7.0 Hz), 3.29 (d, 1H, J = 5.0 Hz), 3.24 (dd, 1H, J = 10.0 and 2.4 Hz), 3.13-3.08 (m, 2H), 3.00-2.96 (m, 1H), 2.48-2.39 (m, 2H), 2.33-2.24 (m, 4H), 2.18 (d, 1H, J = 11.6 Hz), 1.94 (t, 1H, J = 2.7 Hz), 1.87 (d, 1H, J = 12.9 Hz), 1.74-1.63 (m, 2H), 1.37 (t, 3H, J = 7.0 Hz), 1.30 (dd, 1H, J = 12.9 and 6.3 Hz), 1.16 (s, 3H), 0.84 (s, 3H). HRMS calculated for C22H33N2O [M + H]+ 341.2587; found 341.2584. |
| 45 | 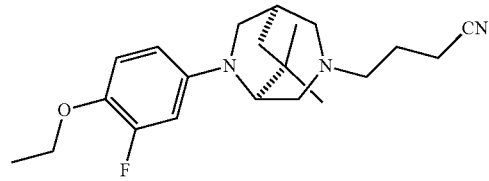 [SMILES: CCOc1ccc(N2C[C@H]3CN(CCCC#N)C[C@@H]2C(C)(C)C3)cc1F] | 4-((1R,5S)-6-(4-Ethoxy-3-fluorophenyl)-9,9-dimethyl-3,6-diazabicyclo[3.2.2]nonan-3-yl)butanenitrile | 1H NMR (500 MHz, CDCl3) δ 6.68 (t, J = 9.1 Hz, 1H), 6.66-6.57 (m, 2H), 3.96 (q, J = 6.9 Hz, 2H), 3.48 (t, J = 9.8 Hz, 1H), 3.20-3.17 (m, 1H), 3.14-3.11 (m, 1H), 3.04 (d, J = 10.1 Hz, 1H), 2.96 (t, J = 9.8 Hz, 1H), 2.59-2.44 (m, 5H), 2.36-2.30 (m, 2H), 1.89-1.78 (m, 3H), 1.39-1.32 (m, 5H), 1.10 (s, 3H), 0.90 (s, 3H). 19F NMR (470 MHz, CDCl3) δ 122.2 (s, 1F). HRMS calculated for C21H31N3OF [M + H]+ 360.2451; found 360.2446. |

Example 46

4-((1R,5S)-6-(4-Ethoxyphenyl)-9,9-dimethyl-3,6-diazabicyclo[3.2.2]nonan-3-yl)-3-hydroxybutanenitrile

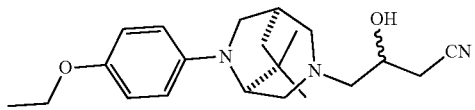 [SMILES: CCOc1ccc(N2C[C@H]3CN(CC(O)CC#N)C[C@@H]2C(C)(C)C3)cc1]

To a solution of (1R,5S)-6-(4-ethoxyphenyl)-9,9-dimethyl-3,6-diazabicyclo[3.2.2]nonane (500 mg, 1.82 mmol) and caesium carbonate (592 mg, 1.82 mmol) in anhydrous acetonitrile (15 mL) was added (R)-4-chloro-3-hydroxybutyronitrile (175 µL, 1.82 mmol) and the resultant mixture heated to 90° C. under microwave irradiation for 4 h. After allowing to cool, the mixture was filtered and the filtrate concentrated under vacuum. Pyridine (7 mL) and acetic anhydride (7 mL) were added and the resultant mixture stirred for 8 h. Water was added and the mixture extracted with ethyl acetate. Combined organic extracts were washed with a saturated aqueous solution of ammonium hydroxide (2×15 mL), dried (magnesium sulphate), filtered and concentrated under vacuum. Silica gel chromatography using a gradient of ethyl acetate in cyclohexane gave (R)-1-cyano-3-((1R,5S)-6-(4-ethoxyphenyl)-9,9-dimethyl-3,6-diazabicyclo[3.2.2]nonan-3-yl)propan-2-yl acetate (383 mg, 53%). To a portion of this material (11 mg, 0.03 mmol) was added tetrahydrofuran (1 mL), methanol (0.5 mL), water (1 mL) and 6M aqueous HCl (0.2 mL) and the resulting mixture heated at reflux for 16 h. The reaction was allowed to cool, quenched with 1 M NaOH (1.2 mL) and extracted with ether. Combined organic extracts were washed with brine, dried (magnesium sulphate), filtered and concentrated under vacuum to give pure 4-((1R,5S)-6-(4-ethoxyphenyl)-9,9-dimethyl-3,6-diazabicyclo[3.2.2]nonan-3-yl)-3-hydroxybutanenitrile (9 mg, 91%).

$^1$H NMR (500 MHz, CDCl$_3$) δ 6.86 (d, J=8.8 Hz, 2H), 6.54 (d, J=8.8 Hz, 2H), 3.99 (p, J=5.4 Hz, 1H), 3.98 (q, J=6.9 Hz, 2H), 3.60 (br s, 1H), 3.35 (d, J=4.4 Hz, 1H), 3.29 (dd, J=10.1 and 2.5 Hz, 1H), 3.16-3.06 (m, 3H), 2.69 (d, J=8.8 Hz, 1H), 2.60 (dd, J=16.7 and 5.4 Hz, 1H), 2.53-2.47 (m, 3H), 2.40 (m, 1H), 2.29 (d, J=11.7 Hz, 1H), 1.77 (d, J=13.6 Hz, 1H), 1.45 (dd, J=12.9 and 6.6 Hz, 1H), 1.39 (t, J=6.9 Hz, 3H), 1.19 (s, 3H), 0.89 (s, 3H). HRMS calculated for $C_{21}H_{31}N_3O_2$ [M+H]$^+$ 358.2489; found 358.2502.

Example 47

(1R,5S)-6-(4-ethoxyphenyl)-9,9-dimethyl-3-(1-methylpiperidin-4-yl)-3,6-diazabicyclo[3.2.2]nonane

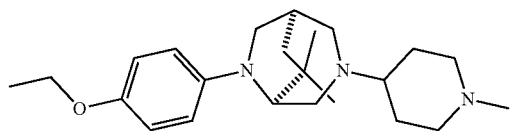 [SMILES: CCOc1ccc(N2C[C@H]3CN(C4CCN(C)CC4)C[C@@H]2C(C)(C)C3)cc1]

A solution of (1R,5S)-6-(4-ethoxyphenyl)-9,9-dimethyl-3,6-diazabicyclo[3.2.2]nonane (750 mg, 2.7 mmol) in dichloromethane (30 mL) and acetic acid (5 mL) was reacted with sodium cyanoborohydride (2.65 g, 42 mmol) and 1-methylpiperidin-4-one (750 mg, 7.6 mmol) at room temperature for 4 days (an additional 4 mL of 1-methylpiperidin-4-one were added at day 3). The reaction mixture was then neutralised with an aqueous solution of sodium bicarbonate and extracted with ethyl acetate. The combined organic layers were dried over anhydrous magnesium sulfate, filtered and evaporated under reduced pressure. The resulting residue was purified by silica gel column chromatography to give 70 mg of (1R,5S)-6-(4-ethoxyphenyl)-9,9-dimethyl-3-(1-methylpiperidin-4-yl)-3,6-diazabicyclo[3.2.2]nonane (7%).

$^1$H NMR (500 MHz, CDCl3) δ 6.89-6.82 (m, 2H), 6.57-6.50 (m, 2H), 3.99 (q, J=7.0 Hz, 2H), 3.33 (d, J=5.1 Hz, 1H), 3.25 (dd, J=10.0 and 2.4 Hz, 1H), 3.16-2.91 (m, 6H), 2.58 (d, J=11.3 Hz, 1H), 2.45 (d, J=11.6 Hz, 1H), 2.36 (s, 3H), 2.09 (s, 1H), 1.86 (d, J=13.0 Hz, 1H), 1.86 (d, J=12.8 Hz, 1H), 1.83-1.65 (m, 5H), 1.39 (t, J=7.0 Hz, 3H), 1.32-1.29 (m, 1H), 1.16 (s, 3H), 0.85 (s, 3H). HRMS calculated for $C_{23}H_{37}N_3O$ [M+H]$^+$ 372.3015; found 372.3384.

Example 48

(1R,5S)-3-(2-(1H-pyrazol-4-yl)ethyl)-6-(4-ethoxyphenyl)-9,9-dimethyl-3,6-diazabicyclo[3.2.2]nonane 6-(4-ethoxyphenyl)-9,9-dimethyl-3-(2-(1-(methylsulfonyl)-1H-pyrazol-4-yl)ethyl)-3,6-diazabicyclo[3.2.2]nonane (420 mg, 94%). $^1$H NMR (500 MHz, DMSO-d$_6$) δ 8.10 (s, 1H), 7.88 (s, 1H), 6.76 (d, J=9.0 Hz, 2H), 6.50 (d, J=7.0 Hz, 2H), 3.89 (q, J=7.0 Hz, 2H), 3.44 (s, 3H), 3.18-3.12 (m, 2H), 3.12-2.98 (m, 2H), 2.68-2.52 (m, 4H), 2.32 (s, 1H), 2.14 (dd, J=11.4, 3.5 Hz, 2H), 1.69 (d, J=12.8 Hz, 1H), 1.26 (t, J=7.0 Hz, 3H), 1.24-1.14 (m, 2H), 0.98 (s, 3H), 0.74 (s, 3H). MS (ESI) m/z 447 [M+H]$^+$.

(1R,5S)-6-(4-ethoxyphenyl)-9,9-dimethyl-3-(2-(1-(methylsulfonyl)-1H-pyrazol-4-yl)ethyl)-3,6-diazabicyclo[3.2.2]nonane (140 mg, 0.31 mmol) was dissolved in ethanol (3 mL) and water (3 mL). KOH (112 mg, 2 mmol) was added, the reaction mixture was refluxed for 12 hrs, then diluted with EtOAc (20 mL) and extracted with saturated aqueous NH4Cl (2×20 mL) and water (20 mL). The organic layer was dried over MgSO$_4$ and filtered. The solvent was

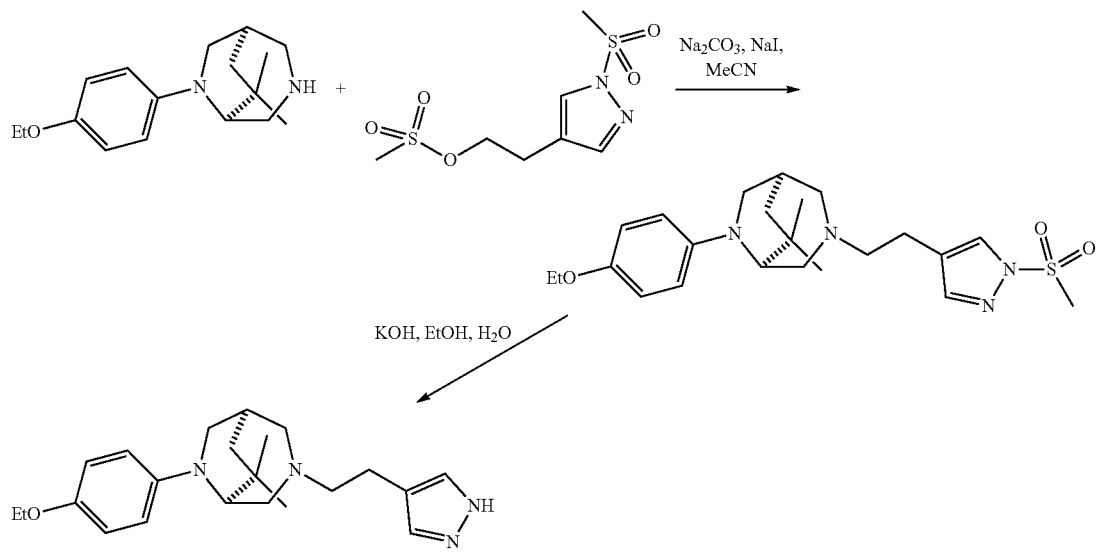

2-(1H-pyrazol-4-yl)ethan-1-ol (300 mg, 2.7 mmol) was dissolved in DCM (10 mL), DIPEA (1.9 mL) was added and the solution cooled at 0° C. Methanesulfonyl chloride (620 μL, 8.3 mmol) was added, the solution was stirred for 1 h, then it was diluted with DCM (20 mL) and extracted with 10% aqueous citric acid (2×20 mL) and water (20 mL). The organic layer was dried over MgSO$_4$ and filtered. The solvent was removed under reduced pressure and the crude was purified by chromatography (cyclohexane/EtOAc 0→100%) to afford 2-(1-(methylsulfonyl)-1H-pyrazol-4-yl)ethyl methanesulfonate (450 mg, 62%). $^1$H NMR (500 MHz, DMSO-d$_6$) δ 8.20 (d, J=0.8 Hz, 1H), 7.92 (d, J=0.8 Hz, 1H), 4.39 (t, J=6.6 Hz, 2H), 3.50 (s, 3H), 3.17 (s, 3H), 2.91 (t, J=6.6, 0.9 Hz, 2H).

(1R,5S)-6-(4-ethoxyphenyl)-9,9-dimethyl-3,6-diazabicyclo[3.2.2]nonane (274 mg, 1 mmol) was dissolved in acetonitrile (10 mL), 2-(1-(methylsulfonyl)-1H-pyrazol-4-yl)ethyl methanesulfonate (450 mg, 1.7 mmol), Na2CO3 (210 mg, 2 mmol) and NaI (300 mg, 2 mmol) were added and the reaction mixture was heated at reflux for 12 hrs. The solvent was evaporated, the residue was partitioned between EtOAc (30 mL) and water (30 mL), the organic layer was dried over MgSO$_4$ and filtered. The solvent was removed under reduced pressure and the crude was purified by chromatography (DCM/EtOAc 0→40%) to afford (1R,5S)- removed under reduced pressure to afford (1R,5S)-3-(2-(1H-pyrazol-4-yl)ethyl)-6-(4-ethoxyphenyl)-9,9-dimethyl-3,6-diazabicyclo[3.2.2]nonane (90 mg, 79%). $^1$H NMR (500 MHz, DMSO-d$_6$) δ 12.48 (s, 1H), 7.50 (br s, 1H), 7.35 (br s, 1H), 6.76 (d, J=8.9 Hz, 2H), 6.51 (d, J=9.0 Hz, 2H), 3.89 (q, J=6.9 Hz, 2H), 3.23-3.11 (m, 2H), 3.11-2.97 (m, 2H), 2.66-2.53 (m, 4H), 2.32 (s, 1H), 2.15 (t, J=12.0 Hz, 2H), 1.77 (d, J=12.8 Hz, 1H), 1.27 (t, J=7.0 Hz, 4H), 1.24-1.20 (m, 1H), 1.07 (s, 3H), 0.76 (s, 3H). MS (ESI) m/z 369 [M+H]$^+$.

VI. General Method for the Synthesis of Compounds with an N-Acyl Linker

Method L

To a mixture of the bridged homopiperazine derivative (1 eq.) and N,N-diisopropylethylamine (1 to 5 eq.) in anhydrous dichloromethane (0.2 to 1 M) was added dropwise the acid chloride (1 to 1.5 eq.). After stirring at room temperature for 2 to 16 h the reaction mixture was diluted with dichloromethane (or ethyl acetate) and washed with water and brine. The organic layer was dried over anhydrous magnesium sulfate, filtered and evaporated under reduced pressure. The resulting residue was purified by silica gel chromatography using a gradient of methanol in ethyl acetate or a gradient of ethyl acetate in cyclohexane.

Example 49

4-((1S,5S)-6-(4-(1,1-Dioxidothiomorpholino)phenyl)-9,9-dimethyl-3,6-diaza bicyclo[3.2.2]nonan-3-yl)-4-oxobutanenitrile

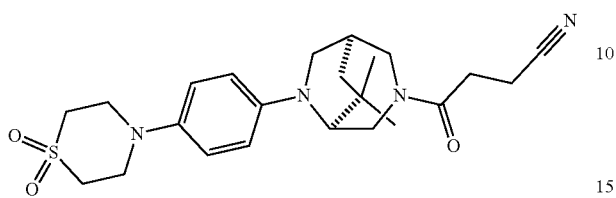

Using method J, a solution of 4-(4-((1R,5S)-9,9-dimethyl-3,6-diazabicyclo[3.2.2]nonan-6-yl)phenyl)thiomorpholine-1,1-dioxide (300 mg, 0.83 mmol) in a mixture of dichloromethane (7 mL) and N,N-diisopropylethylamine (216 µL, 1.24 mmol) was reacted with 3-cyanopropanoyl chloride (97 mg, 0.83 mmol) for 4 h. After work-up and silica gel column chromatography, 241 mg of 4-((1 S,5S)-6-(4-(1,1-dioxido thiomorpholino)phenyl)-9,9-dimethyl-3,6-diazabicyclo[3.2.2]nonan-3-yl)-4-oxobutane nitrile (66%) were obtained.

$^1$H NMR (500 MHz, CDCl$_3$) δ 6.94 (d, J=8.8 Hz, 2H), 6.60 (d, J=8.8 Hz, 2H), 4.87 (dd, J=13.9 and 3.3 Hz, 0.6H), 4.62 (dd, J=13.9 and 7.3 Hz, 0.4H), 3.97-3.90 (m, 1H), 3.63 (t, J=5.0 Hz, 4H), 3.52-3.47 (m, 1H), 3.43-3.40 (d, J=13.2 Hz, 0.4H), 3.47-3.28 (m, 1H), 3.24-3.14 (m, 5.6H), 3.01 (d, J=13.7 Hz, 0.4H), 2.92 (d, J=13.9 Hz, 0.6H), 2.82-2.51 (m, 5H), 1.57-1.43 (m, 2H), 1.06 (s, 1.2H), 1.01, (s, 1.8H), 0.94 (s, 1.2H), 0.91 (s, 1.8H). HRMS calculated for C$_{23}$H$_{33}$N$_4$O$_3$S [M+H]$^+$ 445.2273; found 445.2270.

The following example compounds were prepared by the aforementioned methodology, using the appropriately substituted reagent.

then diluted with dichloromethane, washed with a 1 M aqueous solution of potassium carbonate, a 1 M aqueous solution of hydrochloric acid and brine, dried over anhydrous sodium sulfate, filtered and concentrated under reduced pressure. The resulting residue was purified by silica gel column chromatography using a gradient of ethyl acetate in cyclohexane or a gradient of methanol in ethyl acetate.

Example 51

((1S,5S)-6-(4-ethoxyphenyl)-9,9-dimethyl-3,6-diazabicyclo[3.2.2]nonan-3-yl)(pyridin-2-yl)methanone

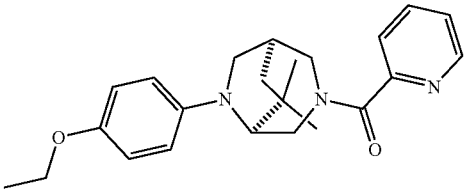 [SMILES: CCOc1ccc(N2C[C@H]3CN(C(=O)c4ccccn4)C[C@@H]2C(C)(C)C3)cc1]

Using method M, a solution of (1R,5S)-6-(4-ethoxyphenyl)-9,9-dimethyl-3,6-diazabicyclo[3.2.2]nonane (200 mg, 0.729 mmol) and picolinic acid (108 mg, 0.87 mmol) in dichloromethane (10 mL) was reacted with triethylamine (0.5 mL, 3.64 mmol), 4-dimethylaminopyridine (89 mg, 0.729 mmol) and ethylcarbodiimide hydrochloride (154 mg, 0.80 mmol) for 24 h. After work-up and silica gel column chromatography, 61 mg of ((1 S,5S)-6-(4-ethoxyphenyl)-9,9-dimethyl-3,6-diazabicyclo[3.2.2]nonan-3-yl)(pyridin-2-yl)methanone (33%) were obtained.

$^1$H NMR (CDCl$_3$, 500 MHz) (major rotamer) δ 8.59 (t, 1H, J=5.0 Hz), 7.79-7.74 (m, 1H), 7.55 (d, 1H, J=7.8 Hz), 7.35-7.29 (m, 1H), 6.87 (d, 2H, J=8.7 Hz), 6.65-6.46 (m,

| Example | Structure | Name | Analytical Data |
|---|---|---|---|
| 50 | 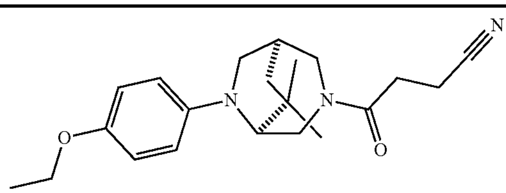 | 4-((1S,5S)-6-(4-Ethoxyphenyl)-9,9-dimethyl-3,6-diazabicyclo[3.2.2]nonan-3-yl)-4-oxobutanenitrile | $^1$H NMR (500 MHz, CDCl$_3$) δ 6.67 (dd, J = 8.8 and 1.9 Hz, 2H), 6.64-6.59 (m, 2H), 4.86 (dd, J = 14.5 and 3.2 Hz, 0.6H), 4.63 (dd, J = 13.9 and 7.6 Hz, 0.4H), 3.99 (q, J = 6.9 Hz, 2H), 3.95-3.88 (m, 1H), 3.50-3.45 (m, 1.4H), 3.38 (d, J = 8.8 Hz, 0.6H), 3.35-3.18 (m, 2H), 3.03 (d, J = 13.9 Hz, 1H), 2.82-2.60 (m, 4H), 2.59-2.49 (m, 1H), 2.18 (br s, 1H), 1.57-1.46 (m, 2H), 1.39 (t, J = 6.9 Hz, 3H), 1.07 (s, 1.4H), 1.00 (s, 1.6H), 0.94-0.88 (m, 3H). HRMS calculated for C$_{21}$H$_{30}$N$_3$O$_2$ [M + H]$^+$ 356.2333; found 356.2340. |

Method M

To a solution of the bridged homopiperazine derivative (1 eq.) and the acid (1.1 eq.) in dichloromethane (0.5 M) were added at 0° C. triethylamine (5 eq.) and 4-dimethylaminopyridine (1 eq.). After 10 mins at 0° C., ethylcarbodiimide hydrochloride (1.1 eq.) was added and the mixture stirred at room temperature for 24 hours. The reaction mixture was 2H), 5.07-4.79 (m, 1H), 4.14-3.87 (m, 3H), 3.64-3.45 (m, 1H), 3.36-3.06 (m, 4H), 2.39 (t, 1H, J=6.4 Hz), 2.02 (d, 1H, J=13.9 Hz), 1.51-1.43 (m, 1H), 1.40-1.36 (m, 3H), 0.92 (s, 3H), 0.86 (s, 3H). HRMS calculated for C$_{28}$H$_{33}$N$_4$O$_2$ [M+H]$^+$ 457.2598; found 457.2586.

The following example compounds were prepared by the aforementioned methodology, using the appropriately substituted reagent.

| Example | Structure | Name | Analytical Data |
|---|---|---|---|
| 52 | 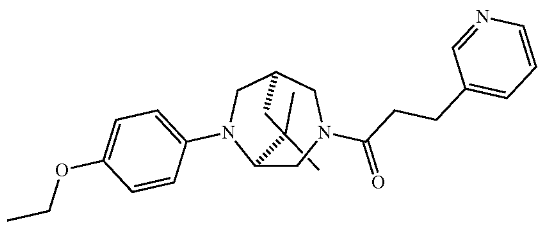 [SMILES: CCOc1ccc(N2C[C@H]3CN(C(=O)CCc4cccnc4)C[C@@H]2C(C)(C)C3)cc1] | 1-((1S,5S)-6-(4-ethoxyphenyl)-9,9-dimethyl-3,6-diazabicyclo[3.2.2]nonan-3-yl)-3-(pyridin-3-yl)propan-1-one | $^1$H NMR (DMSO-d$_6$, 500 MHz) (Major rotamer) δ 8.50 (s, 1H), 8.45 (d, 1H, J = 4.6 Hz), 7.59 (d, 1H, J = 7.8 Hz), 7.22-7.19 (m, 1H), 6.85 (d, 2H, J = 9.1 Hz), 6.56-6.53 (m, 2H), 4.86 (ddd, 1H, J = 13.8, 4.5, 1.7 Hz), 3.99-3.93 (m, 3H), 3.43-3.41 (m, 1H), 3.35-2.86 (m, 6H), 2.74-2.62 (m, 2H), 2.51-2.46 (m, 1H), 1.48-1.34 (m, 2H), 1.37 (t, 3H, J = 7.0 Hz), 0.92 (s, 3H), 0.85 (s, 3H). HRMS calculated for C$_{25}$H$_{33}$N$_3$O$_2$Na$_2$ [M + Na]$^+$ 430.2465; found 430.2450. |

Example 53

2-amino-N-(2-((1S,5S)-6-(4-ethoxyphenyl)-9,9-dimethyl-3,6-diazabicyclo[3.2.2]nonan-3-yl)-2-oxoethyl)acetimidamide

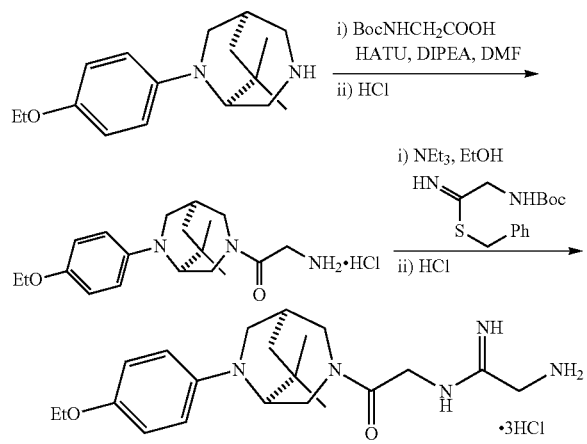

(1R,5S)-6-(4-ethoxyphenyl)-9,9-dimethyl-3,6-diazabicyclo[3.2.2]nonane (411 mg, 1.5 mmol) was dissolved in dry DMF (8 mL), HATU (684 mg, 1.8 mmol), DIPEA (1.7 mL) and Boc-N-glycine (262 mg, 1.5 mmol) were added and the reaction mixture was stirred for 72 hrs at room temperature. The reaction mixture was diluted with AcOEt (100 mL) and extracted with water (50 mL), 10% aqueous citric acid (50 mL), saturated Na$_2$CO$_3$(50 mL) and water (50 mL). The organic layer was dried over MgSO$_4$ and filtered. The solvent was removed under reduced pressure and the crude was purified by chromatography (EtOAc/cyclohexane 0→50%) to afford tert-butyl (2-((1 S,5S)-6-(4-ethoxyphenyl)-9,9-dimethyl-3,6-diazabicyclo[3.2.2]nonan-3-yl)-2-oxoethyl) carbamate (620 mg, 96%). H NMR (500 MHz, DMSO-d$_6$) δ 6.79 (d, J=8.8 Hz, 2H), 6.76-6.67 (m, 1H), 6.58 (d, J=8.7 Hz, 2H), 4.70-4.47 (m, 1H), 3.98-3.81 (m, 4H), 3.79-3.64 (m, 1H), 3.56-3.46 (m, 1H), 3.21-3.14 (m, 1H), 3.17 (d, J=9.5 Hz, 1H), 3.09 (d, J=9.6 Hz, 1H), 2.70 (2d, J=13.8 Hz, 1H), 2.50-2.43 (m, 1H), 1.51-1.31 (m, 2H), 1.39 (s, 9H), 1.27 (t, J=7.0 Hz, 3H), 1.02, 0.89 (2s, 3H), 0.80, 0.78 (2s, 3H). MS (ESI) m/z 432 [M+H]$^+$.

tert-butyl (2-((1 S,5S)-6-(4-ethoxyphenyl)-9,9-dimethyl-3,6-diazabicyclo[3.2.2]nonan-3-yl)-2-oxoethyl) carbamate (350 mg, 0.81 mmol) was dissolved in DCM (4 mL), 4M HCl in dioxane (2 mL) was added and the reaction mixture was stirred for 1.5 hrs. The solvent was evaporated, DCM (5 mL) was added and the solvent was re-evaporated. The addition of DCM and re-evaporation was repeated once more. 2-amino-1-((1 S,5S)-6-(4-ethoxyphenyl)-9,9-dimethyl-3,6-diazabicyclo[3.2.2]nonan-3-yl)ethan-1-one dihydrochloride was obtained as a pink solid (320 mg, 97%). It was used in the next step without purification.

2-amino-1-((1 S,5S)-6-(4-ethoxyphenyl)-9,9-dimethyl-3,6-diazabicyclo[3.2.2]nonan-3-yl)ethan-1-one dihydrochloride (90 mg, 0.22 mmol) was dissolved in ethanol (5 mL), triethylamine (140 μL, 1 mmol) was added followed by benzyl 2-((tert-butoxycarbonyl)amino)ethanimidothioate hydrobromide (Collins, Shearer et al, 1998) (80 mg, 0.22 mmol). The reaction mixture was stirred at room temperature for 12 hrs, then the solvent was evaporated and the residue was purified by chromatography (EtOAc/MeOH 0→20%) to afford tert-butyl (2-((2-((1 S,5S)-6-(4-ethoxyphenyl)-9,9-dimethyl-3,6-diazabicyclo[3.2.2]nonan-3-yl)-2-oxoethyl)amino)-2-iminoethyl)carbamate (95 mg, 86%). $^1$H NMR (500 MHz, DMSO-d$_6$) δ 9.05 (s, 2H), 8.87 (d, J=13.0 Hz, 1H), 7.46 (s, 1H), 6.80 (d, J=9.7 Hz, 2H), 6.60 (d, J=9.3 Hz, 2H), 4.49-4.30 (m, 2H), 4.29-4.09 (m, 2H), 4.04-3.97 (m, 2H), 3.90 (d, J=10 Hz, 2H), 3.88-3.81 (m, 1H), 3.60-3.53 (m, 1H), 3.21 (d, J=10.1 Hz, 1H), 3.17-3.08 (m, 2H), 2.79 (d, J=13.8 Hz, 1H), 1.52-1.33 (m, 2H), 1.41 (s, 9H), 1.27 (t, J=6.9 Hz, 3H), 1.04, 0.91 (2s, 3H), 0.81 (d, J=20.5 Hz, 3H). MS (ESI) m/z 488 [M+H]$^+$.

tert-butyl (2-((2-((1 S,5S)-6-(4-ethoxyphenyl)-9,9-dimethyl-3,6-diazabicyclo[3.2.2]nonan-3-yl)-2-oxoethyl) amino)-2-iminoethyl)carbamate (90 mg, 0.18 mmol) was dissolved in DCM (3 mL), 4M HCl in dioxane (2 mL) was added and the reaction mixture was stirred for 1.5 hrs. The solvent was evaporated, DCM (5 mL) was added and the solvent was re-evaporated. The addition of DCM and re-evaporation was repeated once more. 2-amino-N-(2-((1 S,5S)-6-(4-ethoxyphenyl)-9,9-dimethyl-3,6-diazabicyclo [3.2.2]nonan-3-yl)-2-oxoethyl)acetimidamide trihydrochloride (62 mg, 69%). $^1$H NMR (500 MHz, DMSO-d$_6$) δ 9.78 (br s, 2H), 9.43 (s, 1H), 8.70 (s, 3H), 6.88-6.73 (m, 2H), 6.61 (d, J=9.3 Hz, 2H), 4.67 (d, J=15 Hz, 1H), 4.44 (d, J=17.5 Hz, 1H), 4.36-4.13 (m, 2H), 4.02 (d, J=8.9 Hz, 2H), 3.90 (qd, J=8.7, 8.0, 6.0 Hz, 3H), 3.62-3.53 (m, 1H), 3.24-3.08 (m, 4H), 2.83 (d, J=13.8 Hz, 1H), 1.51-1.34 (m, 2H), 1.27 (t, J=7.0 Hz, 3H), 0.98 (2s, 3H), 0.82 (2s, 3H). MS (ESI) m/z 388 [M+H]$^+$.

VII. General Method for the Synthesis of Compounds with an N-Sulfonyl or N-Sulfonamide Linker Method N To a solution of the bridged homopiperazine derivative (1.0 eq.) in a mixture of dichloromethane (or 1,2-dichloroethane) (0.3 to 0.5M) and triethylamine (or pyridine or N,N-diisopropylethylamine) (1 to 2 eq.) was added the sulfonyl or sulfamoyl chloride (1 to 3 eq.). A catalytic amount of 4-dimethylaminopyridine (0.25 eq.) can also be added. The reaction mixture was stirred at room temperature for 12 to 24 hours, then was diluted with dichloromethane (or ethyl acetate) and washed with a basic aqueous solution (saturated with sodium bicarbonate or a 2.0 M solution of sodium hydroxide), water or brine. The organic phase was then dried over anhydrous magnesium sulfate, filtered and evaporated to dryness. The resulting residue was purified by silica gel column chromatography using a gradient of ethyl acetate in cyclohexane.

Example 54

(1S,5S)-6-(4-ethoxyphenyl)-9,9-dimethyl-3-(propylsulfonyl)-3,6-diazabicyclo[3.2.2]nonane

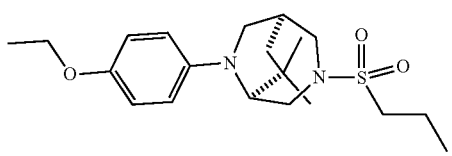 [SMILES: CCCS(=O)(=O)N1C[C@@H]2CN(c3ccc(OCC)cc3)[C@H](C1)C(C)(C)C2]

Using method N, a solution of (1R,5S)-6-(4-ethoxyphenyl)-9,9-dimethyl-3,6-diazabicyclo[3.2.2]nonane (70 mg, 0.26 mmol) in a mixture of dichloromethane (3 mL) and pyridine (25 µL, 0.3 mmol) was reacted with propane-1-sulfonyl chloride (34 µL, 0.3 mmol) and 4-dimethylaminopyridine (5 mg, 0.045 mmol). After work-up and silica gel column chromatography, 30 mg of (1S,5S)-6-(4-ethoxyphenyl)-9,9-dimethyl-3-(propylsulfonyl)-3,6-diazabicyclo[3.2.2]nonane (30%) were obtained.

1H NMR (500 MHz, DMSO-d6) δ 6.78 (d, J=9.0 Hz, 2H), 6.57 (d, J=9.1 Hz, 2H), 3.95 (dd, J=12.3, 4.8 Hz, 1H), 3.90 (q, J=7.0 Hz, 2H), 3.82-3.78 (m, 1H), 3.57 (d, J=4.6 Hz, 1H), 3.20-3.17 (d, J=10.4 Hz, 1H), 3.07 (d, J=10.4 Hz, 1H), 3.03-2.87 (m, 3H), 2.46-2.41 (m, 1H), 1.75-1.52 (m, 5H), 1.35 (dd, J=13.2, 6.4 Hz, 1H), 1.27 (t, J=7.0 Hz, 3H), 1.12 (s, 3H), 0.93 (t, J=7.4 Hz, 3H), 0.79 (s, 3H). HRMS calculated for $C_{20}H_{33}N_2O_3S$ [M+H]+ 381.2341; found 381.2178.

The following example compounds were prepared by the aforementioned methodology, using the appropriately substituted reagent.

| Example | Structure | Name | Analytical Data |
|---|---|---|---|
| 55 | 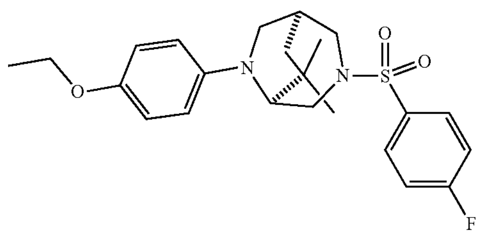 [SMILES: CCOc1ccc(N2C[C@H]3CN(S(=O)(=O)c4ccc(F)cc4)C[C@@H]2C(C)(C)C3)cc1] | (1S,5S)-6-(4-ethoxyphenyl)-3-((4-fluorophenyl)sulfonyl)-9,9-dimethyl-3,6-diazabicyclo[3.2.2]nonane | 1H NMR (500 MHz, DMSO-d6) δ 7.77 (dd, J = 8.9 and 5.2 Hz, 2H), 7.43 (t, J = 8.8 Hz, 2H), 6.73 (d, J = 9.1 Hz, 2H), 6.49 (d, J = 9.1 Hz, 2H), 4.04 (m, 1H), 4.02 (q, J = 7.1 Hz, 2H), 3.95-3.89 (m, 1H), 3.59 (d, J = 4.8 Hz, 1H), 3.12 (dd, J = 10.5 and 2.4 Hz, 1H), 2.95 (d, J = 10.3 Hz, 1H), 2.55 (m, 1H), 2.43-2.34 (m, 2H), 1.71 (d, J = 13.4 Hz, 1H), 1.39 (dd, J = 13.3 and 6.4 Hz, 1H), 1.24 (t, J = 7.0 Hz, 3H), 1.17 (s, 3H), 0.78 (s, 3H). HRMS calculated for C23H30FN2O3S [M + H]+ 433.1961; found 433.2022. |
| 56 | 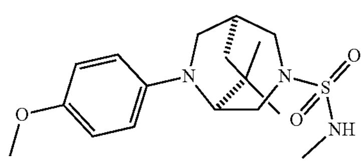 [SMILES: CNS(=O)(=O)N1C[C@@H]2CN(c3ccc(OC)cc3)[C@H](C1)C(C)(C)C2] | (1S,5S)-6-(4-methoxyphenyl)-N,9,9-trimethyl-3,6-diazabicyclo[3.2.2]nonane-3-sulfonamide | 1H NMR (500 MHz, CDCl3) δ 6.92-6.78 (m, 2H), 6.61-6.48 (m, 2H), 4.15 (q, J = 5.3 Hz, 1H), 4.05 (ddd, J = 11.9, 4.8 and 1.7 Hz, 1H), 3.99-3.91 (m, 1H), 3.76 (s, 3H), 3.46 (d, J = 4.6 Hz, 1H), 3.32 (dd, J = 10.3 and 2.3 Hz, 1H), 3.16 (dt, J = 10.3 and 2.6 Hz, 1H), 3.11 (dd, J = 11.9 and 0.7 Hz, 1H), 2.95 (d, J = 12.4 Hz, 1H), 2.70 (d, J = 5.4 Hz, 3H), 2.52 (dd, J = 7.7 and 6.6 Hz, 1H), 1.83 (d, J = 13.5 Hz, 1H), 1.44 (dd, J = 13.6 and 6.6 Hz, 1H), 1.19 (s, 3H), 0.90 (s, 3H). HRMS calculated for C17H28N3O3S [M + H]+ 354.1841; found 354.1851. |
| 57 | 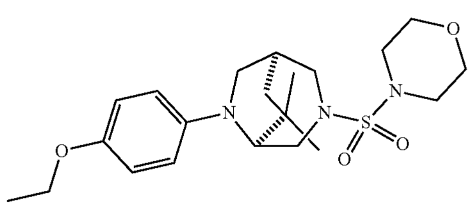 [SMILES: CCOc1ccc(N2C[C@H]3CN(S(=O)(=O)N4CCOCC4)C[C@@H]2C(C)(C)C3)cc1] | 4-(((1S,5S)-6-(4-ethoxyphenyl)-9,9-dimethyl-3,6-diazabicyclo[3.2.2]nonan-3-yl)sulfonyl)morpholine | 1H NMR (CDCl3, 500 MHz) δ 6.86 (d, 2H, J = 9.1 Hz), 6.55 (d, 2H, J = 9.1 Hz), 4.13-4.09 (m, 1H), 4.02-3.95 (m, 3H), 3.69-3.67 (m, 4H), 3.45 (d, 1H, J = 4.3 Hz), 3.30 (dd, 1H, J = 10.3 and 2.1 Hz), 3.18-3.13 (m, 6H), 3.00 (d, 1H, J = 12.6 Hz), 2.53-2.50 (m, 1H), 1.81 (d, 1H, J = 13.7 Hz), 1.44 (dd, 1H, J = 13.7 and 6.6 Hz), 1.38 (t, 3H, J = 7.0 Hz), 1.19 (s, 3H), 0.88 (s, 3H). HRMS calculated for C21H34N3O4S [M + H]+ 424.2265; found 424.2286. |

VIII. Synthesis of Compounds with an N-Aryl Linker

Example 58

N-(4-((1R,5S)-6-(4-ethoxyphenyl)-9,9-dimethyl-3,6-diazabicyclo[3.2.2]nonan-3-yl)phenyl)acetamide (8721)

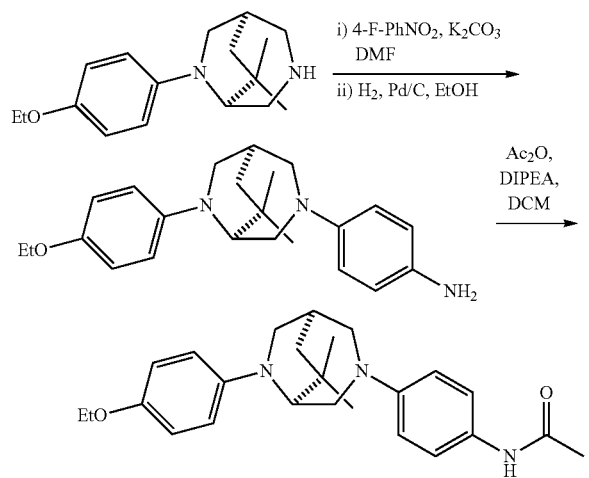

(1R,5S)-6-(4-ethoxyphenyl)-9,9-dimethyl-3,6-diazabicyclo[3.2.2]nonane (274 mg, 1 mmol) was dissolved in dry DMF (3 mL), 4-fluoronitrobenzene (141 mg, 1 mmol) and K2CO3 (166 mg, 1.2 mmol) were added and the reaction mixture was heated at 85° C. for 48 hrs. After cooling down, the reaction mixture was diluted with water (30 mL) and the yellow precipitate recovered by filtration and dried in a dessicator over KOH to afford (1R,5S)-6-(4-ethoxyphenyl)-9,9-dimethyl-3-(4-nitrophenyl)-3,6-diazabicyclo[3.2.2]nonane (350 mg, 89%). MS (ESI) m/z 396 [M+H]$^+$.

(1R,5S)-6-(4-ethoxyphenyl)-9,9-dimethyl-3-(4-nitrophenyl)-3,6-diazabicyclo[3.2.2]nonane (300 mg, 0.76 mmol) was suspended in ethanol (25 mL), palladium 10% on activated carbon (150 mg) was added and the reaction mixture stirred under an atmosphere of hydrogen for 5 hrs. The catalyst was filtered off, the solvent evaporated and the crude was purified by chromatography (DCM/EtOAc 0→30%) to afford 4-((1R,5S)-6-(4-ethoxyphenyl)-9,9-dimethyl-3,6-diazabicyclo[3.2.2]nonan-3-yl)aniline (150 mg, 54%). $^1$H NMR (500 MHz, DMSO-d$_6$) δ 6.77 (d, J=9.1 Hz, 2H), 6.71 (d, J=8.3 Hz, 2H), 6.56 (d, J=9.2 Hz, 2H), 6.47 (d, J=8.3 Hz, 2H), 4.56 (s, 2H), 3.89 (q, J=7.0 Hz, 2H), 3.56 (dd, J=11.6, 4.7 Hz, 1H), 3.48 (s, 2H), 3.22 (dd, J=10.3, 2.6 Hz, 1H), 3.10 (d, J=10.2 Hz, 1H), 2.74 (d, J=12.0 Hz, 2H), 2.44 (s, 1H), 1.83 (d, J=13.0 Hz, 1H), 1.35 (dd, J=13.0, 6.3 Hz, 1H), 1.27 (t, J=7.0 Hz, 3H), 1.14 (s, 3H), 0.82 (s, 3H). MS (ESI) m/z 366 [M+H]$^+$.

4-((1R,5S)-6-(4-ethoxyphenyl)-9,9-dimethyl-3,6-diazabicyclo[3.2.2]nonan-3-yl)aniline (75 mg, 0.2 mmol) was dissolved in DCM (2 mL), DIPEA (92 µL, 0.5 mmol) was added followed by acetic anhydride (19 µL, 0.2 mmol). The reaction mixture was stirred for 48 hrs at room temperature, then it was diluted with DCM (20 mL) and extracted with 10% aqueous citric acid (2×20 mL) and water (20 mL). The organic layer was dried over MgSO$_4$ and filtered. The solvent was removed under reduced pressure and the crude was purified by chromatography (DCM/EtOAc 0→25%) to afford N-(4-((1R,5S)-6-(4-ethoxyphenyl)-9,9-dimethyl-3,6-diazabicyclo[3.2.2]nonan-3-yl)phenyl) acetamide (14 mg, 17%). $^1$H NMR (500 MHz, DMSO-d$_6$) δ 9.66 (s, 1H), 7.37 (d, J=9.1 Hz, 2H), 6.86 (d, J=9.2 Hz, 2H), 6.78 (d, J=9.1 Hz, 2H), 6.59 (d, J=9.1 Hz, 2H), 3.90 (q, J=7.0 Hz, 2H), 3.78 (dd, J=12.3, 7.9 Hz, 2H), 3.55 (d, J=4.5 Hz, 1H), 3.24 (dd, J=10.3, 2.6 Hz, 1H), 3.13 (d, J=10.2 Hz, 1H), 2.83 (d, J=12.0 Hz, 2H), 1.98 (s, 3H), 1.73 (d, J=13.2 Hz, 1H), 1.43-1.36 (m, 1H), 1.27 (t, J=6.9 Hz, 4H), 1.06 (s, 3H), 0.83 (s, 3H). MS (ESI) m/z 408 [M+H]$^+$.

Intermediate:

tert-butyl (1R,5S)-3-(1,1-dioxidothiomorpholine-4-carbonyl)-9,9-dimethyl-3,6-diazabicyclo[3.2.2]nonane-6-carboxylate

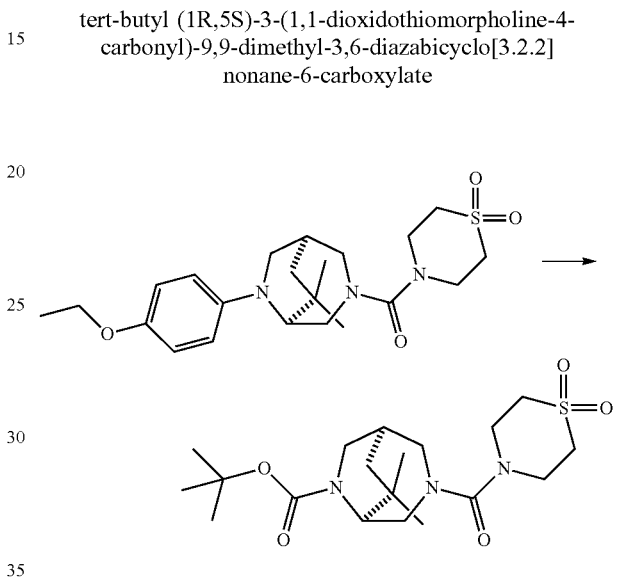

To a solution of (1,1-dioxidothiomorpholino)((1S,5S)-6-(4-ethoxyphenyl)-9,9-dimethyl-3,6-diazabicyclo[3.2.2]nonan-3-yl)methanone (1.07 g, 2.46 mmol) in acetonitrile (30 mL) and water (10 mL) at 0° C. was added portionwise cerium ammonium nitrate (4.03 g, 7.36 mmol) and the mixture stirred at room temperature for 5 h. The acetonitrile was removed under reduced pressure and water (20 mL) and dichloromethane (40 mL) were added. This mixture was stirred strongly then the reaction quenched by the dropwise addition of NaHCO$_3$ (10% aqueous solution) and Na$_2$S$_2$O$_3$ (10% aqueous solution). Di-tert-butyl dicarbonate (2.00 g, 9.16 mmol) was added and the mixture stirred strongly for 16 h. The resulting emulsion was filtered through Celite (dichloromethane). The phases were separated and the aqueous phase was extracted at pH=9 with dichloromethane (3×30 mL). Combined organic phases were washed with brine, dried over anhydrous magnesium sulfate, filtered and evaporated under reduced pressure. Column chromatography (cyclohexane/ethyl acetate) gave tert-butyl (1R,5S)-3-(1,1-dioxidothiomorpholine-4-carbonyl)-9,9-dimethyl-3,6-diazabicyclo[3.2.2]nonane-6-carboxylate (334 mg, 33%). $^1$H NMR (500 MHz, Chloroform-d) Observed as a mixture of rotamers: δ 4.25 (dd, J=13.8, 8.0 Hz, 0.6H), 4.19 (dd, J=13.8, 8.0 Hz, 0.3H), 3.95-3.80 (m, 2H), 3.80-3.71 (m, 2H), 3.69-3.58 (m, 2H), 3.51 (dt, J=12.2, 2.7 Hz, 0.3H), 3.45 (dt, J=12.2, 2.7 Hz, 0.6H), 3.29 (dd, J=12.9, 1.4 Hz, 0.6H), 3.25-3.16 (m, 3.3H), 3.04-2.94 (m, 2H), 2.90 (ps t, J=14.4 Hz, 1H), 2.42 (t, J=7.6 Hz, 0.3H), 2.37 (d, J=7.6 Hz, 0.6H), 1.67-1.59 (m, 1H), 1.41-1.33 (m, 1H), 1.49 (s, 9H), 1.00 (s, 3H), 0.93 (s, 3H). HRMS calculated for C$_{15}$H$_{26}$N$_3$O$_5$S [(M-tBu)+H]$^+$360.1593; found 360.1584.

Method O.

To a solution of Boc-protected homopiperazine (1 eq) in dichloromethane or diethyl ether (0.1 M) was added a half or equal volume of trifluoroacetic acid or HCl (4.0M in dioxane). After stirring for 1-4 h at room temperature, the reaction was concentrated under reduced pressure. tert-Butanol and toluene (1:3 v/v, to 0.1 M in substrate) was added, followed by phosphine ligand (0.1-0.2 eq), palladium (II) acetate (0.05-0.1 eq), sodium tert-butoxide (2-6 eq) and aryl halide (1.2-1.5 eq). The reaction mixture was heated to 110° C. for 4-72 h. After allowing to cool, the volatile components were removed in vacuo, the residue dissolved in dichloromethane and filtered through Celite. The filtrate was concentrated under reduced pressure. The crude was purified by silica gel column chromatography using a gradient of ethyl acetate in cyclohexane or dichloromethane, or a gradient of methanol in ethyl acetate.

Example 63

((1S,5S)-6-(2,3-dihydrobenzo[b][1,4]dioxin-6-yl)-9,9-dimethyl-3,6-diazabicyclo[3.2.2]nonan-3-yl)(1,1-dioxidothiomorpholino)methanone

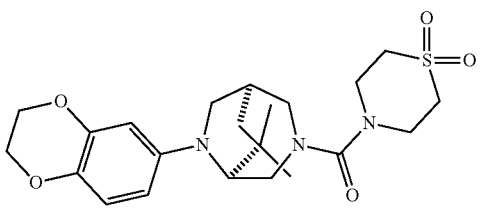 [SMILES: CC1(C)C[C@@H]2CN(C(=O)N3CCS(=O)(=O)CC3)C[C@H]1N(c1ccc3c(c1)OCCO3)C2]

Using method O, tert-butyl (1R,5S)-3-(1,1-dioxidothiomorpholine-4-carbonyl)-9,9-dimethyl-3,6-diazabicyclo[3.2.2]nonane-6-carboxylate (100 mg, 0.24 mmol) was reacted in dichloromethane (2 mL) with trifluoroacetic acid (1 mL) for 1 h. The volatile components were removed under reduced pressure to give crude ((1S,5S)-9,9-dimethyl-3,6-diazabicyclo[3.2.2]nonan-3-yl)(1,1-dioxidothiomorpholino)methanone (83 mg). tert-Butanol and toluene (2 mL, 1:3 v/v) were added, followed by X-Phos (11.5 mg, 0.02 mol), palladium(II) acetate (2.7 mg, 0.01 mol), sodium tert-butoxide (116 mg, 1.20 mmol) and 6-bromo-1,4-benzodioxane (39 µL, 0.29 mmol). The reaction mixture was heated to 110° C. for 24 h. After allowing to cool, the volatile components were removed in vacuo. Workup and column chromatography (cyclohexane/ethyl acetate) gave ((1S,5S)-6-(2,3-dihydrobenzo[b][1,4]dioxin-6-yl)-9,9-dimethyl-3,6-diazabicyclo[3.2.2]nonan-3-yl)(1,1-dioxidothiomorpholino)methanone (25 mg, 23%). $^1$H NMR (500 MHz, Chloroform-d) δ 6.79 (d, J=9.2 Hz, 1H), 6.16 (s, 2H), 4.31-4.16 (m, 6H), 3.92 (d, J=10.0 Hz, 2H), 3.80-3.71 (m, 1H), 3.69-3.58 (m, 1H), 3.36 (d, J=11.8 Hz, 3H), 3.26-3.09 (m, 1H), 3.04-2.91 (m, 1H), 2.53 (t, J=7.5 Hz, 2H), 2.18 (s, 2H), 1.67 (d, J=13.9 Hz, 2H), 1.44 (dd, J=13.9, 6.6 Hz, 1H), 0.96 (s, 3H), 0.90 (s, 3H). HRMS calculated for $C_{22}H_{32}N_3O_5S$ $[M+H]^+$ 450.2063; found 450.2047.

The following example compounds were prepared by the aforementioned methodology, using the appropriately substituted reagent.

| Example | Structure | Name | Analytical Data |
|---|---|---|---|
| 64 | 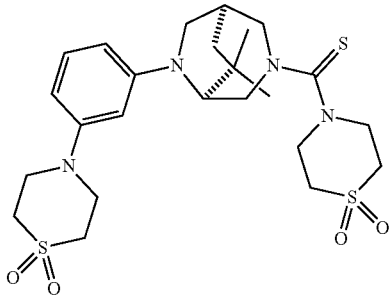 | (1,1-dioxido-thiomorpholino)((1S,5S)-6-(3-(1,1-dioxido-thiomorpholino)phenyl)-9,9-dimethyl-3,6-diazabicyclo[3.2.2]nonan-3-yl)methanone | $^1$H NMR (500 MHz, Chloroform-d) δ 7.19-7.13 (m, 1H), 6.45-6.36 (m, 1H), 6.28 (dd, J = 14.9, 8.2 Hz, 2H), 6.13 (s, 1H), 4.26-4.16 (m, 1H), 3.99 (dd, J = 13.0, 4.1 Hz, 1H), 3.86-3.80 (m, 4H), 3.79-3.72 (m, 2H), 3.67-3.60 (m, 2H), 3.49-3.42 (m, 1H), 3.36 (dd, J = 13.0, 1.6 Hz, 1H), 3.32-3.23 (m, 1H), 3.19-3.09 (m, 5H), 3.04-2.94 (m, 4H), 2.56 (t, J = 7.3 Hz, 1H), 1.71 (d, J = 14.0 Hz, 1H), 1.49 (dd, J = 14.0, 6.6 Hz, 1H), 1.00 (s, 3H), 0.92 (s, 3H). HRMS calculated for $C_{24}H_{37}N_4O_5S_2$ $[M + H]^+$ 525.2205; found 525.2225. |
| 65 | 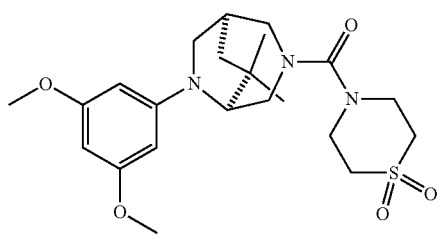 [SMILES: COc1cc(OC)cc(N2C[C@H]3CN(C(=O)N4CCS(=O)(=O)CC4)C[C@@H]2C(C)(C)C3)c1] | ((1S,5S)-6-(3,5-dimethoxyphenyl)-9,9-dimethyl-3,6-diazabicyclo[3.2.2]nonan-3-yl)(1,1-dioxidothiomorpholino)methanone | $^1$H NMR (500 MHz, Chloroform-d) δ 5.93 (s, 1H), 5.83 (s, 2H), 4.21 (dd, J = 13.6, 7.8 Hz, 1H), 4.00-3.86 (m, 1H), 3.81 (s, 6H), 3.78-3.69 (m, 1H), 3.71-3.58 (m, 2H), 3.50-3.32 (m, 2H), 3.32-3.13 (m, 4H), 3.06-2.88 (m, 4H), 2.54 (s, 1H), 1.69 (d, J = 13.8 Hz, 1H), 1.47 (dd, J = 13.8, 7.2 Hz, 1H), 0.98 (s, 3H), 0.92 (s, 3H). HRMS calculated for $C_{22}H_{34}N_3O_5S$ $[M + H]^+$ 452.2219; found 452.2192. |

| Example | Structure | Name | Analytical Data |
|---|---|---|---|
| 66 | 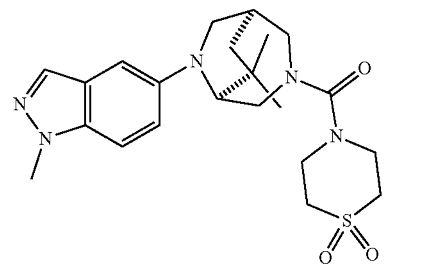 [SMILES: Cn1ncc2cc(N3C[C@H]4CN(C(=O)N5CCS(=O)(=O)CC5)C[C@@H]3C(C)(C)C4)ccc21] | ((1S,5S)-9,9-dimethyl-6-(1-methyl-1H-indazol-5-yl)-3,6-diazabicyclo[3.2.2]nonan-3-yl)(1,1-dioxidothiomorpholino)methanone | $^1$H NMR (500 MHz, Chloroform-d) δ 7.82 (s, 1H), 7.31 (d, J = 9.1 Hz, 1H), 6.96 (dd, J = 9.1, 2.4 Hz, 1H), 6.79 (d, J = 2.4 Hz, 1H), 4.29-4.19 (m, 1H), 4.09-3.99 (m, 4H), 3.85-3.73 (m, 2H), 3.71-3.60 (m, 2H), 3.52 (m, 1H), 3.46 (dd, J = 12.8, 2.0 Hz, 1H), 3.37 (dd, J = 10.1, 2.0 Hz, 1H), 3.25 (dt, J = 10.4, 2.7 Hz, 1H), 3.23-3.15 (m, 2H), 3.07-2.93 (m, 3H), 2.59 (d, J = 7.3 Hz, 1H), 1.72 (d, J = 14.0 Hz, 1H), 1.49 (dd, J = 14.0, 6.6 Hz, 1H), 1.00 (s, 3H), 0.91 (s, 3H). HRMS calculated for $C_{22}H_{32}N_5O_3S$ [M + H]+ 446.2226; found 446.2225. |
| 67 | 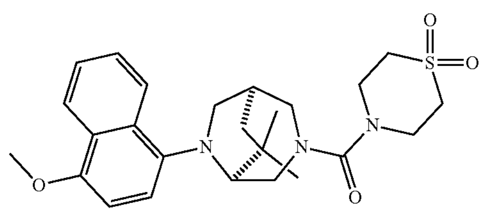 [SMILES: COc1ccc(N2C[C@H]3CN(C(=O)N4CCS(=O)(=O)CC4)C[C@@H]2C(C)(C)C3)c2ccccc12] | (1,1-dioxidothiomorpholino)((1S,5S)-6-(4-methoxynaphthalen-1-yl)-9,9-dimethyl-3,6-diazabicyclo[3.2.2]nonan-3-yl)methanone | $^1$H NMR (300 MHz, Chloroform-d) Observed as a mixture of atropisomers: δ 8.35-8.25 (m, 1H), 8.24-8.17 (m, 1H), 7.61-7.43 (m, 2H), 7.26 (d, J = 8.3 Hz, 0.75H), 7.18 (d, J = 8.3 Hz, 0.25H), 6.79 (d, J = 8.3 Hz, 0.75H), 6.72 (d, J = 8.3 Hz, 0.25H), 4.42 (dd, J = 13.7, 8.0 Hz, 1H), 4.00 (s, 2.25H), 3.98 (s, 0.75H), 3.86-3.68 (m, 3H), 3.67-3.58 (m, 2H), 3.57-3.34 (m, 4H), 3.26-3.12 (m, 3H), 3.10-2.90 (m, 2H), 2.53 (t, J = 6.6 Hz, 0.75H), 2.43 (t, J = 6.6 Hz, 0.25H), 1.74 (d, J = 13.9 Hz, 1H), 1.60-1.47 (m, 1H), 1.43 (s, 3H), 0.96 (s, 3H). LCMS (ES+) m/z = 472.6 ([M + H]+, 100). |

Example 68

(1,1-Dioxidothiomorpholino)((1S,5S)-6-(4-methoxycyclohexyl)-9,9-dimethyl-3,6-diazabicyclo[3.2.2]nonan-3-yl)methanone

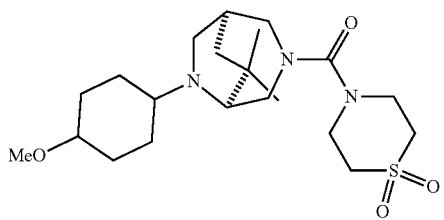 [SMILES: COC1CCC(N2C[C@H]3CN(C(=O)N4CCS(=O)(=O)CC4)C[C@@H]2C(C)(C)C3)CC1]

To tert-butyl (1R,5S)-3-(1,1-dioxidothiomorpholine-4-carbonyl)-9,9-dimethyl-3,6-diazabicyclo[3.2.2]nonane-6-carboxylate (102 mg, 0.25 mmol) in diethyl ether (1 mL) was added HCl (4.0 M in dioxane, 3 mL) and the reaction stirred at room temperature for 1 h. The volatile components were removed under reduced pressure and the residue dissolved in dichloroethane (2.5 mL). 4-Methoxycyclohexanone (38 µL, 0.29 mmol) was added dropwise followed by sodium triacetoxyborohydride (104 mg, 0.49 mmol) and acetic acid (2 drops, catalytic amount) and the reaction stirred for 4 h. Water (3 mL) and diethyl ether (3 mL) were added and the aqueous phase brought to pH=12 with sodium hydroxide (2M solution). The phases were separated and the aqueous phase extracted with diethyl ether (3×5 mL). Combined organic phases were washed with brine, dried over anhydrous magnesium sulfate, filtered and evaporated under reduced pressure. Column chromatography (cyclohexane/ethyl acetate) gave (1,1-dioxidothiomorpholino)((1S,5S)-6-(4-methoxycyclohexyl)-9,9-dimethyl-3,6-diazabicyclo[3.2.2]nonan-3-yl)methanone (25 mg, 24%). $^1$H NMR (500 MHz, Chloroform-d) δ 4.07 (dt, J=13.4, 7.8 Hz, 1H), 3.79-3.69 (m, 3H), 3.69-3.60 (m, 2H), 3.36-3.28 (m, 4H), 3.25-3.15 (m, 2H), 3.14-3.03 (m, 1H), 3.02-2.94 (m, 1H), 2.92-2.76 (m, 2H), 2.70-2.54 (m, 2H), 2.30 (t, J=7.8 Hz, 1H), 2.12-1.60 (m, 5H), 1.59-1.46 (m, 3H), 1.37-1.20 (m, 4H), 1.03 (s, 3H), 0.85 (s, 3H). HRMS calculated for $C_{21}H_{38}N_3O_4S$ [M+H]+ 428.2583; found 428.2579.

Materials and Methods

LOX Activity in Cysts Assay (Tang et al, 2017).
Cell Culture and Transfection

All cell lines used in this study were purchased from American Type Culture Collection (ATCC). *Mycoplasma* contamination was routinely monitored by PCR. Cells used were not found to be *Mycoplasma* positive. MDCK cell lines were cultured in Dulbecco's Modified Eagle Medium (DMEM) supplemented with 10% fetal bovine serum (FBS) and 1% Penicillin Streptomycin solution (Pen Strep). For GFP constructs transfection in MDCK cells, lipofectamine 3000 was used according to manufactures protocols. Cells were either selected with G418 (Life Technologies) at 5 mg/ml. All cell culture reagents were purchased from Life Technologies.

To produce MDCK cysts, cells were cultured on Matrigel (Corning) with 2% Matrigel supplemented in DMEM with 10% FBS. Cysts were allowed to form for 10 days before subsequent studies.
Cloning of LOX Expression Constructs Mouse LOX cDNA was purchased from OriGene. Full length LOX cDNA was then PCR cloned into pEGFP-N1 (Clonetech), or biosensor vector proGFP2-N1 (Hanson, 2004) using the following primers, GAGAGAGCTAGCATGCGTTTCGCCTGGG (forward primer) and TCTCTCCTCGAGATACGGTGAAATTGTGCAGCC (reverse primer). For the insertion into pEGFP-N1 or proGFP2-N1, NheI and XhoI restriction sites were added to forward and reverse primers accordingly. Mutant LOX constructs were made using QuickChange II site-directed mutagenesis kit (Agilent Technologies) following manufacture's protocol using LOX-GFP as template. To generate, roGFP2 versions of LOX mutant constructs, LOX mutant cDNA was transferred from pEGFP-N1 to proGFP2-N1 using NheI and XhoI.

Confocal Imaging and Imaging Analysis

All photomicrographs were taken with a Leica TCS SP8 X confocal system. For LOX biosensor imaging, live MDCK cysts were used. The oxidised biosensor was excited using a 405 nm laser, while the reduced biosensor was excited with a 488 nm laser. Emission of the biosensor was recorded at 500 nm~530 nm range using sequential scans. Ratio images were generated following a published protocol {Kardash, 2011 #376}. Note, while the published protocol generates YFP/CFP ratio images, we used it to generate Oxidised/Reduced (roGFP2 ratio) ratio images. The roGFP2 ratio at the basal surface of MDCK cysts was used to indicate LOX inhibition. LOX inhibitors were added 30 min prior to imaging.

The inhibition of LOX in cysts assay by LOX inhibitors as compared to control (DMSO vehicle treated) cysts is shown in Table 1. For clarity, readout for DMSO treated cysts represents 0% inhibition (no inhibition) and readout for BAPN at 1 mM is used as 100% inhibition (full inhibition).

TABLE 1

Inhibition of LOX in the cyst

| Structure | Example | LOX biosensor inhibition (cyst) @ 10 uM | LOX biosensor IC50 (cyst) |
|---|---|---|---|
| [structure] | 1 | 91% | — |
| [structure] | 2 | 92% (@ 2.5 uM) | — |
| [structure] | 3 | 88% | — |
| [structure] | 4 | 88% | 0.61 |
| [structure] | 5 | 62% | — |
| [structure] | 6 | 50% | — |
| [structure] | 7 | 88% | 0.54 |

TABLE 1-continued
Inhibition of LOX in the cyst
| Structure | Example | LOX biosensor inhibition (cyst) @ 10 uM | LOX biosensor IC50 (cyst) |
|---|---|---|---|
| 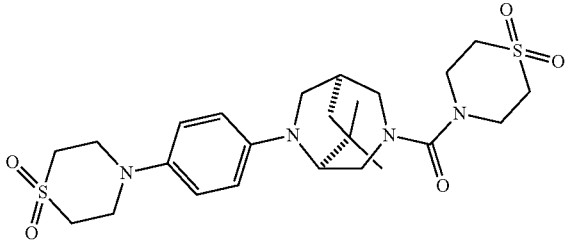 [SMILES: CC1(C)C[C@@H]2CN(C(=O)N3CCS(=O)(=O)CC3)C[C@H]1N(c1ccc(N3CCS(=O)(=O)CC3)cc1)C2] | 8 | 100% (@ 2.5 uM) | 0.54 |
| 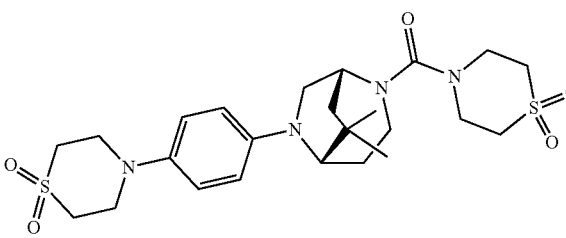 | 9 | 100% | 0.69 |
| 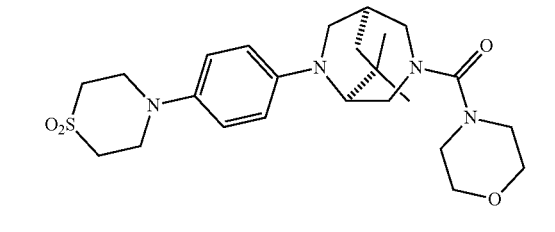 [SMILES: CC1(C)C[C@@H]2CN(C(=O)N3CCOCC3)C[C@H]1N(c1ccc(N3CCS(=O)(=O)CC3)cc1)C2] | 10 | 100% | <0.18 |
| 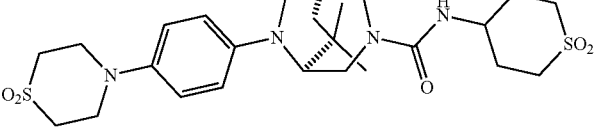 | 11 | 100% | — |
| 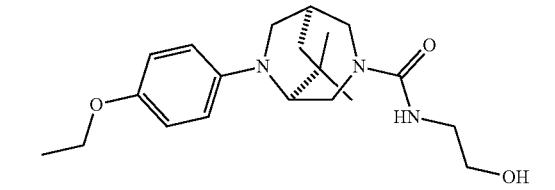 [SMILES: CCOc1ccc(N2C[C@H]3CN(C(=O)NCCO)C[C@@H]2C(C)(C)C3)cc1] | 12 | — | 0.89 |
| 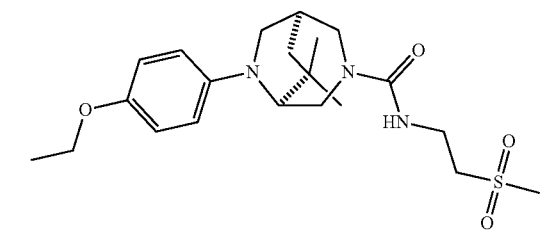 [SMILES: CCOc1ccc(N2C[C@H]3CN(C(=O)NCCS(C)(=O)=O)C[C@@H]2C(C)(C)C3)cc1] | 13 | — | 1.02 |

TABLE 1-continued
Inhibition of LOX in the cyst
| Structure | Example | LOX biosensor inhibition (cyst) @ 10 uM | LOX biosensor IC50 (cyst) |
|---|---|---|---|
| 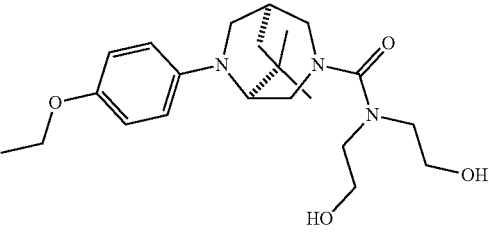 [SMILES: CCOc1ccc(N2C[C@H]3CN(C(=O)N(CCO)CCO)C[C@@H]2C(C)(C)C3)cc1] | 14 | 75% | |
| 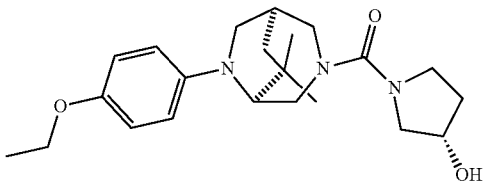 [SMILES: CCOc1ccc(N2C[C@H]3CN(C(=O)N4CC[C@H](O)C4)C[C@@H]2C(C)(C)C3)cc1] | 15 | 84% | — |
| 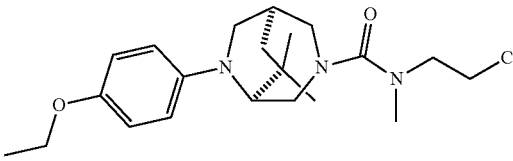 | 16 | 88% | — |
| 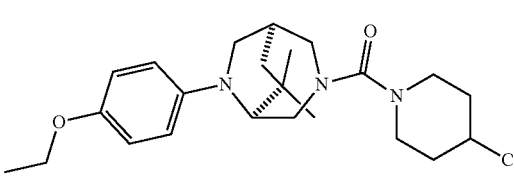 | 17 | 77% (@ 2.5 uM) | — |
| 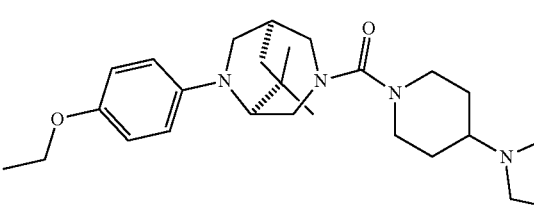 | 18 | 84% | — |
| 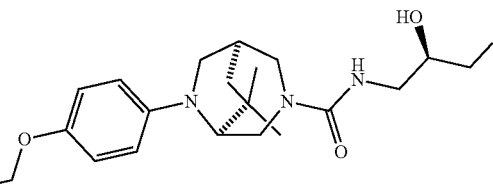 | 19 | 100% | — |
| 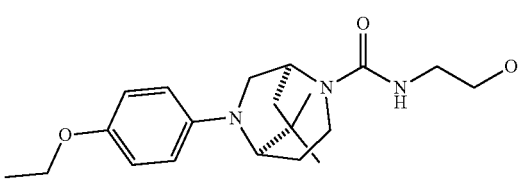 | 20 | 79% | — |

TABLE 1-continued
Inhibition of LOX in the cyst
| Structure | Example | LOX biosensor inhibition (cyst) @ 10 uM | LOX biosensor IC50 (cyst) |
|---|---|---|---|
| 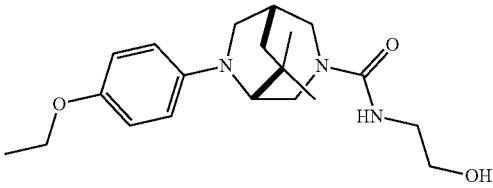 [SMILES: CCOc1ccc(N2C[C@@H]3CN(C(=O)NCCO)C[C@H]2C(C)(C)C3)cc1] | 21 | 94% | — |
| 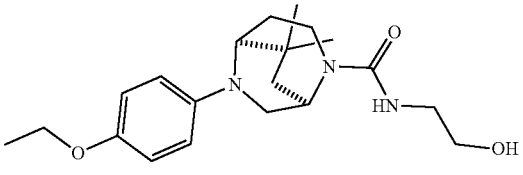 | 22 | 100% | — |
| 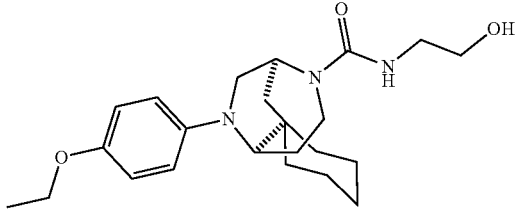 [SMILES: CCOc1ccc(N2C[C@@H]3CC4(CCCCC4)[C@H]2CCN3C(=O)NCCO)cc1] | 23 | 100% | 0.37 |
| 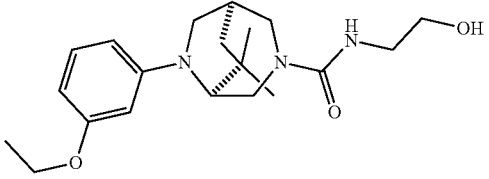 [SMILES: CCOc1cccc(N2C[C@H]3CN(C(=O)NCCO)C[C@@H]2C(C)(C)C3)c1] | 24 | 100% | <0.63 |
| 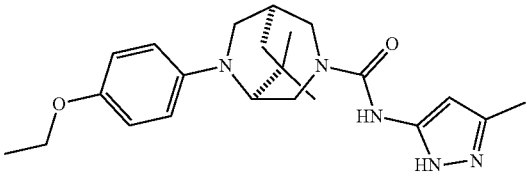 [SMILES: CCOc1ccc(N2C[C@H]3CN(C(=O)Nc4cc(C)n[nH]4)C[C@@H]2C(C)(C)C3)cc1] | 25 | 73% | — |
| 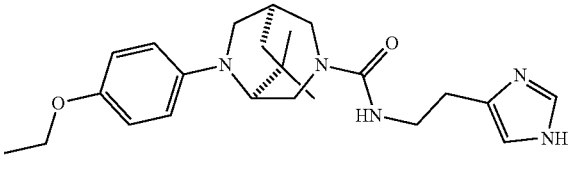 [SMILES: CCOc1ccc(N2C[C@H]3CN(C(=O)NCCc4c[nH]cn4)C[C@@H]2C(C)(C)C3)cc1] | 26 | | 0.34 |
| 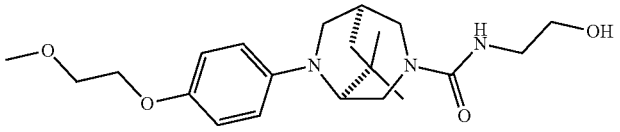 [SMILES: COCCOc1ccc(N2C[C@H]3CN(C(=O)NCCO)C[C@@H]2C(C)(C)C3)cc1] | 27 | 88% | 0.99 |
| 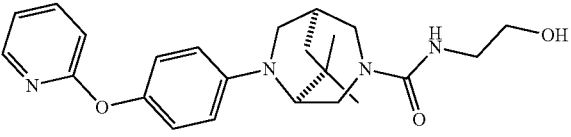 [SMILES: CC1(C)C[C@@H]2CN(C(=O)NCCO)C[C@H]1N(c1ccc(Oc3ccccn3)cc1)C2] | 28 | 100% | — |

TABLE 1-continued

Inhibition of LOX in the cyst

| Structure | Example | LOX biosensor inhibition (cyst) @ 10 uM | LOX biosensor IC50 (cyst) |
| --- | --- | --- | --- |
| 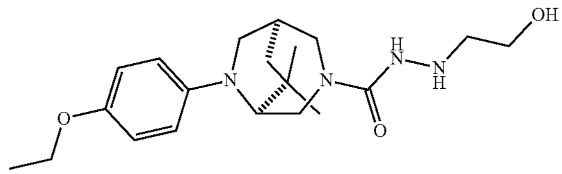 [SMILES: CCOc1ccc(N2C[C@H]3CN(C(=O)NNCCO)C[C@@H]2C(C)(C)C3)cc1] | 29 | 100% | — |
| 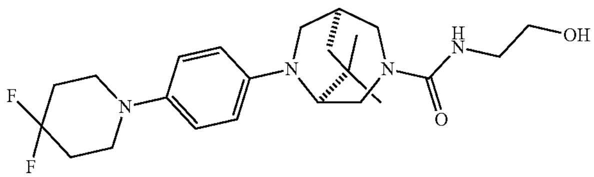 [SMILES: CC1(C)C[C@@H]2CN(C(=O)NCCO)C[C@H]1N(c1ccc(N3CCC(F)(F)CC3)cc1)C2] | 30 | 100% | 0.33 |
| 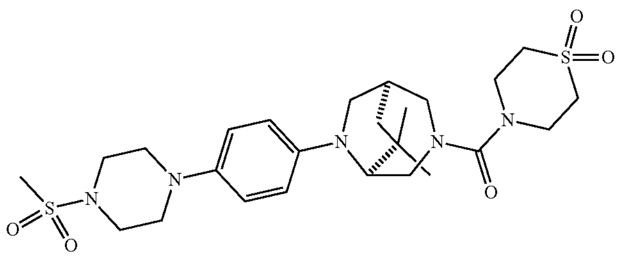 [SMILES: CC1(C)C[C@@H]2CN(C(=O)N3CCS(=O)(=O)CC3)C[C@H]1N(c1ccc(N3CCN(S(C)(=O)=O)CC3)cc1)C2] | 31 | 100% | <0.18 |
| 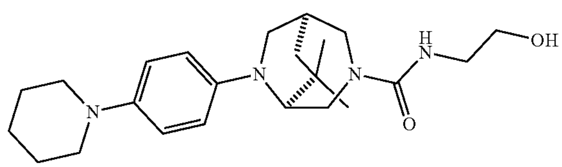 [SMILES: CC1(C)C[C@@H]2CN(C(=O)NCCO)C[C@H]1N(c1ccc(N3CCCCC3)cc1)C2] | 32 | 90% | <0.18 |
| 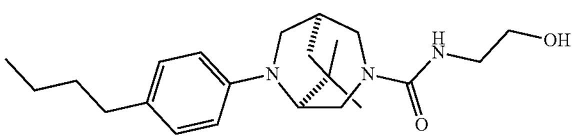 [SMILES: CCCCc1ccc(N2C[C@H]3CN(C(=O)NCCO)C[C@@H]2C(C)(C)C3)cc1] | 33 | 69.3% | — |
| 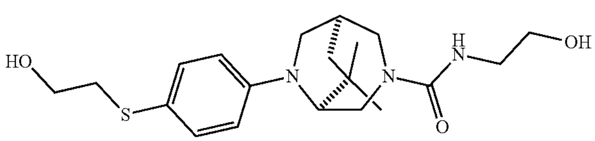 [SMILES: CC1(C)C[C@@H]2CN(C(=O)NCCO)C[C@H]1N(c1ccc(SCCO)cc1)C2] | 34 | 100% | — |
| 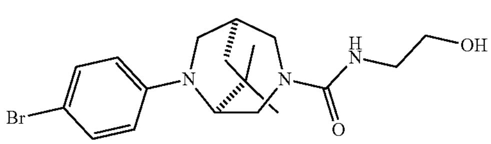 [SMILES: CC1(C)C[C@@H]2CN(C(=O)NCCO)C[C@H]1N(c1ccc(Br)cc1)C2] | 35 | 84.1% | — |
| 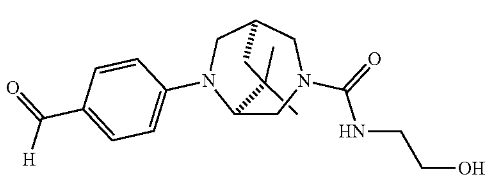 [SMILES: CC1(C)C[C@@H]2CN(C(=O)NCCO)C[C@H]1N(c1ccc(C=O)cc1)C2] | 37 | 86% | — |
| 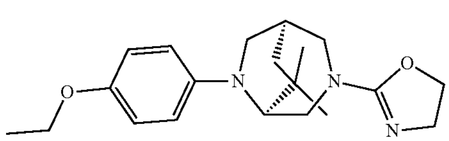 [SMILES: CCOc1ccc(N2C[C@H]3CN(C4=NCCO4)C[C@@H]2C(C)(C)C3)cc1] | 38 | 59% | — |

TABLE 1-continued
Inhibition of LOX in the cyst
| Structure | Example | LOX biosensor inhibition (cyst) @ 10 uM | LOX biosensor IC50 (cyst) |
|---|---|---|---|
| 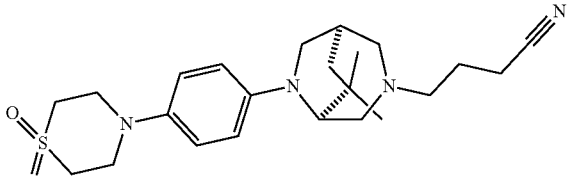 | 39 | 75% | 3.18 |
| 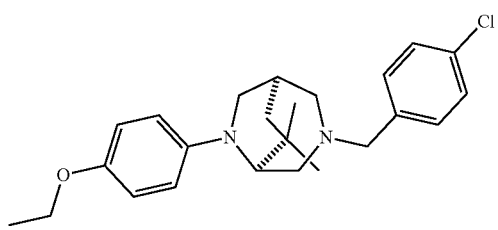 [SMILES: CCOc1ccc(N2C[C@H]3CN(Cc4ccc(Cl)cc4)C[C@@H]2C(C)(C)C3)cc1] | 40 | 68% | — |
| 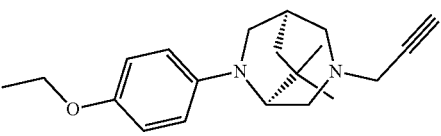 [SMILES: C#CCN1C[C@@H]2CN(c3ccc(OCC)cc3)[C@H](C1)C(C)(C)C2] | 41 | 87% | — |
| 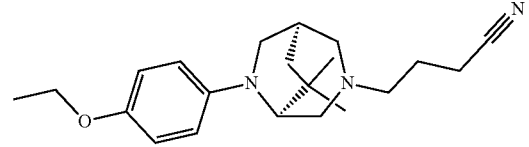 [SMILES: CCOc1ccc(N2C[C@H]3CN(CCCC#N)C[C@@H]2C(C)(C)C3)cc1] | 42 | — | <0.63 |
| 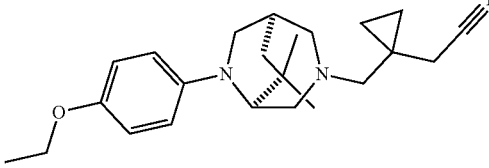 | 43 | 59% | — |
| 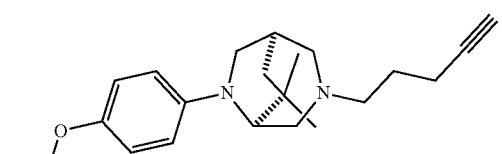 | 44 | 66% (@ 2.5 uM) | 0.31 |
| 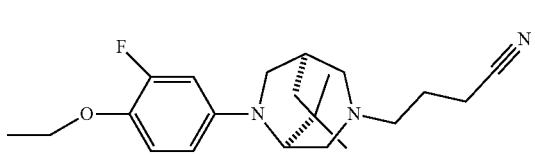 [SMILES: CCOc1ccc(N2C[C@H]3CN(CCCC#N)C[C@@H]2C(C)(C)C3)cc1F] | 45 | 42% | — |
| 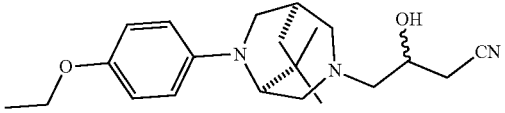 [SMILES: CCOc1ccc(N2C[C@H]3CN(CC(O)CC#N)C[C@@H]2C(C)(C)C3)cc1] | 46 | 72% | — |

TABLE 1-continued
Inhibition of LOX in the cyst
| Structure | Example | LOX biosensor inhibition (cyst) @ 10 uM | LOX biosensor IC50 (cyst) |
|---|---|---|---|
| 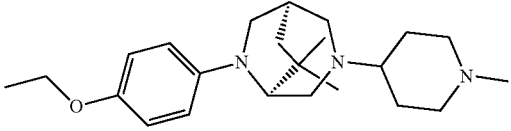 [SMILES: CCOc1ccc(N2C[C@H]3CN(C4CCN(C)CC4)C[C@@H]2C(C)(C)C3)cc1] | 47 | 90% | — |
| 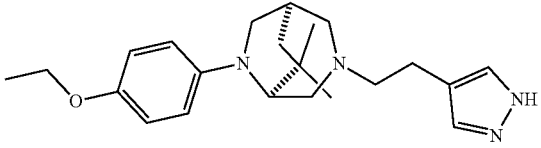 [SMILES: CCOc1ccc(N2C[C@H]3CN(CCc4cn[nH]c4)C[C@@H]2C(C)(C)C3)cc1] | 48 | 100% | — |
| 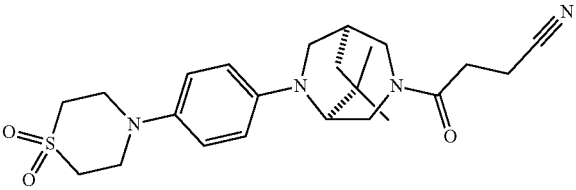 [SMILES: CC1(C)C[C@@H]2CN(C(=O)CCC#N)C[C@H]1N(c1ccc(N3CCS(=O)(=O)CC3)cc1)C2] | 49 | 100% | — |
| 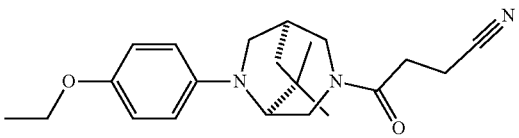 [SMILES: CCOc1ccc(N2C[C@H]3CN(C(=O)CCC#N)C[C@@H]2C(C)(C)C3)cc1] | 50 | 57% | — |
| 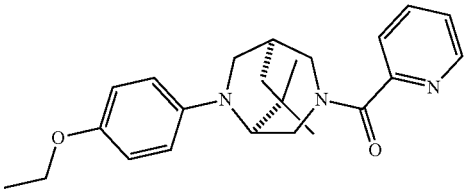 [SMILES: CCOc1ccc(N2C[C@H]3CN(C(=O)c4ccccn4)C[C@@H]2C(C)(C)C3)cc1] | 51 | 75% | — |
| 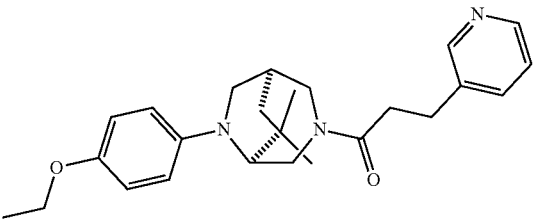 [SMILES: CCOc1ccc(N2C[C@H]3CN(C(=O)CCc4cccnc4)C[C@@H]2C(C)(C)C3)cc1] | 52 | 100% | — |
| 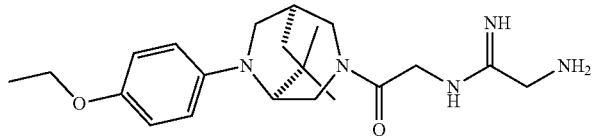 [SMILES: CCOc1ccc(N2C[C@H]3CN(C(=O)CNC(=N)CN)C[C@@H]2C(C)(C)C3)cc1] | 53 | 100% | — |
| 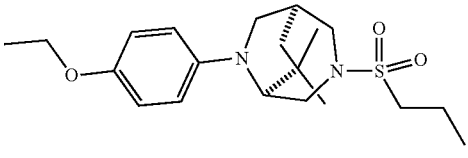 [SMILES: CCCS(=O)(=O)N1C[C@@H]2CN(c3ccc(OCC)cc3)[C@H](C1)C(C)(C)C2] | 54 | 54% | — |

TABLE 1-continued

Inhibition of LOX in the cyst

| Structure | Example | LOX biosensor inhibition (cyst) @ 10 uM | LOX biosensor IC50 (cyst) |
|---|---|---|---|
| 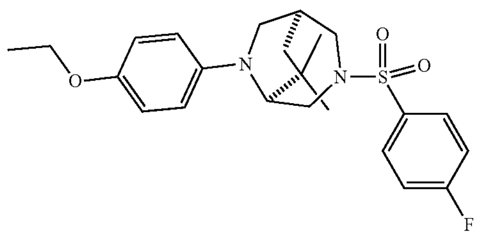 [SMILES: CCOc1ccc(N2C[C@H]3CN(S(=O)(=O)c4ccc(F)cc4)C[C@@H]2C(C)(C)C3)cc1] | 55 | 100% | — |
| 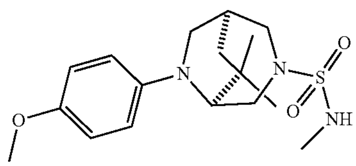 [SMILES: CNS(=O)(=O)N1C[C@@H]2CN(c3ccc(OC)cc3)[C@H](C1)C(C)(C)C2] | 56 | 74% | — |
| 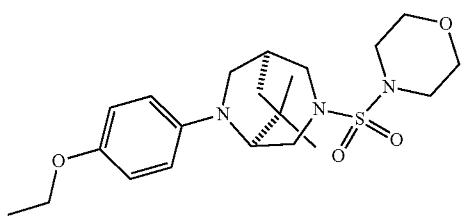 [SMILES: CCOc1ccc(N2C[C@H]3CN(S(=O)(=O)N4CCOCC4)C[C@@H]2C(C)(C)C3)cc1] | 57 | 93% | — |
| 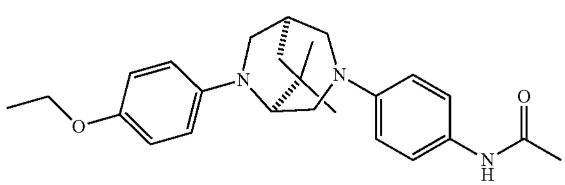 [SMILES: CCOc1ccc(N2C[C@H]3CN(c4ccc(NC(C)=O)cc4)C[C@@H]2C(C)(C)C3)cc1] | 58 | 100% | — |
| 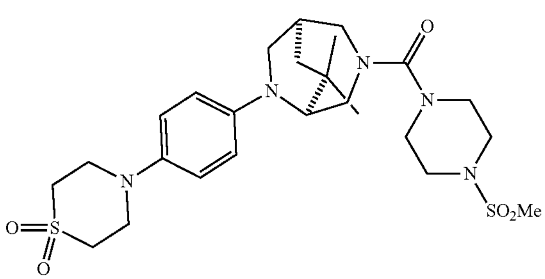 [SMILES: CC1(C)C[C@@H]2CN(C(=O)N3CCN(S(C)(=O)=O)CC3)C[C@H]1N(c1ccc(N3CCS(=O)(=O)CC3)cc1)C2] | 61 | 79% | — |
| 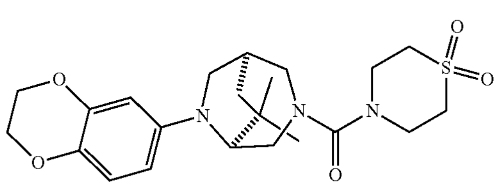 [SMILES: CC1(C)C[C@@H]2CN(C(=O)N3CCS(=O)(=O)CC3)C[C@H]1N(c1ccc3c(c1)OCCO3)C2] | 63 | 100% | — |

TABLE 1-continued

Inhibition of LOX in the cyst

| Structure | Example | LOX biosensor inhibition (cyst) @ 10 uM | LOX biosensor IC50 (cyst) |
|---|---|---|---|
| [structure] | 64 | 100% | — |
| [structure] | 65 | 88% | — |

In Vivo Assessment of LOX Inhibitors
Animal Procedures

All procedures involving animals were approved by the Animal Welfare and Ethical Review Body of the Institute of Cancer Research and Cancer Research UK Manchester Institute in accordance with National Home Office regulations under the Animals (Scientific Procedures) Act 1986 and according to the guidelines of the Committee of the National Cancer Research Institute Tumour size was determined by caliper measurements of tumour length, width and depth and volume was calculated as volume=0.5236×length×width×depth (mm). In accordance with our licence to perform animal experiments, animals were excluded from the experiments if they displayed signs of distress, excessive bodyweight loss (>20%) or illness.

Oral Tolerability of LOX Inhibitors

Two CD1, NCR or Balb/c female mice at 6 weeks of age were dosed po by metal gavage once a day for 4 consecutive days with suspension of the test compound at the dose planned for therapy (200 mg/kg/day) in 5.25% Tween20/saline (v:v) or 5% DMSO in water at 0.2 ml per 20 g bodyweight.

The mice were observed for up to 15 days after last dose and their bodyweight measured every 4 days. A compound is considered tolerated if the bodyweight does not fall by >20% for over 72 hrs.

Compounds of this invention tested in vivo show good tolerability at the dose tested and exhibit <5% bodyweight loss or show bodyweight gain in the tolerability study and in further longer therapy studies.

In Vivo Tumour Models Studies

PDAC allografts: CD1 nu/nu female mice at 6 weeks of age were inoculated subcutaneously in the right flank with $2 \times 10^6$ PDAC TRP53R172H (p53 mut) cells at 100 ul suspension per animal. In some examples, the oral dosing by metal gavage commences one day after cells inoculation, at 0.2 ml/20 g bodyweight per animal once daily for 2-4 weeks, with compound dissolved in 5.25% tween20/saline or 5% DMSO/water. In other examples, groups of 7-8 mice were assigned to treatment following stratified allocation of tumour volumes with a median size of circa 100 mm$^3$. Oral dosing by metal gavage commenced around day 10, at 0.2 ml/20 g bodyweight per animal once daily for 2 weeks, with compound dissolved in 5.25% tween20/saline or 5% DMSO/water. Control animals received a similar dosage of vehicle (5.25% tween20/saline). Tumours and weights are measured twice weekly using calipers. At the end of the study the animals are culled, and samples taken, fixed or snap frozen in liquid nitrogen. Frozen samples kept at −80 degree centigrade until being analysed and the fixed samples stained according to the desired marker.

SW620 xenografts: NCr mice were inoculated subcutaneously in the right flank with $5 \times 10^6$ SW620 cells at 100 ul suspension per animal. Groups of 7-8 mice were assigned to treatment following stratified allocation of tumour volumes with a median size of circa 100 mm$^3$. Dosing commenced around day 10-13 at 0.2 ml/20 g bodyweight per animal once daily for 2 weeks. Dosing was administrated orally by metal gavage, at 0.2 ml/20 g bodyweight, compound dissolved in 5.25% tween20/saline or 5% DMSO/water. Control animals received a similar dosage of vehicle (5.25% tween20/saline or 5% DMSO/water). Tumours and weights are measured twice weekly using calipers. At the end of the study the animals are culled, and samples taken, fixed or snap frozen in liquid nitrogen. Frozen samples are kept at −80 degree centigrade until being analysed and the fixed samples stained according to the desired marker.

MDA-MB-231 xenografts. Ncr nude female mice at 6 weeks old from Charles River were injected into the third upper nipple mammary fat pad with MDA-MB-231 Luc 4×10^6 in 100 ul PB (50:50 Matrigel). When tumours reach a mean of 80 mm$^3$ around 10 days post cell inoculation the animals are allocated in 4 groups of 8. LOX inhibitor treatment is then administrated by oral gavage dosing, at 0.2 ml/20 g bodyweight once daily for up to 28 consecutive days. Tumours and weights are measured twice weekly using calipers and the animals can be imaged using non invasive method by bioluminescence using IVIS 200 imaging machine, weekly using 150 mg/kg luciferin administrate intraperitoneal or subcutaneous. At the end of the study the animals are culled, and samples taken, fixed or snap frozen in liquid nitrogen. Frozen samples kept at −80 degree centigrade until being analyzed and the fixed samples stained according to desired marker.

compound treated and vehicle control treated (TIC) is calculated. The ratio of average metastases numbers between compound treated and vehicle control treated (T/C) is also calculated. Reduction in metastases area and/or in metastases number in the compound treated group compared to vehicle-treated control group results in T/C<1. The antimetastatic efficacy of LOX inhibitors described in this invention, as measured by T/C in a model of breast cancer metastasising to lungs is shown in Table 2 and is significant (p<0.05) for all the data presented.

TABLE 2

| Example | PDAC R172H (p53 mut) (mouse pancreatic carcinoma)- primary tumour | SW620 human colorectal carcinoma cells (mutant RAS)- primary tumour | MDA-MB-231 human breast adenocarcinoma- primary tumour | MMT-PyMT breast transgenic model- primary tumour | MMT-PyMT breast transgenic model- metastases a) Count b) Area |
|---|---|---|---|---|---|
| 4 | | | 0.35 | | |
| 7 | | | 0.34 | 0.25 | |
| 8 | | 0.48 | 0.54 | 0.22 | a) 0.1 b) 0.012 |
| 10 | | | 0.39 | 0.11 | a) 0.02 b) 0.0006 |
| 12 | 0.47 | | | 0.26 | |
| 13 | 0.56 (100 mg/kg bid) | | 0.63 | | |
| 26 | 0.46 | | | | |
| 27 | | | 0.60 | | |
| 39 | | | 0.48 | | |
| 42 | 0.44 | 0.54 | 0.41 | 0.50 | a) 0.16 b) 0.013 |
| 49 | | | 0.62 | | |

LOX Inhibitor Treatment of a Transgenic Mouse Breast Cancer Model

MMTV-PyMT (Guy et al, 1992) (FVB) female mice were randomized by non-statistical methods to LOX inhibitor treatment groups from day 70 post-birth, when animals had no detectable tumour. Mice were treated daily by oral gavage with LOX inhibitor in vehicle, or daily vehicle (5% DMSO/2.5% Tween20 in water) by oral gavage. Tumour size was determined unblinded by caliper measurements of tumour length, width and depth and volume was calculated as 0.5236×length×width×depth (mm). In all experiments, mice were humanely killed and mammary tumours and lungs were collected when the primary tumours reached ethical limits or signs of ill health.

For therapeutic efficacy assessment, the ratio of average tumour volume between compound treated and vehicle control treated (T/C) is calculated. Reduction in tumour volume in the compound treated group compared to vehicle-treated control group results in T/C<1. The efficacy of LOX inhibitors described in this invention, as measured by T/C in a pancreatic cancer model, a colorectal cancer model and a breast cancer model is shown in Table 2 and is significant (p<0.05) for all the data presented.

For lung metastases quantification, all mouse tissue samples were fixed in 10% formalin (Sigma) and embedded in paraffin. Samples were sectioned and hematoxylin and eosin (H&E) stained. Samples were imaged with a Leica CN400 slide scanner. Lung metastases were manually selected using Pen tool in ImageScope. Lung metastases number was counted and area was measured using ImageScope. The investigator was blinded to the experimental groups. The ratio of average metastases surface between Significant, p<0.05
All values are T/C, all doses are 200 mg/kg po qd unless otherwise stated

REFERENCES

Guy, C. T., Cardiff, R. D. & Muller, W. J. Induction of mammary tumors by expression of polyomavirus middle T oncogene: a transgenic mouse model for metastatic disease. Mol Cell Biol 12, 954-961 (1992)

Hanson, G. T., Aggeler, R., Oglesbee, D., Cannon, M., Capaldi, R. A., Tsien, R. Y., Remington J. S. (2004). Investigating mitochondrial redox potential with redox-sensitive green fluorescent protein indicators. J. Biol. Chem. 279, 13044-13053.

REFERENCES

Abourbih, D. A., et al. (2010). "Lysyl oxidase expression and inhibition in uveal melanoma." *Melanoma research* 20(2): 97-106.

Adam, O., et al. (2011). "Increased lysyl oxidase expression and collagen cross-linking during atrial fibrillation." *J. Mol. Cell. Cardiol.* 50(4): 678-685.

Akiri, G., et al. (2003). "Lysyl oxidase-related protein-1 promotes tumor fibrosis and tumor progression in vivo." *Cancer research* 63(7): 1657-1666.

Albinger-Hegyi, A., et al. (2010). "Lysyl oxidase expression is an independent marker of prognosis and a predictor of lymph node metastasis in oral and oropharyngeal squamous cell carcinoma (OSCC)." *International journal of cancer Journal international du cancer* 126(11): 2653-2662.

Alexandrescu, D. T. (2009). "Treatment of skin disorders with EGFR inhibitors". WO2009091889A1

Anderson, C., et al. (2007). "Chemical genetics suggests a critical role for lysyl oxidase in zebrafish notochord morphogenesis." *Mol Biosyst* 3(1): 51-59.

Aslam, T., et al. (2015). "Optical molecular imaging of lysyl oxidase activity—detection of active fibrogenesis in human lung tissue." *Chemical Science* 6(8): 4946-4953.

Baker, A.-M., et al. (2013). "Lysyl oxidase plays a critical role in endothelial cell stimulation to drive tumor angiogenesis." *Cancer research* 73(2): 583-594.

Baker, A.-M., et al. (2011). "The role of lysyl oxidase in SRC-dependent proliferation and metastasis of colorectal cancer." *Journal of the National Cancer Institute* 103(5): 407-424.

Barker, H. E., et al. (2013). "Tumor-Secreted LOXL2 Activates Fibroblasts through FAK Signaling." *Molecular Cancer Research* 11(11): 1425-1436.

Barker, H. E., et al. (2011). "LOXL2-mediated matrix remodeling in metastasis and mammary gland involution." *Cancer research* 71(5): 1561-1572.

Barker, H. E., et al. (2012). "The rationale for targeting the LOX family in cancer." *Nature reviews Cancer* 12(8): 540-552.

Barry-Hamilton, V., et al. (2010). "Allosteric inhibition of lysyl oxidase-like-2 impedes the development of a pathologic microenvironment." *Nat Med* 16(9): 1009-1017.

Beerlage, C., et al. (2013). "Hypoxia-inducible factor 1-regulated lysyl oxidase is involved in *Staphylococcus aureus* abscess formation." *Infect. Immun.* 81(7): 2562-2573.

Bianco, R., et al. (2007). "Rational bases for the development of EGFR inhibitors for cancer treatment." *The International Journal of Biochemistry & Cell Biology* 39(7-8): 1416-1431.

Bondareva, A., et al. (2009). "The lysyl oxidase inhibitor, beta-aminopropionitrile, diminishes the metastatic colonization potential of circulating breast cancer cells." *PLoS One* 4(5): e5620.

Borad, M. J., et al. (2014). "Targeted chemotherapy of cancer using EGFR inhibitors". WO2014145751A2

Boufraqech, M., et al. (2015). "miR30a Inhibits LOX Expression and Anaplastic Thyroid Cancer Progression." *Cancer research* 75(2): 367-377.

Brasselet, C., et al. (2005). "Collagen and elastin cross-linking: A mechanism of constrictive remodeling after arterial injury." *Am. J. Physiol.* 289(5, Pt. 2): H2228-H2233.

Burchardt, E. R. (2006). "Preparation of 2-phenyl-3-pyridazinones as lysyl oxidase inhibitors". DE102004056226A1

Burke A. A., et al (2017) Comparing hydrazine-derived reactive groups as inhibitors of quinone-dependent amine oxidases, *Journal of Enzyme Inhibition and Medicinal Chemistry*, 32:1, 496-503, Carrington, M. J., et al. (1984). "The inhibition of lysyl oxidase in vivo by isoniazid and its reversal by pyridoxal. Effect on collagen cross-linking in the chick embryo." *Biochem J* 221(3): 837-843.

Chang, J. et al (2017) Pre-clinical evaluation of small molecule LOXL2 inhibitors in breast cancer. Oncotarget, Advance Publication Chanoki, M., et al. (1995). "Increased expression of lysyl oxidase in skin with scleroderma." *Br J Dermatol* 133(5): 710-715.

Chen, W.-C., et al. (2015). "Matrix-Stiffness-Regulated Inverse Expression of Krüppel-Like Factor 5 and Krüppel-Like Factor 4 in the Pathogenesis of Renal Fibrosis." *The American Journal of Pathology* 185(9): 2468-2481.

Chen, R T et al. (2017) "Blocking Surgically Induced Lysyl Oxidase Activity Reduces the Risk of Lung Metastases". Cell Reports 19(4), 774-784

Chien, J. W., et al. (2014). "Serum lysyl oxidase-like 2 levels and idiopathic pulmonary fibrosis disease progression." *European Respiratory Journal* 43(5): 1430-1438.

Cox, T. R., et al. (2013). "LOX-Mediated Collagen Cross-linking Is Responsible for Fibrosis-Enhanced Metastasis." *Cancer research* 73(6): 1721-1732.

Cox, T. R., et al. (2015). "The hypoxic cancer secretome induces pre-metastatic bone lesions through lysyl oxidase." *Nature* 522(7554): 106-110.

Crowley, V. et al. (2016). "Development of Glucose Regulated Protein 94-Selective Inhibitors Based on the Bnlm and Radamide Scaffold." *J Med. Chem.* 59, 3471-3488.

Curtis, M. et al. (2013). "Phenicol antibacterials." US2013/0237502A1.

da Silva, R., et al. (2015). "LOX Expression and Functional Analysis in Astrocytomas and Impact of IDH1 Mutation." *PLoS One* 10(3): e0119781.

Decitre, M., et al. (1998). "Lysyl oxidase-like protein localizes to sites of de novo fibrinogenesis in fibrosis and in the early stromal reaction of ductal breast carcinomas." *Lab. Invest.* 78(2): 143-151.

Dentillo, D. B., et al. (2010). "Deregulation of LOXL1 and HTRA1 Gene Expression in Endometriosis." *Reproductive Sciences* 17(11): 1016-1023.

Di Donato, A., et al. (1997). "Lysyl oxidase expression and collagen cross-linking during chronic adriamycin nephropathy." *Nephron* 76(2): 192-200.

Dong, K.-f., et al. (2014). "Effects on apoptosis and chemosensitivity in human laryngeal cancer Hep-2 cells by silencing the lysyl oxidase gene expression." *Zhoncicuo Xiandai Yixue Zazhi* 24(29): 13-17.

Dong, K., et al. (2014). "Effects of lox gene expression on proliferation, invasion and radiosensitivity of laryngeal cancer hep-2 cells." *Tianiin Yivao* 42(5): 417-420.

Erler, J. T., et al. (2009). "Hypoxia-induced lysyl oxidase is a critical mediator of bone marrow cell recruitment to form the premetastatic niche." *Cancer Cell* 15(1): 35-44.

Erler, J. T., et al. (2006). "Lysyl oxidase is essential for hypoxia-induced metastasis." *Nature* 440(7088): 1222-1226.

Fong, S. F., et al. (2007). "Lysyl oxidase-like 2 expression is increased in colon and esophageal tumors and associated with less differentiated colon tumors." *Genes Chromosomes Cancer* 46(7): 644-655.

Gao, Y., et al. (2010). "LKB1 inhibits lung cancer progression through lysyl oxidase and extracellular matrix remodeling." *Proceedings of the National Academy of Sciences* 107(44): 18892-18897.

Georges, P. C., et al. (2007). "Increased stiffness of the rat liver precedes matrix deposition: implications for fibrosis." *Am. J. Physiol.* 293(6, Pt. 1): G1147-G1154.

Giboda, M., et al. (1992). "Experimental schistosomiasis mansoni: modulation of granulomas by inhibition of collagen cross-link formation. Preliminary report." *Ann Trop Med Parasitol* 86(6): 631-636.

Gilad, G. M. and V. H. Gilad (2001). "β-Aminopropionitrile treatment can accelerate recovery of mice after spinal cord injury." *Eur. J. Pharmacol.* 430(1): 69-72.

Gilad, G. M., et al. (2001). "Lysyl oxidase, the extracellular matrix-forming enzyme, in rat brain injury sites." *Neurosci. Lett.* 310(1): 45-48.

Gilad, G. M., et al. (2005). "Evidence for increased lysyl oxidase, the extracellular matrix-forming enzyme, in Alzheimer's disease brain." *Neurosci Lett* 376(3): 210-214.

Goeroegh, T., et al. (2007). "Selective upregulation and amplification of the lysyl oxidase like-4 (LOXL4) gene in head and neck squamous cell carcinoma." *J Pathol* 212 (1): 74-82.

Gonzalez-Santamaria, J et al, (2016) "Matrix cross-linking lysyl oxidases are induced in response to myocardial infarction and promote cardiac dysfunction". Cardiovascular Research 109, (1), 67-78.

Gonzalez, G. E., et al. (2014). "N-acetyl-seryl-aspartyl-lysyl-proline reduces cardiac collagen cross-linking and inflammation in angiotensin II-induced hypertensive rats." *Clin. Sci.* 126(1): 85-94.

Gopalan Balasubramanian. (1990) "Biphenyl-substituted guanidine derivatives useful as hypoglycaemic agents." U.S. Pat. No. 5,302,720.

Haase, V. H. (2009). "Pathophysiological Consequences of HIF Activation." *Annals of the New York Academy of Sciences* 1177(1): 57-65.

Halberg, N., et al. (2009). "Hypoxia-inducible factor 1α induces fibrosis and insulin resistance in white adipose tissue." *Mol. Cell. Biol.* 29(16): 4467-4483.

Hase, H., et al. (2014). "LOXL2 Status Correlates with Tumor Stage and Regulates Integrin Levels to Promote Tumor Progression in ccRCC." *Molecular Cancer Research* 12(12): 1807-1817.

He, Z. and V. Koprivica (2007). "EGFR inhibitors promote axon regeneration". WO2007008338A1

Herranz, N., et al. (2012). "Lysyl Oxidase-like 2 Deaminates Lysine 4 in Histone H3." *Molecular Cell* 46(3): 369-376.

Hornstra, I. K., et al. (2003). "Lysyl oxidase is required for vascular and diaphragmatic development in mice." *J Biol Chem* 278(16): 14387-14393.

Huang, C.-S., et al. (2013). "Long-term ethanol exposure-induced hepatocellular carcinoma cell migration and invasion through lysyl oxidase activation are attenuated by combined treatment with pterostilbene and curcumin analogues." *Journal of Agricultural and Food Chemistry* 61(18): 4326-4335.

Hynes, J. et al. (2009). "Imidazopyridine and imidazopyrazine compounds useful as kinase inhibitors." WO2009/155388A1.

Ingber, D. E. and A. Mammoto (2014). "Methods of altering vascular permeability by changing the mechanical properties of extracellular matrixes using agents such as lysyl oxidase (LOX)-modulating agents and uses for treatment of diseases". WO2014152122A2

Jiang, W.-P., et al. (2014). "Identification of the involvement of LOXL4 in generation of keratocystic odontogenic tumors by RNA-Seq analysis." In *J Oral Sci* 6(1): 31-38.

Jourdan-Le Saux, C., et al. (1994). "Lysyl oxidase cDNA of myofibroblast from mouse fibrotic liver." *Biochem Biophys Res Commun* 199(2): 587-592.

Jung, B. (2010). "Use of quinazoline derivatives for the treatment of viral diseases". WO2010026029A1

Kagan, H. M. (1994). "Lysyl oxidase: mechanism, regulation and relationship to liver fibrosis." *Pathol Res Pract* 190(9-10): 910-919.

Kagan, H. M. and W. Li (2003). "Lysyl oxidase: properties, specificity, and biological roles inside and outside of the cell." *Journal of cellular biochemistry* 88(4): 660-672.

Kagan, H. M., et al. (1981). "Changes in aortic lysyl oxidase activity in diet-induced atherosclerosis in the rabbit." *Arteriosclerosis* 1(4): 287-291.

Karagiannis, G. S., et al. (2012). "Cancer-Associated Fibroblasts Drive the Progression of Metastasis through both Paracrine and Mechanical Pressure on Cancer Tissue." *Molecular Cancer Research* 10(11): 1403-1418.

Kasashima, H., et al. (2014). "Lysyl oxidase-like 2 (LOXL2) from stromal fibroblasts stimulates the progression of gastric cancer." *Cancer Letters* 354(2): 438-446.

Kasashima, H., et al. (2015). "Lysyl oxidase is associated with the epithelial-mesenchymal transition of gastric cancer cells in hypoxia." *Gastric Cancer:* 1-12.

Kim, Y.-M., et al. (2010). "The human lysyl oxidase-like 2 protein functions as an amine oxidase toward collagen and elastin." *Mol. Biol. Rep.* 38(1): 145-149.

Kim, Y., et al. (1999). "Coexpression of the lysyl oxidase-like gene (LOXL) and the gene encoding type III procollagen in induced liver fibrosis." *Journal of cellular biochemistry* 72(2): 181-188.

Kirschmann, D. A., et al. (2002). "A molecular role for lysyl oxidase in breast cancer invasion." *Cancer research* 62(15): 4478-4483.

Kumarasamy, A., et al. (2009). "Lysyl oxidase activity is dysregulated during impaired alveolarization of mouse and human lungs." *Am. J. Respir. Crit. Care Med.* 180 (12): 1239-1252.

Lee, G.-H., et al. (2011). "Lysyl oxidase-like-1 enhances lung metastasis when lactate accumulation and monocarboxylate transporter expression are involved." *Oncology Letters* 2(5): 831-838.

Levene, C. I., et al. (1992). "Inhibition of chick embryo lysyl oxidase by various lathyrogens and the antagonistic effect of pyridoxal." *Int J Exp Pathol* 73(5): 613-624.

Levental, K. R., et al. (2009). "Matrix crosslinking forces tumor progression by enhancing integrin signaling." *Cell* 139(5): 891-906.

Li, R.-k., et al. (2015). "Lysyl oxidase-like 4 (LOXL4) promotes proliferation and metastasis of gastric cancer via FAK/Src pathway." *Journal of Cancer Research and Clinical Oncology* 141(2): 269-281.

Li, W., et al. (2003). "Lysyl oxidase oxidizes basic fibroblast growth factor and inactivates its mitogenic potential." *Journal of cellular biochemistry* 88(1): 152-164.

Liu, G., et al. (1997). "Irreversible inhibition of lysyl oxidase by homocysteine thiolactone and its selenium and oxygen analogues. Implications for homocystinuria." *J Biol Chem* 272(51): 32370-32377.

Liu, J., et al. (2014). "Correlations of lysyl oxidase with MMP2/MMP9 expression and its prognostic value in non-small cell lung cancer." *Int J Clin Exp Pathol* 7(9): 6040-6047.

Lopez, B., et al. (2010). "Role of lysyl oxidase in myocardial fibrosis: from basic science to clinical aspects." *Am. J. Physiol.* 299(1, Pt. 2): H1-H9.

Lopez, B., et al. (2013). "Osteopontin-mediated myocardial fibrosis in heart failure: a role for lysyl oxidase?" *Cardiovasc. Res.* 99(1): 111-120.

Lopez, B., et al. (2012). "Collagen Cross-Linking But Not Collagen Amount Associates With Elevated Filling Pressures in Hypertensive Patients With Stage C Heart Failure: Potential Role of Lysyl Oxidase." *Hypertension* 60(3): 677-683.

Lucero, H. A. and H. M. Kagan (2006). "Lysyl oxidase: an oxidative enzyme and effector of cell function." *Cellular and molecular life sciences: CMLS* 63(19-20): 2304-2316.

Lucero, H. A., et al. (2008). "Lysyl oxidase oxidizes cell membrane proteins and enhances the chemotactic response of vascular smooth muscle cells." *J Biol Chem* 283(35): 24103-24117.

Ma, W. (2013). "Methods for treating alzheimer's disease by administering certain synthetic compounds". WO2013111013A2

Maki, J. M., et al. (2002). "Inactivation of the lysyl oxidase gene Lox leads to aortic aneurysms, cardiovascular dysfunction, and perinatal death in mice." *Circulation* 106 (19): 2503-2509.

Mambetsariev, I., et al. (2014). "Stiffness-activated GEF-H1 expression exacerbates LPS-induced lung inflammation." *PLoS One* 9(4): e92670/92671-e92670/92612, 92612 pp.

Mammoto, A., et al. (2013). "Control of lung vascular permeability and endotoxin-induced pulmonary oedema by changes in extracellular matrix mechanics." *Nature communications* 4: 1759.

Mammoto, T., et al. (2013). "Role of Collagen Matrix in Tumor Angiogenesis and Glioblastoma Multiforme Progression." *The American Journal of Pathology* 183(4): 1293-1305.

Marshall, D. and V. Smith (2011). "In vivo screening assays for identifying inhibitors of LOXL2 activity". WO 2011022670

Marshall, D., et al. (2012). "Anti-LOXL2 antibody, siRNA, shRNA, ribozyme and triplex oligonucleotide to increase efficacy of antitumor agent and treat cancer". WO2012139045A1

Martinez-Martinez, E et al. (2016). The lysyl oxidase inhibitor (β-aminopropionitrile) reduces leptin profibrotic effects and ameliorates cardiovascular remodeling in diet-induced obesity in rats. *Journal of Molecular and Cellular* Cardiology, 92, 96-104

Miana, M., et al. (2015). "The lysyl oxidase inhibitor β-aminopropionitrile reduces body weight gain and improves the metabolic profile in diet-induced obesity in rats." *Dis. Models Mech.* 8(6): 543-551.

Millanes-Romero, A., et al. (2013). "Regulation of Heterochromatin Transcription by Snail1/LOXL2 during Epithelial-to-Mesenchymal Transition." *Molecular Cell* 52(5): 746-757.

Miller, B. W., et al. (2015). "Targeting the LOX/hypoxia axis reverses many of the features that make pancreatic cancer deadly: inhibition of LOX abrogates metastasis and enhances drug efficacy." *EMBO Mol Med* 7(8): 1063-1076.

Moreno-Bueno, G., et al. (2011). "Lysyl oxidase-like 2 (LOXL2), a new regulator of cell polarity required for metastatic dissemination of basal-like breast carcinomas." *EMBO Mol Med* 3(9): 528-544.

Murawaki, Y., et al. (1991). "Serum lysyl oxidase activity in chronic liver disease in comparison with serum levels of prolyl hydroxylase and laminin." *Hepatology* 14(6): 1167-1173.

Nave, A. H., et al. (2014). "Lysyl Oxidases Play a Causal Role in Vascular Remodeling in Clinical and Experimental Pulmonary Arterial Hypertension." *Arterioscler., Thromb., Vasc. Biol.* 34(7): 1446-1458.

Neufeld, G. and V. Brekhman (2009). "Use of shRNA targeting LOXL2 gene in modulating angiogenesis and treating tumors, metastasis, fibrosis, and pulmonary alveolar proteinosis". WO2009010974A2

Nicholson, R. I., et al. (2001). "EGFR and cancer prognosis." *European Journal of Cancer* 37, Supplement 4: 9-15.

Nishikawa, R., et al. (2015). "Tumour-suppressive microRNA-29s directly regulate LOXL2 expression and inhibit cancer cell migration and invasion in renal cell carcinoma." *FEBS letters* 589(16): 2136-2145.

Nuthakki, V. K., et al. (2004). "Lysyl oxidase expression in a rat model of arterial balloon injury." *J Vasc Surg* 40(1): 123-129.

Offenberg, H., et al. (2008). "TIMP-1 expression in human colorectal cancer is associated with TGF-B1, LOXL2, INHBA1, TNF-AIP6 and TIMP-2 transcript profiles." *Mol Oncol* 2(3): 233-240.

Ohmura, H., et al. (2012). "Cardiomyocyte-specific transgenic expression of lysyl oxidase-like protein-1 induces cardiac hypertrophy in mice." *Hypertens. Res.* 35(11): 1063-1068.

Osawa, T., et al. (2013). "Lysyl oxidase secreted by tumour endothelial cells promotes angiogenesis and metastasis." *Br J Cancer* 109(8): 2237-2247.

Palfreyman, M. G., et al. (1989). "Preparation of allylamines, inhibitors of lysyl oxidase". EP330218A2

Papadantonakis, N., et al. (2012). "Megakaryocyte pathology and bone marrow fibrosis: the lysyl oxidase connection." *Blood* 120(9): 1774-1781.

Park, H.-Y. L., et al. (2014). "Lysyl oxidase-like 2 level and glaucoma surgical outcomes." *Invest. Ophthalmol. Visual Sci.* 55(5): 3337-3343.

Peinado, H., et al. (2005). "A molecular role for lysyl oxidase-like 2 enzyme in snail regulation and tumor progression." *EMBO J* 24(19): 3446-3458.

Peinado, H., et al. (2008). "Lysyl Oxidase-Like 2 as a New Poor Prognosis Marker of Squamous Cell Carcinomas." *Cancer research* 68(12): 4541-4550.

Peng, L., et al. (2009). "Secreted LOXL2 is a novel therapeutic target that promotes gastric cancer metastasis via the Src/FAK pathway." *Carcinogenesis* 30(10): 1660-1669.

Pickup, M. W., et al. (2013). "Stromally Derived Lysyl Oxidase Promotes Metastasis of Transforming Growth Factor-β-Deficient Mouse Mammary Carcinomas." *Cancer Res.* 73(17): 5336-5346.

Pinnell, S. R. and G. R. Martin (1968). "The cross-linking of collagen and elastin: enzymatic conversion of lysine in peptide linkage to alpha-aminoadipic-delta-semialdehyde (allysine) by an extract from bone." *Proceedings of the National Academy of Sciences* 61(2): 708-716.

Priyanka, T. et al. (2016) "Lysyl oxidase (LOX) inhibitors as anti-scarring agents" Abstracts of Papers, 252nd ACS National Meeting & Exposition, Philadelphia, PA, United States, Aug. 21-25, 2016, BIOL-98

Ree, A. H., et al. (2008). "Treatment and diagnosis of metastatic prostate cancer with inhibitors of epidermal growth factor receptor (EGFR)". WO2008125633A2

Reynault, O. et al. (1997). "A convenient synthesis of new halothienyl β-aminoacids as versatile building block." *Org. Prep. Proc. Int.* 29(4): 488-494.

Ricard-Blum, S., et al. (1996). "Mechanism of collagen network stabilization in human irreversible granulomatous liver fibrosis." *Gastroenterology* 111(1): 172-182.

Rimar, D., et al. (2014). "Brief report: lysyl oxidase is a potential biomarker of fibrosis in systemic sclerosis." *Arthritis Rheumatol* 66(3): 726-730.

Roehrig, F et al. (2017) "VEGF-ablation therapy reduces drug delivery and therapeutic response in ECM-dense tumors" *Oncogene* 36(1), 1-12.

Romero, F. et al. (2016). "4,5,6,7-Tetrahydro-1-H-pyrazolo [4,3-C]pyrimidine-3-amine compounds as CBP and/or EP300 inhibitors." WO2016/086200A1

Rosin, N. L., et al. (2015). "Disruption of Collagen Homeostasis Can Reverse Established Age-Related Myocardial Fibrosis." *Am. J. Pathol.* 185(3): 631-642.

Rowbottom, M. W. et al. (2016a). "Preparation of substituted pyridinylmethylamine compounds as lysyl oxidase-like 2 inhibitors". WO2016144702

Rowbottom, M. W. et al. (2016b). "Preparation of fluorinated pyridine derivatives as lysyl oxidase-like 2 inhibitors and uses thereof." WO2016144703

Rowbottom, M. W.; Hutchinson, J. H. (2017a). "Preparation of pyrimidine derivatives as Lysyl oxidase-like 2 inhibitors useful for the treatment of fibrosis." WO2017003862

Rowbottom, M. W.; Hutchinson, J. H. (2017b). "Lysyl oxidase-like 2 inhibitors and uses thereof." WO2017015221

Ruiz, L. A., et al. (2011). "Single-nucleotide polymorphisms in the lysyl oxidase-like protein 4 and complement component 3 genes are associated with increased risk for endometriosis and endometriosis-associated infertility." *Fertil Steril* 96(2): 512-515.

Sansom, O. (2012). *Targeting the tumour microenvironment in pancreatic cancer*. EACR-IACR Joint Conference: Tumour Microenvironment, Dublin, Ireland.

Sayre, L. M. (2007). "Amine compounds for amine oxidase inhibitors, and therapeutic use". WO2007005737A2

Schietke, R., et al. (2010). "The lysyl oxidases LOX and LOXL2 are necessary and sufficient to repress E-cadherin in hypoxia: insights into cellular transformation processes mediated by HIF-1." *J Biol Chem* 285(9): 6658-6669.

Schlotzer-Schrehardt, U., et al. (2008). "Genotype-correlated expression of lysyl oxidase-like 1 in ocular tissues of patients with pseudoexfoliation syndrome/glaucoma and normal patients." *American Journal of Pathology* 173(6): 1724-1735.

Schohe-Loop, R., et al. (2003). "Preparation of 2-phenyl-3 (2H)-pyridazinones as lysyl oxidase inhibitors for preventing and treating fibrosis". DE10216144A1

Schuetze, F., et al. (2015). "Inhibition of Lysyl Oxidases Improves Drug Diffusion and Increases Efficacy of Cytotoxic Treatment in 3D Tumor Models." *Sci. Rep.* 5: 17576.

Schweighauser, L., et al. (2015). "Attraction or Repulsion? London Dispersion Forces Control Azobenzene Switches." *Angew. Chem. Int ed* 54(45): 13436-13439.

Scola, N. and T. Gorogh (2010). "LOXL4 as a selective molecular marker in primary and metastatic head/neck carcinoma." *Anticancer Res* 30(11): 4567-4571.

Se, L Y et al. (2017) "Expression of Lysyl Oxidase Predictive of Distant Metastasis of Laryngeal Cancer". Otolaryngology—head and neck surgery; 156(3), 489-497

Shen, C. J., et al. (2014). "Ionizing radiation induces tumor cell lysyl oxidase secretion." *BMC Cancer* 14: 532/531-532/510.

Shinobu, M et al. (2016) "Lysyl oxidase is associated with increased thrombosis and platelet reactivity". Blood; 127 (11), 1493-1501

Siegel, R. C., et al. (1978). "Biochemical and immunochemical study of lysyl oxidase in experimental hepatic fibrosis in the rat." *Proceedings of the National Academy of Sciences* 75(6): 2945-2949.

Smith, V. and A. K. Holzer (2010). "Chemotherapeutic methods and compositions for treating cancer by inhibiting activity of lysyl oxidase-type enzyme". WO2010080769A2

Smith, V. and P. Van Vlasselaer (2011). "Tumor therapy by inhibiting the activity or expression of lysyl oxidase-like 2 with antibodies or inhibitory nucleic acids". WO2011022710A1

Stalmans, I., et al. (2010). "Use of lysyl oxidase related protein inhibitors for treatment of ocular neovascularization and fibrotic damage". WO2010091279A1

Stalmans, I., et al. (2011). "Methods of treatmenting ocular fibrosis by modulating the activity of lysyl oxidase-type enzymes". US20110076285A1

Stewart, G. D., et al. (2008). "Analysis of hypoxia-associated gene expression in prostate cancer: lysyl oxidase and glucose transporter-1 expression correlate with Gleason score." *Oncol Rep* 20(6): 1561-1567.

Tadmor, T., et al. (2013). "The expression of lysyl-oxidase gene family members in myeloproliferative neoplasms." *American Journal of Hematology* 88(5): 355-358.

Tang, H et al. "Lysyl oxidase drives tumour progression by trapping EGF receptors at the cell surface." Nat Commun. 8:14909

Tang, S. S., et al. (1984). "Beta-substituted ethylamine derivatives as suicide inhibitors of lysyl oxidase." *J Biol Chem* 259(2): 975-979.

Threadgill, D. and C. J. Barrick (2007). "Use of EGFR inhibitors to prevent or treat obesity". WO2007011702A2

Toustrup, K., et al. (2011). "Development of a hypoxia gene expression classifier with predictive impact for hypoxic modification of radiotherapy in head and neck cancer." *Cancer research* 71(17): 5923-5931.

Tsang, A. W. and C. M. Furdui (2015). "Methods and compositions comprising epidermal growth factor receptor (EGFR) inhibitors for the treatment of *Chlamydia* infection and related diseases and disorders". WO2015038755A1

Uzel, M. I., et al. (2001). "Multiple bone morphogenetic protein 1-related mammalian metalloproteinases process pro-lysyl oxidase at the correct physiological site and control lysyl oxidase activation in mouse embryo fibroblast cultures." *J Biol Chem* 276(25): 22537-22543.

Vadasz, Z., et al. (2005). "Abnormal deposition of collagen around hepatocytes in Wilson's disease is associated with hepatocyte specific expression of lysyl oxidase and lysyl oxidase like protein-2." *J Hepatol* 43(3): 499-507.

Van Bergen, T., et al. (2013). "The role of LOX and LOXL2 in scar formation after glaucoma surgery." *Invest. Ophthalmol. Visual Sci.* 54(8): 5788-5796.

Van Bierbeek, A and Gingras, M. (1998) "Polysulfurated branched molecules containing functionalized m-phenylene sulfides." *Tetrahedron Lett,* 39(35): 6283-6286.

van Nimwegen, M. J. and B. van de Water (2007). "Focal adhesion kinase: a potential target in cancer therapy." *Biochem Pharmacol* 73(5): 597-609.

Vitalba, D S et al. (2016). "Major Action of Endogenous Lysyl Oxidase in Clear Cell Renal Cell Carcinoma Progression and Collagen Stiffness Revealed by Primary Cell Cultures" *Am. J. Pathol.*; 186(9), 2473-2485

Weihua, Z., et al. (2008). "Survival of Cancer Cells Is Maintained by EGFR Independent of Its Kinase Activity." *Cancer Cell* 13(5): 385-393.

Wiel, C., et al. (2013). "Lysyl oxidase activity regulates oncogenic stress response and tumorigenesis." *Cell Death Dis* 4: e855.

Wilgus, M.-L., et al. (2011). "Lysyl oxidase: A lung adenocarcinoma biomarker of invasion and survival." *Cancer* 117(10): 2186-2191.

Wilhelmus, M. M. M., et al. (2013). "Extracellular matrix modulator lysyl oxidase colocalizes with amyloid-beta pathology in Alzheimer's disease and hereditary cerebral hemorrhage with amyloidosis-Dutch type." *Exp. Gerontol.* 48(2): 109-114.

Williamson, P. R. and H. M. Kagan (1987). "Electronegativity of aromatic amines as a basis for the development of ground state inhibitors of lysyl oxidase." *J Biol Chem* 262(30): 14520-14524.

Wong, C. C.-L., et al. (2011). "Hypoxia-inducible factor 1 is a master regulator of breast cancer metastatic niche formation." *Proceedings of the National Academy of Sciences* 108(39): 16369-16374.

Wong, C. C.-L., et al. (2014). "Lysyl oxidase-like 2 is critical to tumor microenvironment and metastatic niche formation in hepatocellular carcinoma." *Hepatology* (Hoboken, NJ, U. S.) 60(5): 1645-1658.

Xiao Q and Ge G. (2012) "Lysyl Oxidase, Extracellular Matrix Remodeling and Cancer Metastasis" *Cancer Microenviron.* 5(3): 261-273

Xu, J., et al. (2014). "67 laminin receptor promotes the malignant potential of tumour cells up-regulating lysyl oxidase-like 2 expression in cholangiocarcinoma." *Digestive and Liver Disease* 46(8): 750-757.

Yang, X., et al. (2013). "Inactivation of lysyl oxidase by β-aminopropionitrile inhibits hypoxia-induced invasion and migration of cervical cancer cells." *Oncol Rep* 29(2): 542-548.

Yang, Z., et al. (2010). "Uric acid increases fibronectin synthesis through upregulation of lysyl oxidase expression in rat renal tubular epithelial cells." *Am. J. Physiol.* 299(2, Pt. 2): F336-F346.

Zaffryar-Eilot, S., et al. (2013). "Lysyl oxidase-like-2 promotes tumour angiogenesis and is a potential therapeutic target in angiogenic tumours." *Carcinogenesis* 34(10): 2370-2379.

Zenkel, M., et al. (2011). "Regulation of lysyl oxidase-like 1 (LOXL1) and elastin-related genes by pathogenic factors associated with pseudoexfoliation syndrome." *Invest Ophthalmol Vis Sci* 52(11): 8488-8495.

Zhao X and Subramaian S. (2017). "Intrinsic Resistance of Solid Tumors to Immune Checkpoint Blockade Therapy" *Cancer Res*; 77(4), 817-822

Zhi, C et al. (2017) "Elevated ischaemia-associated lysyl oxidase activity in delayed graft failure 6-12 months after renal transplantation" Experimental Physiology 102(2), 282-287

Zhu, J., et al. (2015). "Lysyl Oxidase Is Predictive of Unfavorable Outcomes and Essential for Regulation of Vascular Endothelial Growth Factor in Hepatocellular Carcinoma." *Digestive Diseases and Sciences:* 1-13.

Zibadi, S., et al. (2010). "T lymphocyte regulation of lysyl oxidase in diet-induced cardiac fibrosis." *Cardiovasc Toxicol* 10(3): 190-198.

The invention claimed is:

1. A compound according to formula IIId, or a pharmaceutically acceptable salt thereof:

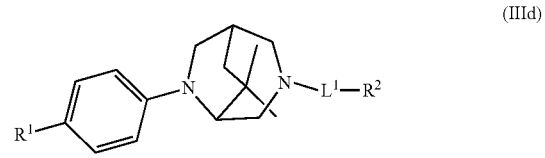

(IIId)

wherein $R^1$ is selected from hydrogen, halo, —CN, —NO$_2$, —OR$^{41}$, —NR$^{41}$R$^{42}$, —SR$^{41}$, —C(O)R$^{41}$, —C(O)OR$^{41}$, —OC(O)R$^{41}$, —O(CR$^{43}$R$^{44}$)$_o$OR$^{41}$, —C(O)NR$^{41}$R$^{42}$, —NR$^{41}$C(O)R$^{43}$, NR$^{41}$C(O)NR$^{41}$R$^{42}$, —OC(O)NR$^{41}$R$^{42}$, —NR$^{41}$C(O)OR$^{42}$, —SO$_2$NR$^{41}$R$^{42}$, —NR$^{41}$SO$_2$R$^{42}$, —SO$_2$R$^{41}$, optionally substituted C$_{1-6}$ alkyl, optionally substituted C$_{1-6}$ haloalkyl, optionally substituted C$_{2-6}$ alkenyl, optionally substituted C$_{2-6}$ alkynyl, optionally substituted C$_{3-6}$ cycloalkyl, optionally substituted 3- to 7-membered heterocyclyl including 1, 2 or 3 heteroatoms selected from N, O or S, optionally substituted aryl, optionally substituted 5- to 10-membered heteroaryl including 1, 2 or 3 heteroatoms selected from N, O or S;

o is selected from 1 to 6;

$R^{A1}$ and $R^{A2}$ are each independently selected from H, optionally substituted $C_{1-6}$ alkyl, $C_{1-6}$ haloalkyl, $C_{2-6}$ alkenyl, $C_{2-6}$ alkynyl, $C_{3-6}$ cycloalkyl, 3- to 7-membered heterocyclyl including 1, 2 or 3 heteroatoms selected from N, O or S, 6-membered aryl, 3- to 7-membered heteroaryl including 1, 2 or 3 heteroatoms selected from N, O or S, or $R^{A1}$ and $R^{A2}$ together with the nitrogen atom to which they are attached form a 3- to 7-membered heterocyclyl including 1, 2 or 3 heteroatoms selected from N, O or S, wherein when $C_{1-6}$ alkyl is substituted it is substituted with $SR^{A3}$, $SO_2R^{A3}$, $NR^{A3}R^{A4}$ and $OR^{A3}$;

$R^{A3}$ and $R^{A4}$ are each independently selected from H, halo, $C_{1-6}$ alkyl, $C_{1-6}$ haloalkyl, $C_{2-6}$ alkenyl, $C_{2-6}$ alkynyl, $C_{3-6}$ cycloalkyl, 3- to 7-membered heterocyclyl including 1, 2 or 3 heteroatoms selected from N, O or S, aryl, heteroaryl including 1, 2 or 3 heteroatoms selected from N, O or S, or $R^{A1}$ and $R^{A2}$ together with the nitrogen atom to which they are attached form a 4- to 6-membered heterocyclyl including 1, 2 or 3 heteroatoms selected from N, O or S;

$L^1$ is selected from a bond, —C(O)—, —C(O)O—, —C(O)NR$^{A5}$—, —C(O)NR$^{A5}$NR$^{A6}$—, —C(S)—, —C(S)NR$^{A5}$—, —S(O)$_2$—, —S(O)$_2$NR$^{A5}$—, —C(=NR$^{A5}$)—, —C(=N—CN)NR$^{A5}$—, —C(=NR$^{A5}$)NR$^{A6}$—, —C(O)(CR$^{A7}$R$^{A8}$)$_r$—, —C(O)NR$^{A6}$(CR$^{A7}$R$^{A8}$)$_r$—, —S(O)$_2$(CR$^{A7}$R$^{A8}$)$_r$—, —(CR$^{A7}$R$^{A8}$)$_r$—;

r is 1, 2, 3 or 4;

each of $R^{A5}$ and $R^{A6}$, is independently selected at each occurrence from H, optionally substituted $C_{1-6}$ alkyl, optionally substituted $C_{1-6}$ haloalkyl, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkenyl, optionally substituted 3- to 6-membered heterocyclyl including 1, 2 or 3 heteroatoms selected from N, O or S, optionally substituted aryl and optionally substituted heteroaryl including 1, 2 or 3 heteroatoms selected from N, O or S;

each of $R^{A7}$ and $R^{A8}$ is independently selected at each occurrence from H, halo, —OR$^{A5}$, optionally substituted $C_{1-6}$ alkyl, optionally substituted $C_{1-6}$ haloalkyl, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkenyl, optionally substituted 3- to 6-membered heterocyclyl including 1, 2 or 3 heteroatoms selected from N, O or S, optionally substituted aryl and optionally substituted heteroaryl including 1, 2 or 3 heteroatoms selected from N, O or S, or $R^{A7}$ and $R^{A8}$ together with the carbon atom to which they are attached form a $C_{3-6}$-cycloalkyl;

$R^2$ is selected from H, CN, OH, —NR$^{B1}$R$^{B2}$, halo, optionally substituted $C_{1-6}$ alkyl, $C_{1-6}$ haloalkyl, $C_{2-6}$ alkenyl, optionally substituted $C_{2-6}$ alkynyl, $C_{3-6}$ cycloalkyl, $C_{3-6}$ cycloalkenyl, optionally substituted 3- to 7-membered heterocyclyl including 1, 2 or 3 heteroatoms selected from N, O or S, optionally substituted aryl and optionally substituted 5- to 10-membered heteroaryl including 1, 2 or 3 heteroatoms selected from N, O or S, provided that when $L^1$ is a bond, $R^2$ is not H; and each of $R^{B1}$ and $R^{B2}$ is independently selected at each occurrence from H, optionally substituted $C_{1-6}$ alkyl, or optionally substituted $C_{1-6}$ haloalkyl;

wherein the optional substituents are independently selected from the group consisting of halo, —CN, —NO$_2$, —OR$^{A1}$, —NR$^{A1}$R$^{A2}$, —SR$^{A1}$, —C(O)R$^{A1}$, —C(O)OR$^{A1}$, —OC(O)R$^{A1}$, —O(CR$^{A1}$R$^{A2}$)$_m$OR$^{A3}$, —C(O)NR$^{A1}$R$^{A2}$, —NR$^{A1}$C(O)R$^{A2}$, —SO$_2$R$^{A3}$, —SO$_2$NR$^{A1}$R$^{A2}$, —NR$^{A1}$SO$_2$R$^{A2}$, $C_{1-6}$ alkyl, $C_{1-6}$ haloalkyl, $C_{2-6}$ alkenyl, $C_{2-6}$ alkynyl, =O, =S, =NR$^{A1}$, $C_{3-6}$ cycloalkyl, aryl and 3- to 6-membered heterocyclyl including 1, 2 or 3 heteroatoms selected from N, O and S.

2. The compound according to claim 1, wherein $R^1$ is selected from halo, CN, OR$^{A1}$, C(O)R$^{A1}$, —NR$^{A1}$R$^{A2}$, —SR$^{A1}$, optionally substituted $C_{1-6}$ alkyl and optionally substituted 4 to 7 membered heterocyclyl.

3. The compound according to claim 1, wherein $R^1$ is ethoxy or an optionally substituted 6-membered heterocycloalkyl.

4. The compound according to claim 1, wherein $R^1$ is thiomorpholine dioxide, morpholine, or ethoxy.

5. The compound according to claim 1, wherein $L^1$ is selected from a bond, —SO$_2$—, —C(O)—, —C(O)NR$^{A5}$— and —C(O)NR$^{A6}$(CR$^{A7}$R$^{A8}$)$_r$—.

6. The compound according to claim 1, wherein L' is selected from —C(O)— or —C(O)NH—.

7. The compound according to claim 1, wherein $R^2$ is selected from H, CN, OH, —NR$^{B1}$R$^{B2}$, halo, optionally substituted $C_{1-6}$ alkyl, optionally substituted $C_{2-6}$ alkynyl, optionally substituted 3- to 6-membered heterocyclyl, optionally substituted aryl and optionally substituted heteroaryl including 1, 2 or 3 heteroatoms selected from N, O or S.

8. The compound according to claim 1, wherein $R^2$ is optionally substituted 5- to 6-membered heterocyclyl including 1, 2 or 3 heteroatoms selected from N, O or S.

9. The compound according to claim 1, wherein $R^2$ is $C_{1-6}$ alkyl substituted with CN.

10. The compound according to claim 1, wherein $R^2$ is $C_{1-6}$ alkyl substituted with OH.

11. The compound according to claim 1, wherein $R^1$ is ethoxy, —N(Me)CH$_2$CH$_2$S(O)$_2$Me, or optionally substituted 6-membered heterocycloalkyl; $L^1$ is selected from a bond, —C(O)—, —C(O)NH—, —C(O)NR$^{A6}$(CR$^{A7}$R$^{A8}$)$_r$—, and —(CR$^{A7}$R$^{A8}$)$_r$—; and $R^2$ is selected from —NHCH$_2$CH$_2$OH, —CH$_2$CH$_2$OH, thiomorpholine dioxide, morpholine or methylsulfonyl piperazine.

12. A pharmaceutical composition comprising a compound according to claim 1, or a pharmaceutically acceptable salt thereof, and a pharmaceutically acceptable excipient.

13. A combination comprising a compound according to claim 1 and one or more additional anti-tumour agent and/or radiotherapy.

14. A method of treating a cancer in a subject in need thereof, said method comprising administering to said subject a therapeutically effective amount of a compound of claim 1; wherein the cancer is selected from the group consisting of lung cancer, pancreatic cancer, squamous cells carcinoma, skin cancer, thyroid cancer, colorectal cancer, prostate cancer, renal cancer, breast cancer, head & neck cancer, ovarian cancer, oesophageal cancer, and cholangiocarcinoma, and hepatocellular carcinoma.

15. A method of treating a fibrotic disorder in a subject in need thereof, said method comprising administering to said subject a therapeutically effective amount of a compound of claim 1; wherein the fibrotic disorder is selected from the group consisting of renal fibrosis, lung fibrosis and liver fibrosis; or wherein the fibrotic disorder is characterized by excess fibrous connective tissue in a tissue or organ in response to injury.

16. The method of claim 14, wherein the cancer is selected from the group consisting of breast cancer, pancreatic cancer, and colorectal cancer.

* * * * *